(12) United States Patent
Crouse et al.

(10) Patent No.: US 9,018,136 B2
(45) Date of Patent: Apr. 28, 2015

(54) PESTICIDAL COMPOSITIONS AND PROCESSES RELATED THERETO

(71) Applicant: Dow AgroSciences LLC, Indianapolis, IN (US)

(72) Inventors: Gary D. Crouse, Noblesville, IN (US); Thomas C. Sparks, Greenfield, IN (US); William H. Dent, III, Indianapolis, IN (US); CaSandra L. McLeod, Indianapolis, IN (US); Lawrence C. Creemer, Greenfield, IN (US); David A. Demeter, Fishers, IN (US); Amanda E. Fritz, Carmel, IN (US); Lindsey G. Fischer, Indianapolis, IN (US); Erich W. Baum, Greenwood, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/314,457

(22) Filed: Jun. 25, 2014

(65) Prior Publication Data

US 2014/0315721 A1    Oct. 23, 2014

Related U.S. Application Data

(62) Division of application No. 13/366,602, filed on Feb. 6, 2012, now Pat. No. 8,815,922.

(60) Provisional application No. 61/440,003, filed on Feb. 7, 2011.

(51) Int. Cl.
| | | |
|---|---|---|
| *A01N 25/02* | (2006.01) | |
| *A01N 43/60* | (2006.01) | |
| *A61K 31/427* | (2006.01) | |
| *A61K 31/422* | (2006.01) | |
| *C07D 263/30* | (2006.01) | |
| *C07D 277/04* | (2006.01) | |
| *A61K 45/06* | (2006.01) | |
| *C07F 7/08* | (2006.01) | |
| *C07D 403/12* | (2006.01) | |
| *C07D 401/12* | (2006.01) | |
| *C07D 405/12* | (2006.01) | |
| *C07D 413/12* | (2006.01) | |
| *C07D 417/12* | (2006.01) | |

(Continued)

(52) U.S. Cl.
CPC .............. *A01N 43/60* (2013.01); *A61K 45/06* (2013.01); *C07F 7/0812* (2013.01); *C07D 403/12* (2013.01); *C07D 401/12* (2013.01); *C07D 405/12* (2013.01); *C07D 413/12* (2013.01); *C07D 417/12* (2013.01); *C07D 417/14* (2013.01); *C07D 249/08* (2013.01); *C07D 495/04* (2013.01); *A01N 43/78* (2013.01); *A01N 43/86* (2013.01); *A01N 47/42* (2013.01); *A01N 43/72* (2013.01); *A01N 47/34* (2013.01); *A01N 43/80* (2013.01); *A01N 43/653* (2013.01); *A01N 43/76* (2013.01); *A01N 43/90* (2013.01)

(58) Field of Classification Search
USPC ............ 514/369, 374; 548/184, 235; 504/358
See application file for complete search history.

(56) References Cited

U.S. PATENT DOCUMENTS

| | | | |
|---|---|---|---|
| 3,932,436 A | 1/1976 | Grohe et al. | |
| 4,833,158 A | 5/1989 | Twydell et al. | |

(Continued)

FOREIGN PATENT DOCUMENTS

| | | | |
|---|---|---|---|
| WO | WO 2009/102736 A1 | 8/2009 | |
| WO | WO 2011/017504 A1 | 10/2011 | |
| WO | PCT/US2012/023932 A1 | 5/2012 | |

OTHER PUBLICATIONS

Kagabu S and Medej S, "Stability Comparison of Imidacloprid and Related Compounds under Simulated Sunlight, Hydrolysis Conditions, and to Oxygen" Biosci. Biotech. Biochem., 59 (6), 980-985, (1995).

Kagabu S, Murata N, Hibino R, Hanzawa M, and Nishimura K, "Insecticidal and Neuroblocking Activities of Thiamethoxam-Type Compounds in the American Cockroach (*Periplaneta americana* L.)" J. Pesticide Sci. 30 (2), 111-115 (2005).

(Continued)

*Primary Examiner* — Samantha Shterengarts
(74) *Attorney, Agent, or Firm* — Carl D. Corvin

(57) ABSTRACT

This document discloses molecules having the following formulas ("Formula One" & "Formula Two" and "Formula Three")

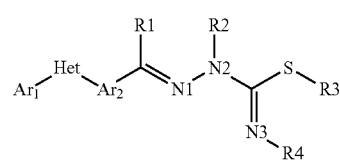

Formula 1

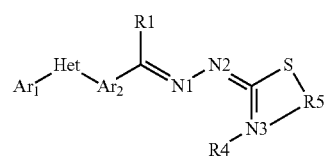

Formula 2

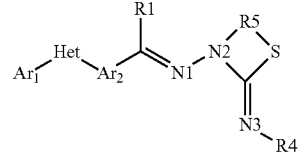

Formula 3

The $Ar_1$, Het, $Ar_2$, R1, R2, R3, R4, and R5 are further described herein.

15 Claims, No Drawings

(51) Int. Cl.
  C07D 417/14 (2006.01)
  C07D 249/08 (2006.01)
  C07D 495/04 (2006.01)
  A01N 43/78 (2006.01)
  A01N 43/86 (2006.01)
  A01N 47/42 (2006.01)
  A01N 43/72 (2006.01)
  A01N 47/34 (2006.01)
  A01N 43/80 (2006.01)
  A01N 43/653 (2006.01)
  A01N 43/76 (2006.01)
  A01N 43/90 (2006.01)

(56) References Cited

U.S. PATENT DOCUMENTS

2007/0027034 A1 2/2007 Tank et al.
2008/0262057 A1 10/2008 Tisdell et al.
2009/0137667 A1 5/2009 Kabanov et al.
2009/0209476 A1 8/2009 Crouse et al.

OTHER PUBLICATIONS

Kollmeyer, WD, Flattum RF, Foster JP, Powell JE, Schroeder ME, and Soloway SB, "Discovery of the Nitromethylene Heterocycle Insecticides" Nicotinoid Insecticides and the Nicotinic Acetylcholine Receptor (pp. 71-89) Eds Yamamoto I, and Casida JE.

Shiga Y, Okada I, and Fukuchi T, "Synthesis and Acaricidal Activity of N-(1,3,4-Thiadiazol-2-yl) cyclopropanecarboxamides" J. Pesticide Sci. 28, 61-63 (2003).

Sparks TC, Crouse GD, and Durst D, "Natural products as insecticides: the biology, biochemistry and quantitative structure-activity relationships of spinosyns and spinosoids" Pest Manag Sci 57:896-905 (2001).

Wakita T, Kinoshita K, Kodaka K, Yasui N, Naoi A, and Banba S "Synthesis and Structure Activity Relationships of Dinotefuran Derivatives: Modification in the Tetrahydro-3-furylmethyl Part" J. Pesticide Sci. 29 (4), 356-363 (2004).

Ertl P. "Cheminformatics Analysis of Organic Substituents: Identification of the Most Common Substituents, Calculation of Substituents Properties, and Automatic Identification of Drug-like Bioisosteric Groups" J. Chem Inf. Comput. Sci. 2003, 43, 374-380.

PESTICIDAL COMPOSITIONS AND PROCESSES RELATED THERETO

CROSS REFERENCE TO RELATED APPLICATIONS

This Application is a divisional application of U.S. non-provisional application Ser. No. 13/366,602, which was filed on Feb. 6, 2012, and which claims priority from U.S. provisional application 61/440,003, which was filed on Feb. 7, 2011. The entire content of these applications are hereby incorporated by reference into this Application.

FIELD OF THE INVENTION

The invention disclosed in this document is related to the field of processes to produce molecules that are useful as pesticides (e.g., acaricides, insecticides, molluscicides, and nematicides), such molecules, and processes of using such molecules to control pests.

BACKGROUND OF THE INVENTION

Pests cause millions of human deaths around the world each year. Furthermore, there are more than ten thousand species of pests that cause losses in agriculture. The world-wide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known, but resistance has even developed to some of the newer pesticides.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Acaricide Group" is defined under the heading "ACARICIDES".

"AI Group" is defined after the place in this document where the "Herbicide Group" is defined.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbornenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbornyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Fungicide Group" is defined under the heading "FUNGICIDES."

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Herbicide Group" is defined under the heading "HERBICIDES."

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

"Insecticide Group" is defined under the heading "INSECTICIDES."

"Nematicide Group" is defined under the heading "NEMATICIDES"

"Synergist Group" is defined under the heading "SYNERGISTIC MIXTURES AND SYNERGISTS"

DETAILED DESCRIPTION OF THE INVENTION

This document discloses molecules having the following formulas ("Formula One" & "Formula Two" and "Formula Three"): (In the following formulas the nitrogens are numbered 1, 2, and 3, solely for the purpose of identifying them and being able to refer to them throughout this document for clarity purposes)

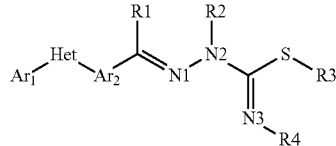

Formula 1

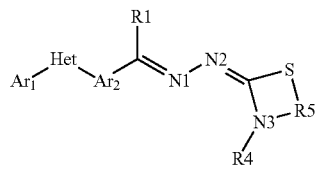

Formula 2

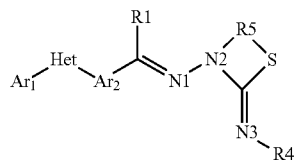

Formula 3 wherein:
(a) $Ar_1$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl, and substituted phenoxy,
wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O$ $(C_1$-$C_6$ alkyl)phenyl, and phenoxy;

(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other (but may be meta or para, such as, for a five membered ring they are 1,3 and for a 6 membered ring they are either 1, 3 or 1,4), and where said heterocyclic ring may also be substituted with one or more substituents independently selected from H, F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O$ $(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy,
wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O$ $(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(c) $Ar_e$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy, wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_1$-C$_6$ haloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, and phenoxy;

(d) R1 is selected from H, CN, F, Cl, Br, I, C$_1$-C$_6$ alkyl, C$_3$-C$_6$ cycloalkyl, C$_3$-C$_6$ cycloalkoxy, C$_1$-C$_6$ alkoxy, C$_2$-C$_6$ alkenyl, C$_2$-C$_6$ alkynyl, S(=O)$_n$(C$_1$-C$_6$ alkyl), OSO$_2$(C$_1$-C$_6$ alkyl), C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, or phenoxy, wherein each alkyl, cycloalkyl, cycloalkoxy, alkoxy, alkenyl, alkynyl, phenyl, and phenoxy, are optionally substituted with one or more substituents independently selected from F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O (C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, and phenoxy;

(e) R2 is H, C$_1$-C$_6$ alkyl, C$_3$-C$_6$ cycloalkyl, C$_2$-C$_6$ alkenyl, C$_2$-C$_6$ alkynyl, C(=O)H, C(=O)(C$_1$-C$_6$ alkyl), C(=O)O (C$_1$-C$_6$ alkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, C$_1$-C$_6$ alkylphenyl, C$_1$-C$_6$ alkyl-O-phenyl, C(=O)Het-1, Het-1, C$_1$-C$_6$ alkylHet-1, or C$_1$-C$_6$ alkyl-O-Het-1, wherein each alkyl, cycloalkyl, alkenyl, alkynyl, phenyl, and Het-1 are optionally substituted with one or more substituents independently selected from F, Cl, Br, I, CN, NO$_2$, NR$_x$R$_y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S (C$_1$-C$_6$ alkyl), C(=O)(C$_1$-C$_6$ alkyl)C(=O)O(C$_1$-C$_6$ alkyl), phenyl, phenoxy, and Het-1;

(f) R3 is C$_1$-C$_6$ alkyl, C$_3$-C$_6$ cycloalkyl, C$_2$-C$_6$ alkenyl, C$_2$-C$_6$ alkynyl, C(=O)H, C(=O)(C$_1$-C$_6$ alkyl), C(=O)O (C$_1$-C$_6$ alkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, C$_1$-C$_6$ alkylphenyl, C$_1$-C$_6$ alkyl-O-phenyl, C(=O)Het-1, Het-1, C$_1$-C$_6$ alkylHet-1, C$_1$-C$_6$ alkyl-O—C(=O)C$_1$-C$_6$ alkyl-O—C$_1$-C$_6$ alkyl, C$_1$-C$_6$ alkyl-O—C(=O)C$_1$-C$_6$ alkyl-O—C$_1$-C$_6$ alkyl-O—C$_1$-C$_6$ alkyl, C$_1$-C$_6$ alkyl-O—C(=O) C$_1$-C$_6$ alkyl-O—C$_1$-C$_6$ haloalkyl, C$_1$-C$_6$ alkyl-O—C(=O) C$_1$-C$_6$ alkyl-N(R$_x$)C(=O)—O-phenyl, C$_1$-C$_6$ alkyl-O—C (=O)C$_1$-C$_6$ alkyl-N(R$_x$)C(=O)—O—C$_1$-C$_6$ alkylphenyl, C$_1$-C$_6$ alkylC(=O)N(R$_x$)C$_1$-C$_6$ alkyl, C$_1$-C$_6$ alkylC(=O)N (R$_x$)C$_1$-C$_6$ alkylHet-1C(=O)—O—C$_1$-C$_6$ alkyl, C$_1$-C$_6$ alkylC(=O)N(R$_x$)C$_1$-C$_6$ alkylHet-1, C$_1$-C$_6$ alkylC(=O) Het-1, C$_1$-C$_6$ alkylC(=O)N(R$_x$)C$_1$-C$_6$ alkyl(N(R$_x$)(R$_y$))(C (=O)OH), C$_1$-C$_6$ alkylC(=O)N(R$_x$)C$_1$-C$_6$ alkylN(R$_x$)(R$_y$), C$_1$-C$_6$ alkylC(=O)N(R$_x$)C$_1$-C$_6$ alkylN(ROC(=O)—O— C$_1$-C$_6$ alkyl, C$_1$-C$_6$ alkylC(=O)N(R$_x$)C$_1$-C$_6$ alkyl(N(ROC (=O)—O—C$_1$-C$_6$ alkyl)(C(=O)OH), C$_1$-C$_6$ alkylC(=O) Het-1C(=O)—O—C$_1$-C$_6$ alkyl, C$_1$-C$_6$ alkyl-O—C(=O)— O—C$_1$-C$_6$ alkyl, C$_1$-C$_6$ alkyl-O—C(=O)C$_1$-C$_6$ alkyl, C$_1$-C$_6$ alkyl-O—C(=O)C$_3$-C$_6$ cycloalkyl, C$_1$-C$_6$ alkyl-O—C(=O) Het-1, C$_1$-C$_6$ alkyl-O—C(=O)C$_1$-C$_6$ alkyl-N(R$_x$)C(=O)— O—C$_1$-C$_6$ alkyl, C$_1$-C$_6$ alkyl-NR$_x$R$_y$, or C$_1$-C$_6$ alkyl-O-Het-1, wherein each alkyl, cycloalkyl, alkenyl, alkynyl, phenyl, and Het-1 are optionally substituted with one or more substituents independently selected from F, Cl, Br, I, CN, NO$_2$, NR$_x$R$_y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O) (C$_1$-C$_6$ alkyl)C(=O)O(C$_1$-C$_6$ alkyl), phenyl, phenoxy, Si(C$_1$-C$_6$ alkyl)$_3$, S(=O)$_n$NR$_x$R$_y$, and Het-1;

(g) R4 is H, C$_1$-C$_6$ alkyl, C$_3$-C$_6$ cycloalkyl, C$_2$-C$_6$ alkenyl, C$_2$-C$_6$ alkynyl, C(=O)H, C(=O)(C$_1$-C$_6$ alkyl), C(=O)O (C$_1$-C$_6$ alkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, C$_1$-C$_6$ alkylphenyl, C$_1$-C$_6$ alkyl-O-phenyl, C(=O)Het-1, Het-1, C$_1$-C$_6$ alkylHet-1, or C$_1$-C$_6$ alkyl-O-Het-1, wherein each alkyl, cycloalkyl, alkenyl, alkynyl, phenyl, and Het-1 are optionally substituted with one or more substituents independently selected from F, Cl, Br, I, CN, NO$_2$, NR$_x$R$_y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S (C$_1$-C$_6$ alkyl), C(=O)(C$_1$-C$_6$ alkyl), C(=O)O(C$_1$-C$_6$ alkyl), phenyl, phenoxy, and Het-1;

(h) R5 is a 2 to 4 membered saturated or unsaturated hydrocarbyl linkage where said linkage may also be substituted with F, Cl, Br, I, CN, NO$_2$, oxo, NR$_x$R$_y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, and Het-1, wherein each alkyl, cycloalkyl, cycloalkoxy, alkoxy, alkenyl, alkynyl, phenyl, phenoxy, and Het-1, are optionally substituted with one or more substituents independently selected from F, Cl, Br, I, CN, NO$_2$, oxo, NR$_x$R$_y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$_x$R$_y$, (C$_1$-C$_6$ alkyl)NR$_x$R$_y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, halophenyl, phenoxy, and Het-1;

(i) n=0, 1, or 2;

(j) R$_x$ and R$_y$ are independently selected from H, C$_1$-C$_6$ alkyl, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), and phenyl, wherein each alkyl, cycloalkyl, cycloalkoxy, alkoxy, alkenyl, alkynyl, phenyl, phenoxy, and Het-1, are optionally substituted with one or more substituents independently selected from F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, halophenyl, phenoxy, and Het-1, or R$_x$ and R$_y$ together can optionally form a 5- to 7-membered saturated or unsaturated cyclic group which may contain one or more heteroatoms selected from nitrogen, sulfur, and oxygen, and where said cyclic group can contain >C=O or >C=S, and where said cyclic group may be substituted with F, Cl, Br, I, CN, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, substituted phenyl, phenoxy, and Het-1; and (k) Het-1 is a 5- or 6-membered, saturated or unsaturated, heterocyclic ring, containing one or more heteroatoms independently selected from nitrogen, sulfur or oxygen.

It is understood that in Formula 1, when R2 is H, the compounds may exist in more than one tautomeric or isomeric form, wherein the hydrogen is attached to either of the nitrogen atoms; further, both E and Z isomers may exist. Any and all isomeric forms of the compounds of this invention are claimed.

In another embodiment Ar$_1$ is a substituted phenyl, wherein said substituted phenyl has one or more substituents independently selected from C$_1$-C$_6$ haloalkyl and C$_1$-C$_6$ haloalkoxy.

In another embodiment Ar$_1$ is a substituted phenyl, wherein said substituted phenyl has one or more substituents independently selected from CF$_3$, OCF$_3$, and OCF$_2$CF$_3$.

In another embodiment Het is selected from triazolyl, imidazolyl, or pyrazolyl, which can be substituted or unsubstituted.

In another embodiment Het is a 1,2,4-triazolyl

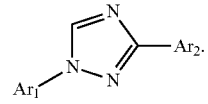

In another embodiment Het is 1,4-imidazolyl

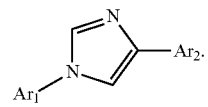

In another embodiment Het is 1,3-pyrazolyl

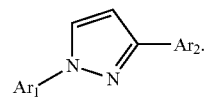

In another embodiment Het is a substituted 1,3-pyrazolyl.
In another embodiment Het is 1,4-pyrazolyl

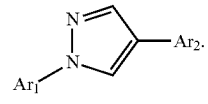

In another embodiment Ar$_2$ is a phenyl.
In another embodiment R1 is H or C$_1$-C$_6$ alkyl.

In another embodiment R1 is H or $CH_3$.

In another embodiment R2 is H.

In another embodiment R3 is selected from $C_1$-$C_6$ alkyl, $C_2$-$C_6$ alkenyl, $C_2$-$C_6$ alkynyl, $C_1$-$C_6$ alkylphenyl, $C_1$-$C_6$ alkylHet-1, $C_1$-$C_6$ alkyl-O—C(═O)$C_1$-$C_6$ alkyl-O—$C_1$-$C_6$ alkyl, $C_1$-$C_6$ alkyl-O—C(═O)$C_1$-$C_6$ alkyl-O—$C_1$-$C_6$ alkyl-O—$C_1$-$C_6$ alkyl, $C_1$-$C_6$ alkyl-O—C(═O)$C_1$-$C_6$ alkyl-O—$C_1$-$C_6$ haloalkyl, $C_1$-$C_6$ alkyl-O—C(═O)$C_1$-$C_6$ alkyl-N($R_x$)C(═O)—O-phenyl, $C_1$-$C_6$ alkyl-O—C(═O)$C_1$-$C_6$ alkyl-N($R_x$)C(═O)—O—$C_1$-$C_6$ alkylphenyl, $C_1$-$C_6$ alkylC(═O)N($R_x$)$C_1$-$C_6$ alkyl, $C_1$-$C_6$ alkylC(═O)N($R_x$)$C_1$-$C_6$ alkylHet-1C(═O)—O—$C_1$-$C_6$ alkyl, $C_1$-$C_6$ alkylC(═O)N($R_x$)$C_1$-$C_6$ alkylHet-1, $C_1$-$C_6$ alkylC(═O)Het-1, $C_1$-$C_6$ alkylC(═O)N($R_x$)$C_1$-$C_6$ alkyl(N($R_x$)($R_y$))(C(═O)OH), $C_1$-$C_6$ alkylC(═O)N($R_x$)$C_1$-$C_6$ alkylN($R_x$)($R_y$), $C_1$-$C_6$ alkylC(═O)N($R_x$)$C_1$-$C_6$ alkylN($R_x$)C(═O)—O—$C_1$-$C_6$ alkyl, $C_1$-$C_6$ alkylC(═O)N($R_x$)$C_1$-$C_6$ alkyl(N($R_x$)C(═O)—O—$C_1$-$C_6$ alkyl)(C(═O)OH), $C_1$-$C_6$ alkylC(═O)Het-1C(═O)—O—$C_1$-$C_6$ alkyl, $C_1$-$C_6$ alkyl-O—C(═O)—O—$C_1$-$C_6$ alkyl, $C_1$-$C_6$ alkyl-O—C(═O)$C_1$-$C_6$ alkyl, $C_1$-$C_6$ alkyl-O—C(═O)$C_3$-$C_6$ cycloalkyl, $C_1$-$C_6$ alkyl-O—C(═O)Het-1, or $C_1$-$C_6$ alkyl-O—C(═O)$C_1$-$C_6$ alkyl-N($R_x$)C(═O)—O—$C_1$-$C_6$ alkyl, wherein each alkyl, alkenyl, alkynyl, phenyl, and Het-1 are optionally substituted with one or more substituents independently selected from F, Cl, Br, $C_1$-$C_6$ alkyl, $C_1$-$C_6$ haloalkyl, $C_1$-$C_6$ haloalkoxy, S(═O)$_n$($C_1$-$C_6$ alkyl), C(═O)OH, C(═O)O($C_1$-$C_6$ alkyl), phenyl, Si($C_1$-$C_6$ alkyl)$_3$, and S(═O)$_n$NR$_x$R$_y$.

In another embodiment $R_4$ is phenyl, $C_1$-$C_6$ alkylphenyl, Het-1, or $C_1$-$C_6$ alkyl-O-phenyl, wherein each alkyl, Het-1, and phenyl are optionally substituted with one or more substituents independently selected from F, Cl, NR$_x$R$_y$, $C_1$-$C_6$ alkyl, $C_3$-$C_6$ cycloalkyl, $C_1$-$C_6$ haloalkoxy, C(═O)OC$_1$-$C_6$ alkyl, or $C_1$-$C_6$ alkoxy.

In another embodiment R5 is substituted with oxo, C(═O)OH, phenyl, and Het-1, wherein each phenyl and Het-1, may be optionally substituted with one or more substituents independently selected from oxo, $C_1$-$C_6$ haloalkyl, $C_1$-$C_6$ haloalkoxy, C(═O)OH, and halophenyl.

In another embodiment $R_x$ and $R_y$ are independently selected from H and phenyl, wherein said phenyl, may be optionally substituted with one or more substituents independently selected from F and Cl.

In another embodiment:
$Ar_1$ is a substituted phenyl wherein said substituted phenyl, has one or more $C_1$-$C_6$ haloalkoxy;
Het is a triazolyl;
$Ar_2$ is a phenyl;
R1 is H;
R2 is H;
R3 is $C_1$-$C_6$ alkylHet-1 wherein said alkyl and Het-1 are optionally substituted with one or more substituents independently selected from F, Cl, Br, $C_1$-$C_6$ alkyl, $C_1$-$C_6$ haloalkyl, $C_1$-$C_6$ haloalkoxy, S(═O)$_n$($C_1$-$C_6$ alkyl), C(═O)OH, C(═O)O($C_1$-$C_6$ alkyl), phenyl, Si($C_1$-$C_6$ alkyl)$_3$, and S(═O)$_n$NR$_x$R$_y$;
R4 is phenyl, wherein said phenyl is optionally substituted with one or more substituents independently selected from F, Cl, NR$_x$R$_y$, $C_1$-$C_6$ alkyl, or $C_1$-$C_6$ alkoxy; and n=0, 1, or 2;
$R_x$ and $R_y$ are independently selected from H and phenyl, wherein said phenyl, may be optionally substituted with one or more substituents independently selected from F and Cl; and
Het-1 is a 5- or 6-membered, saturated or unsaturated, heterocyclic ring, containing one or more heteroatoms independently selected from nitrogen, sulfur or oxygen.

In another embodiment Het-1 is selected from benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, triazolyl, piperazinyl, piperidinyl, morpholinyl, pyrrolidinyl, tetrahydrofuranyl, tetrahydropyranyl, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

In another embodiment Het is selected benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, triazolyl, piperazinyl, piperidinyl, morpholinyl, pyrrolidinyl, tetrahydrofuranyl, tetrahydropyranyl, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

In another embodiment Het-1 is selected from benzofuranyl, benzoisothiazolyl, benzoisoxazolyl, benzoxazolyl, benzothienyl, benzothiazolyl, benzothiadizolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, thienylpyrazolyl, triazinyl, triazolyl, piperazinyl, piperidinyl, morpholinyl, pyrrolidinyl, tetrahydrofuranyl, tetrahydropyranyl, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

In another embodiment Het-1 is selected from benzothiadizolyl, furanyl, oxazolyl, and thienylpyrazolyl.

While these embodiments have been expressed, other embodiments and combinations of these expressed embodiments and other embodiments are possible.

The Molecules of Formulae One, Two and Three will generally have a molecular mass of about 100 Daltons to about 1200 Daltons. However, it is generally preferred if the molecular mass is from about 120 Daltons to about 900 Daltons, and it is even more generally preferred if the molecular mass is from about 400 Daltons to about 800 Daltons.

Preparation of Triaryl-Intermediates

Compounds of this invention can be prepared by making a triaryl intermediate, $Ar_1$-Het-$Ar_2$, and then linking it to the desired intermediate to form the desired compound. A wide variety of triaryl intermediates can be used to prepare compounds of this invention, provided that such triaryl intermediates contain a suitable functional group on $Ar_2$ to which the rest of the desired intermediate can be attached. Suitable functional groups include an oxoalkyl or a formyl group. These triaryl intermediates can be prepared by methods previously described in the chemical literature, including Crouse et al. PCT Int. Appl. Publ. WO2009/102736 A1.

Preparation of Hydrazone-Linked Compounds

Hydrazone-linked compounds can be prepared from the corresponding aryl aldehydes or ketones by one of three methods: (1) by reaction with a hydrazine, followed by reaction with an aryl isothiocyanate in tetrahydrofuran (THF), at temperatures between 0 and 100° C. (Reaction A); (2) by reaction with methyl hydrazinecarbodithioate, followed by reaction with an aniline in a polar aprotic solvent such as N,N-dimethylformamide (DMF), at temperatures between 25 and 150° C. (Reaction B); or (3) by reaction with an aryl thiosemicarbazide, that is either commercially available or can be prepared by one who is skilled in the art, in a polar protic solvent such as ethyl alcohol (EtOH), at temperatures between 0 and 100° C. (Reaction C).

Compounds of Formula Two, wherein R5 forms a ring with $N_3$ (see Scheme below) or of Formula Three, wherein R5 forms a ring with $N_2$, can be prepared from a suitable acyclic precursor by using α-halo acids, acid halides, esters, or ketones (F or G or H). For example, treatment of the thiosemicarbazone with a slight excess of an α-halo ester, in a protic solvent such as EtOH or methyl alcohol ($CH_3OH$) results in S-alkylation and subsequent ring closure exclusively onto $N_3$ (Reaction F; see for example, *J. Indian Chemical Society* 1966, 43, 275-276, or *J. Heterocycl. Chem.* 1978, 15, 335-336). When an aprotic solvent such as $CH_2Cl_2$ or dichloroethane ($ClCH_2CH_2Cl$) is used at temperatures from 30° C. to 80° C., the orientation of addition of a halo ketones also favors closure onto $N_3$, with subsequent dehydration to form an imino thiazoline (Reaction G). With α-halo acids or acid halides or esters in a halocarbon solvent such as $CH_2Cl_2$ or $ClCH_2CH_2Cl$, ring closure onto both $N_2$ (Reaction H) and $N_3$ is observed. Though these reactions often proceed in the absence of added base, a base such as sodium bicarbonate, sodium carbonate or sodium acetate, or an amine base such as pyridine or triethylamine, can be added.

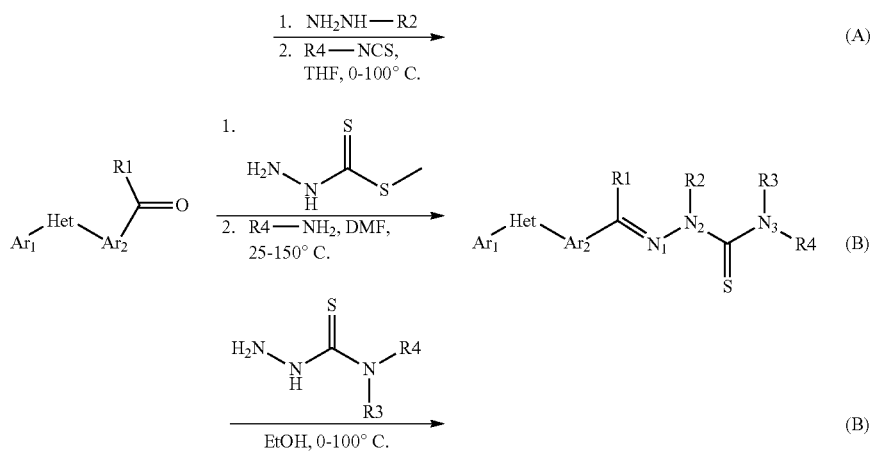

Preparation of Alkylated Hydrazone-Linked Compounds

Alkylated hydrazone-linked compounds can be prepared from the corresponding hydrazone-linked compounds by one of two methods: (1) by reaction with an alkylating agent in EtOH or acetone, at temperatures between 0 and 100° C. for from 1 to 24 h or (2) by reaction with an alkylating agent in chloroform ($CHCl_3$), dichloromethane ($CH_2Cl_2$), or other halocarbon solvent, with or without a base such as sodium bicarbonate, at from 20 to 60° C.

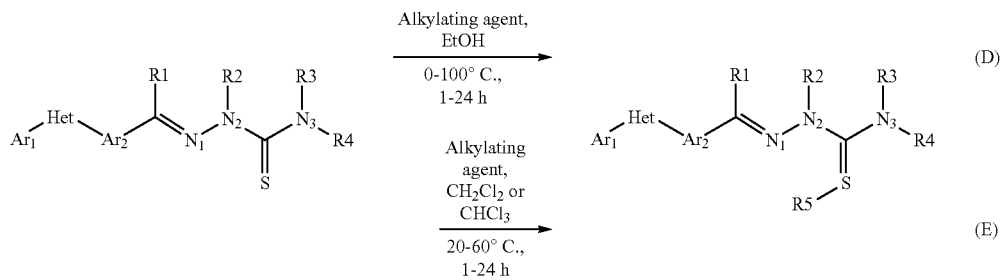

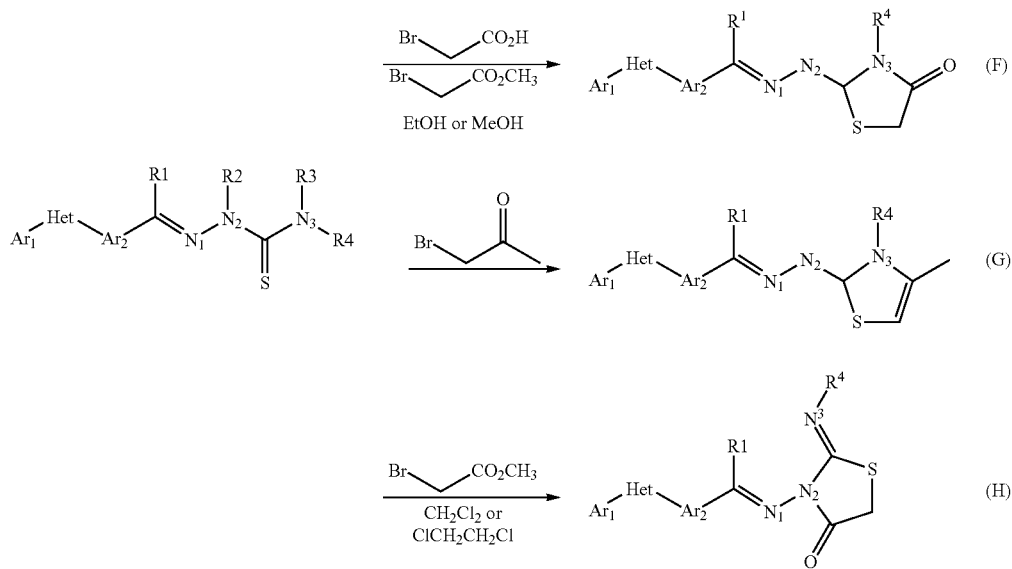

Alternatively, 3-arylidineimino-2-aryliminothiazolin-4-ones can be prepared by treating an aldehyde or ketone, wherein R1 is as previously described, with a 3-amino-2-(arylimino)thiazolidin-4-one in acetic acid at from 30 to 70° C. as shown in the following scheme (I). The intermediate 1-amino-2-aryliminothiazolin-5-one, wherein R4 is phenyl, has been described (see for example, *J. Org. Chem.* 1962, 27, 2878); it was prepared in 80% yield by treatment of 4-phenyl thiosemicarbazide with ethyl 2-chloroacetate and sodium acetate in hot EtOH.

(I)

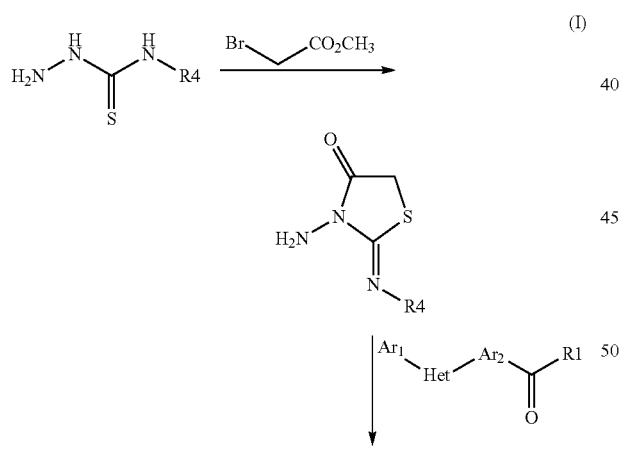

-continued

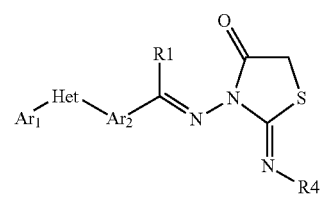

Alternatively, compounds of Formula 2 and Formula 3 may be formed by heating a thiosemicarbazone precursor with a di-halo group Hal1-R5-Hal2 such as 1-bromo-2-chloro ethane, in acetone or 2-butanone or other suitable solvent, using a base such as potassium carbonate or triethylamine, at temperatures between ambient and 100° C. for from 1 to 72 hours. The S-alkylated intermediate undergoes cyclization at N2 or N3 to generate compounds of Formula Two or Formula Three (Reaction J). In some cases, addition of KI may be required to accelerate the cyclization of the intermediate S-alkylated derivatives to the ring-closed products.

(J)

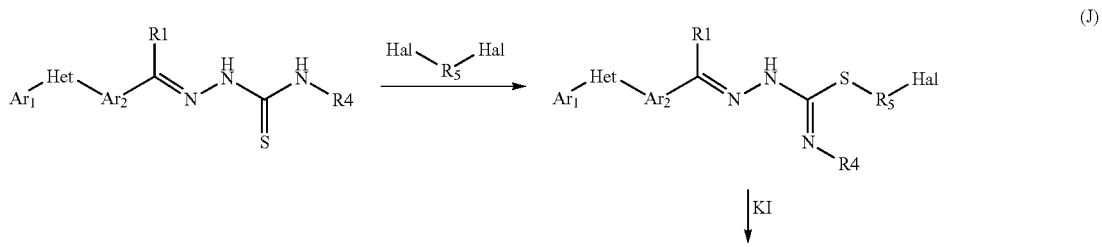

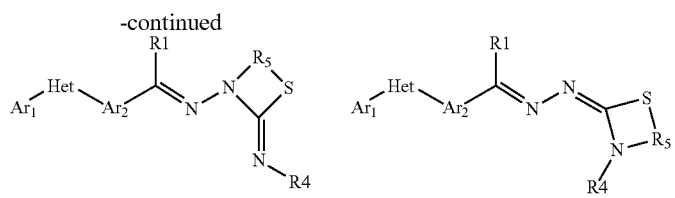

An alternative method of preparing compounds of this invention is by treatment of a thiosemicarbazone precursor with an unsaturated ester or acid chloride (Reaction L).

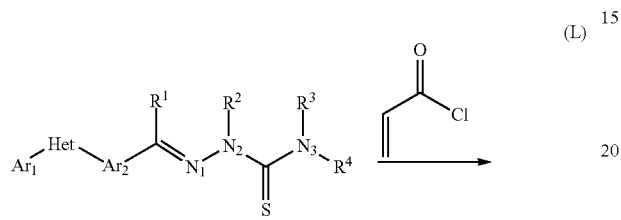

-continued

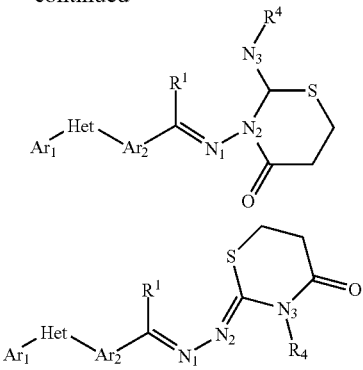

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within MDL ISIS™/Draw 2.5, ChemBioDraw Ultra 12.0 or ACD Name Pro. If such programs are unable to name a molecule, the molecule is named using conventional naming rules. $^1$H NMR spectral data are in ppm ($\delta$) and were recorded at 300, 400 or 600 MHz, and $^{13}$C NMR spectral data are in ppm ($\delta$) and were recorded at 75, 100 or 150 MHz, unless otherwise stated.

Example 1

Preparation of (E)-N-(4-dimethylamino)phenyl)-2-(4-(1-(4-(trifluoromethoxy)phenyl)-1H-1,2,4-triazol-3-yl)benzylidene)hydrazine-carbothioamide (Compound I-1) [Synthesis Method A]

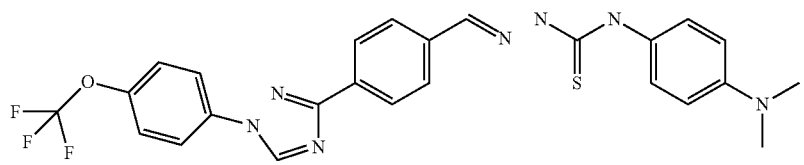

Step 1. (E)-3-(4-(Hydrazonomethyl)phenyl)-1-(4-(trifluoromethoxy)phenyl)-1H-1,2,4-triazole To a 250 milliliter (mL) round-bottomed flask containing hydrazine hydrate (64% aqueous (aq) solution; 7.27 mL, 15.0 millimoles (mmol)) in EtOH (100 mL) at 80° C. was added 4-[1-(4-trifluoromethoxyphenyl)-1H-[1,2,4]triazol-3-yl]-benzaldehyde (5.00 grams (g), 1.50 mmol) portionwise over 5 minutes (min). The solution was stirred at reflux for an additional 3 hours (h) before being diluted with water (H$_2$O; 300 mL) and cooled to 0° C. The precipitated product was collected by vacuum filtration as a white solid (4.89 g, 93%): mp 222-226° C.; $^1$H NMR (400 MHz, DMSO-d$_6$) $\delta$ 8.59 (s, 1H), 8.22 (d, J=8.2 Hz, 2H), 7.84-7.79 (m, 3H), 7.66 (d, J=8.3 Hz, 2H), 7.41 (d, J=8.2 Hz, 2H), 7.29 (s, 1H), 5.63 (br s, 2H); ESIMS m/z 348 (M+H).

Step 2

To a 25 mL round-bottomed flask containing (E)-3-(4-(hydrazonomethyl)-phenyl)-1-(4-(trifluoromethoxy)phenyl)-1H-1,2,4-triazole (250 mg, 0.720 mmol) in THF (10 mL) was added 4-isothiocyanato-N,N-dimethylaniline (385 mg, 2.16 mmol). The contents were heated at 65° C. with stirring for 2 h before the solvent was removed under reduced pressure. The residue was slurried in CH$_2$Cl$_2$ (10 mL) resulting in precipitation of product material. The desired product was obtained as a yellow solid via vacuum filtration (350 mg, 93%): mp 205-208° C.; $^1$H NMR (400 MHz, DMSO-d$_6$) $\delta$ 11.78 (s, 1H), 10.02 (s, 1H), 9.42 (s, 1H), 8.19-7.99 (m, 6H), 7.64 (d, J=8.3 Hz, 2H), 7.28 (d, J=8.3 Hz, 2H), 7.73 (d, J=8.3 Hz, 2H), 2.92 (s, 6H); ESIMS m/z 526 (M+H).

Example 2

Preparation of N-(3-(dimethylamino)phenyl)-2-(4-(1-(4-(trifluoromethoxy)phenyl)-1H-1,2,4-triazol-3-yl)benzylidene)hydrazinecarbothioamide (Compound I-2) [Synthesis Method B]

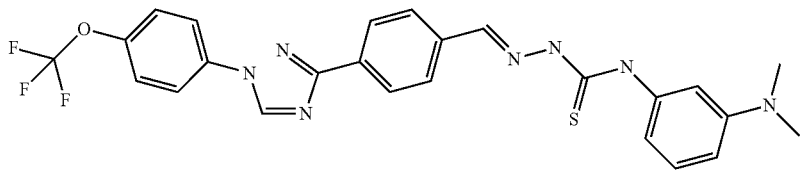 [SMILES: CN(C)c1cccc(NC(=S)N/N=C/c2ccc(C(=N)/N=C\Nc3ccc(OC(F)(F)F)cc3)cc2)c1]

Step 1. (E)-Methyl 2-(4-(1-(4-(trifluoromethoxy)phenyl)-1H-1,2,4-triazol-3-yl)benzylidene)hydrazinecarbodithioate To a 250 mL round-bottom flask containing hydrazinecarbodithioic acid methyl ester (2.38 g, 1.95 mmol) in EtOH (100 mL) was added 4-[1-(4-trifluoromethoxyphenyl)-1H-[1,2,4]triazol-3-yl]-benzaldehyde (5.00 g, 1.50 mmol). The vessel was heated at 80° C. for 3 h before being diluted with H$_2$O (300 mL) and cooled to 0° C. The precipitated product was collected by vacuum filtration as an off-white solid (6.13 g, 93%): mp 204-206° C.; $^1$H NMR (400 MHz, DMSO-d$_6$) δ 13.39 (s, 1H), 9.43 (s, 1H), 8.38 (s, 1H), 8.21 (d, J=8.3 Hz, 2H), 8.09 (d, J=8.4 Hz, 2H), 7.88 (d, J=8.4 Hz, 2H), 7.62 (d, J=8.3 Hz, 2H), 2.57 (s, 3H); ESIMS m/z 438 (M+H).

Step 2

To a 50 mL round-bottomed flask containing (E)-methyl 2-(4-(1-(4-(trifluoromethoxy)phenyl)-1H-1,2,4-triazol-3-yl)benzylidene)hydrazinecarbodithioate (250 mg, 0.571 mmol) in DMF (3 mL) was added N1,N1-dimethylbenzene-1,3-diamine (195 mg, 1.43 mmol). The contents were heated at 150° C. with stirring for 5 h before the solution was allowed to cool overnight. The mixture was filtered, and the filtrate was purified via RP-HPLC to afford the desired material (235 mg, 78%) as an off-white solid: mp 192-194° C.; $^1$H NMR (400 MHz, DMSO-d$_6$) δ 11.82 (s, 1H), 10.04 (s, 1H), 9.41 (s, 1H), 8.19 (s, 1H), 8.16-7.99 (m, 6H), 7.61 (d, J=8.3 Hz, 2H), 7.16 (t, J=7.2 Hz, 1H), 7.01 (m, 1H), 6.87 (m, 1H), 6.58 (m, 1H), 2.88 (s, 6H); ESIMS m/z 526 ([M+H]$^+$).

Example 3

Preparation of N-benzyl-2-(4-(1-(4-(trifluoromethoxy)phenyl)-1H-1,2,4-triazol-3-yl)benzylidene)hydrazinecarbothioamide (Compound I-3) [Synthesis Method C]

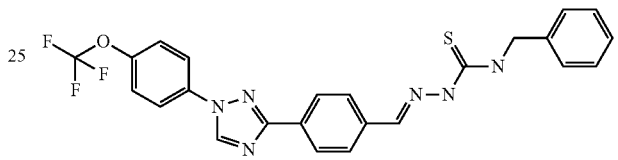

To a 50 mL round-bottomed flask containing 4-[1-[4-(trifluoromethoxy)phenyl]-1,2,4-triazol-3-yl]benzaldehyde (500 mg, 1.5 mmol) in EtOH (3 mL) was added 4-benzylthiosemicarbazide (650 mg, 3.6 mmol). The reaction mixture was heated at 80° C. overnight. H$_2$O was added upon completion of the reaction, and the crude product material was isolated by vacuum filtration. The title compound was isolated via RP-HPLC as a white solid (390 mg, 52%): mp 220-224° C.; $^1$H NMR (400 MHz, CDCl$_3$) δ 9.29 (s, 1H), 8.59 (s, 1H), 8.21 (d, J=8.4 Hz, 2H), 7.85-7.79 (m, 3H), 7.71 (d, J=8.4 Hz, 2H), 7.46-7.30 (m, 8H), 5.01 (d, J=5.8 Hz, 2H); ESIMS m/z 497.2 (M+H).

Compounds I-4 through I-31 in Table 1 were synthesized in accordance with the examples above. Other intermediates used in the preparation of compounds of this invention were prepared in accordance with the procedures described in Brown, et al, WO 2011017504, or by other known routes.

Example 4

Preparation of N-(4-dimethylaminophenyl)-S-methyl-2-{4-[1-(4-trifluoromethoxyphenyl)-1H-[1,2,4]-triazol-3-yl]-benzylidene}-hydrazine-carbothioamide (Compound 1C) (Synthesis Method D)

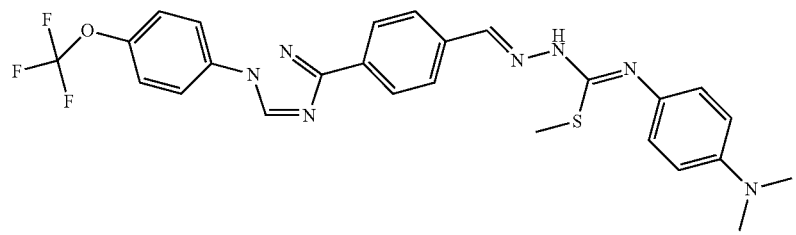 [SMILES: CS/C(=N\c1ccc(N(C)C)cc1)N/N=C/c1ccc(C(=N)/N=C\Nc2ccc(OC(F)(F)F)cc2)cc1]

A solution containing (E)-N-(4-(dimethylamino)phenyl)-2-(4-(1-(4-(trifluoromethoxy)-phenyl)-1H-1,2,4-triazol-3-yl)benzylidene)hydrazinecarbothioamide (150 mg, 0.285 mmol) and iodomethane (0.054 mL, 0.856 mmol) in EtOH (5 mL) was heated at 80° C. for 3 h before the solvent was removed under reduced pressure. The residue was purified via normal phase flash chromatography (gradient elution with hexanes/EtOAc) to afford the title compound as an orange foam (93 milligrams (mg), 60%): $^1$H NMR (400 MHz, DMSO-$d_6$) δ 8.61 (s, 1H), 8.48 (s, 1H), 8.22 (d, J=8.24 Hz, 2H), 8.17 (s, 1H), 7.89 (d, J=8.24 Hz, 2H), 7.80 (d, J=8.28 Hz, 2H), 7.41 (d, J=8.28 Hz, 2H), 7.19 (d, J=8.24 Hz, 2H), 6.71 (d, J=8.24 Hz, 2H), 2.99 (s, 6H), 2.42 (s, 3H); EIMS m/z 540 (M$^+$).

Example 5

General Procedure for S-Alkylation of Triaryl Thiosemicarbazones (Synthesis Method E)

A stirred solution of the thiosemicarbazone and alkylating reagent in $CH_2Cl_2$ or chloroform ($CHCl_3$) was heated at from 35 to 50° C. for from 10 to 24 h. The cooled solution was concentrated under reduced pressure. The residue was generally purified via chromatography using a chloroform/methanol ($CHCl_3/CH_3OH$) or EtOAc-hexane solution as the eluent to afford the S-alkylated products.

Example 6

Preparation of (S)-tert-butyl 3-((2-(Z)-(2,6-dimethylphenylimino)-((E)-2-(4-(1-(4-(trifluoromethoxy)phenyl)-1H-1,2,4-triazol-3-yl)benzylidene)hydrazinyl)-methylthio)acetamido)methyl)piperidine-1-carboxylate (Compound 56C) (Synthesis Method E)

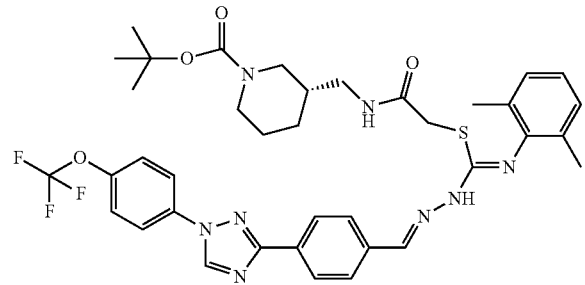 [SMILES: Cc1cccc(C)c1/N=C(/N/N=C/c1ccc(-c2ncn(-c3ccc(OC(F)(F)F)cc3)n2)cc1)SCC(=O)NC[C@@H]1CCCN(C(=O)OC(C)(C)C)C1]

To a solution of bromoacetyl bromide (26 microliters (μL), 0.299 mmol) in dichloroethane (3 mL) was added dropwise a solution of (S)-tert-butyl 3-(aminomethyl)piperidine-1-carboxylate (63.9 mg, 0.298 mmol) in dichloromethane (1 mL), followed by N-ethyl-N-isopropylpropan-2-amine (76 mg, 0.588 mmol). This mixture was stirred at room temperature for 30 min, then (E)-N-(2,6-dimethylphenyl)-2-(4-(1-(4-(trifluoromethoxy)phenyl)-1H-1,2,4-triazol-3-yl)benzylidene)hydrazine-carbothioamide (100 mg, 0.196 mmol) was added as a solid and the mixture was heated to 40° C. for 90 min. It was then allowed to cool to room temperature and evaporated under reduced pressure, giving a light yellow glass, which was dissolved in acetonitrile (2 mL) and allowed to stand at room temperature. The resulting precipitate was isolated by centrifuge and decanting, washing with fresh acetonitrile. The solid was dried under a nitrogen stream and then under high vacuum. The crude product was recrystallized from acetone-isopropyl alcohol. The title compound was isolated as a white solid (36.5 mg, 24%): mp 148-151° C.; $^1$H NMR (400 MHz, methanol-$d^4$) δ 9.18 (s, 1H), 8.59 (s, 1H), 8.30 (d, J=8.1 Hz, 2H), 8.12 (m, 2H), 8.07-8.00 (m, 2H), 7.58-7.43 (m, 2H), 7.33 (dd, J=8.6, 6.5 Hz, 1H), 7.25 (d, J=7.6 Hz, 2H), 4.02 (m, 2H), 3.97-3.75 (m, 2H), 3.21 (d, J=6.9 Hz, 2H), 2.90 (m, 1H), 2.59 (m, 1H), 2.35 (s, 6H), 1.84 (m, 2H), 1.78-1.63 (m, 2H), 1.44 (s, 9H), 1.29 (m, 3H); ESIMS m/z 765 (M+H).

Example 7

Preparation of (1Z,2E)-2-oxo-2-((((R)-piperidin-3-ylmethyl)amino)ethyl N-(2,6-dimethylphenyl)-2-(4-(1-(4-(trifluoromethoxy)phenyl)-1H-1,2,4-triazol-3-yl)benzylidene)hydrazinecarbimidothioate trifluoroacetic acid (Compound 62C) (Synthesis Method K)

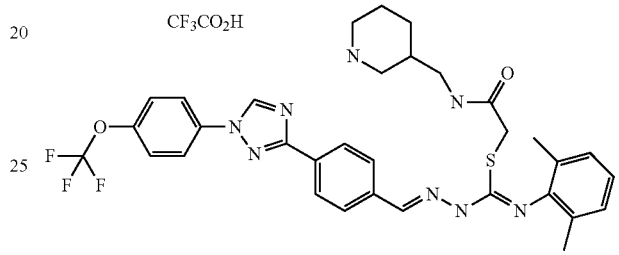

A solution of (S)-tert-butyl 3-((2-((Z)-(2,6-dimethylphenylimino)-((E)-2-(4-(1-(4-(trifluoromethoxy)phenyl)-1H-1,2,4-triazol-3-yl)benzylidene)hydrazinyl)methylthio)-acetamido)methyl)piperidine-1-carboxylate (32.0 mg, 0.042 mmol) in TFA (250 μL, 3.24 mmol) was stirred at room temperature for 10 min $Et_2O$ (10 mL) was then added giving a white precipitate, which was isolated by centrifuge and decanting, then rinsing with fresh $Et_2O$ (5 mL). The solid was dried under nitrogen stream and then under high vacuum giving the title compound as a white solid (19.8 mg, 60%): mp 110-120° C.; $^1$H NMR (400 MHz, methanol-$d_4$) δ 9.18 (s, 1H), 8.56 (m, 1H), 8.26 (m, 2H), 8.16-7.84 (m, 4H), 7.52 (m, 2H), 7.27 (m, 1H), 7.22 (m, 2H), 4.00 (s, 2H), 3.28 (m, 3H), 3.06-2.83 (m, 1H), 2.75 (t, J=12.2 Hz, 1H), 2.34 (s, 6H), 2.21-1.83 (m, 4H), 1.72 (m, 1H), 1.47-1.19 (m, 2H); ESIMS m/z 665 (M+H).

Example 8

Preparation of 2-(((Z)-((4-methoxy-2,6-dimethylphenyl)imino)((E)-2-(4-(1-(4-(trifluoromethoxy)phenyl)-1H-1,2,4-triazol-3-yl)benzylidene)hydrazinyl)methyl)-thio)acetic acid sodium salt (Compound 68C)

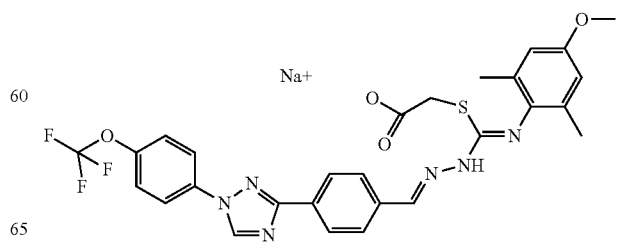

To a solution of 2-((Z)-(4-methoxy-2,6-dimethylphenylimino)((E)-2-(4-(1-(4-(trifluoromethoxy)phenyl)-1H-1,2,4-triazol-3-yl)benzylidene)hydrazinyl)methylthio)acetic acid (77.7 mg, 0.130 mmol) in THF (10 mL) was added slowly sodium methanolate (0.5 M in methanol; 260 µL, 0.130 mmol) at room temperature. The mixture immediately turned a darker yellow and was then evaporated at room temperature under vacuum giving a light orange solid. This material was triturated with Et$_2$O (2×) and isolated by decanting using a centrifuge and drying under a nitrogen stream and then under high vacuum. The title compound was isolated as a light orange solid (32 mg, 39%). mp 146-154° C.; $^1$H NMR (400 MHz, methanol-d$_4$) δ 9.11 (s, 1H), 8.64-7.68 (m, 7H), 7.51 (m, 2H), 6.70 (s, 2H), 3.85-3.70 (m, 4H), 3.61 (m, 1H), 2.29 (s, 6H); ESIMS m/z 599 (M+H).

Example 9

Preparation of (Z)-3-(4-methoxy-2,6-dimethylphenyl)-2-((E)-(4-(1-(4-(trifluoromethoxy)phenyl)-1H-1,2,4-triazol-3-yl)benzylidene)hydrazono)thiazolidin-4-one (Compound 69C) (Synthesis Method F)

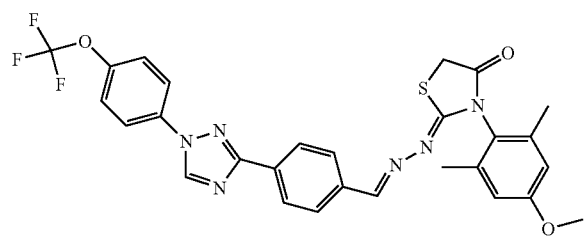 [SMILES: COc1cc(C)c(N2C(=O)CS/C2=N\N=C\c2ccc(-c3ncn(-c4ccc(OC(F)(F)F)cc4)n3)cc2)c(C)c1]

To a solution of (E)-N-(4-methoxy-2,6-dimethylphenyl)-2-(4-(1-(4-(trifluoromethoxy)phenyl)-1H-1,2,4-triazol-3-yl)benzylidene)hydrazine-carbothioamide (250 mg, 0.462 mmol) in EtOH (5 mL) was added methyl bromoacetate (100 mg, 0.65 mmol), and the mixture was heated to 70° C. for 4 h. The mixture was allowed to cool to room temperature and diluted with water (1 mL). The precipitate was vacuum filtered, giving the title compound as a white solid (204 mg, 76%): mp 188-190° C.; $^1$H NMR (400 MHz, CDCl$_3$) δ 8.56 (s, 1H), 8.33 (s, 1H), 8.22 (d, J=8.1 Hz, 2H), 7.90-7.70 (m, 4H), 7.39 (d, J=8.7 Hz, 2H), 6.72 (s, 2H), 4.01 (s, 2H), 3.87-3.73 (s, 3H), 2.18 (s, 6H); ESIMS m/z 581 (M+H).

Example 10

Preparation of 4-((2Z)-3-(2,6-dimethylphenyl)-2-((4-(1-(4-(trifluoromethoxy)phenyl)-1H-1,2,4-triazol-3-yl)benzylidene)hydrazono)-2,3-dihydrothiazol-4-yl)-N,N-diethylaniline (Compound 74C) (Synthesis Method G)

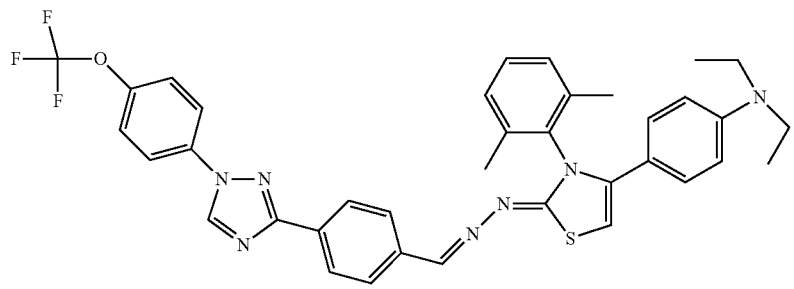 [SMILES: CCN(CC)c1ccc(-c2cs/c(=N\N=Cc3ccc(-c4ncn(-c5ccc(OC(F)(F)F)cc5)n4)cc3)n2-c2c(C)cccc2C)cc1]

To a solution of (E)-N-(2,6-dimethylphenyl)-2-(4-(1-(4-(trifluoromethoxy)phenyl)-1H-1,2,4-triazol-3-yl)benzylidene)hydrazine-carbothioamide (74.7 mg, 0.144 mmol) in dichloroethane (5 mL), was added α-bromo-4-diethylamino)acetophenone (53.9 mg, 0.199 mmol), and the mixture was heated to 40° C. for 4 h. The mixture was then cooled to room temperature and evaporated under vacuum. The crude material was triturated with acetonitrile and decanted (2×). The resulting solid was dried under a stream of nitrogen, giving the title compound as a pale yellow solid (25 mg, 25%): mp 190-193° C. dec; $^1$H NMR (400 MHz, methanol-d$_4$) δ 9.20 (s, 1H), 8.38 (s, 1H), 8.31-8.24 (m, 2H), 8.08-8.00 (m, 2H), 7.95-7.88 (m, 2H), 7.55-7.48 (m, 3H), 7.48-7.36 (m, 5H), 7.31 (d, J=7.7 Hz, 2H), 3.60 (q, J=7.2 Hz, 4H), 2.20 (s, 6H), 1.07 (t, J=7.2 Hz, 6H); ESIMS m/z 682 (M+H).

Example 11

Preparation of (Z)-2-(2,6-dimethylphenylimino)-3-((E)-4-(1-(4-(trifluoromethoxy)phenyl)-1H-1,2,4-triazol-3-yl)benzylideneamino)thiazolidin-4-one (Compound 81C) (Synthesis Method I)

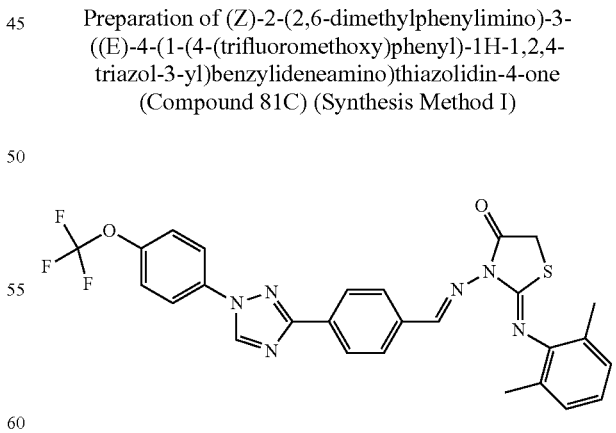

To a solution of 1-(2,6-dimethylphenyl)thiourea (1.0 g, 5.55 mmol) in EtOH (10 mL) was added methyl 2-bromoacetate (1.0 g, 6.5 mmol) and sodium acetate (1.0 g, 12.2 mmol). The solution was stirred and heated to reflux for 1 h, then it was cooled and the liquid was decanted from a small amount of solid material and the liquid was then diluted with water (10 mL). The precipitate was isolated by filtration to give (1.1 g, 83%) of (Z)-3-amino-2-(2,6-dimethylphenylimino)thiazolidin-4-one: mp 149-152° C.; $^1$H NMR (400 MHz, CDCl$_3$) δ 7.06 (d, J=7.2 Hz, 2H), 6.98 (m, 1H), 4.75 (s, 2H), 3.80 (s, 2H), 2.12 (s, 6H); ESIMS m/z 236 (M+H).

A portion of this material (0.07 g, 0.3 mmol) was dissolved in glacial acetic acid (3 mL) and treated with 4-(1-(4-(trifluoromethoxy)phenyl)-1H-1,2,4-triazol-3-yl)benzaldehyde (0.10 g, 0.30 mmol), and the solution was heated to 60° C. for 2 h. The solution was then cooled and diluted with water (1 mL), and the resulting solid was filtered and air-dried to give the title compound (0.12 g, 67%): mp 209-213° C.; $^1$H NMR (400 MHz, CDCl$_3$) δ 9.42 (s, 1H), 8.59 (s, 1H), 8.28 (d, J=8.4 Hz, 2H), 8.01 (d, J=8.3 Hz, 2H), 7.80-7.77 (m, 2H), 7.43-7.34 (m, 2H), 7.07 (d, J=7.5 Hz, 2H), 6.98 (dd, J=8.2, 6.7 Hz, 1H), 3.90 (s, 2H), 2.17 (s, 6H); ESIMS m/z 551 (M+H).

Example 12

Preparation of (2Z,NE)-2-(2-isopropylphenyl) imino)-N-(4-(1-(4-(trifluoromethyl)phenyl)-1H-1,2, 4-triazol-3-yl)benzylidene)-1,3-thiazinan-3-amine and (Z)-3-(2-isopropylphenyl)-2-(E)-(4-(1-(4-(trifluoromethyl)phenyl)-1H-1,2,4-triazol-3-yl)benzylidene)hydrazono)-1,3-thiazinane (Compound 87C and 179C) (Synthesis Method J)

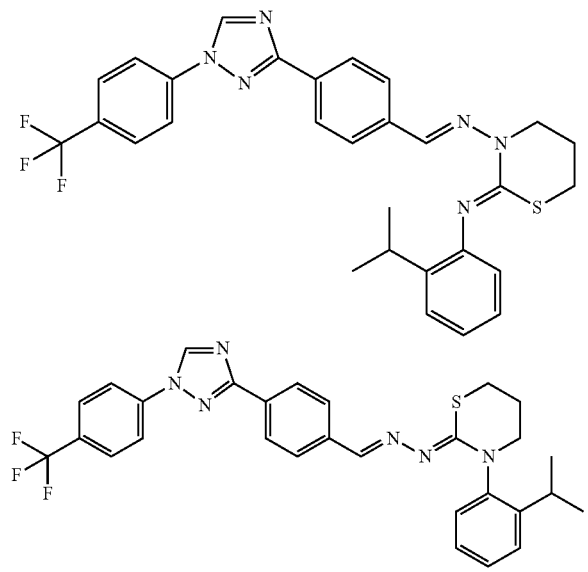

To (E)-N-(2-isopropylphenyl)-2-(4-(1-(4-(trifluoromethyl)phenyl)-1H-1,2,4-triazol-3-yl)benzylidene)hydrazinecarbothioamide (200 mg, 0.393 mmol) and potassium carbonate (217 mg, 1.57 mmol) in butanone (10 ml) in a 25 mL vial equipped with a stir bar and vigruex column was added 1-bromo-3-chloropropane (0.047 ml, 0.472 mmol). The reaction was heated to 60° C. overnight. The reaction was determined to be complete by LCMS. The reaction mixture was diluted with DCM and washed with water. The aqueous layer was extracted with DCM. The organic layers were poured through a phase separator and concentrated. Purification by flash column chromatography provided two compounds. The minor compound was dried overnight under house vacuum providing the title compound 87C (2Z,NE)-2-((2-isopropylphenyl)imino)-N-(4-(1-(4-(trifluoromethyl)phenyl)-1H-1, 2,4-triazol-3-yl)benzylidene)-1,3-thiazinan-3-amine (28.5 mg, 13%) as a yellow solid: mp 187-189° C.; $^1$H NMR (400 MHz, CDCl$_3$) δ 8.81 (s, 1H), 8.66 (s, 1H), 8.21 (d, J=8.3 Hz, 2H), 7.92 (d, J=8.4 Hz, 2H), 7.81 (t, J=10.2 Hz, 4H), 7.30-7.26 (m, 2H), 7.17-7.04 (m, 1H), 6.83 (d, J=6.4 Hz, 1H), 3.96 (t, J=6.1 Hz, 2H), 3.13 (heptet, J=6.9 Hz, 1H), 2.97-2.90 (m, 2H), 2.47-2.38 (m, 2H), 1.25 (d, J=7.5 Hz, 6H); ESIMS m/z 550 (M+H). The major compound was recrystallized with MeOH. The solid was filtered, washed with MeOH and dried at 50° C. under vacuum. The solid was then azeotroped with acetone (3×) and the resultant solid was dried at 50° C. under vacuum providing the title compound 179C (Z)-3-(2-isopropylphenyl)-2-((E)-(4-(1-(4-(trifluoromethyl)phenyl)-1H-1, 2,4-triazol-3-yl)benzylidene)hydrazono)-1,3-thiazinane as a yellow solid (92.3 mg, 0.168 mmol, 43%): mp 212-213° C.; $^1$H NMR (400 MHz, CDCl$_3$) δ 8.64 (s, 1H), 8.15 (d, J=8.4 Hz, 2H), 8.06 (s, 1H), 7.91 (d, J=8.5 Hz, 2H), 7.79 (d, J=8.6 Hz, 2H), 7.75 (d, J=8.4 Hz, 2H), 7.38 (dd, J=7.8, 1.6 Hz, 1H), 7.33 (td, J=7.5, 1.4 Hz, 1H), 7.29-7.23 (m, 1H), 7.18 (dd, J=7.8, 1.4 Hz, 1H), 3.78-3.72 (m, 1H), 3.59-3.48 (m, 1H), 3.18-3.04 (m, 3H), 2.40-2.30 (m, 2H), 1.26-1.20 (m, 6H); ESIMS m/z 550 (M+H).

Example 13

Preparation of (Z)-3-(2-cyclopropylphenyl)-5-methyl-2-((E)-(4-(1-(4-(trifluoromethoxy)phenyl)-1H-1, 2,4-triazol-3-yl)benzylidene)hydrazono)thiazolidin-4-one (Compound 127C) (Synthesis Method F)

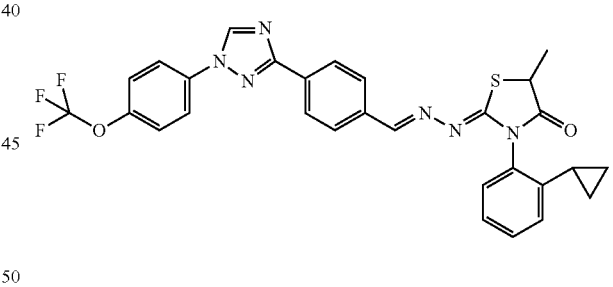

To (E)-N-(2-cyclopropylphenyl)-2-(4-(1-(4-(trifluoromethoxy)phenyl)-1H-1,2,4-triazol-3-yl)benzylidene)hydrazinecarbothioamide (100 mg, 0.191 mmol) and sodium acetate (63.0 mg, 0.765 mmol) in EtOH (4 mL) was added methyl 2-bromopropanoate (0.026 mL, 0.230 mmol). The reaction was heated to 60° C. overnight. The reaction was then heated to 85° C. for 72 hours. The reaction mixture was diluted with DCM and washed with water. The aqueous layer was extracted with DCM. The organic layers were poured through a phase separator and concentrated. Purification by flash column chromatography provided the title compound as a white solid (32.5 mg, 0.056 mmol, 30%): mp 112-115° C.; $^1$H NMR (400 MHz, CDCl$_3$) δ 8.58 (s, 1H), 8.32 (s, 1H), 8.22 (d, J=8.3 Hz, 2H), 7.87-7.75 (m, 4H), 7.43-7.32 (m, 4H), 7.26-7.24 (m, 2H), 4.23 (q, J=7.3 Hz, 1H), 1.85-1.78 (m, 4H), 0.90-0.78 (m, 2H), 0.78-0.69 (m, 1H), 0.65-0.55 (m, 1H); ESIMS m/z 578 (M+H).

Example 14

Preparation of (Z)-3-(2-isopropylphenyl)-2-(E)-(4-(1-(4-(trifluoromethoxy)phenyl)-1H-1,2,4-triazol-3-yl)benzylidene)hydrazono)thiazolidine (Compound 132C) (Synthesis Method J)

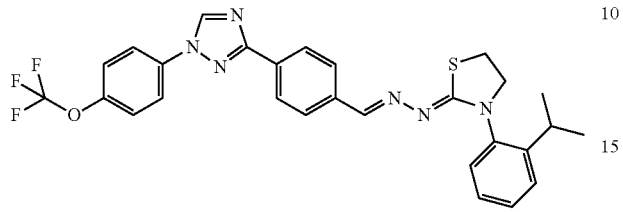

To (E)-N-(2-isopropylphenyl)-2-(4-(1-(4-(trifluoromethoxy)phenyl)-1H-1,2,4-triazol-3-yl)benzylidene)hydrazinecarbothioamide (214 mg, 0.407 mmol) and potassium carbonate (225 mg, 1.63 mmol) in butanone (4 ml) was added 1-bromo-2-chloroethane (70.0 mg, 0.489 mmol). The reaction was heated to 90° C. overnight. The reaction was determined to be complete by LCMS. The reaction mixture was cooled, diluted with DCM and washed with water. The aqueous layer was extracted with DCM. The organic layers were filtered through a phase separator and concentrated. Separation by flash column chromatography and drying the recovered solid at 55° C. under vacuum provided the title compound as a white solid (137 mg, 0.249 mmol, 61%): mp 193-196° C.; $^1$H NMR (400 MHz, CDCl$_3$) δ 8.56 (s, 1H), 8.22 (s, 1H), 8.17 (d, J=8.4 Hz, 2H), 7.80 (ddd, J=9.5, 6.9, 4.9 Hz, 4H), 7.43-7.33 (m, 4H), 7.31-7.21 (m, 2H), 4.05 (td, J=9.4, 7.1 Hz, 1H), 3.97-3.87 (m, 1H), 3.42-3.33 (m, 1H), 3.33-3.24 (m, 1H), 3.12 (heptet, J=6.8 Hz, 1H), 1.27 (d, J=6.8 Hz, 3H), 1.22 (d, J=6.9 Hz, 3H); ESIMS m/z 552 (M+H).

Example 15

Preparation of (Z)-3-(2-isopropylphenyl)-4-methyl-2-((E)-(4-(1-(4-(trifluoromethoxy)phenyl)-1H-1,2,4-triazol-3-yl)benzylidene)hydrazono)thiazolidine (Compound 155C) (Synthesis Method J)

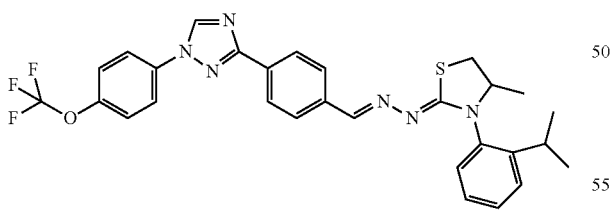

To (E)-N-(2-isopropylphenyl)-2-(4-(1-(4-(trifluoromethoxy)phenyl)-1H-1,2,4-triazol-3-yl)benzylidene)hydrazinecarbothioamide (300 mg, 0.572 mmol) and potassium carbonate (316 mg, 2.29 mmol) in butanone (4 ml) was added 1,2-dibromopropane (0.072 ml, 0.686 mmol). The reaction was heated to 85° C. overnight. The reaction was determined to be complete by LCMS. The reaction mixture was diluted with DCM and washed with water. The aqueous layer was extracted with DCM. The organic layers were poured through a phase separator and concentrated. Purification by flash column chromatography provided a yellow solid. The solid was recrystallized from MeOH. The solid was filtered, washed with MeOH, and dried to provide the title compound as a yellow solid which was dissolved in acetone and concentrated (3×). The light yellow solid was collected and dried under to provide the title compound as a 1:1 mixture of rotational diastereoisomers (75.1 mg, 0.133 mmol, 23%): mp 201-204° C.; $^1$H NMR of mixture (400 MHz, CDCl$_3$) δ 8.56 (s, 2H), 8.18 (dd, J=10.8, 7.4 Hz, 6H), 7.84-7.73 (m, 8H), 7.45-7.30 (m, 8H), 7.30-7.23 (m, 2H), 7.20 (d, J=6.7 Hz, 1H), 7.12 (dd, J=7.8, 1.2 Hz, 1H), 4.43-4.33 (m, 1H), 4.16 (dd, J=12.6, 6.3 Hz, 1H), 3.48 (dt, J=13.3, 6.7 Hz, 1H), 3.37 (dd, J=10.8, 6.2 Hz, 1H), 3.24 (dt, J=13.7, 6.9 Hz, 1H), 3.08-2.92 (m, 3H), 1.33-1.16 (m, 18H); ESIMS m/z 566 (M+H).

Example 16

Preparation of (Z)-3-(2,6-dimethylphenyl)-4-methyl-2-((E)-(4-(1-(4-(trifluoromethoxy)phenyl)-1H-1,2,4-triazol-3-yl)benzylidene)hydrazono)-2,3-dihydrothiazole (Compound 173C) (Synthesis Method G)

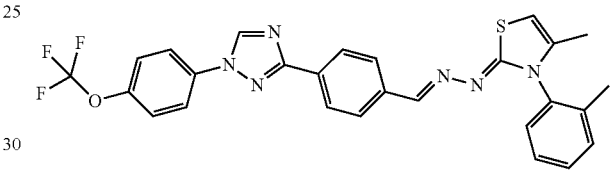

To a solution of (E)-N-(o-tolyl)-2-(4-(1-(4-(trifluoromethoxy)phenyl)-1H-1,2,4-triazol-3-yl)benzylidene)hydrazinecarbothioamide (257 mg, 0.520 mmol) in butanone (5 mL) was added triethylamine (0.14 mL, 1.0 mmol) and chloroacetone (0.06 mL, 0.73 mmol) and refluxed at 75° C. for 15 h. The mixture was allowed to cool to room temperature and then transferred to a separatory funnel containing water (5 mL) and extracted twice with dichloromethane. The organic layers were filtered through a phase separator, adsorbed onto silica gel, and purified by flash column chromatography to afford the title compound as a yellow solid (229 mg, 83%): mp 87° C. (dec); $^1$H NMR (400 MHz, CDCl$_3$) δ 8.56 (s, 1H), 8.19-8.15 (m, 3H), 7.82-7.75 (m, 4H), 7.43-7.30 (m, 5H), 7.24 (d, J=7.3 Hz, 1H), 5.88 (d, J=1.3 Hz, 1H), 2.21 (s, 3H), 1.80 (d, J=1.2 Hz, 3H); ESIMS m/z 536 (M+H).

Example 17

Preparation of (Z)-3-(2-isopropylphenyl)-5-methyl-2-((E)-(4-(1-(4-(trifluoromethoxy)phenyl)-1H-1,2,4-triazol-3-yl)benzylidene)hydrazono)-1,3-thiazinane (Compound 178C) (Synthesis Method J)

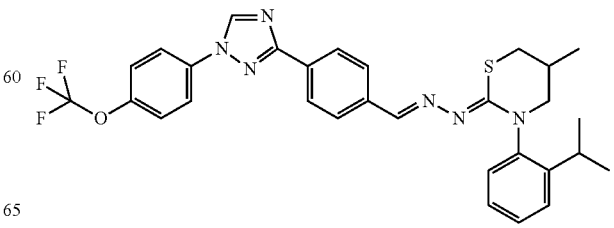

To (E)-N-(2-isopropylphenyl)-2-(4-(1-(4-(trifluoromethoxy)phenyl)-1H-1,2,4-triazol-3-yl)benzylidene)hydrazinecarbothioamide (100 mg, 0.191 mmol) and potassium carbonate (105 mg, 0.763 mmol) in butanone (4 ml) was added 1-bromo-3-chloro-2-methylpropane (39.0 mg, 0.229 mmol). The reaction was heated to 80° C. overnight. The reaction mixture was then diluted with DCM and washed with water. The aqueous layer was extracted with DCM. The organic layers were poured through a phase separator and concentrated. Purification by flash column chromatography provided the title compound as a light yellow solid as a mixture of rotational diastereoisomers: mp 186-190° C.; $^1$H NMR (400 MHz, CDCl$_3$) δ 8.55 (d, J=3.6 Hz, 1H), 8.14 (d, J=8.4 Hz, 2H), 8.06 (s, 1H), 7.84-7.77 (m, 2H), 7.74 (d, J=8.4 Hz, 2H), 7.38 (d, J=9.0 Hz, 3H), 7.32 (td, J=7.5, 1.4 Hz, 1H), 7.26 (s, 1H), 7.17 (t, J=7.1 Hz, 1H), 3.69-3.26 (m, 1H), 3.55-3.37 (m, 1H), 3.18-2.98 (m, 2H), 2.93-2.80 (m, 1H), 2.47 (d, J=35.9 Hz, 1H), 1.31-1.12 (m, 9H); ESIMS m/z 580 (M+H).

Example 18

Preparation of (Z)-3-(2,6-dimethylphenyl)-2-((E)-(4-(1-(4-(trifluoromethoxy)phenyl)-1H-1,2,4-triazol-3-yl)benzylidene)hydrazono)-1,3-thiazepane (Compound 211C) (Synthesis Method J)

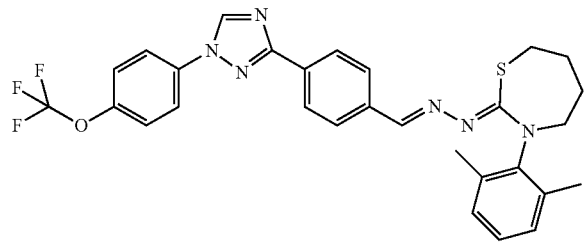 [SMILES: Cc1cccc(C)c1N1CCCCS/C1=N\N=C\c1ccc(-c2ncn(-c3ccc(OC(F)(F)F)cc3)n2)cc1]

To (E)-N-(2,6-dimethylphenyl)-2-(4-(1-(4-(trifluoromethoxy)phenyl)-1H-1,2,4-triazol-3-yl)benzylidene)hydrazinecarbothioamide (500 mg, 0.979 mmol) and potassium carbonate (541 mg, 3.92 mmol) in acetone (4 ml) was added 1-bromo-4-chlorobutane (0.135 ml, 1.18 mmol). The reaction was heated to 60° C. overnight. The alkylation was determined to be complete by ultra performance liquid chromatography ("UPLC"). The reaction mixture was diluted with DCM and washed with water. The aqueous layer was extracted with DCM. The organic layers were poured through a phase separator and concentrated. Purification by flash column chromatography provided (1Z,N'E)-4-chlorobutyl N-(2,6-dimethylphenyl)-N'-(4-(1-(4-(trifluoromethoxy)phenyl)-1H-1,2,4-triazol-3-yl)benzylidene) carbamohydrazonothioate (427 mg, 0.710 mmol, 73%) as a yellow gum which was used without further purification. To (1Z,N'E)-4-chlorobutyl N-(2,6-dimethylphenyl)-N-(4-(1-(4-(trifluoromethoxy)phenyl)-1H-1,2,4-triazol-3-yl)benzylidene)-carbamohydrazonothioate (427 mg, 0.710 mmol), potassium iodide (236 mg, 1.42 mmol) and potassium carbonate (393 mg, 2.84 mmol) was added acetone (7 ml). The reaction was heated to 65° C. for 72 h. The reaction was cooled to room temperature, diluted with DCM and washed with water. The aqueous layer was extracted with DCM. The organic layers were poured through a phase separator and concentrated. Purification by flash column chromatography provided a yellow oil. The yellow oil was recrystallized from MeOH, filtered, washed with MeOH and dried to provide the title compound as a yellow solid (100 mg, 0.177 mmol, 25%): mp 100-106° C.; $^1$H NMR (400 MHz, CDCl$_3$) δ 8.55 (s, 1H), 8.15 (d, J=8.4 Hz, 2H), 8.10 (s, 1H), 7.79 (dt, J=10.4, 5.8 Hz, 4H), 7.38 (d, J=8.3 Hz, 2H), 7.11 (s, 3H), 3.85-3.78 (m, 2H), 3.20-3.12 (m, 2H), 2.30 (s, 6H), 2.13-2.07 (m, 2H), 1.87-1.82 (m, 2H); ESIMS m/z 566 (M+H).

Example 19

Preparation of (Z)-3-(2-isopropylphenyl)-2-((E)-(4-(1-(4-(trifluoromethoxy)phenyl)-1H-1,2,4-triazol-3-yl)benzylidene)hydrazono)-1,3-thiazinan-4-one (Compound 224C) (Synthesis Method L)

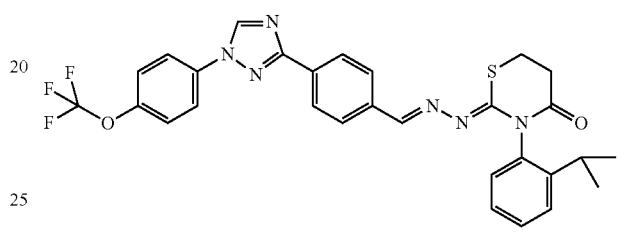

To (E)-N-(2-isopropylphenyl)-2-(4-(1-(4-(trifluoromethoxy)phenyl)-1H-1,2,4-triazol-3-yl)benzylidene)hydrazinecarbothioamide (500 mg, 0.953 mmol) in butanone (9.5 ml) was added acryloyl chloride (0.077 ml, 0.953 mmol). The reaction was stirred at ambient temperature for 10 min followed by 50° C. for 2 h. The reaction was cooled to 40° C. overnight. The reaction was determined to be complete by LCMS. The reaction mixture was diluted with DCM and washed with saturated sodium bicarbonate. The aqueous layer was extracted with DCM. The organic layers were poured through a phase separator and concentrated. Purification by flash column chromatography provided a yellow oil. The oil was recrystallized with diethyl ether/hexanes to provide the title compound as a light yellow solid (125 mg, 0.217 mmol, 23%): mp 118° C. (dec); $^1$H NMR (400 MHz, CDCl$_3$) δ 8.57 (s, 1H), 8.21 (d, J=8.4 Hz, 2H), 8.16 (s, 1H), 7.85-7.75 (m, 4H), 7.46-7.36 (m, 4H), 7.33-7.26 (m, 1H), 7.10 (d, J=7.6 Hz, 1H), 3.26-3.14 (m, 4H), 2.81 (heptet, J=6.9 Hz, 1H), 1.21 (t, J=7.2 Hz, 6H); ESIMS m/z 580 (M+H).

Example 20

Separation of Rotationally Stable Atropisomers from Racemic Mixtures

Separation of constituent isomers from racemic mixtures can be carried out utilizing one of the following chiral HPLC methods.

Separation Method A:

The column used for separation was a Chiral Technologies INC Chiral Pak 1A 5 μm, 4.6×250 mm column (Part number 80325). The method consists of a 1.0 mL/min flow rate from 0 to 30 min with an isocratic hold at 25% B for the duration of the run. The A eluent is n-hexane, the B eluent is iso-propyl alcohol.

Separation Method B:

The column used for separation was a Chiral Technologies INC Chiral Pak 1B 5 μm, 4.6×250 mm column (Part number 81325). The method consists of a 1.0 mL/min flow rate from 0 to 30 min with an isocratic hold at 15% B for the duration of the run. The A eluent is n-pentane, the B eluent is n-butyl alcohol.

Example 21

Bioassays on Beet Armyworm ("BAW") and Corn Earworm ("CEW")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. CEW is known to attack corn and tomatoes, but it also attacks artichoke, asparagus, cabbage, cantaloupe, collards, cowpeas, cucumbers, eggplant, lettuce, lima beans, melon, okra, peas, peppers, potatoes, pumpkin, snap beans, spinach, squash, sweet potatoes, and watermelon, among other plants. CEW is also known to be resistant to certain insecticides. Consequently, because of the above factors control of these pests is important. Furthermore, molecules that control these pests are useful in controlling other pests.

Certain molecules disclosed in this document were tested against BAW and CEW using procedures described in the following examples. In the reporting of the results, the "BAW & CEW Rating Table" was used (See Table Section).

Bioassays on BAW (*Spodoptera exigua*)

Bioassays on BAW were conducted using a 128-well diet tray assay. One to five second instar BAW larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table 5: Biological Results" (See Table Section).

Bioassays on CEW (*Helicoverpa zea*)

Bioassays on CEW were conducted using a 128-well diet tray assay. One to five second instar CEW larvae were placed in each well (3 mL) of the diet tray that had been previously filled with 1 mL of artificial diet to which 50 µg/cm² of the test compound (dissolved in 50 µL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table 5: Biological Results" (See Table Section).

Example 22

Bioassays on Green Peach Aphid ("GPA") (*Myzus persicae*)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the nightshade/potato family Solanaceae, and various mosaic viruses to many other food crops. GPA attacks such plants as broccoli, burdock, cabbage, carrot, cauliflower, daikon, eggplant, green beans, lettuce, *macadamia*, papaya, peppers, sweet potatoes, tomatoes, watercress, and zucchini, among other plants. GPA also attacks many ornamental crops such as carnation, chrysanthemum, flowering white cabbage, poinsettia, and roses. GPA has developed resistance to many pesticides.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/methanol (1:1) solvent, forming stock solutions of 1000 ppm test compound. The stock solutions were diluted 5× with 0.025% Tween 20 in $H_2O$ to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/methanol (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

$$\text{Corrected \% Control}=100*(X-Y)/X$$

where
X=No. of live aphids on solvent check plants and
Y=No. of live aphids on treated plants The results are indicated in the table entitled "Table 5: Biological Results" (See Table Section).

Pesticidally Acceptable Acid Addition Salts, Salt Derivatives, Solvates, Ester Derivatives, Polymorphs, Isotopes and Radionuclides Molecules of Formulas One, Two and Three may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formulas One, Two and Three may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formulas One, Two and Three may be formulated into stable complexes with a solvent, such that the complex remains intact after the non-complexed solvent is removed. These complexes are often referred to as "solvates." However, it is particularly desirable to form stable hydrates with water as the solvent.

Molecules of Formulas One, Two and Three may be made into ester derivatives. These ester derivatives can then be applied in the same manner as the invention disclosed in this document is applied.

Molecules of Formulas One, Two and Three may be made as various crystal polymorphs. Polymorphism is important in the development of agrochemicals since different crystal polymorphs or structures of the same molecule can have vastly different physical properties and biological performances.

Molecules of Formulas One, Two and Three may be made with different isotopes. Of particular importance are molecules having $^2$H (also known as deuterium) in place of $^1$H.

Molecules of Formulas One, Two and Three may be made with different radionuclides. Of particular importance are molecules having $^{14}$C.

Stereoisomers

Molecules of Formulas One, Two and Three may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures.

Insecticides

Molecules of Formulas One, Two and Three may also be used in combination (such as, in a compositional mixture, or a simultaneous or sequential application) with one or more of the following insecticides-1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthionethyl, fenvalerate, fipronil, flometoquin, flonicamid, flubendiamide (additionally resolved isomers thereof), flucofuron, flucycloxuron, flucythrinate, flufenerim, flufenoxuron, flufenprox, flufiprole, flupyradifurone, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemetonmethyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, and zolaprofos (collectively these commonly named insecticides are defined as the "Insecticide Group").

Acaricides

Molecules of Formulas One, Two and Three may also be used in combination (such as, in a compositional mixture, or a simultaneous or sequential application) with one or more of the following acaricides-acequinocyl, amidoflumet, arsenous oxide, azobenzene, azocyclotin, benomyl, benoxafos, benzoximate, benzyl benzoate, bifenazate, binapacryl, bromopropylate, chinomethionat, chlorbenside, chlorfenethol, chlorfenson, chlorfensulphide, chlorbenzilate, chloromebuform, chloromethiuron, chloropropylate, clofentezine, cyenopyrafen, cyflumetofen, cyhexatin, dichlofluanid, dicofol, dienochlor, diflovidazin, dinobuton, dinocap, dinocap-4, dinocap-6, dinocton, dinopenton, dinosulfon, dinoterbon, diphenyl sulfone, disulfuram, dofenapyn, etoxazole, fenazaquin, fenbutatin oxide, fenothiocarb, fenpyroximate, fenson, fentrifanil, fluacrypyrim, fluazuron, flubenzimine, fluenetil, flumethrin, fluorbenside, hexythiazox, mesulfen, MNAF, nikkomycins, proclonol, propargite, quintiofos, spirodiclofen, sulfuram, sulfur, tetradifon, tetranactin, tetrasul, and thioquinox (collectively these commonly named acaricides are defined as the "Acaricide Group").

Nematicides

Molecules of Formulas One, Two and Three may also be used in combination (such as, in a compositional mixture, or a simultaneous or sequential application) with one or more of the following nematicides-1,3-dichloropropene, benclothiaz, dazomet, dazomet-sodium, DBCP, DCIP, diamidafos, fluensulfone, fosthiazate, furfural, imicyafos, isamidofos, isazofos, metam, metam-ammonium, metam-potassium, metam-sodium, phosphocarb, and thionazin (collectively these commonly named nematicides are defined as the "Nematicide Group")

Fungicides

Molecules of Formulas One, Two and Three may also be used in combination (such as, in a compositional mixture, or a simultaneous or sequential application) with one or more of the following fungicides-(3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarb, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfuram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothal-isopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, zoxamide (collectively these commonly named fungicides are defined as the "Fungicide Group").

Herbicides

Molecules of Formulas One, Two and Three may also be used in combination (such as, in a compositional mixture, or a simultaneous or sequential application) with one or more of the following herbicides-2,3,6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorfenazole, chlorflurenol, chlorflurenol-methyl, chloridazon, chlorimuron, chlorimuron-ethyl, chlornitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, fluorochloridone, fluoroxypyr, fluoroxypyr-butomethyl, fluoroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluoron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyr-butotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifop-methyl, trifopsime, trihydroxytriazine, trimeturon, tripropindan, tritac, tritosulfuron, vernolate, xylachlor, (collectively these commonly named herbicides are defined as the "Herbicide Group").

Biopesticides

Molecules of Formulas One, Two and Three may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinemema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the Molecules of Formula One, Two or Three may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of*

*Biocontrol Agents* (formerly the *Biopesticide Manual*) 3rd Edition. British Crop Production Council (BCPC), Farnham, Surrey UK.

Other Active Compounds

Molecules of Formulas One, Two and Three may also be used in combination (such as in a compositional mixture, or a simultaneous or sequential application) with one or more of the following:
1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N-2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Molecules of Formulas One, Two and Three may also be used in combination (such as in a compositional mixture, or a simultaneous or sequential application) with one or more compounds in the following groups: algicides, antifeedants, avicides, bactericides, bird repellents, chemosterilants, herbicide safeners, insect attractants, insect repellents, mammal repellents, mating disrupters, molluscicides, plant activators, plant growth regulators, rodenticides, and/or virucides (collectively these commonly named groups are defined as the "AI Group"). It should be noted that compounds falling within the AI Group, Insecticide Group, Fungicide Group, Herbicide Group, Acaricide Group, or Nematicide Group might be in more than one group, because of multiple activities the compound has. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Synergistic Mixtures and Synergists

Molecules of Formulas One, Two and Three may be used with the compounds in the Insecticide Group to form synergistic mixtures where the mode of action of such compounds compared to the mode of action of the Molecules of Formula One and Two are the same, similar, or different. Examples of modes of action include, but are not limited to: acetylcholinesterase inhibitor; sodium channel modulator; chitin biosynthesis inhibitor; GABA-gated chloride channel antagonist; GABA and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs). Additionally, Molecules of Formula One and Two may be used with compounds in the Fungicide Group, Acaricide Group, Herbicide Group, or Nematicide Group to form synergistic mixtures. Furthermore, Molecules of Formulas One, Two and Three may be used with other active compounds, such as the compounds under the heading "OTHER ACTIVE COMPOUNDS", algicides, avicides, bactericides, molluscicides, rodenticides, virucides, herbicide safeners, adjuvants, and/or surfactants to form synergistic mixtures. Generally, weight ratios of the Molecules of Formulas One, Two and Three in a synergistic mixture with another compound are from about 10:1 to about 1:10, preferably from about 5:1 to about 1:5, and more preferably from about 3:1, and even more preferably about 1:1. Additionally, the following compounds are known as synergists and may be used with the molecules disclosed in Formula One: piperonyl butoxide, piprotal, propyl isome, sesamex, sesamolin, sulfoxide, and tribufos (collectively these synergists are defined as the "Synergists Group").

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formulas One, Two and Three are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment-Retrospects and Prospects" by A. S. Perry, I. Yamamoto, I. Ishaaya, and R. Perry, copyright 1998 by Springer-Verlag.

Bests

In general, the Molecules of Formula Formulas One, Two and Three may be used to control pests e.g. beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

In another embodiment, the Molecules of Formulas One, Two and Three may be used to control pests in the Phyla Nematoda and/or Arthropoda.

In another embodiment, the Molecules of Formulas One, Two and Three may be used to control pests in the Subphyla Chelicerata, Myriapoda, and/or Hexapoda.

In another embodiment, the Molecules of Formulas One, Two and Three may be used to control pests in the Classes of Arachnida, Symphyla, and/or Insecta.

In another embodiment, the Molecules of Formulas One, Two and Three may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the Molecules of Formulas One, Two and Three may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the Molecules of Formulas One, Two and Three may be used to control pests of the Order Dermaptera.

In another embodiment, the Molecules of Formulas One, Two and Three may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the Molecules of Formulas One, Two and Three may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the Molecules of Formulas One, Two and Three may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera,*

*Trialeurodes vaporariorum, Trialeurodes abutiloneus, Unaspis yanonensis*, and *Zulia entrerriana*.

In another embodiment, the Molecules of Formulas One, Two and Three may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richteri, Solenopsis xyloni*, and *Tapinoma sessile*.

In another embodiment, the Molecules of Formulas One, Two and Three may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the Molecules of Formulas One, Two and Three may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spoodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the Molecules of Formulas One, Two and Three may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the Molecules of Formulas One, Two and Three may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the Molecules of Formulas One, Two and Three may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the Molecules of Formulas One, Two and Three may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci*.

In another embodiment, the Molecules of Formulas One, Two and Three may be used to control pests of the Order Thysanura. A non-exhaustive list of particular genera includes, but is not limited to, *Lepisma* spp. and *Thermobia* spp.

In another embodiment, the Molecules of Formulas One, Two and Three may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panony-*

*chus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor.*

In another embodiment, the Molecules of Formulas One, Two and Three may be used to control pest of the Order Symphyla. A non-exhaustive list of particular sp. includes, but is not limited to, *Scutigerella immaculata.*

In another embodiment, the Molecules of Formulas One, Two and Three may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis.*

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formulas One, Two and Three are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formulas One, Two and Three is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use aluminum sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The Molecules of Formulas One, Two and Three may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP).

The Molecules of Formulas One, Two and Three can be applied to the foliar and fruiting portions of plants to control pests. The molecules will either come in direct contact with the pest, or the pest will consume the pesticide when eating leaf, fruit mass, or extracting sap, that contains the pesticide. The Molecules of Formulas One, Two and Three can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One, Two or Three.

The Molecules of Formulas One, Two and Three can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the Formula One, Two or Three may be desirable to control newly emerged larvae.

Systemic movement of pesticides in plants may be utilized to control pests on one portion of the plant by applying (for example by spraying an area) the Molecules of Formula One, Two or Three to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the Molecules of Formula One, Two or Three may further enhance the ability of a plant to better withstand stressful growing conditions. This results in a healthier, more vigorous plant, which can lead to higher yields at harvest time. Generally, about 1 gram of the Molecules of Formula One, Two or Three to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the Molecules of Formulas One, Two and Three may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The Molecules of Formulas One, Two and Three may be used for controlling endoparasites and ectoparasites in the veterinary medicine sector or in the field of non-human animal keeping. The Molecules of Formulas One, Two and Three are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The Molecules of Formulas One, Two and Three may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The Molecules of Formulas One, Two and Three may also be used for controlling parasitic worms, especially of the intestine, in the animals listed above.

The Molecules of Formula One, Two, and Three may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The Molecules of Formula One and Two may also be used on such new invasive species to control them in such new environment.

The Molecules of Formula One, Two, and Three may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One, Two, and Three can be tested to determine its efficacy against pests. Furthermore, mode of action studies can be conducted to determine if said molecule has a different mode of action than other pesticides. Thereafter, such acquired data can be disseminated, such as by the internet, to third parties.

The headings in this document are for convenience only and must not be used to interpret any portion hereof.

TABLE SECTION

| BAW & CEW Rating Table | |
|---|---|
| % Control (or Mortality) | Rating |
| 50-100 | A |
| More than 0-Less than 50 | B |
| Not Tested | C |
| No activity noticed in this bioassay | D |

| GPA Rating Table | |
|---|---|
| % Control (or Mortality) | Rating |
| 80-100 | A |
| More than 0-Less than 80 | B |
| Not Tested | C |
| No activity noticed in this bioassay | D |

TABLE 1

Structures for Compounds

| ID | Structure |
|---|---|
| I-4 | 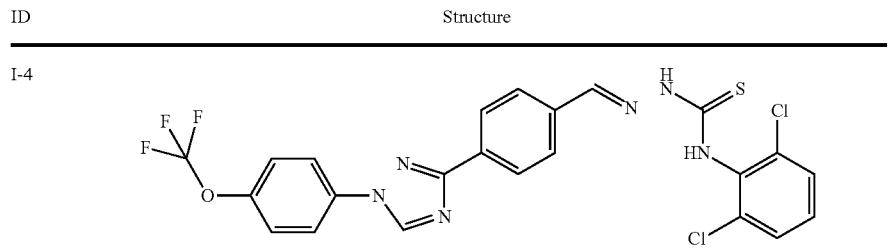 |
| I-5 | 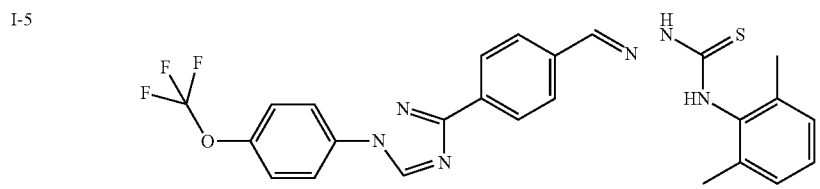 |

TABLE 1-continued

Structures for Compounds

| ID | Structure |
|---|---|
| I-6 | 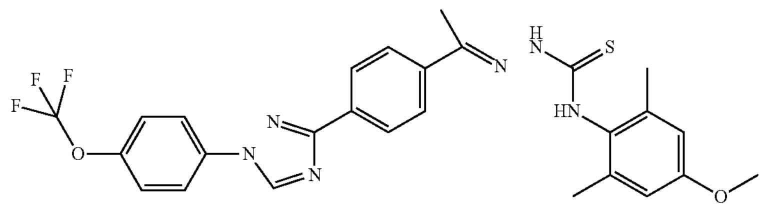 |
| I-7 | 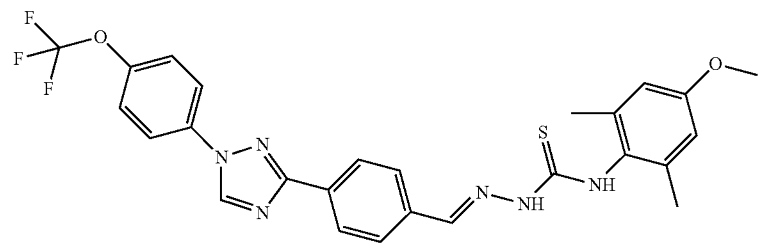 [SMILES: COc1cc(C)c(NC(=S)N/N=C/c2ccc(-c3ncn(-c4ccc(OC(F)(F)F)cc4)n3)cc2)c(C)c1] |
| I-8 | 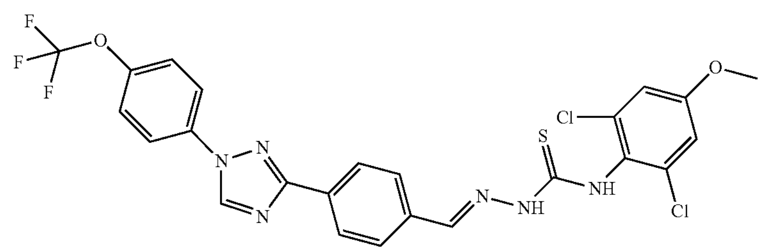 [SMILES: COc1cc(Cl)c(NC(=S)N/N=C/c2ccc(-c3ncn(-c4ccc(OC(F)(F)F)cc4)n3)cc2)c(Cl)c1] |
| I-9 | 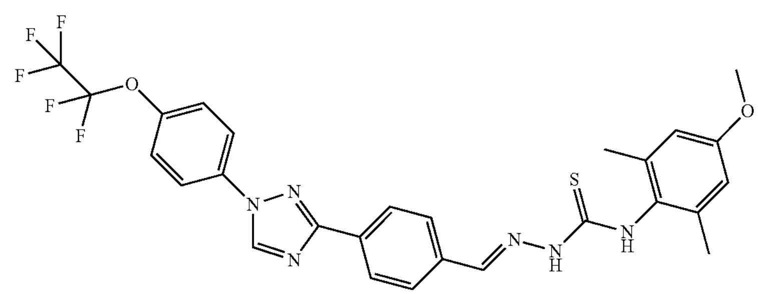 [SMILES: COc1cc(C)c(NC(=S)N/N=C/c2ccc(-c3ncn(-c4ccc(OC(F)(F)C(F)(F)F)cc4)n3)cc2)c(C)c1] |
| I-10 | 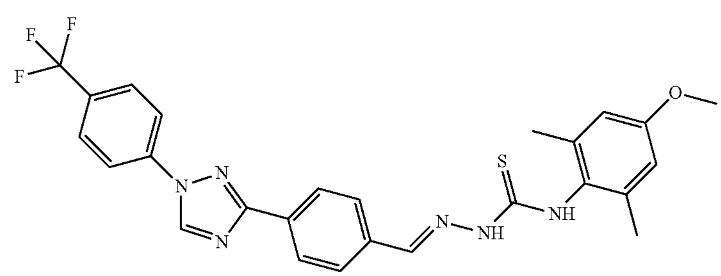 [SMILES: COc1cc(C)c(NC(=S)N/N=C/c2ccc(-c3ncn(-c4ccc(C(F)(F)F)cc4)n3)cc2)c(C)c1] |
| I-11 | 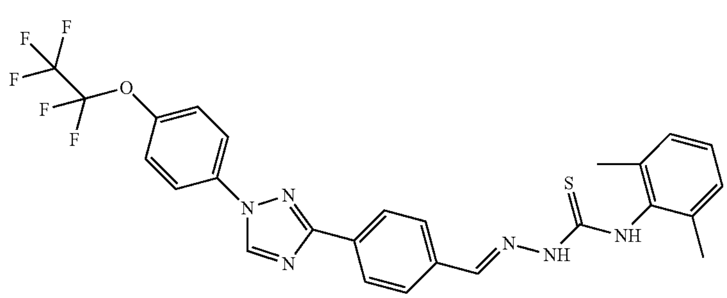 [SMILES: Cc1cccc(C)c1NC(=S)N/N=C/c1ccc(-c2ncn(-c3ccc(OC(F)(F)C(F)(F)F)cc3)n2)cc1] |

TABLE 1-continued
Structures for Compounds
| ID | Structure |
|---|---|
| I-12 | 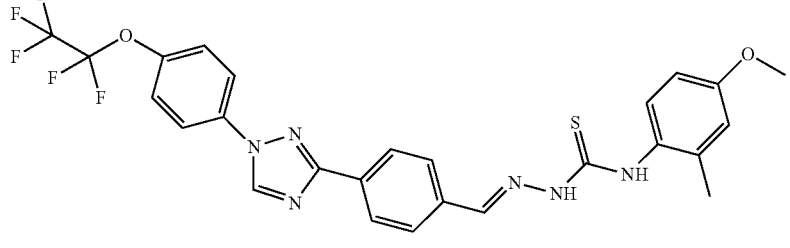 |
| I-13 | 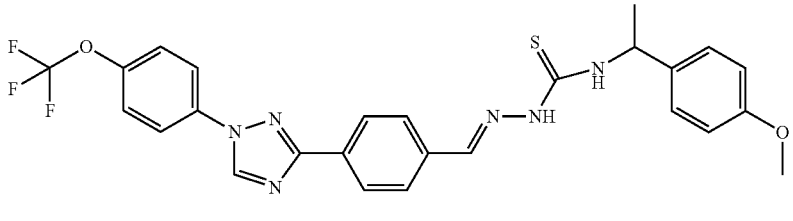 [SMILES: COc1ccc(C(C)NC(=S)N/N=C/c2ccc(-c3ncn(-c4ccc(OC(F)(F)F)cc4)n3)cc2)cc1] |
| I-14 | 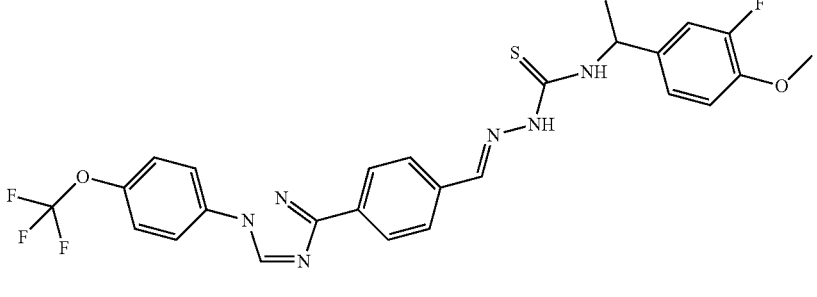 [SMILES: COc1ccc(C(C)NC(=S)N/N=C/c2ccc(C(=N)/N=C\Nc3ccc(OC(F)(F)F)cc3)cc2)cc1F] |
| I-15 | 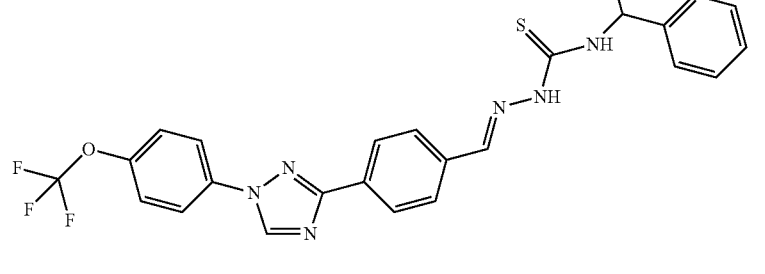 |
| I-16 | 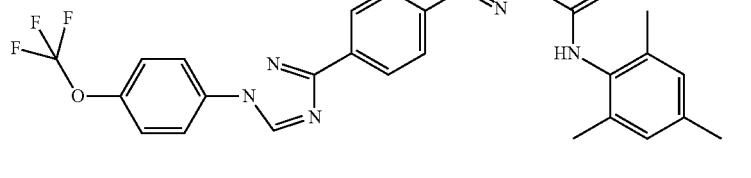 |
| I-17 | 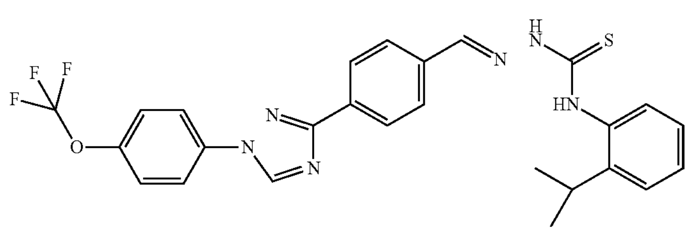 |

TABLE 1-continued

Structures for Compounds

| ID | Structure |
|---|---|
| I-18 | 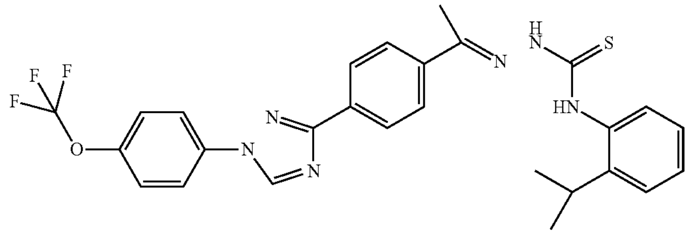 |
| I-19 | 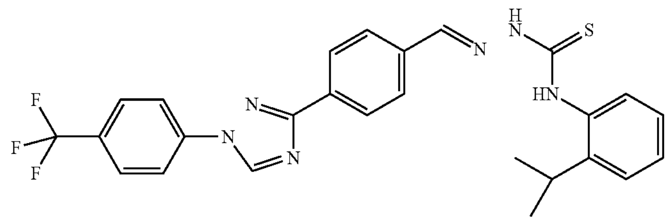 |
| I-20 | 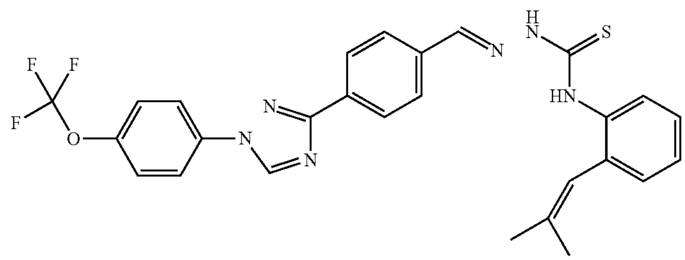 |
| I-21 | 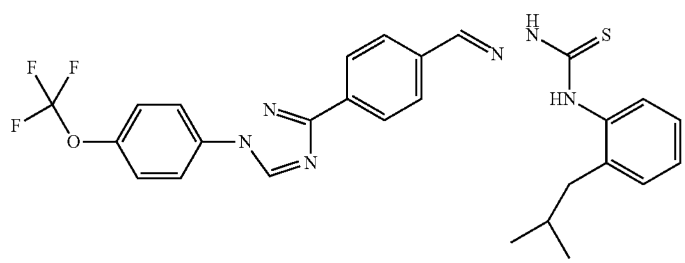 |
| I-22 | 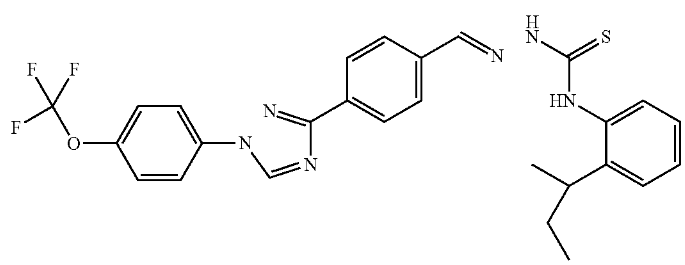 |
| I-23 | 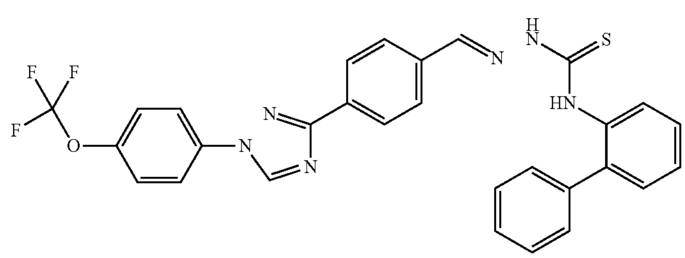 |

TABLE 1-continued
Structures for Compounds
| ID | Structure |
|---|---|
| I-24 | 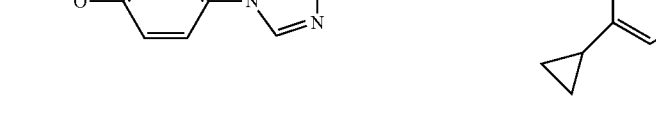 |
| I-25 | 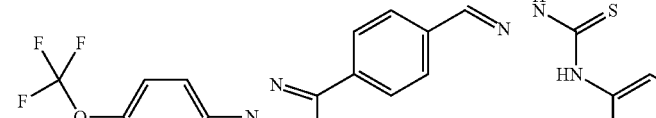 |
| I-26 | 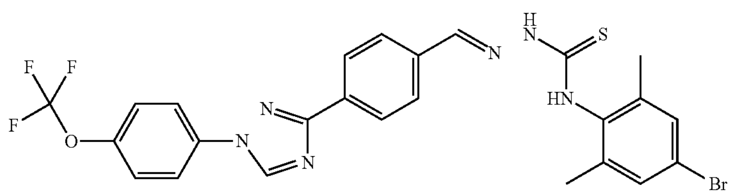 |
| I-27 | 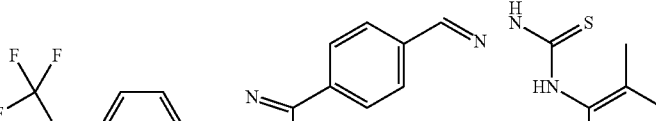 |
| I-28 | 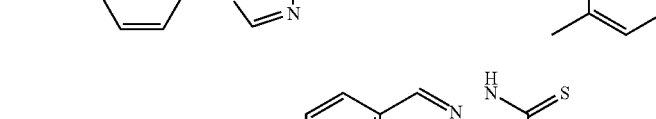 |
| I-29 | 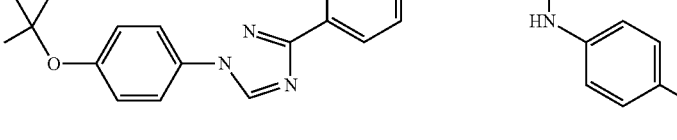 |
| I-30 | 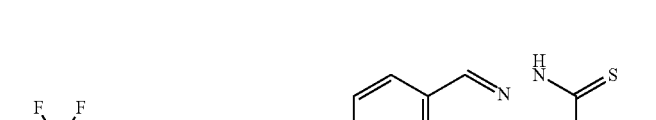 |

TABLE 1-continued

Structures for Compounds

| ID | Structure |
|---|---|
| I-31 | (structure) |

TABLE 2

Analytical Data for Compounds in Table 1.

| ID | Synthesis Method | MS | mp (° C.) | ¹H NMR (δ)¹ |
|---|---|---|---|---|
| I-4 | A | 551 (M + 1) | 209-211 | (DMSO-d$_6$) 12.06 (s, 1H), 10.19 (s, 1H), 9.42 (s, 1H), 8.22 (s, 1H), 8.17-8.03 (m, 5H), 7.66-7.57 (m, 4H), 7.42-7.38 (m, 2H) |
| I-5 | C | 511 (M + 1) | 220-225 | (CDCl$_3$) 9.30 (s, 1H), 8.69 (s, 1H), 8.60 (s, 1H), 8.26 (d, J = 8.4 Hz, 2H), 7.89 (s, 1H), 7.81 (m, 4H), 7.41 (d, J = 8.4 Hz, 2H), 7.19 (m, 3H), 2.35 (s, 6H) |
| I-6 | C | 555 (M + H) | 206-209 | (CDCl$_3$) 8.90 (s, 1H), 8.80 (s, 1H), 8.6 (s, 1H), 8.28 (d, J = 8.4 Hz, 2H), 8.9-8.7 (m, 4H), 7.4 (d, J = 8.6 Hz, 2H), 6.7 (s, 2H), 3.80 (s, 3H), 2.39 (s, 3H), 2.32 (s, 6H) |
| I-7 | C | 541 (M + H) | 202-210 | (CDCl$_3$) 9.88 (s, 1H), 8.61 (s, 1H), 8.60 (s, 1H), 8.27 (d, J = 8.4 Hz, 2H), 7.9 (s, 1H), 7.9-7.7 (m, 4H), 7.4 (d, J = 8.6 Hz, 2H), 6.7 (s, 2H), 3.81 (s, 3H), 2.33 (s, 6H) |
| I-8 | B | 581 | 195-199 | (CDCl$_3$) 10.2 (s, 1H), 8.7 (s, 1H), 8.6 (s, 1H), 8.25 (d, J = 8.4 Hz, 2H), 8.0 (s, 1H), 7.82 (m, 4H), 7.4 (d, J = 8.4 Hz, 2H), 7.0 (s, 2H), 3.82 (s, 3H) |
| I-9 | C | 591 (M + H) | 233-236 | (CDCl$_3$) 9.89 (s, 1H), 8.60 (s, 2H), 8.25 (d, J = 8.5 Hz, 2H), 7.95 (s, 1H), 7.88-7.70 (m, 4H), 7.41 (d, J = 9.0 Hz, 2H), 6.70 (s, 2H), 3.81 (s, 3H), 2.31 (s, 6H) |
| I-10 | C | 525 (M + H) | 230-240 | (CDCl$_3$) 9.93 (s, 1H), 8.69 (s, 1H), 8.60 (s, 1H), 8.26 (d, J = 8.4 Hz, 2H), 7.93 (d, J = 9.5 Hz, 2H), 7.95 (s, 1H), 7.86-7.75 (m, 4H), 6.69 (s, 2H), 3.81 (s, 3H), 2.31 (s, 6H) |
| I-11 | C | 561 (M + H) | 234-238 | (CDCl$_3$) 9.62 (s, 1H), 8.70 (s, 1H), 8.60 (s, 1H), 8.26 (d, J = 8.4 Hz, 2H), 7.92 (s, 1H), 7.86-7.75 (m, 4H), 7.41 (d, J = 9.0 Hz, 2H), 7.18 (m, 3H), 2.35 (s, 6H) |
| I-12 | C | 577 (M + H) | 197-200 | (CDCl$_3$) 10.2 (s, 1H), 8.90 (s, 1H), 8.62 (s, 1H), 8.25 (d, J = 8.4 Hz, 2H), 7.98 (s, 1H), 7.9-7.7 (m, 4H), 7.4 (m, 3H), 6.8 (m, 2H), 3.82 (s, 3H), 2.37 (s, 3H) |
| I-13 | B | 541 (M + H) | 180-186 | (CDCl$_3$) 9.9 (s, 1H), 8.6 (s, 1H), 8.23 (d, J = 8.4 Hz, 2H), 7.9 (s, 1H), 7.8 (d, J = 8.6 Hz, 2H), 7.75 (d, J = 8.4 Hz, 2H), 7.7 (d, J = 7 Hz, 1H), 7.45-7.35 (m, 4H), 6.91 (d, J = 8 Hz, 2H), 5.73 (m, 1H), 3.80 (s, 3H), 1.65 (d, J = 7.2 Hz, 3H) |
| I-14 | B | 559 (M + H) | 196-203 | (CDCl$_3$) 9.32 (s, 1H), 8.6 (s, 1H), 8.22 (d, J = 8.4 Hz, 2H), 7.85-7.7 (m, 5H), 7.6 (d, J = 6 Hz, 1H), 7.4 (d, J = 8.5 Hz, 2H), 7.25-7.15 (m, 2H), 6.93 (m, 1H), 5.7 (m, 1H), 3.89 (s, 3H), 1.67 (d, J = 6 Hz, 3H) |
| I-15 | B | 511 (M + H) | 201-206 | (CDCl$_3$) 9.32 (s, 1H), 8.61 (s, 1H), 8.27 (d, J = 8.4 Hz, 2H), 7.9-7.7 (m, 6H), 7.5-7.3 (m, 7H), 5.76 (m, 1H), 1.67 (d, J = 7 Hz, 3H) |
| I-16 | C | 525 (M + 1) | 218-225 | (CDCl$_3$) 9.37 (s, 1H), 8.63 (s, 1H), 8.60 (s, 1H), 8.26 (d, J = 8.4 Hz, 2H), 7.89 (s, 1H), 7.85-7.76 (m, 4H), 7.41 (d, J = 8.4 Hz, 2H), 6.97 (s, 2H), 2.32 (s, 3H), 2.30 (s, 6H) |
| I-17 | C | 525 (M + H) | 168-180 | (CDCl$_3$) 10.2 (s, 1H), 9.07 (s, 1H), 8.63 (s, 1H), 8.25 (d, J = 8.4 Hz, 2H), 8.0 (s, 1H), 7.9-7.7 (m, 4H), 7.65 (d, J = 8 Hz, 1H), |

TABLE 2-continued

Analytical Data for Compounds in Table 1.

| ID | Synthesis Method | MS | mp (° C.) | ¹H NMR (δ)¹ |
|---|---|---|---|---|
| I-18 | C | 539 (M + 1) | 216-221 | 7.4-7.25 (m, 5H), 3.25 (heptet, J = 7 Hz, 1H), 1.35 (d, J = 7 Hz, 6H) (CDCl₃) δ 9.29 (s, 1H), 8.87 (s, 1H), 8.59 (s, 1H), 8.31-8.19 (m, 2H), 7.90-7.84 (m, 2H), 7.85-7.79 (m, 2H), 7.73 (dd, J = 7.5, 1.7 Hz, 1H), 7.39 (dd, J = 12.6, 5.1 Hz, 3H), 7.35-7.27 (m, 2H), 3.37-3.04 (m, 1H), 2.40 (s, 3H), 1.29 (d, J = 7.5 Hz, 6H) |
| I-19 | C | 509 (M + 1) | 223-225 | (CDCl₃) δ 9.74 (s, 1H), 9.06 (s, 1H), 8.69 (s, 1H), 8.31-8.20 (m, 2H), 7.98-7.84 (m, 3H), 7.80 (m, 4H), 7.65 (d, J = 1.4 Hz, 1H), 7.43-7.28 (m, 3H), 3.19 (heptet, J = 6.9 Hz, 1H), 1.32 (d, J = 6.9 Hz, 6H) |
| I-20 | C | 538 (M + H) | 220 (dec) | (CDCl₃) δ 9.52 (s, 1H), 9.31 (s, 1H), 8.66 (d, J = 8.2 Hz, 1H), 8.60 (s, 1H), 8.25 (d, J = 8.4 Hz, 2H), 7.87 (s, 1H), 7.86-7.80 (m, 2H), 7.77 (d, J = 8.4 Hz, 2H), 7.41 (d, J = 8.3 Hz, 2H), 7.32 (ddd, J = 13.9, z 7.2, 4.3 Hz, 1H), 7.24-7.15 (m, 2H), 6.27 (s, 1H), 2.03 (d, J = 1.3 Hz, 3H), 1.73 (d, J = 1.1 Hz, 3H) |
| I-21 | C | 540 (M + H) | 207-210; 215-218 | (CDCl₃) δ 9.48 (s, 1H), 9.14 (s, 1H), 8.60 (s, 1H), 8.26 (d, J = 8.4 Hz, 2H), 7.92 (s, 1H), 7.87 (d, J = 7.7 Hz, 1H), 7.84-7.76 (m, 4H), 7.40 (d, J = 8.3 Hz, 2H), 7.30 (dt, J = 8.2, 3.7 Hz, 1H), 7.28-7.23 (m, 2H), 2.57 (d, J = 7.2 Hz, 2H), 1.93 (dq, J = 13.6, 6.7 Hz, 1H), 0.98 (d, J = 6.6 Hz, 6H) |
| I-22 | C | 540 (M + H) | 210-215 | (CDCl₃) δ 9.46 (s, 1H), 9.05 (s, 1H), 8.60 (s, 1H), 8.26 (d, J = 8.4 Hz, 2H), 7.91 (s, 1H), 7.84-7.74 (m, 4H), 7.69 (d, J = 7.4 Hz, 1H), 7.40 (d, J = 8.3 Hz, 2H), 7.36-7.27 (m, 3H), 2.91 (dt, J = 13.9, 6.9 Hz, 1H), 1.75-1.58 (m, 2H), 1.30 (d, J = 6.9 Hz, 3H), 0.92 (t, J = 7.4 Hz, 3H). |
| I-23 | C | 560 (M + H) | 213-216 | (CDCl₃) δ 9.41 (s, 1H), 9.01 (s, 1H), 8.74 (d, J = 7.7 Hz, 1H), 8.60 (s, 1H), 8.15 (d, J = 8.4 Hz, 2H), 7.86-7.78 (m, 2H), 7.69 (s, 1H), 7.57-7.44 (m, 6H), 7.42 (d, J = 9.1 Hz, 2H), 7.37-7.27 (m, 4H). |
| I-24 | C | 524 (M + H) | 200-206; 210-211 | (CDCl₃) δ 9.65 (d, J = 17.9 Hz, 1H), 9.20 (s, 1H), 8.60 (s, 1H), 8.27 (dd, J = 8.0, 4.5 Hz, 3H), 7.89 (s, 1H), 7.86-7.75 (m, 4H), 7.41 (d, J = 8.3 Hz, 2H), 7.30-7.27 (m, 1H), 7.18 (q, J = 7.8 Hz, 2H), 2.00-1.90 (m, 1H), 1.09-1.01 (m, 2H), 0.81-0.73 (m, 2H). |
| I-25 | C | 550 (M + H) | 221-223 | (DMSO-d₆) δ 12.13 (s, 1H), 10.07 (s, 1H), 9.44 (s, 1H), 8.23 (s, 1H), 8.16 (d, J = 8.4 Hz, 2H), 8.13-8.06 (m, 2H), 8.01-7.98 (m, 3H), 7.63 (d, J = 8.4 Hz, 2H), 7.38-7.26 (m, 3H), 7.23 (t, J$_{HF}$ = 74.1 Hz, 1H) |
| I-26 | C | 590 (M + H) | 230-231 | (CDCl₃) δ 9.37 (s, 1H), 8.60 (s, 1H), 8.57 (s, 1H), 8.27 (d, J = 8.4 Hz, 2H), 7.90 (s, 1H), 7.81 (dt, J = 8.5, 4.8 Hz, 4H), 7.41 (d, J = 8.3 Hz, 2H), 7.31 (s, 2H), 2.31 (s, 6H) |
| I-27 | C | 556 (M + H) | 190-192 | (CDCl₃) δ 9.39 (s, 1H), 9.15 (s, 1H), 8.61 (s, 1H), 8.29 (d, J = 8.4 Hz, 2H), 8.16-8.05 (m, 2H), 7.95-7.85 (m, 3H), 7.85-7.76 (m, 4H), 7.41 (d, J = 8.3 Hz, 2H), 4.39 (q, J = 7.1 Hz, 2H), 1.41 (t, J = 7.1 Hz, 3H) |
| I-28 | C | 528 (M + H) | 219-221 | (300 MHz, CDCl₃) δ 10.17 (s, 1H), 9.09 (s, 1H), 9.03 (t, J = 5.4 Hz, 1H), 8.60 (s, 1H), 8.23 (t, J = 8.9 Hz, 2H), 7.89-7.76 (m, 5H), 7.39 (t, J = 7.2 Hz, 2H), 7.17-7.07 (m, 1H), 7.03 (d, J = 7.8 Hz, 1H), 6.94 (d, J = 6.9 Hz, 1H), 4.18 (q, J = 7.1 Hz, 2H), 1.61 (t, J = 7.0 Hz, 3H) |
| I-29 | C | 499 (M + 1) | 195-200 | (DMSO-d₆) δ 9.44 (s, 1H), 8.49 (s, 1H), 8.42 (d, J = 5.2 Hz, 1H), 8.29-8.21 (m, 2H), 8.16 (d, J = 8.5 Hz, 2H), 8.10 (d, J = 2.3 Hz, 1H), 8.08 (d, J = 3.0 Hz, 1H), 8.04 (t, J = 6.5 Hz, 2H), 7.63 (d, J = 8.3 Hz, 3H), 2.29 (s, 3H). |
| I-30 | C | 499 (M + 1) | 114-118 | (CDCl₃) δ 8.60 (s, 1H), 8.31 (s, 1H), 8.24 (d, J = 8.4 Hz, 2H), 8.16 (d, J = 3.9 Hz, 1H), 7.95 (d, J = 8.4 Hz, 2H), 7.82 (d, J = 9.0 Hz, |

TABLE 2-continued

Analytical Data for Compounds in Table 1.

| ID | Synthesis Method | MS | mp (° C.) | $^1$H NMR (δ)[1] |
|---|---|---|---|---|
| I-31 | C | 513 (M + 1) | 122-125 | 2H), 7.55 (d, J = 6.7 Hz, 1H), 7.41 (s, 2H), 6.99 (dd, J = 7.4, 5.1 Hz, 1H), 2.35 (s, 3H). (CDCl$_3$) δ 8.60 (s, 1H), 8.32 (s, 1H), 8.25 (d, J = 8.4 Hz, 2H), 8.19-8.16 (m, 1H), 7.97 (d, J = 8.4 Hz, 2H), 7.84-7.81 (m, 2H), 7.58 (d, J = 7.5 Hz, 1H), 7.40 (d, J = 8.3 Hz, 2H), 7.03 (dd, J = 7.5, 5.1 Hz, 1H), 2.67 (s, 2H), 1.35 (t, J = 7.5 Hz, 3H). |

[1] H NMR spectral data were acquired using a 400 MHz instrument.

TABLE 3

Structures for Compounds

| ID | Structure |
|---|---|
| 1C | 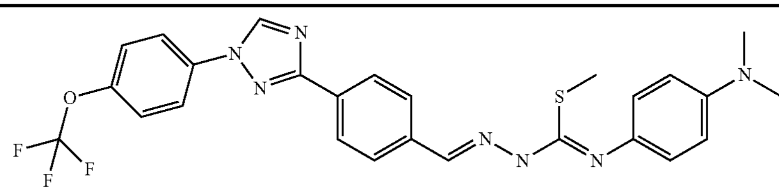 |
| 2C | 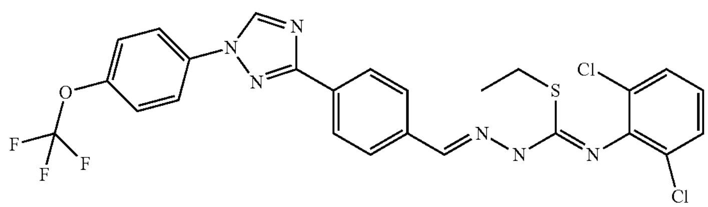 [SMILES: CCS/C(=N\c1c(Cl)cccc1Cl)N/N=C/c1ccc(-c2ncn(-c3ccc(OC(F)(F)F)cc3)n2)cc1] |
| 3C | 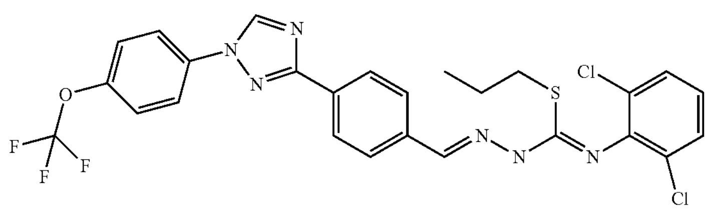 [SMILES: CCCS/C(=N\c1c(Cl)cccc1Cl)N/N=C/c1ccc(-c2ncn(-c3ccc(OC(F)(F)F)cc3)n2)cc1] |
| 4C | 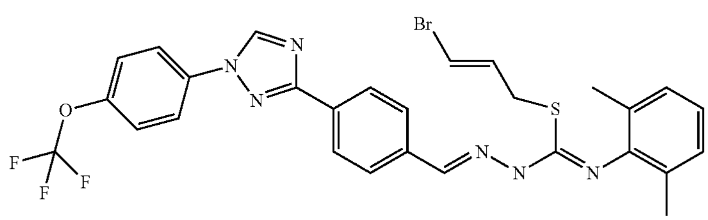 [SMILES: Cc1cccc(C)c1/N=C(/N/N=C/c1ccc(-c2ncn(-c3ccc(OC(F)(F)F)cc3)n2)cc1)SC/C=C/Br] |
| 5C | 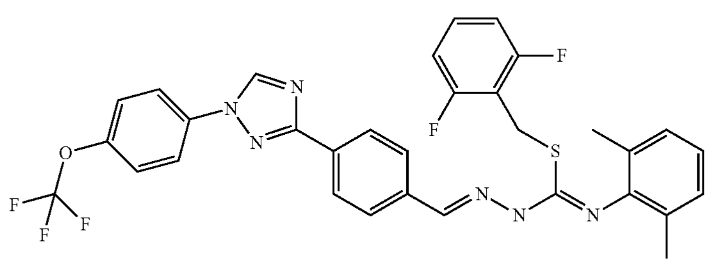 [SMILES: Cc1cccc(C)c1/N=C(/N/N=C/c1ccc(-c2ncn(-c3ccc(OC(F)(F)F)cc3)n2)cc1)SCc1c(F)cccc1F] |

TABLE 3-continued
Structures for Compounds
| ID | Structure |
|---|---|
| 6C | 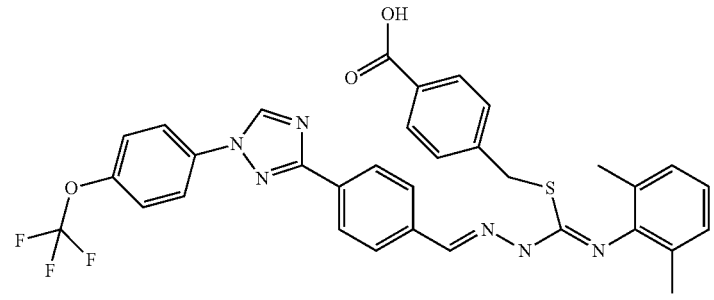 [SMILES: Cc1cccc(C)c1/N=C(/N/N=C/c1ccc(-c2ncn(-c3ccc(OC(F)(F)F)cc3)n2)cc1)SCc1ccc(C(=O)O)cc1] |
| 7C | 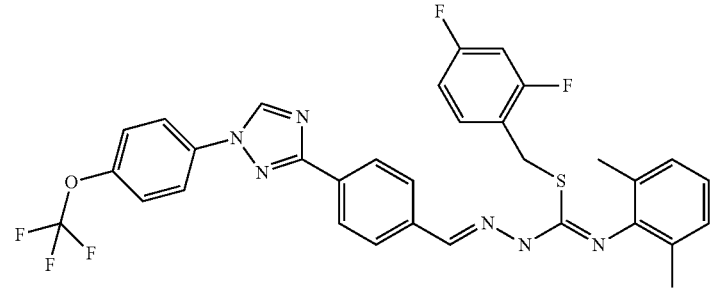 [SMILES: Cc1cccc(C)c1/N=C(/N/N=C/c1ccc(-c2ncn(-c3ccc(OC(F)(F)F)cc3)n2)cc1)SCc1ccc(F)cc1F] |
| 8C | 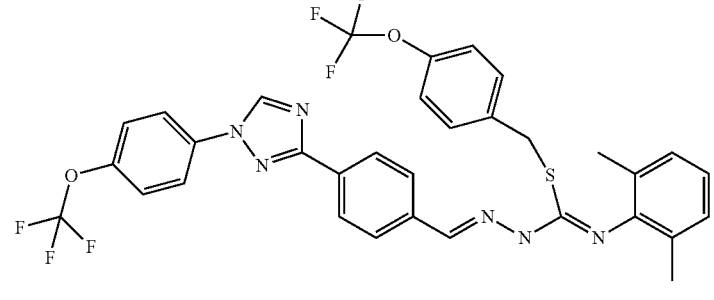 |
| 9C | 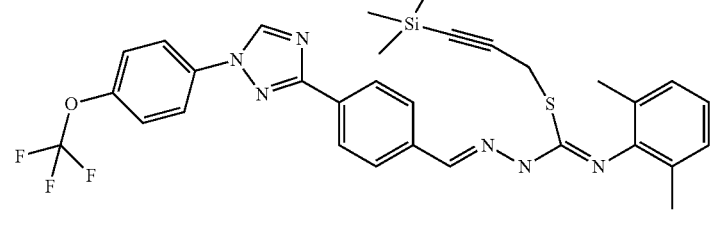 |
| 10C | 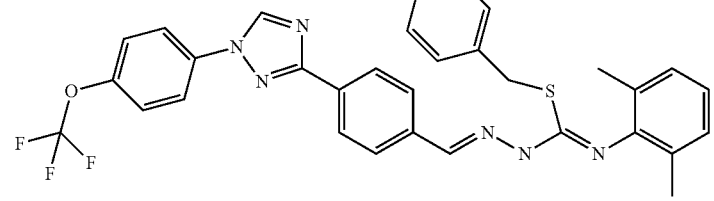 |

TABLE 3-continued

Structures for Compounds

| ID | Structure |
|---|---|
| 11C | 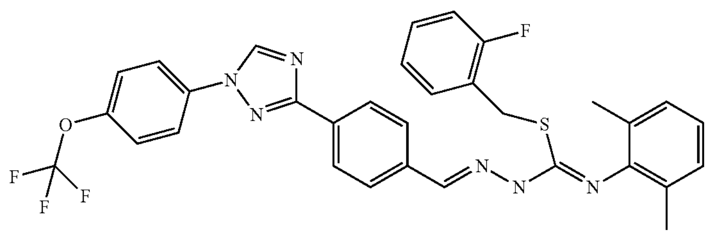 [SMILES: Cc1cccc(C)c1/N=C(/N/N=C/c1ccc(-c2ncn(-c3ccc(OC(F)(F)F)cc3)n2)cc1)SCc1ccccc1F] |
| 12C | 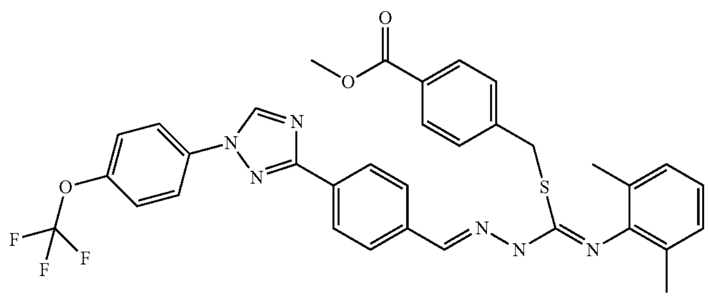 [SMILES: COC(=O)c1ccc(CS/C(=N\c2c(C)cccc2C)N/N=C/c2ccc(-c3ncn(-c4ccc(OC(F)(F)F)cc4)n3)cc2)cc1] |
| 13C | 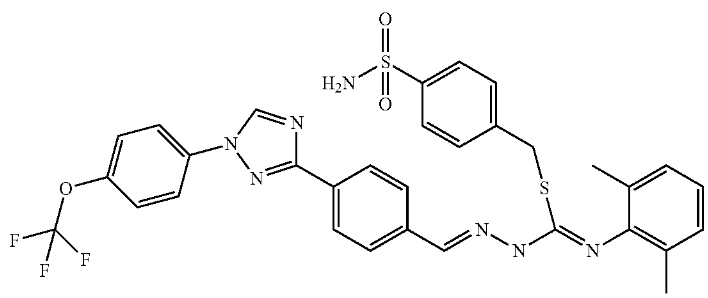 [SMILES: Cc1cccc(C)c1/N=C(/N/N=C/c1ccc(-c2ncn(-c3ccc(OC(F)(F)F)cc3)n2)cc1)SCc1ccc(S(N)(=O)=O)cc1] |
| 14C | 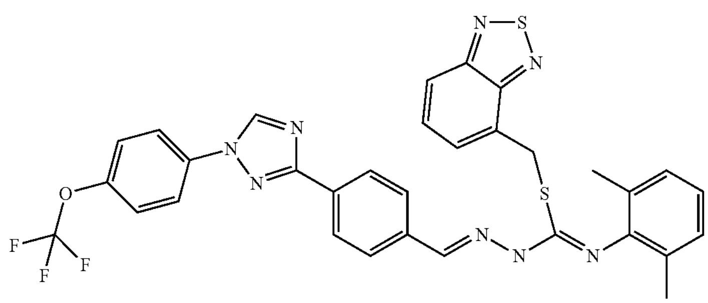 [SMILES: Cc1cccc(C)c1/N=C(/N/N=C/c1ccc(-c2ncn(-c3ccc(OC(F)(F)F)cc3)n2)cc1)SCc1cccc2nsnc12] |
| 15C | 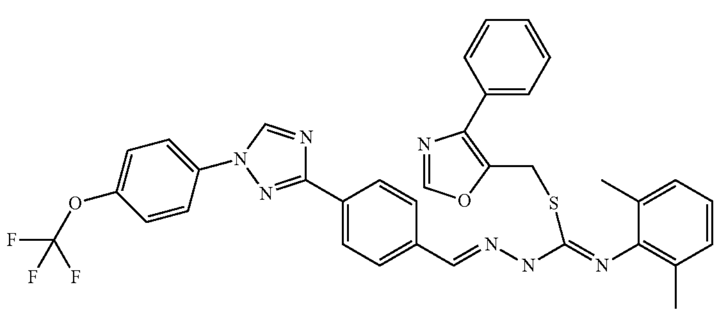 [SMILES: Cc1cccc(C)c1/N=C(/N/N=C/c1ccc(-c2ncn(-c3ccc(OC(F)(F)F)cc3)n2)cc1)SCc1ocnc1-c1ccccc1] |

TABLE 3-continued
Structures for Compounds
| ID | Structure |
|---|---|
| 16C | 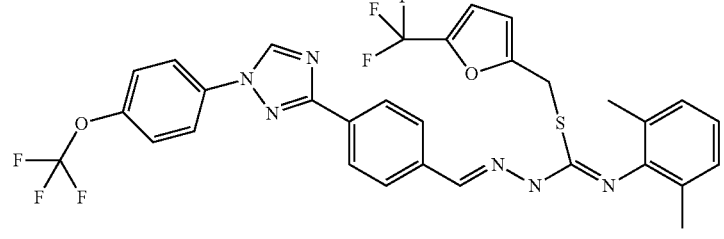 |
| 17C | 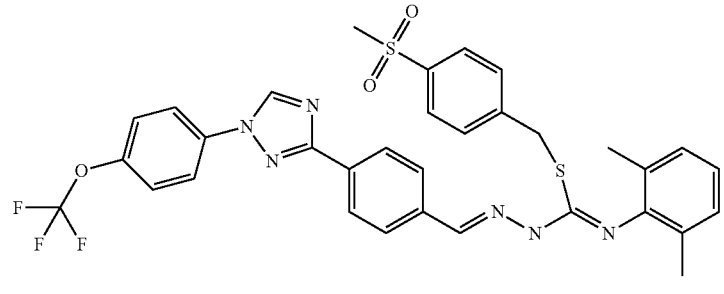 [SMILES: Cc1cccc(C)c1/N=C(/N/N=C/c1ccc(-c2ncn(-c3ccc(OC(F)(F)F)cc3)n2)cc1)SCc1ccc(S(C)(=O)=O)cc1] |
| 18C | 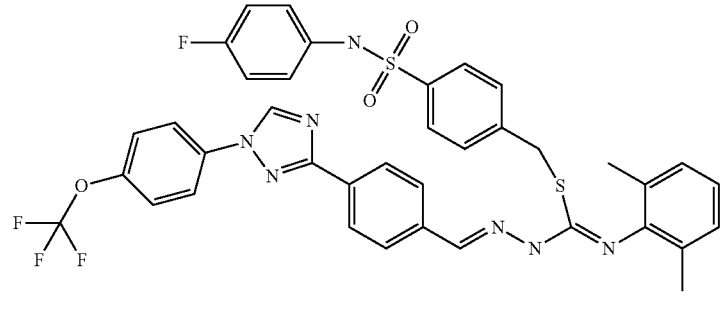 [SMILES: Cc1cccc(C)c1/N=C(/N/N=C/c1ccc(-c2ncn(-c3ccc(OC(F)(F)F)cc3)n2)cc1)SCc1ccc(S(=O)(=O)Nc2ccc(F)cc2)cc1] |
| 19C | 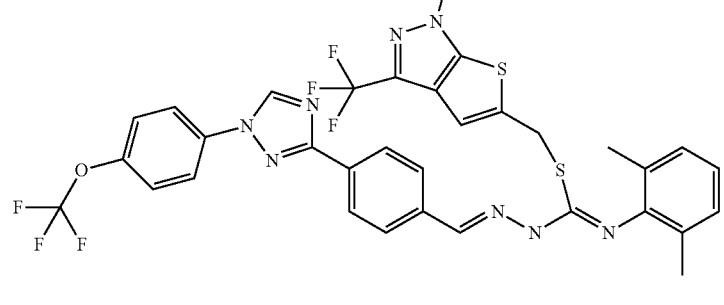 |
| 20C | 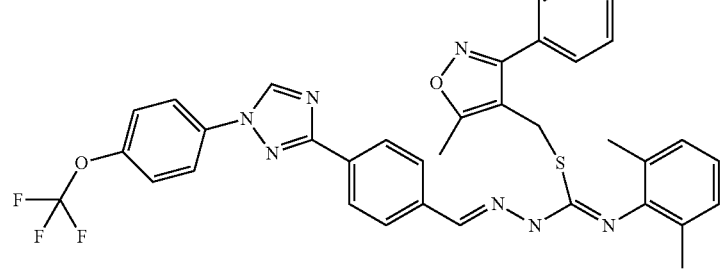 |

TABLE 3-continued

Structures for Compounds

| ID | Structure |
|---|---|
| 21C | 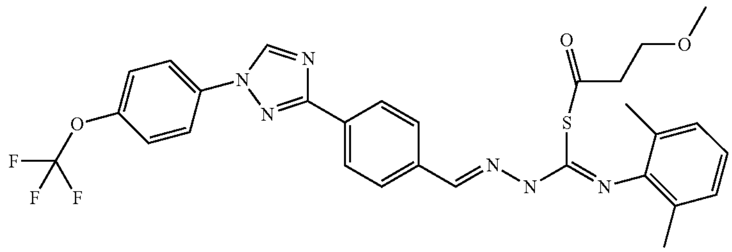 [SMILES: COCCC(=O)S/C(=N\c1c(C)cccc1C)N/N=C/c1ccc(-c2ncn(-c3ccc(OC(F)(F)F)cc3)n2)cc1] |
| 22C | 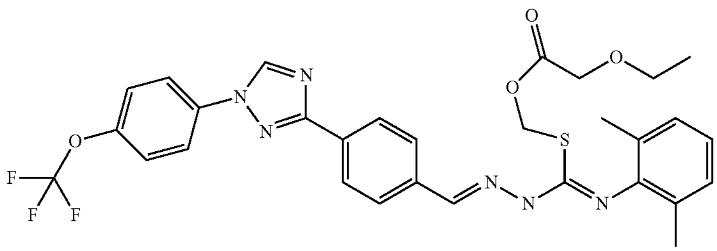 [SMILES: CCOCC(=O)OCS/C(=N\c1c(C)cccc1C)N/N=C/c1ccc(-c2ncn(-c3ccc(OC(F)(F)F)cc3)n2)cc1] |
| 23C | 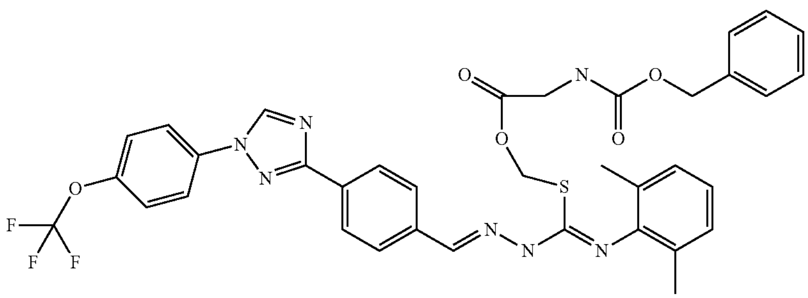 [SMILES: Cc1cccc(C)c1/N=C(/N/N=C/c1ccc(-c2ncn(-c3ccc(OC(F)(F)F)cc3)n2)cc1)SCOC(=O)CNC(=O)OCc1ccccc1] |
| 24C | 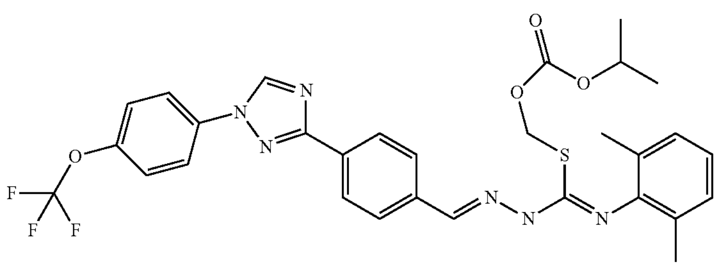 [SMILES: Cc1cccc(C)c1/N=C(/N/N=C/c1ccc(-c2ncn(-c3ccc(OC(F)(F)F)cc3)n2)cc1)SCOC(=O)OC(C)C] |
| 25C | 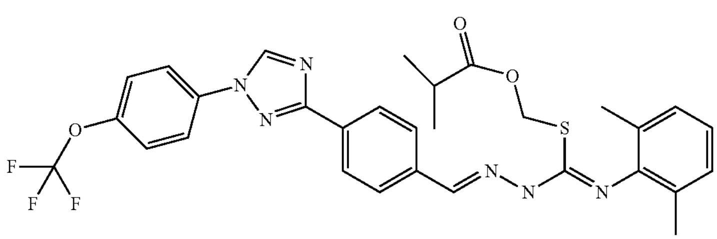 [SMILES: Cc1cccc(C)c1/N=C(/N/N=C/c1ccc(-c2ncn(-c3ccc(OC(F)(F)F)cc3)n2)cc1)SCOC(=O)C(C)C] |
| 26C | 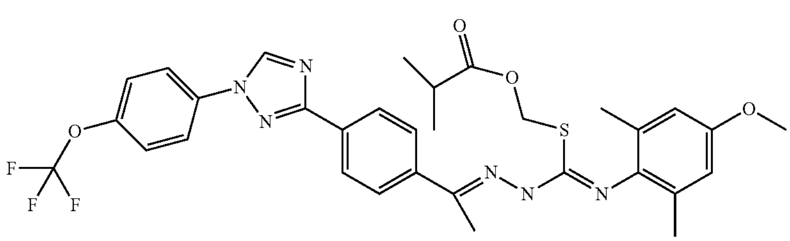 [SMILES: COc1cc(C)c(/N=C(/N/N=C(\C)c2ccc(-c3ncn(-c4ccc(OC(F)(F)F)cc4)n3)cc2)SCOC(=O)C(C)C)c(C)c1] |

TABLE 3-continued

Structures for Compounds

| ID | Structure |
|---|---|
| 27C | 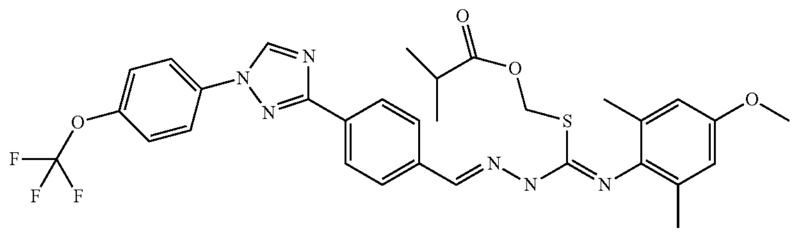 [SMILES: COc1cc(C)c(/N=C(/N/N=C/c2ccc(-c3ncn(-c4ccc(OC(F)(F)F)cc4)n3)cc2)SCOC(=O)C(C)C)c(C)c1] |
| 28C | 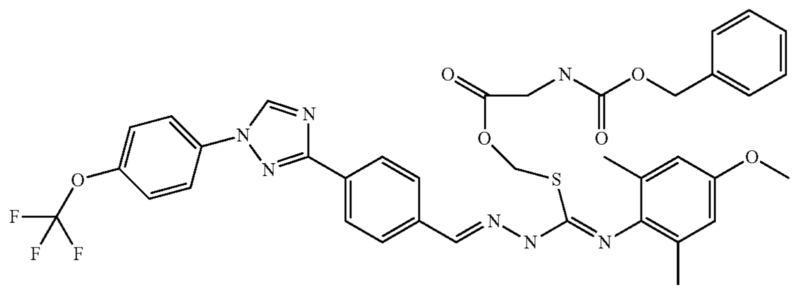 [SMILES: COc1cc(C)c(/N=C(/N/N=C/c2ccc(-c3ncn(-c4ccc(OC(F)(F)F)cc4)n3)cc2)SCOC(=O)CNC(=O)OCc2ccccc2)c(C)c1] |
| 29C | 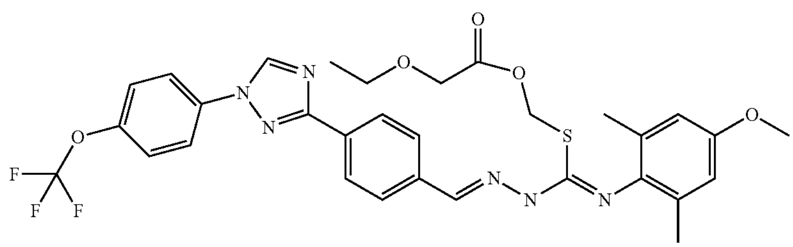 [SMILES: CCOCC(=O)OCS/C(=N\c1c(C)cc(OC)cc1C)N/N=C/c1ccc(-c2ncn(-c3ccc(OC(F)(F)F)cc3)n2)cc1] |
| 30C | 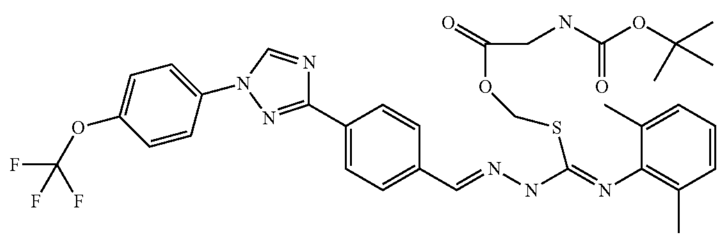 [SMILES: Cc1cccc(C)c1/N=C(/N/N=C/c1ccc(-c2ncn(-c3ccc(OC(F)(F)F)cc3)n2)cc1)SCOC(=O)CNC(=O)OC(C)(C)C] |
| 31C | 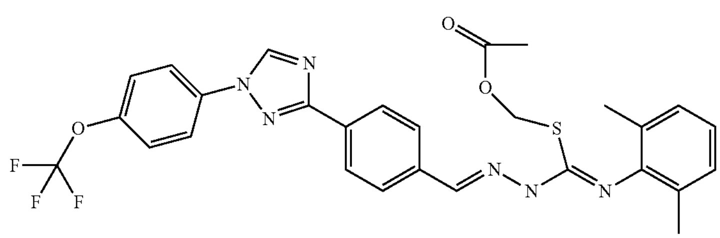 [SMILES: CC(=O)OCS/C(=N\c1c(C)cccc1C)N/N=C/c1ccc(-c2ncn(-c3ccc(OC(F)(F)F)cc3)n2)cc1] |
| 32C | 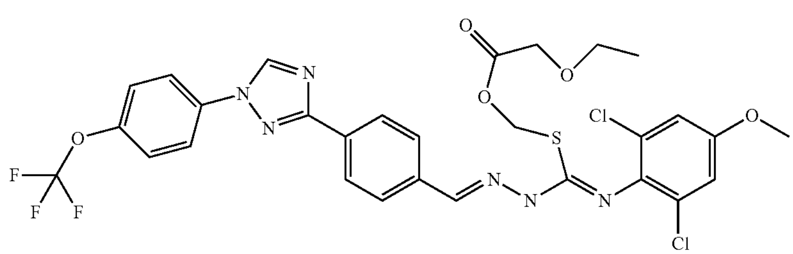 [SMILES: CCOCC(=O)OCS/C(=N\c1c(Cl)cc(OC)cc1Cl)N/N=C/c1ccc(-c2ncn(-c3ccc(OC(F)(F)F)cc3)n2)cc1] |

TABLE 3-continued

Structures for Compounds

| ID  | Structure |
|-----|-----------|
| 33C | 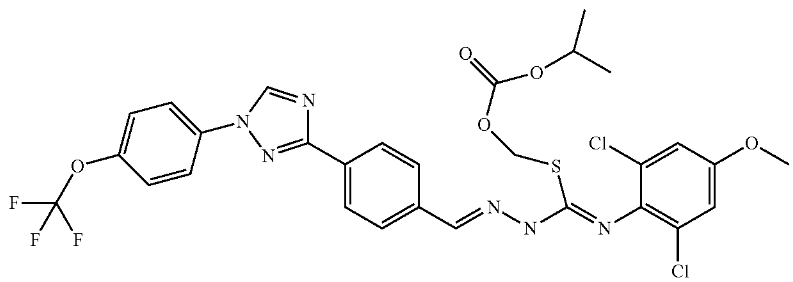 [SMILES: COc1cc(Cl)c(/N=C(/N/N=C/c2ccc(-c3ncn(-c4ccc(OC(F)(F)F)cc4)n3)cc2)SCOC(=O)OC(C)C)c(Cl)c1]          |
| 34C | 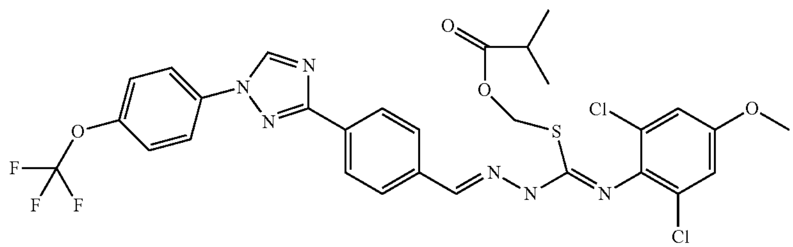 [SMILES: COc1cc(Cl)c(/N=C(/N/N=C/c2ccc(-c3ncn(-c4ccc(OC(F)(F)F)cc4)n3)cc2)SCOC(=O)C(C)C)c(Cl)c1]          |
| 35C | 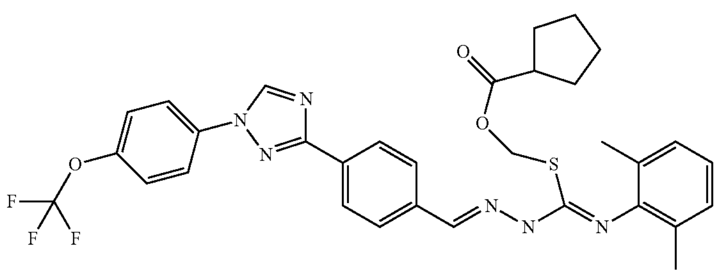 [SMILES: Cc1cccc(C)c1/N=C(/N/N=C/c1ccc(-c2ncn(-c3ccc(OC(F)(F)F)cc3)n2)cc1)SCOC(=O)C1CCCC1]          |
| 36C | 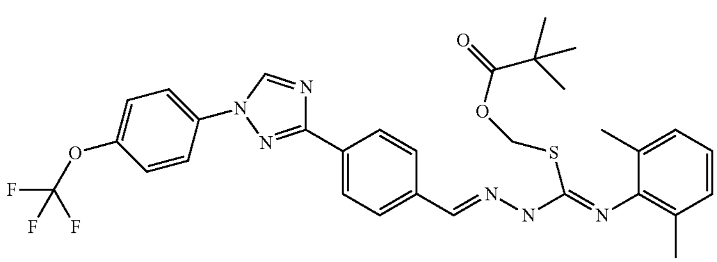 [SMILES: Cc1cccc(C)c1/N=C(/N/N=C/c1ccc(-c2ncn(-c3ccc(OC(F)(F)F)cc3)n2)cc1)SCOC(=O)C(C)(C)C]          |
| 37C | 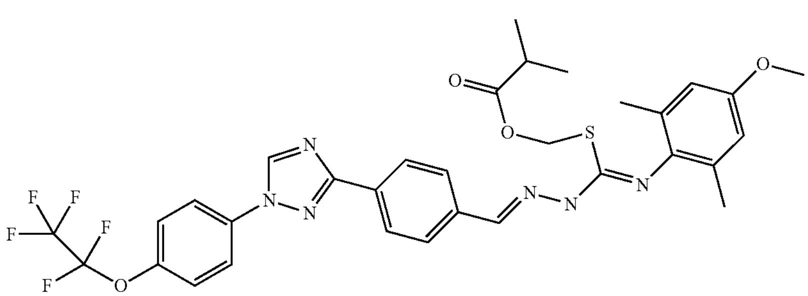 [SMILES: COc1cc(C)c(/N=C(/N/N=C/c2ccc(-c3ncn(-c4ccc(OC(F)(F)C(F)(F)F)cc4)n3)cc2)SCOC(=O)C(C)C)c(C)c1]          |

TABLE 3-continued

Structures for Compounds

| ID | Structure |
|---|---|
| 38C | 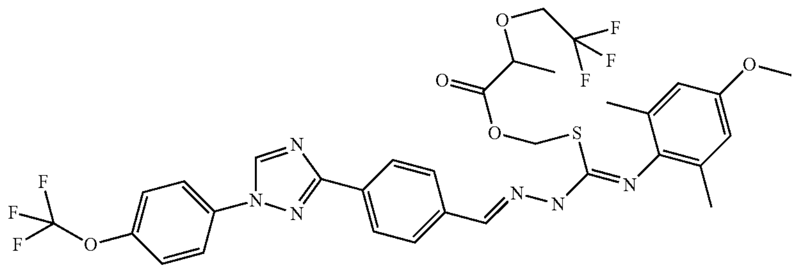 [SMILES: COc1cc(C)c(/N=C(/N/N=C/c2ccc(-c3ncn(-c4ccc(OC(F)(F)F)cc4)n3)cc2)SCOC(=O)C(C)OCC(F)(F)F)c(C)c1] |
| 39C | 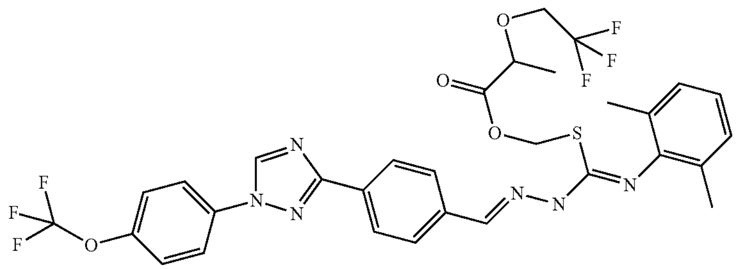 [SMILES: Cc1cccc(C)c1/N=C(/N/N=C/c1ccc(-c2ncn(-c3ccc(OC(F)(F)F)cc3)n2)cc1)SCOC(=O)C(C)OCC(F)(F)F] |
| 40C | 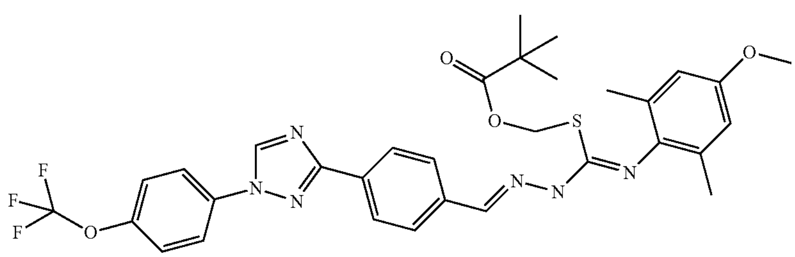 [SMILES: COc1cc(C)c(/N=C(/N/N=C/c2ccc(-c3ncn(-c4ccc(OC(F)(F)F)cc4)n3)cc2)SCOC(=O)C(C)(C)C)c(C)c1] |
| 41C | 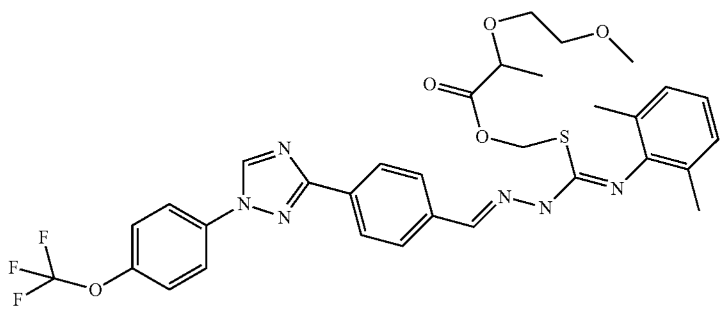 [SMILES: COCCOC(C)C(=O)OCS/C(=N\c1c(C)cccc1C)N/N=C/c1ccc(-c2ncn(-c3ccc(OC(F)(F)F)cc3)n2)cc1] |
| 42C | 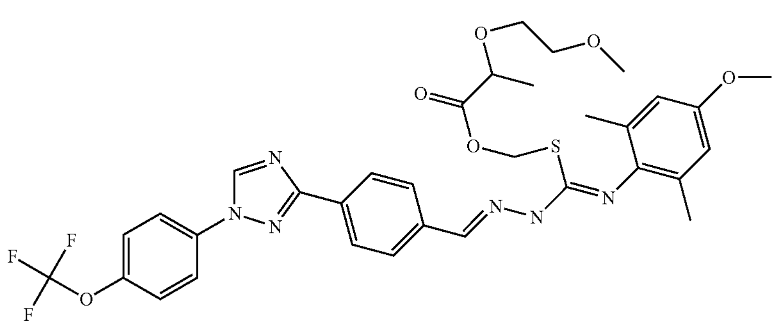 [SMILES: COCCOC(C)C(=O)OCS/C(=N\c1c(C)cc(OC)cc1C)N/N=C/c1ccc(-c2ncn(-c3ccc(OC(F)(F)F)cc3)n2)cc1] |

TABLE 3-continued

Structures for Compounds

| ID | Structure |
|---|---|
| 43C | 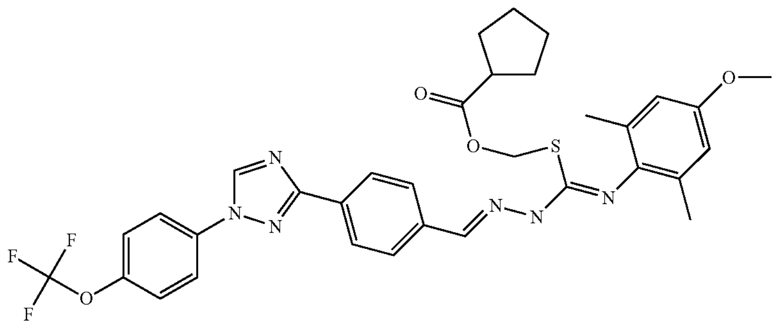 [SMILES: COc1cc(C)c(/N=C(/N/N=C/c2ccc(-c3ncn(-c4ccc(OC(F)(F)F)cc4)n3)cc2)SCOC(=O)C2CCCC2)c(C)c1] |
| 44C | 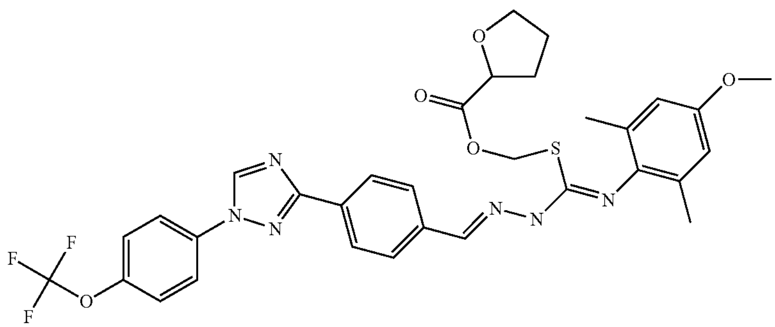 [SMILES: COc1cc(C)c(/N=C(/N/N=C/c2ccc(-c3ncn(-c4ccc(OC(F)(F)F)cc4)n3)cc2)SCOC(=O)C2CCCO2)c(C)c1] |
| 45C | 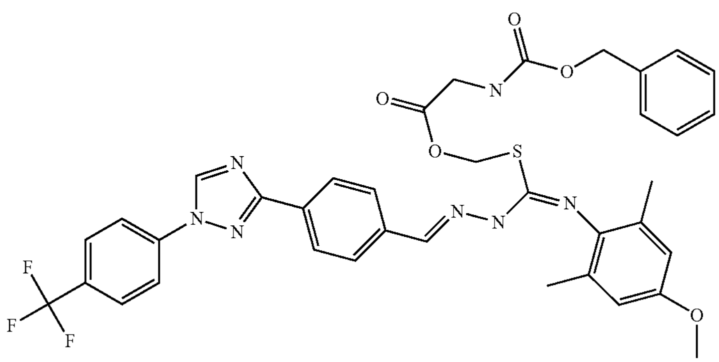 [SMILES: COc1cc(C)c(/N=C(\N/N=C/c2ccc(-c3ncn(-c4ccc(C(F)(F)F)cc4)n3)cc2)SCOC(=O)CNC(=O)OCc2ccccc2)c(C)c1] |
| 46C | 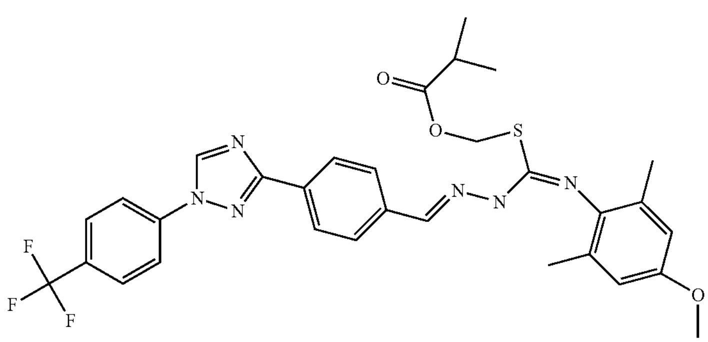 [SMILES: COc1cc(C)c(/N=C(\N/N=C/c2ccc(-c3ncn(-c4ccc(C(F)(F)F)cc4)n3)cc2)SCOC(=O)C(C)C)c(C)c1] |
| 47C | 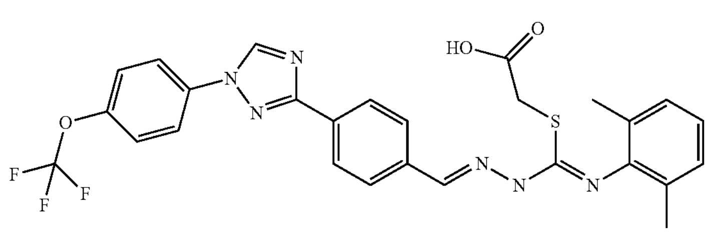 [SMILES: Cc1cccc(C)c1/N=C(/N/N=C/c1ccc(-c2ncn(-c3ccc(OC(F)(F)F)cc3)n2)cc1)SCC(=O)O] |

TABLE 3-continued
Structures for Compounds
| ID | Structure |
|---|---|
| 48C | 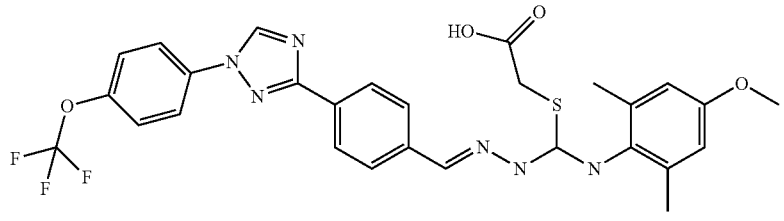 [SMILES: COc1cc(C)c(NC(N/N=C/c2ccc(-c3ncn(-c4ccc(OC(F)(F)F)cc4)n3)cc2)SCC(=O)O)c(C)c1] |
| 49C | 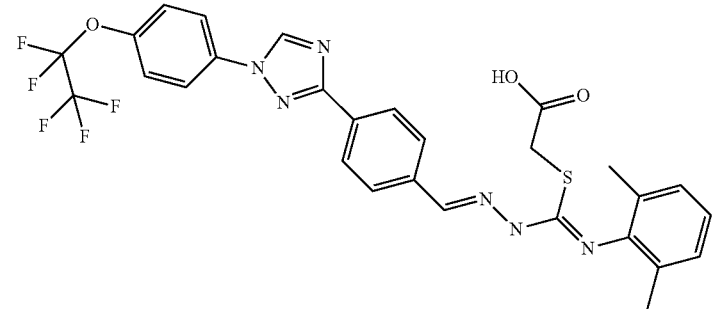 [SMILES: Cc1cccc(C)c1/N=C(/N/N=C/c1ccc(-c2ncn(-c3ccc(OC(F)(F)C(F)(F)F)cc3)n2)cc1)SCC(=O)O] |
| 50C | 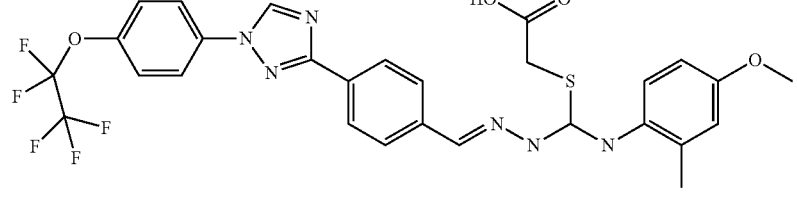 |
| 51C | 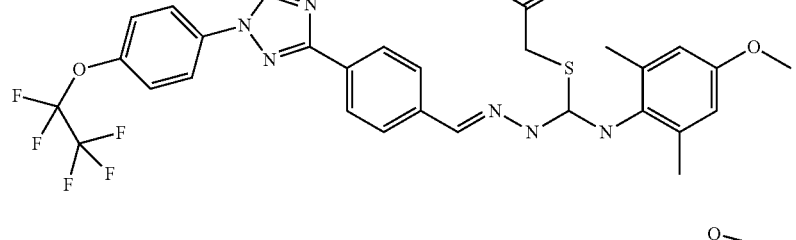 |
| 52C | 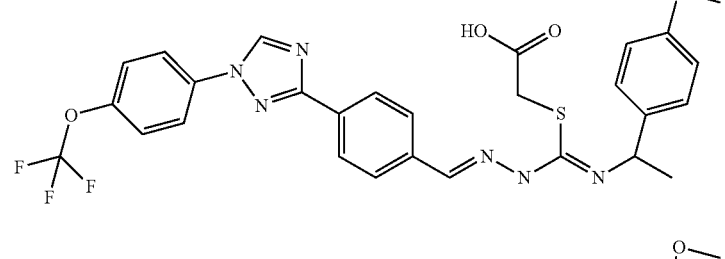 |
| 53C | 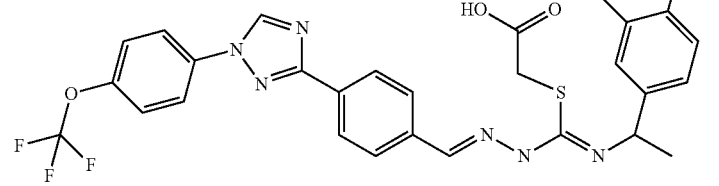 |

TABLE 3-continued

Structures for Compounds

| ID | Structure |
|----|-----------|
| 54C | 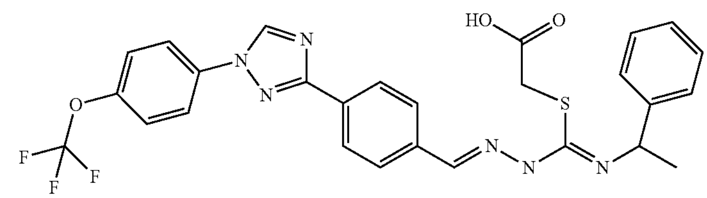 [SMILES: CC(/N=C(/N/N=C/c1ccc(-c2ncn(-c3ccc(OC(F)(F)F)cc3)n2)cc1)SCC(=O)O)c1ccccc1] |
| 55C | 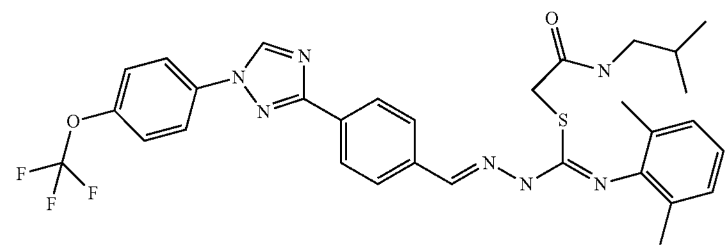 [SMILES: Cc1cccc(C)c1/N=C(/N/N=C/c1ccc(-c2ncn(-c3ccc(OC(F)(F)F)cc3)n2)cc1)SCC(=O)NCC(C)C] |
| 56C | 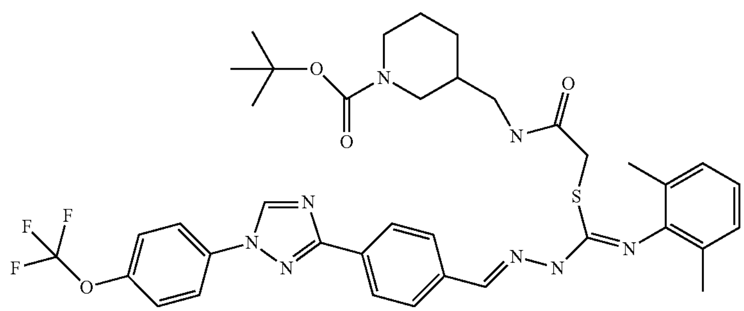 [SMILES: Cc1cccc(C)c1/N=C(/N/N=C/c1ccc(-c2ncn(-c3ccc(OC(F)(F)F)cc3)n2)cc1)SCC(=O)NCC1CCCN(C(=O)OC(C)(C)C)C1] |
| 57C | 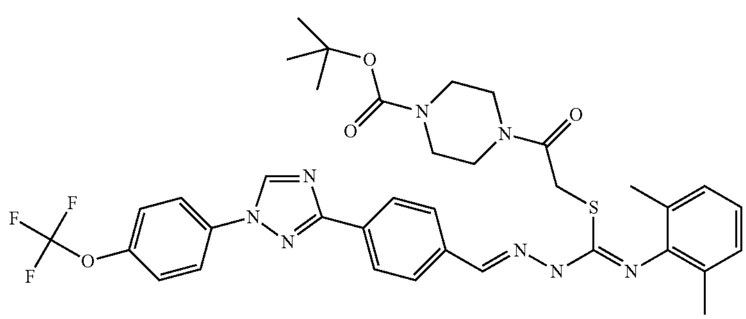 [SMILES: Cc1cccc(C)c1/N=C(/N/N=C/c1ccc(-c2ncn(-c3ccc(OC(F)(F)F)cc3)n2)cc1)SCC(=O)N1CCN(C(=O)OC(C)(C)C)CC1] |
| 58C | 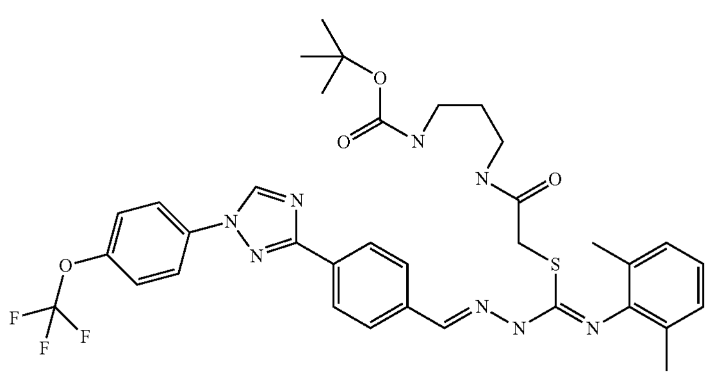 [SMILES: Cc1cccc(C)c1/N=C(/N/N=C/c1ccc(-c2ncn(-c3ccc(OC(F)(F)F)cc3)n2)cc1)SCC(=O)NCCCNC(=O)OC(C)(C)C] |

TABLE 3-continued

Structures for Compounds

| ID | Structure |
|----|-----------|
| 59C | 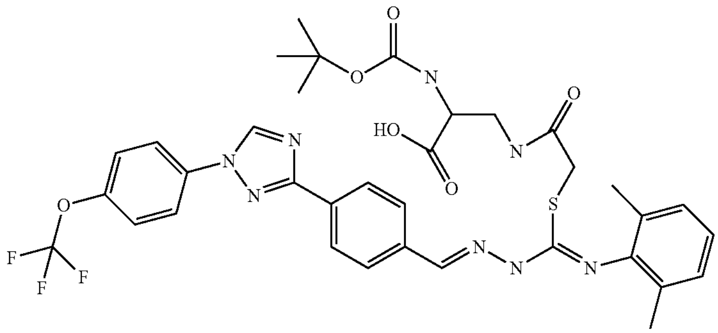 [SMILES: Cc1cccc(C)c1/N=C(/N/N=C/c1ccc(-c2ncn(-c3ccc(OC(F)(F)F)cc3)n2)cc1)SCC(=O)NCC(NC(=O)OC(C)(C)C)C(=O)O] |
| 60C | 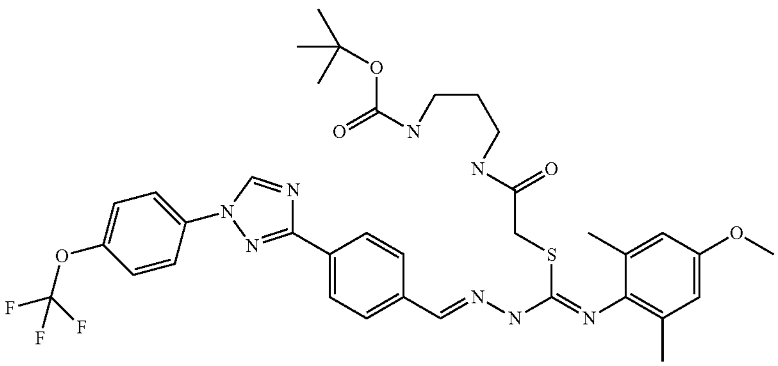 [SMILES: COc1cc(C)c(/N=C(/N/N=C/c2ccc(-c3ncn(-c4ccc(OC(F)(F)F)cc4)n3)cc2)SCC(=O)NCCCNC(=O)OC(C)(C)C)c(C)c1] |
| 61C | 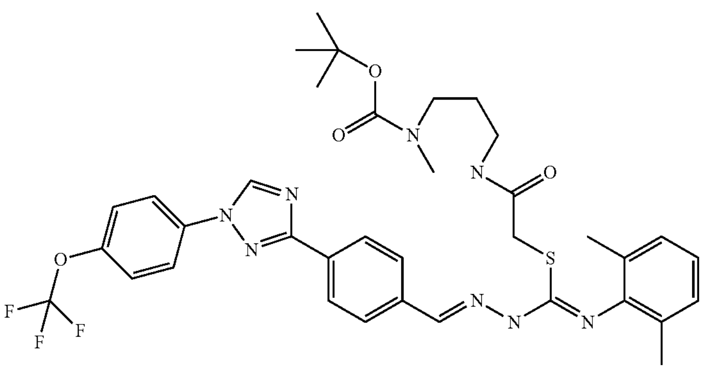 [SMILES: Cc1cccc(C)c1/N=C(/N/N=C/c1ccc(-c2ncn(-c3ccc(OC(F)(F)F)cc3)n2)cc1)SCC(=O)NCCCN(C)C(=O)OC(C)(C)C] |
| 62C | 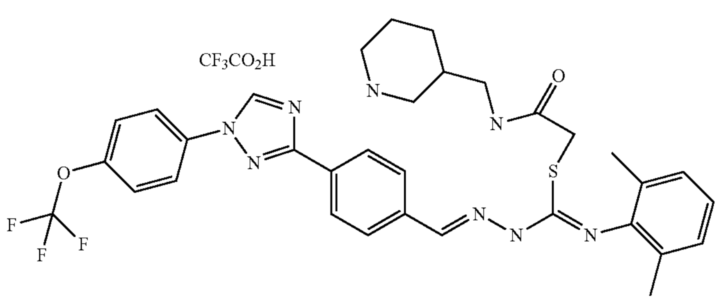 [SMILES: Cc1cccc(C)c1/N=C(/N/N=C/c1ccc(-c2ncn(-c3ccc(OC(F)(F)F)cc3)n2)cc1)SCC(=O)NCC1CCCNC1 ; "CF3CO2H"] |

TABLE 3-continued

Structures for Compounds

| ID | Structure |
|---|---|
| 63C | 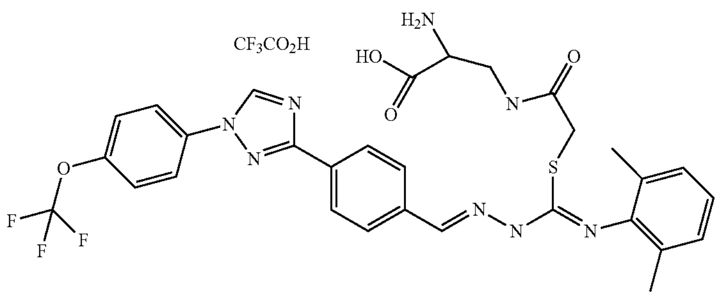 [SMILES: Cc1cccc(C)c1/N=C(/N/N=C/c1ccc(-c2ncn(-c3ccc(OC(F)(F)F)cc3)n2)cc1)SCC(=O)NCC(N)C(=O)O ; "CF3CO2H"] |
| 64C | 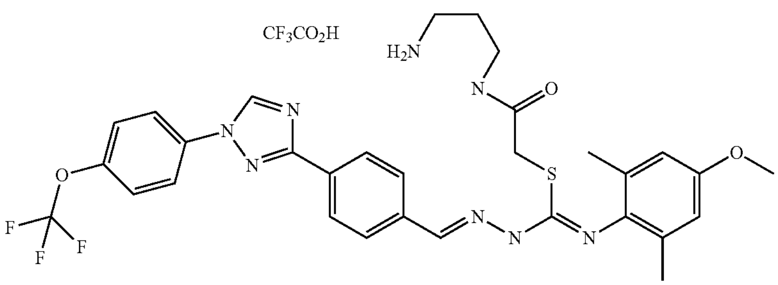 [SMILES: COc1cc(C)c(/N=C(/N/N=C/c2ccc(-c3ncn(-c4ccc(OC(F)(F)F)cc4)n3)cc2)SCC(=O)NCCCN)c(C)c1 ; "CF3CO2H"] |
| 65C | 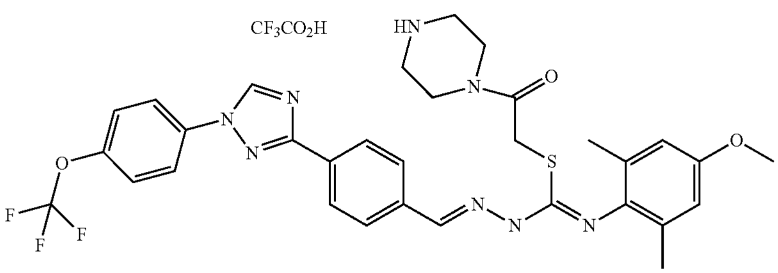 [SMILES: COc1cc(C)c(/N=C(/N/N=C/c2ccc(-c3ncn(-c4ccc(OC(F)(F)F)cc4)n3)cc2)SCC(=O)N2CCNCC2)c(C)c1 ; "CF3CO2H"] |
| 66C | 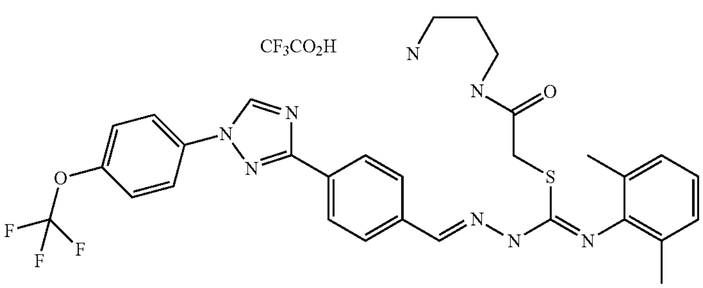 [SMILES: Cc1cccc(C)c1/N=C(/N/N=C/c1ccc(-c2ncn(-c3ccc(OC(F)(F)F)cc3)n2)cc1)SCC(=O)NCCCN ; "CF3CO2H"] |
| 67C | 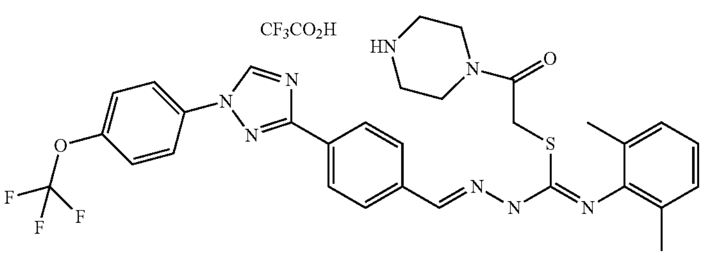 [SMILES: Cc1cccc(C)c1/N=C(/N/N=C/c1ccc(-c2ncn(-c3ccc(OC(F)(F)F)cc3)n2)cc1)SCC(=O)N1CCNCC1 ; "CF3CO2H"] |

TABLE 3-continued

Structures for Compounds

| ID | Structure |
|---|---|
| 68C | (structure with CF$_3$CO$_2$H and Na+ salt) |
| 69C | (structure) |
| 70C | (structure) |
| 71C | (structure) |
| 72C | (structure) |
| 73C | (structure) |

TABLE 3-continued
Structures for Compounds
| ID | Structure |
|---|---|
| 74C | 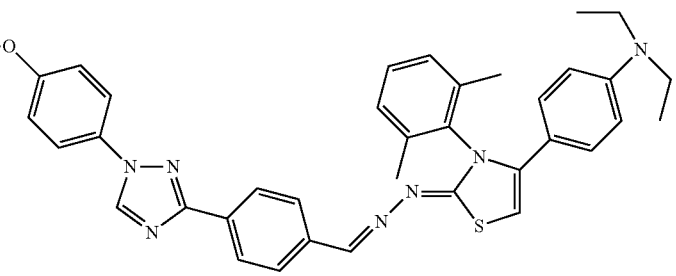 |
| 75C | 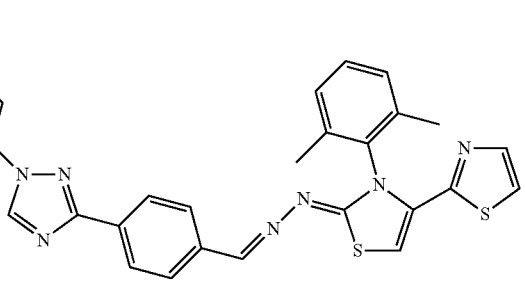 |
| 76C | 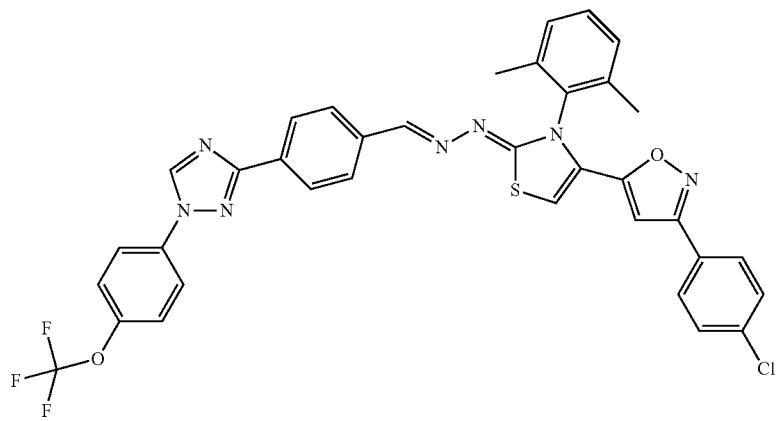 [SMILES: Cc1cccc(C)c1-n1c(-c2cc(-c3ccc(Cl)cc3)no2)cs/c1=N\N=C\c1ccc(-c2ncn(-c3ccc(OC(F)(F)F)cc3)n2)cc1] |
| 77C | 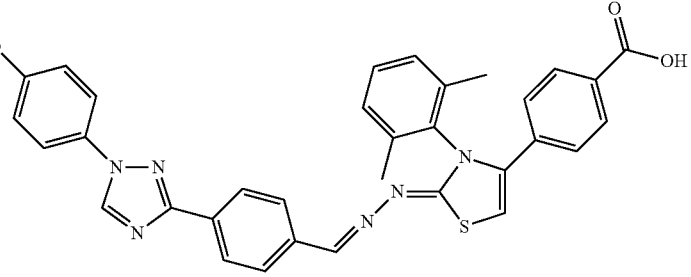 |
| 78C | 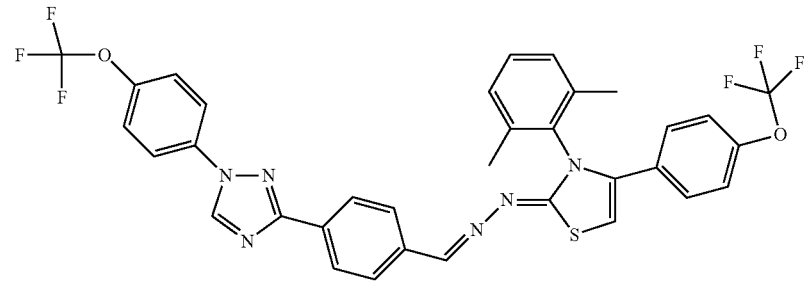 [SMILES: Cc1cccc(C)c1-n1c(-c2ccc(OC(F)(F)F)cc2)cs/c1=N\N=Cc1ccc(-c2ncn(-c3ccc(OC(F)(F)F)cc3)n2)cc1] |

TABLE 3-continued

Structures for Compounds

| ID | Structure |
|---|---|
| 79C | 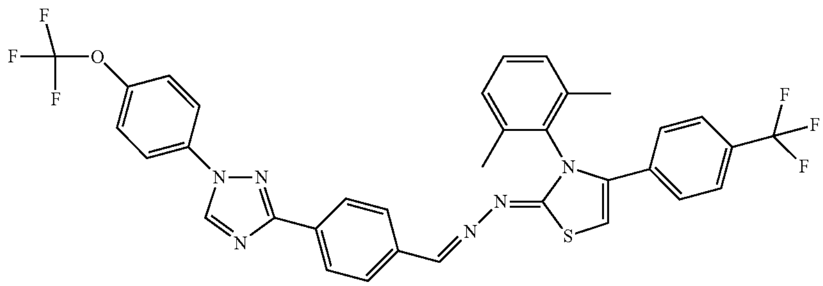 [SMILES: Cc1cccc(C)c1-n1c(-c2ccc(C(F)(F)F)cc2)cs/c1=N\N=Cc1ccc(-c2ncn(-c3ccc(OC(F)(F)F)cc3)n2)cc1] |
| 80C | 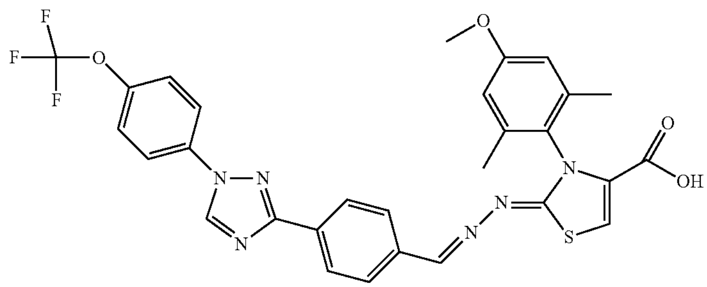 [SMILES: COc1cc(C)c(-n2c(C(=O)O)cs/c2=N\N=Cc2ccc(-c3ncn(-c4ccc(OC(F)(F)F)cc4)n3)cc2)c(C)c1] |
| 81C | 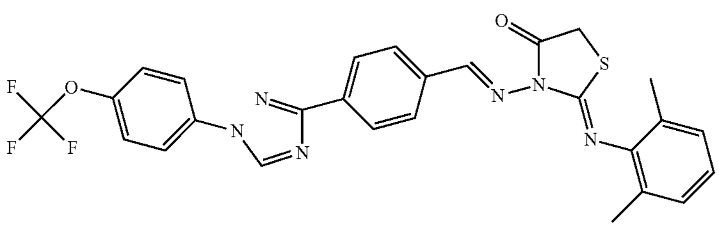 [SMILES: Cc1cccc(C)c1/N=C1\SCC(=O)N1/N=C/c1ccc(C(=N)/N=C\Nc2ccc(OC(F)(F)F)cc2)cc1] |
| 82C | 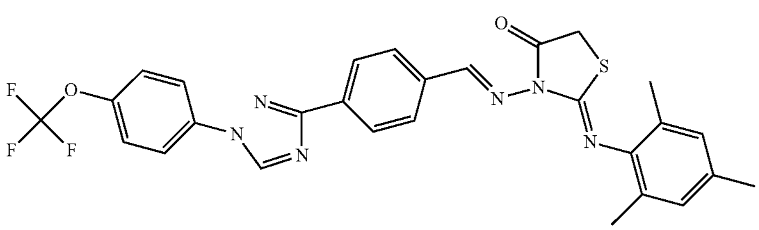 [SMILES: Cc1cc(C)c(/N=C2\SCC(=O)N2/N=C/c2ccc(C(=N)/N=C\Nc3ccc(OC(F)(F)F)cc3)cc2)c(C)c1] |
| 83C | 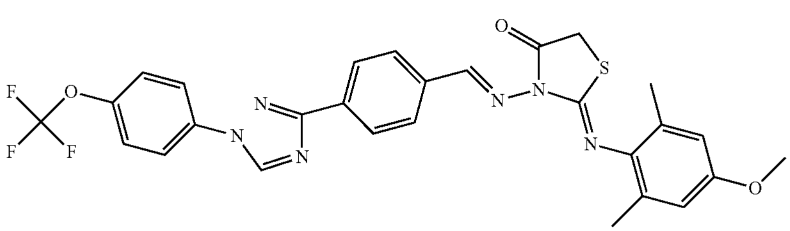 [SMILES: COc1cc(C)c(/N=C2\SCC(=O)N2/N=C/c2ccc(C(=N)/N=C\Nc3ccc(OC(F)(F)F)cc3)cc2)c(C)c1] |
| 84C | 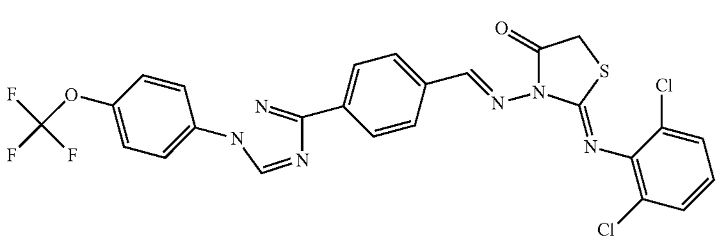 [SMILES: N=C(/N=C\Nc1ccc(OC(F)(F)F)cc1)c1ccc(/C=N/N2C(=O)CS/C2=N\c2c(Cl)cccc2Cl)cc1] |

TABLE 3-continued

Structures for Compounds

| ID | Structure |
|---|---|
| 85C | 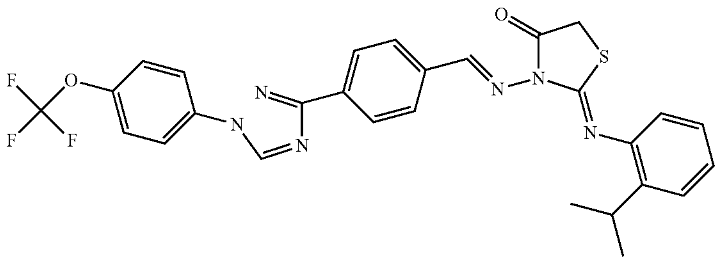 [SMILES: CC(C)c1ccccc1/N=C1\SCC(=O)N1/N=C/c1ccc(C(=N)/N=C\Nc2ccc(OC(F)(F)F)cc2)cc1] |
| 86C | 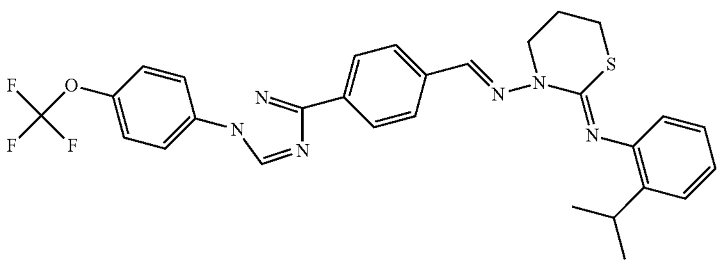 [SMILES: CC(C)c1ccccc1/N=C1\SCCCN1/N=C/c1ccc(C(=N)/N=C\Nc2ccc(OC(F)(F)F)cc2)cc1] |
| 87C | 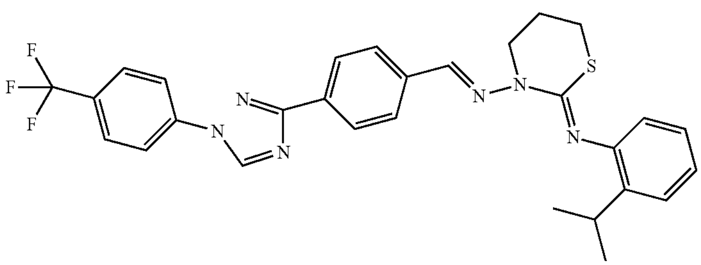 [SMILES: CC(C)c1ccccc1/N=C1\SCCCN1/N=C/c1ccc(C(=N)/N=C\Nc2ccc(C(F)(F)F)cc2)cc1] |
| 88C | 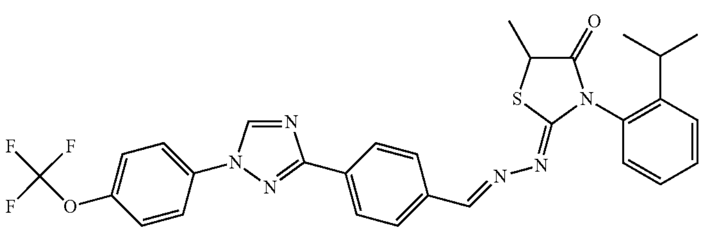 [SMILES: CC1S/C(=N\N=C\c2ccc(-c3ncn(-c4ccc(OC(F)(F)F)cc4)n3)cc2)N(c2ccccc2C(C)C)C1=O] |
| 89C | 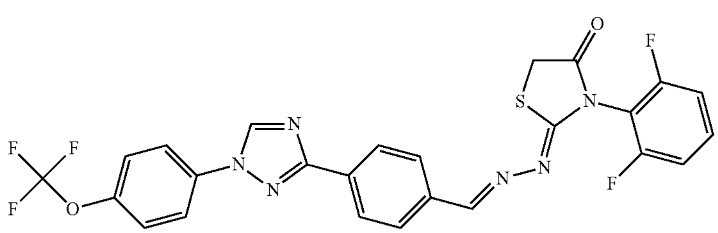 |
| 90C | 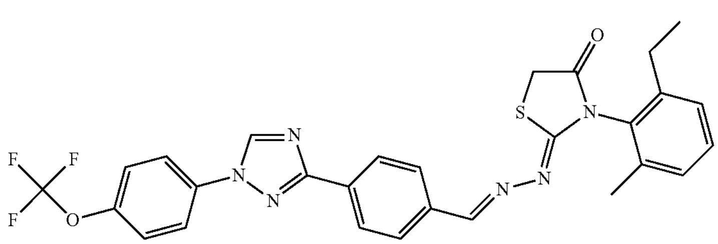 [SMILES: CCc1cccc(C)c1N1C(=O)CS/C1=N\N=C\c1ccc(-c2ncn(-c3ccc(OC(F)(F)F)cc3)n2)cc1] |

TABLE 3-continued

| ID | Structure |
|---|---|
| 91C | (structure) |
| 92C | (structure) |
| 93C | (structure) |
| 94C | (structure) |
| 95C | (structure) |
| 96C | (structure) |

TABLE 3-continued

Structures for Compounds

| ID | Structure |
|---|---|
| 97C | 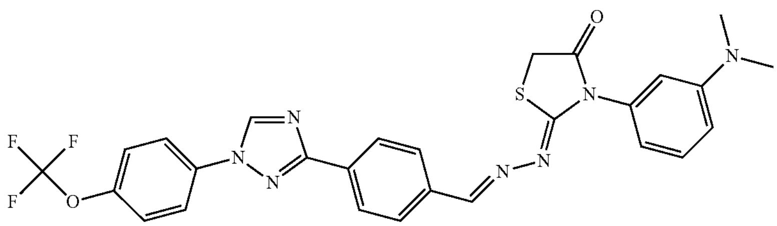 [SMILES: CN(C)c1cccc(N2C(=O)CS/C2=N\N=C\c2ccc(-c3ncn(-c4ccc(OC(F)(F)F)cc4)n3)cc2)c1] |
| 98C | 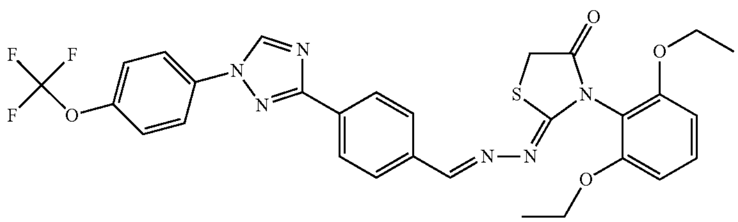 [SMILES: CCOc1cccc(OCC)c1N1C(=O)CS/C1=N\N=C\c1ccc(-c2ncn(-c3ccc(OC(F)(F)F)cc3)n2)cc1] |
| 99C | 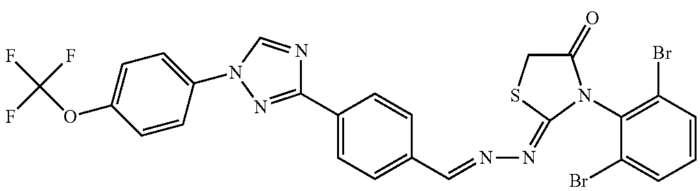 [SMILES: O=C1CS/C(=N\N=C\c2ccc(-c3ncn(-c4ccc(OC(F)(F)F)cc4)n3)cc2)N1c1c(Br)cccc1Br] |
| 100C | 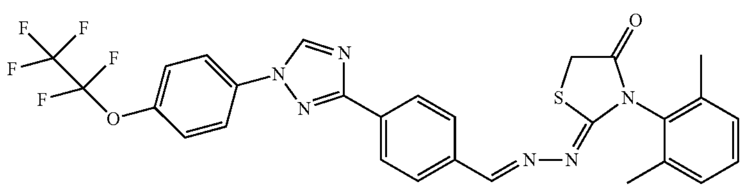 [SMILES: Cc1cccc(C)c1N1C(=O)CS/C1=N\N=C\c1ccc(-c2ncn(-c3ccc(OC(F)(F)C(F)(F)F)cc3)n2)cc1] |
| 101C | 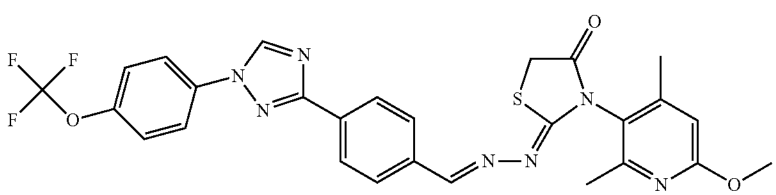 [SMILES: COc1cc(C)c(N2C(=O)CS/C2=N\N=C\c2ccc(-c3ncn(-c4ccc(OC(F)(F)F)cc4)n3)cc2)c(C)n1] |
| 102C | 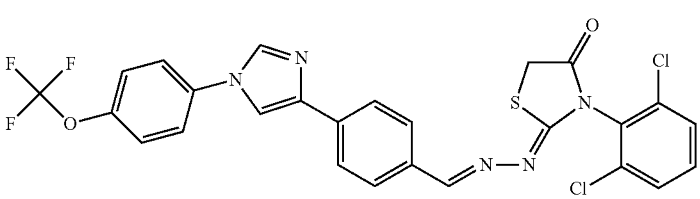 |
| 103C | 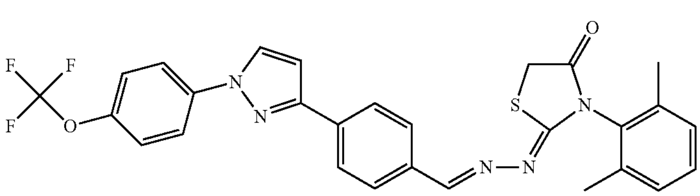 [SMILES: Cc1cccc(C)c1N1C(=O)CS/C1=N\N=C\c1ccc(-c2ccn(-c3ccc(OC(F)(F)F)cc3)n2)cc1] |

TABLE 3-continued
Structures for Compounds
| ID | Structure |
|---|---|
| 104C | 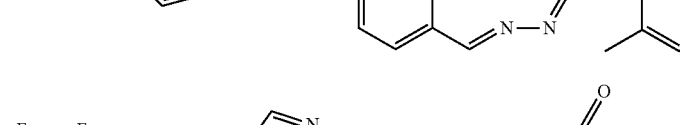 |
| 105C | 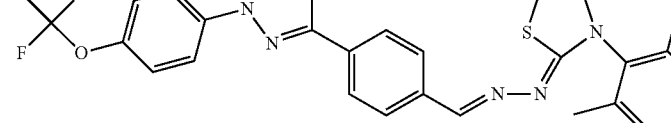 |
| 106C | 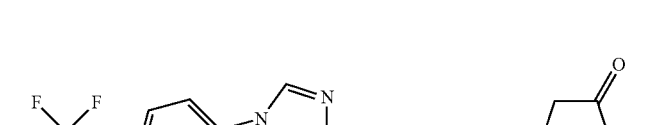 |
| 107C | 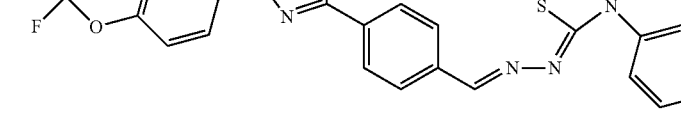 |
| 108C | 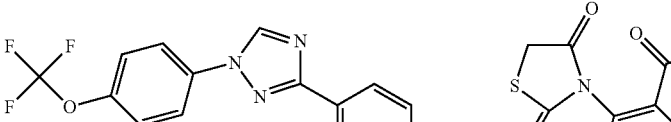 |
| 109C | 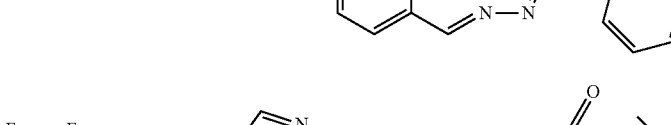 |
| 110C | 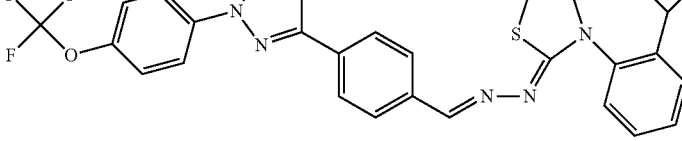 |

TABLE 3-continued
Structures for Compounds
| ID | Structure |
|---|---|
| 111C | 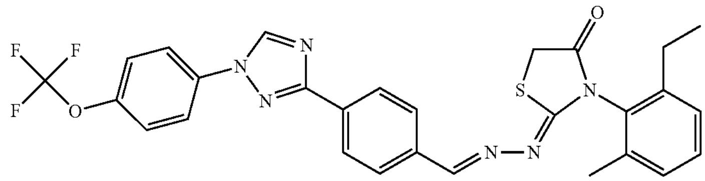 [SMILES: CCc1cccc(C)c1N1C(=O)CS/C1=N\N=C\c1ccc(-c2ncn(-c3ccc(OC(F)(F)F)cc3)n2)cc1] |
| 112C | 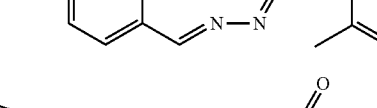 |
| 113C | 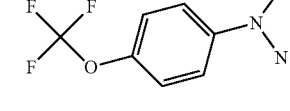 |
| 114C | 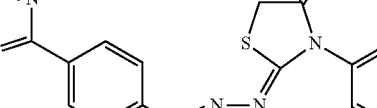 |
| 115C | 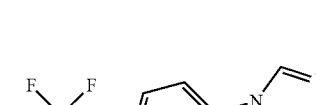 |
| 116C | 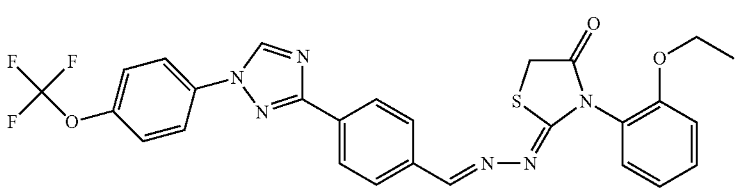 [SMILES: CCOc1ccccc1N1C(=O)CS/C1=N\N=C\c1ccc(-c2ncn(-c3ccc(OC(F)(F)F)cc3)n2)cc1] |
| 117C | 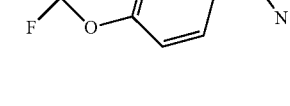 |
| 118C | 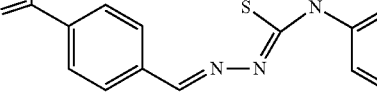 |

TABLE 3-continued
Structures for Compounds
| ID | Structure |
|---|---|
| 119C | 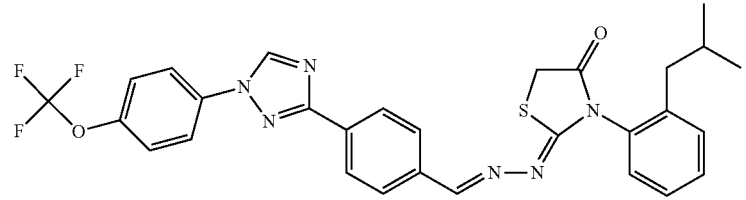 [SMILES: CC(C)Cc1ccccc1N1C(=O)CS/C1=N\N=C\c1ccc(-c2ncn(-c3ccc(OC(F)(F)F)cc3)n2)cc1] |
| 120C | 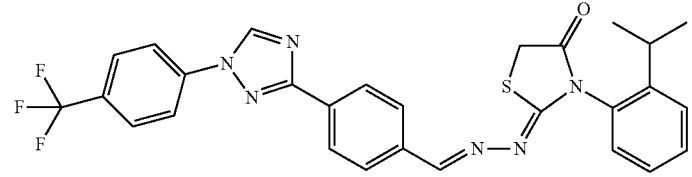 [SMILES: CC(C)c1ccccc1N1C(=O)CS/C1=N\N=C\c1ccc(-c2ncn(-c3ccc(C(F)(F)F)cc3)n2)cc1] |
| 121C | 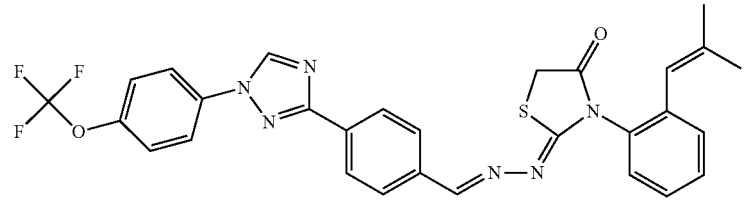 [SMILES: CC(C)=Cc1ccccc1N1C(=O)CS/C1=N\N=C\c1ccc(-c2ncn(-c3ccc(OC(F)(F)F)cc3)n2)cc1] |
| 122C | 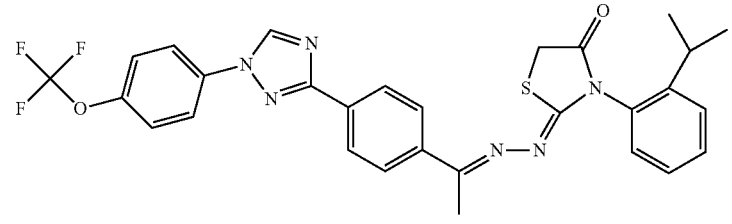 [SMILES: C/C(=N\N=C1/SCC(=O)N1c1ccccc1C(C)C)c1ccc(-c2ncn(-c3ccc(OC(F)(F)F)cc3)n2)cc1] |
| 123C | 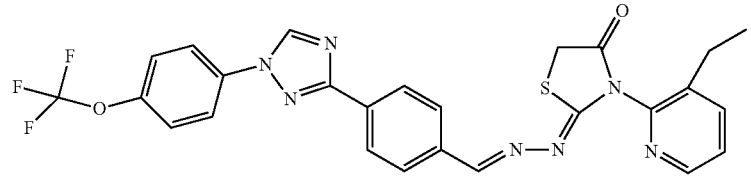 [SMILES: CCc1cccnc1N1C(=O)CS/C1=N\N=C\c1ccc(-c2ncn(-c3ccc(OC(F)(F)F)cc3)n2)cc1] |
| 124C | 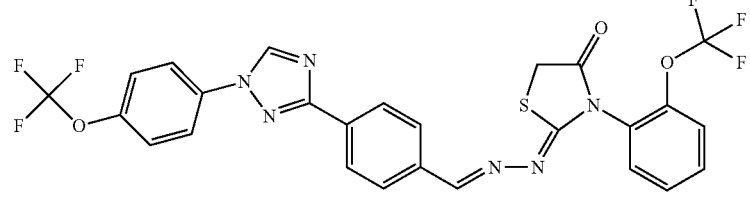 |
| 125C | 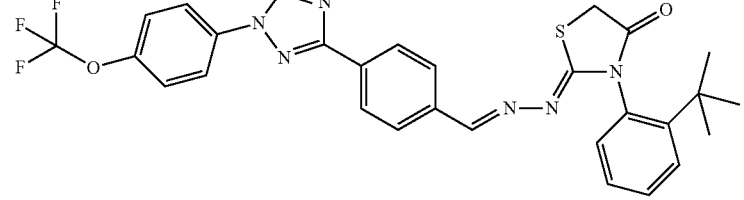 |

TABLE 3-continued

Structures for Compounds

| ID | Structure |
|---|---|
| 126C | 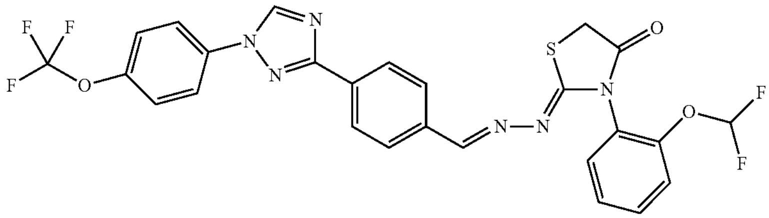 [SMILES: O=C1CS/C(=N\N=C\c2ccc(-c3ncn(-c4ccc(OC(F)(F)F)cc4)n3)cc2)N1c1ccccc1OC(F)F] |
| 127C | 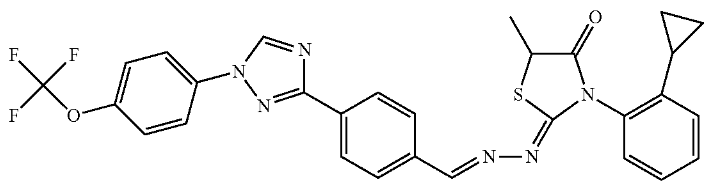 [SMILES: CC1S/C(=N\N=C\c2ccc(-c3ncn(-c4ccc(OC(F)(F)F)cc4)n3)cc2)N(c2ccccc2C2CC2)C1=O] |
| 128C | 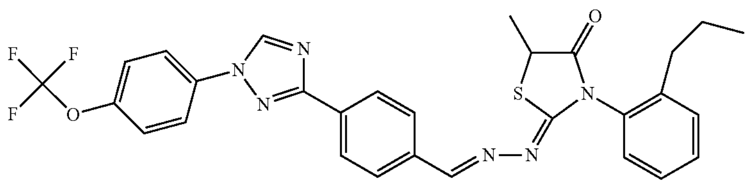 [SMILES: CCCc1ccccc1N1C(=O)C(C)S/C1=N\N=C\c1ccc(-c2ncn(-c3ccc(OC(F)(F)F)cc3)n2)cc1] |
| 129C | 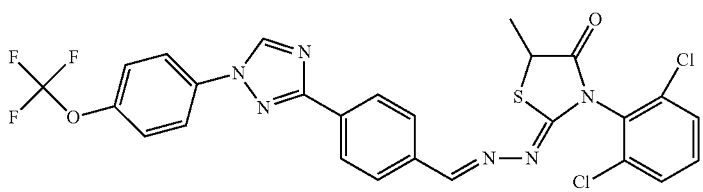 [SMILES: CC1S/C(=N\N=C\c2ccc(-c3ncn(-c4ccc(OC(F)(F)F)cc4)n3)cc2)N(c2c(Cl)cccc2Cl)C1=O] |
| 130C | 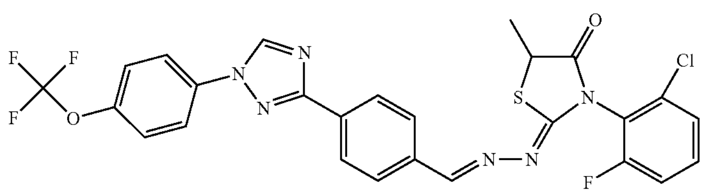 |
| 131C | 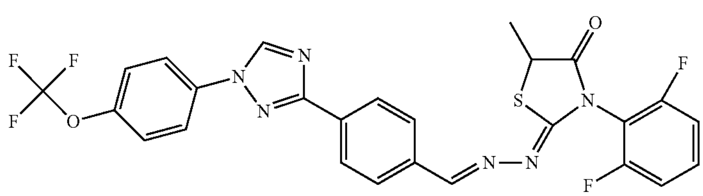 [SMILES: CC1S/C(=N\N=C\c2ccc(-c3ncn(-c4ccc(OC(F)(F)F)cc4)n3)cc2)N(c2c(F)cccc2F)C1=O] |
| 132C | 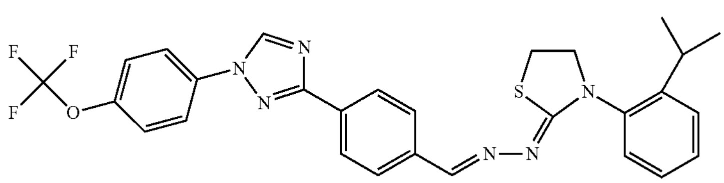 [SMILES: CC(C)c1ccccc1N1CCS/C1=N\N=C\c1ccc(-c2ncn(-c3ccc(OC(F)(F)F)cc3)n2)cc1] |
| 133C | 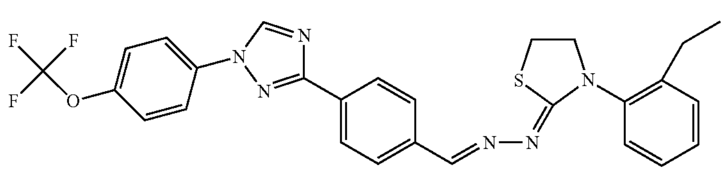 [SMILES: CCc1ccccc1N1CCS/C1=N\N=C\c1ccc(-c2ncn(-c3ccc(OC(F)(F)F)cc3)n2)cc1] |

TABLE 3-continued

| ID | Structure |
|---|---|
| 134C | (structure) |
| 135C | (structure) |
| 136C | (structure) |
| 137C | (structure) |
| 138C | (structure) |
| 139C | (structure) |
| 140C | (structure) |
| 141C | (structure) |

TABLE 3-continued

| ID | Structure |
|---|---|
| 142C | (structure) |
| 143C | (structure) |
| 144C | (structure) |
| 145C | (structure) |
| 146C | (structure) |
| 147C | (structure) |
| 148C | (structure) |
| 149C | (structure) |

TABLE 3-continued
Structures for Compounds
| ID | Structure |
|---|---|
| 150C | 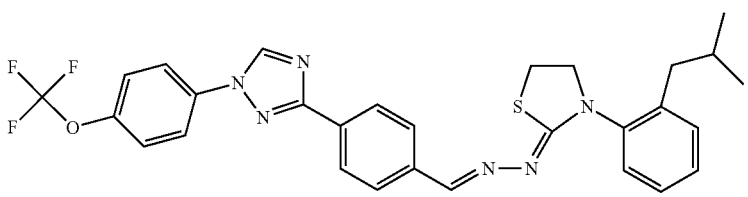 [SMILES: CC(C)Cc1ccccc1N1CCS/C1=N\N=C\c1ccc(-c2ncn(-c3ccc(OC(F)(F)F)cc3)n2)cc1] |
| 151C | 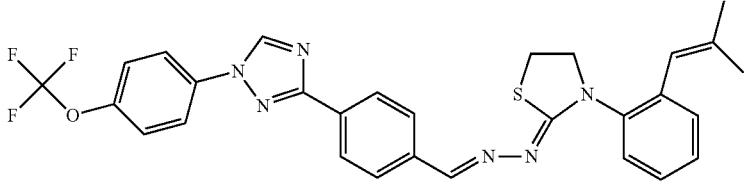 [SMILES: CC(C)=Cc1ccccc1N1CCS/C1=N\N=C\c1ccc(-c2ncn(-c3ccc(OC(F)(F)F)cc3)n2)cc1] |
| 152C | 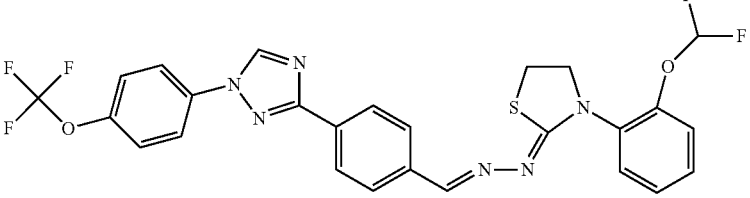 |
| 153C | 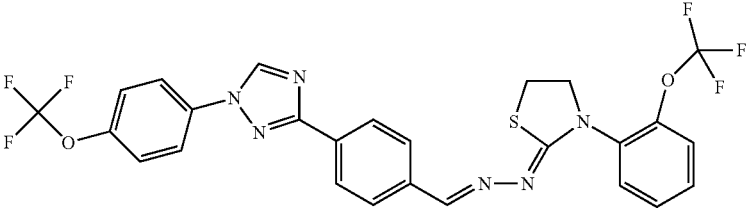 [SMILES: FC(F)(F)Oc1ccc(-n2cnc(-c3ccc(/C=N/N=C4\SCCN4c4ccccc4OC(F)(F)F)cc3)n2)cc1] |
| 154C | 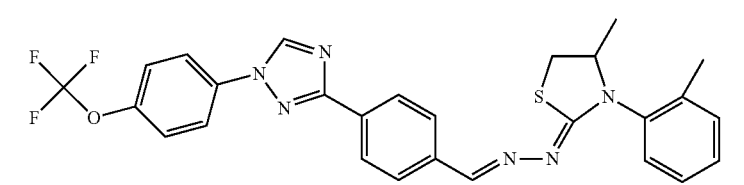 [SMILES: Cc1ccccc1N1/C(=N/N=C/c2ccc(-c3ncn(-c4ccc(OC(F)(F)F)cc4)n3)cc2)SCC1C] |
| 155C | 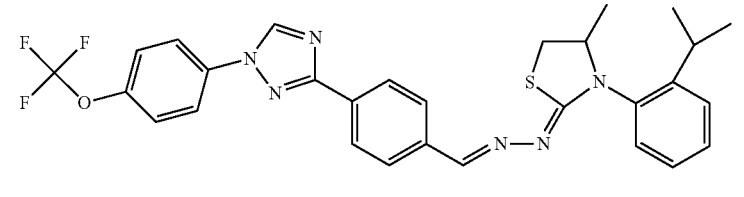 [SMILES: CC(C)c1ccccc1N1/C(=N/N=C/c2ccc(-c3ncn(-c4ccc(OC(F)(F)F)cc4)n3)cc2)SCC1C] |
| 156C | 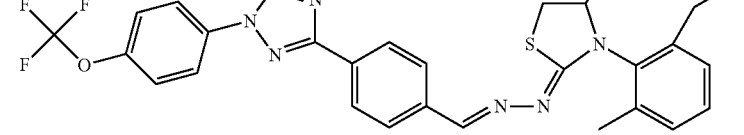 |

TABLE 3-continued

Structures for Compounds

| ID | Structure |
|---|---|
| 157C | 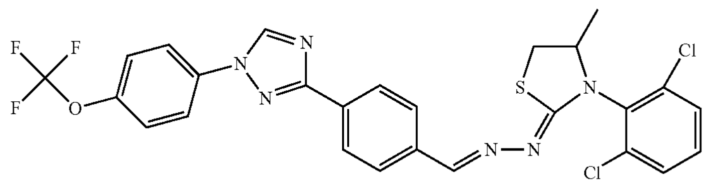 [SMILES: CC1CS/C(=N\N=C\c2ccc(-c3ncn(-c4ccc(OC(F)(F)F)cc4)n3)cc2)N1c1c(Cl)cccc1Cl] |
| 158C | 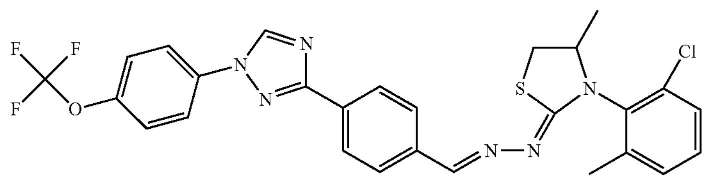 [SMILES: Cc1cccc(Cl)c1N1/C(=N/N=C/c2ccc(-c3ncn(-c4ccc(OC(F)(F)F)cc4)n3)cc2)SCC1C] |
| 159C | 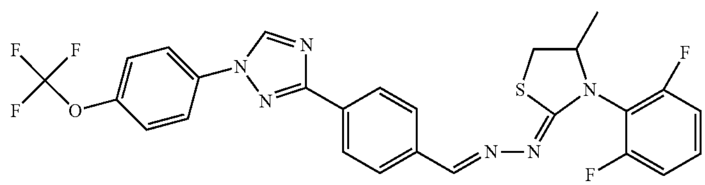 [SMILES: CC1CS/C(=N\N=C\c2ccc(-c3ncn(-c4ccc(OC(F)(F)F)cc4)n3)cc2)N1c1c(F)cccc1F] |
| 160C | 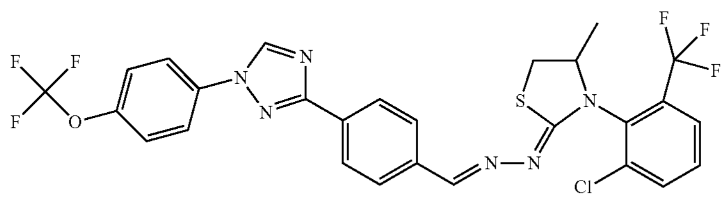 [SMILES: CC1CS/C(=N\N=C\c2ccc(-c3ncn(-c4ccc(OC(F)(F)F)cc4)n3)cc2)N1c1c(Cl)cccc1C(F)(F)F] |
| 161C | 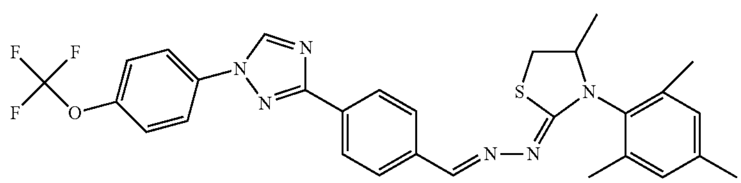 [SMILES: Cc1cc(C)c(N2/C(=N/N=C/c3ccc(-c4ncn(-c5ccc(OC(F)(F)F)cc5)n4)cc3)SCC2C)c(C)c1] |
| 162C | 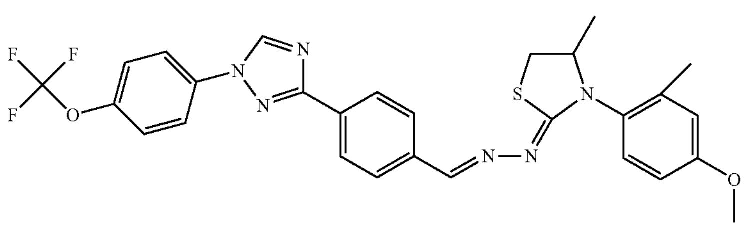 [SMILES: COc1ccc(N2/C(=N/N=C/c3ccc(-c4ncn(-c5ccc(OC(F)(F)F)cc5)n4)cc3)SCC2C)c(C)c1] |
| 163C | 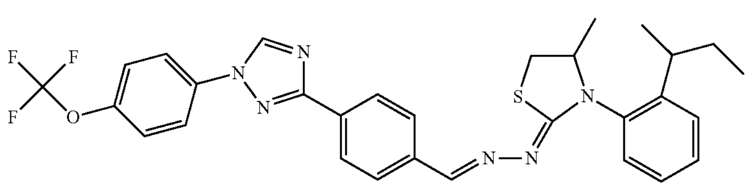 [SMILES: CCC(C)c1ccccc1N1/C(=N/N=C/c2ccc(-c3ncn(-c4ccc(OC(F)(F)F)cc4)n3)cc2)SCC1C] |
| 164C | 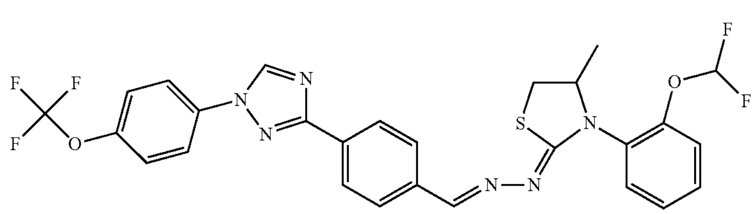 [SMILES: CC1CS/C(=N\N=C\c2ccc(-c3ncn(-c4ccc(OC(F)(F)F)cc4)n3)cc2)N1c1ccccc1OC(F)F] |

TABLE 3-continued

Structures for Compounds

| ID | Structure |
|---|---|
| 165C | 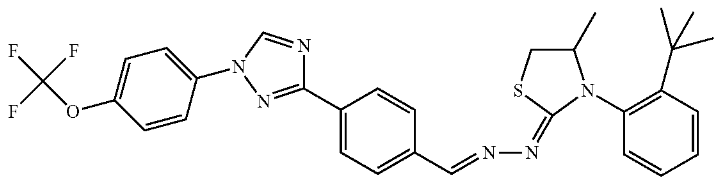 [SMILES: CC1CS/C(=N\N=C\c2ccc(-c3ncn(-c4ccc(OC(F)(F)F)cc4)n3)cc2)N1c1ccccc1C(C)(C)C] |
| 166C | 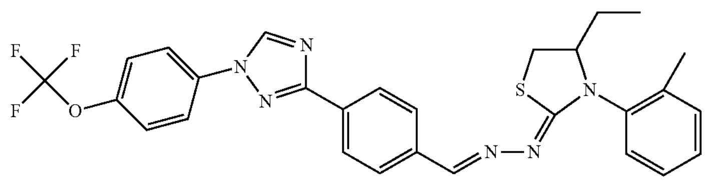 [SMILES: CCC1CS/C(=N\N=C\c2ccc(-c3ncn(-c4ccc(OC(F)(F)F)cc4)n3)cc2)N1c1ccccc1C] |
| 167C | 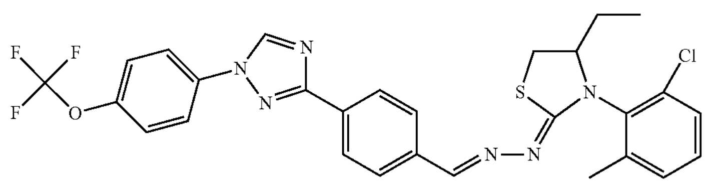 [SMILES: CCC1CS/C(=N\N=C\c2ccc(-c3ncn(-c4ccc(OC(F)(F)F)cc4)n3)cc2)N1c1c(C)cccc1Cl] |
| 168C | 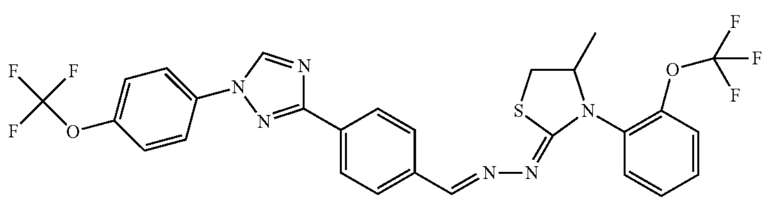 [SMILES: CC1CS/C(=N\N=C\c2ccc(-c3ncn(-c4ccc(OC(F)(F)F)cc4)n3)cc2)N1c1ccccc1OC(F)(F)F] |
| 169C | 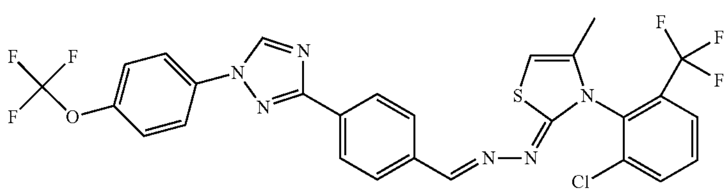 [SMILES: Cc1cs/c(=N\N=C\c2ccc(-c3ncn(-c4ccc(OC(F)(F)F)cc4)n3)cc2)n1-c1c(Cl)cccc1C(F)(F)F] |
| 170C | 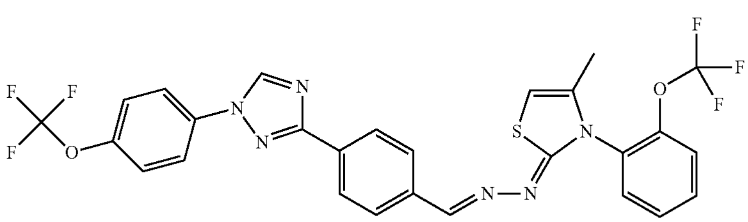 [SMILES: Cc1cs/c(=N\N=C\c2ccc(-c3ncn(-c4ccc(OC(F)(F)F)cc4)n3)cc2)n1-c1ccccc1OC(F)(F)F] |
| 171C | 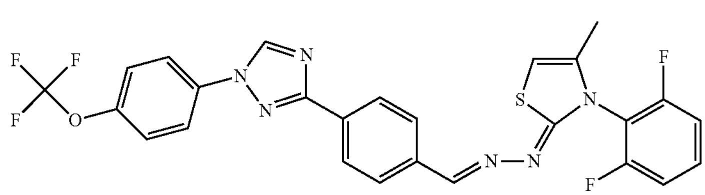 [SMILES: Cc1cs/c(=N\N=C\c2ccc(-c3ncn(-c4ccc(OC(F)(F)F)cc4)n3)cc2)n1-c1c(F)cccc1F] |

TABLE 3-continued

Structures for Compounds

| ID | Structure |
|---|---|
| 172C | 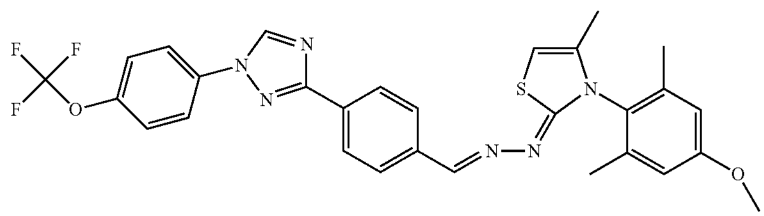 [SMILES: COc1cc(C)c(-n2c(C)cs/c2=N\N=C\c2ccc(-c3ncn(-c4ccc(OC(F)(F)F)cc4)n3)cc2)c(C)c1] |
| 173C | 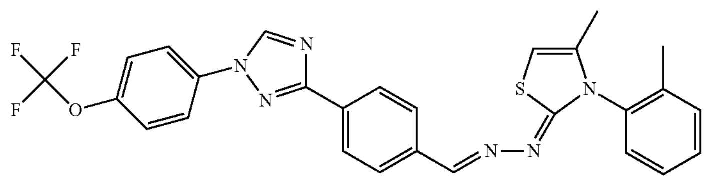 [SMILES: Cc1ccccc1-n1c(C)cs/c1=N\N=C\c1ccc(-c2ncn(-c3ccc(OC(F)(F)F)cc3)n2)cc1] |
| 174C | 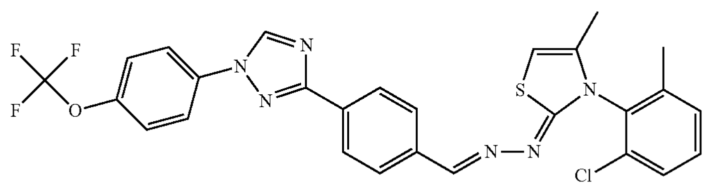 [SMILES: Cc1cccc(Cl)c1-n1c(C)cs/c1=N\N=C\c1ccc(-c2ncn(-c3ccc(OC(F)(F)F)cc3)n2)cc1] |
| 175C | 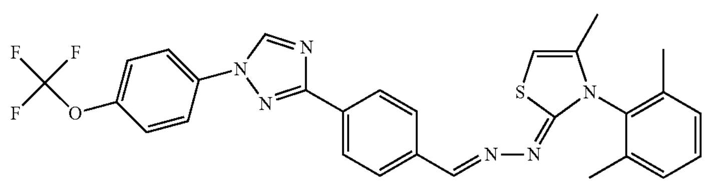 [SMILES: Cc1cccc(C)c1-n1c(C)cs/c1=N\N=C\c1ccc(-c2ncn(-c3ccc(OC(F)(F)F)cc3)n2)cc1] |
| 176C | 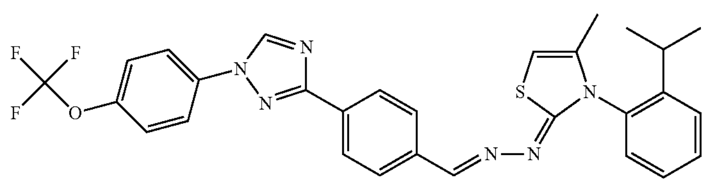 [SMILES: Cc1cs/c(=N\N=C\c2ccc(-c3ncn(-c4ccc(OC(F)(F)F)cc4)n3)cc2)n1-c1ccccc1C(C)C] |
| 177C | 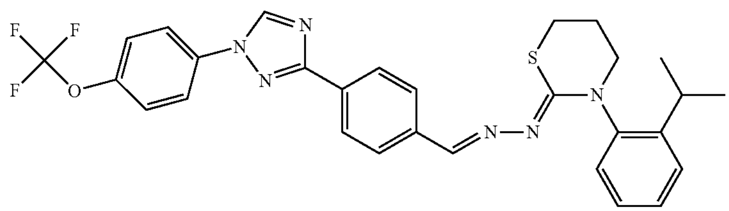 [SMILES: CC(C)c1ccccc1N1CCCS/C1=N\N=C\c1ccc(-c2ncn(-c3ccc(OC(F)(F)F)cc3)n2)cc1] |
| 178C | 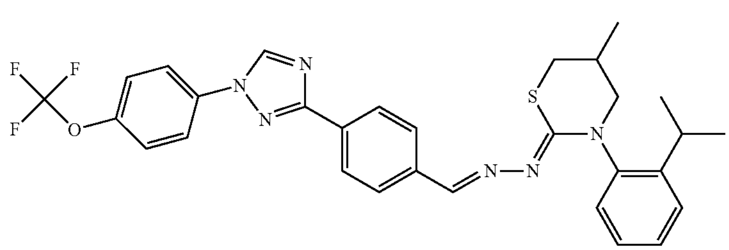 [SMILES: CC1CS/C(=N\N=C\c2ccc(-c3ncn(-c4ccc(OC(F)(F)F)cc4)n3)cc2)N(c2ccccc2C(C)C)C1] |

TABLE 3-continued
Structures for Compounds
| ID | Structure |
|---|---|
| 179C | 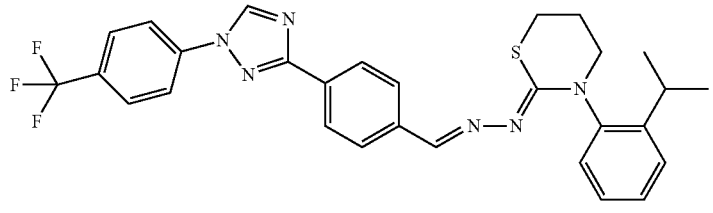 [SMILES: CC(C)c1ccccc1N1CCCS/C1=N\N=C\c1ccc(-c2ncn(-c3ccc(C(F)(F)F)cc3)n2)cc1] |
| 180C | 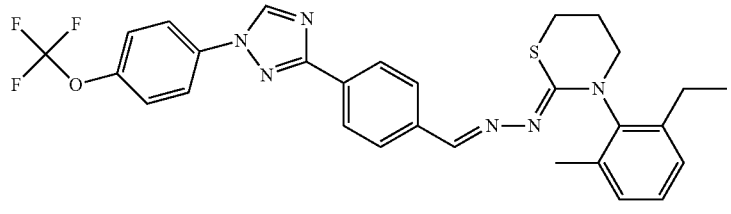 [SMILES: CCc1cccc(C)c1N1CCCS/C1=N\N=C\c1ccc(-c2ncn(-c3ccc(OC(F)(F)F)cc3)n2)cc1] |
| 181C | 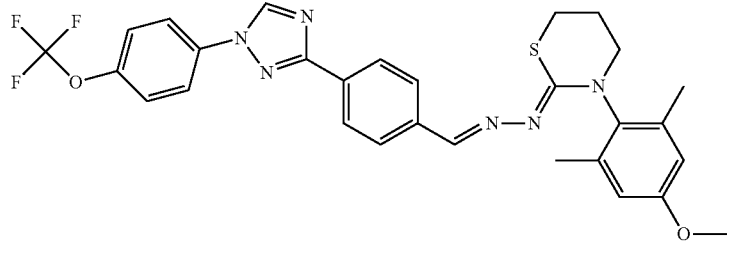 [SMILES: COc1cc(C)c(N2CCCS/C2=N\N=C\c2ccc(-c3ncn(-c4ccc(OC(F)(F)F)cc4)n3)cc2)c(C)c1] |
| 182C | 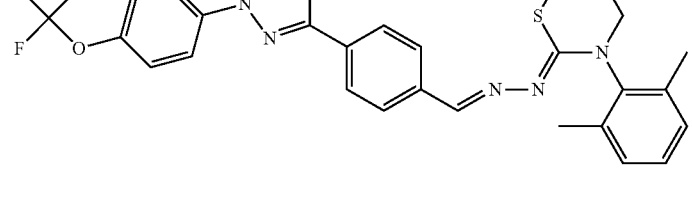 |
| 183C | 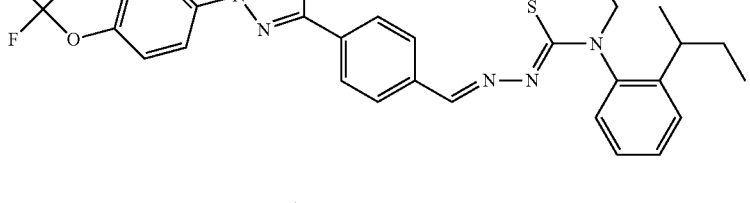 |
| 184C | 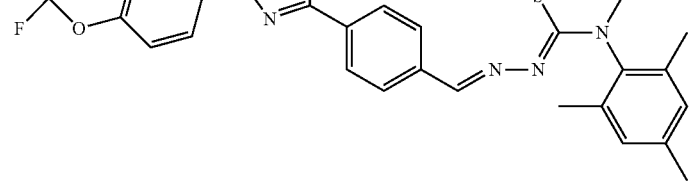 |

TABLE 3-continued

Structures for Compounds

| ID | Structure |
|---|---|
| 185C | 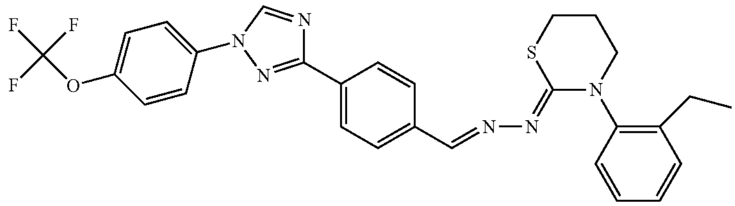 [SMILES: CCc1ccccc1N1CCCS/C1=N\N=C\c1ccc(-c2ncn(-c3ccc(OC(F)(F)F)cc3)n2)cc1] |
| 186C | 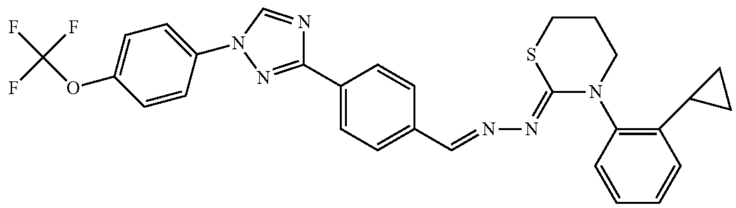 [SMILES: FC(F)(F)Oc1ccc(-n2cnc(-c3ccc(/C=N/N=C4\SCCCN4c4ccccc4C4CC4)cc3)n2)cc1] |
| 187C | 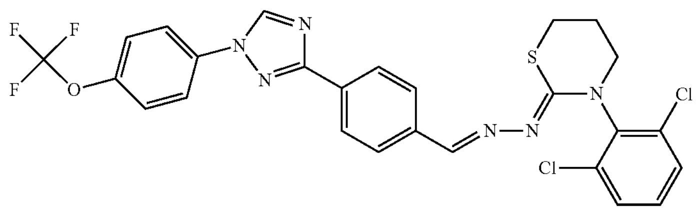 |
| 188C | 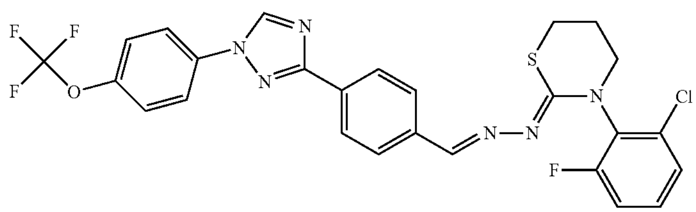 [SMILES: FC(F)(F)Oc1ccc(-n2cnc(-c3ccc(/C=N/N=C4\SCCCN4c4c(Cl)cccc4Cl)cc3)n2)cc1] |
| 189C | 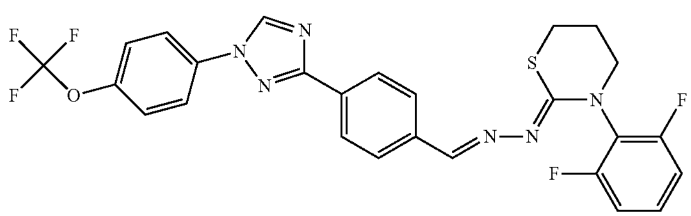 [SMILES: Fc1cccc(F)c1N1CCCS/C1=N\N=C\c1ccc(-c2ncn(-c3ccc(OC(F)(F)F)cc3)n2)cc1] |
| 190C | 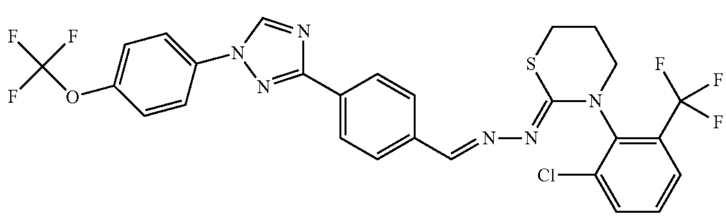 [SMILES: FC(F)(F)Oc1ccc(-n2cnc(-c3ccc(/C=N/N=C4\SCCCN4c4c(Cl)cccc4C(F)(F)F)cc3)n2)cc1] |
| 191C | 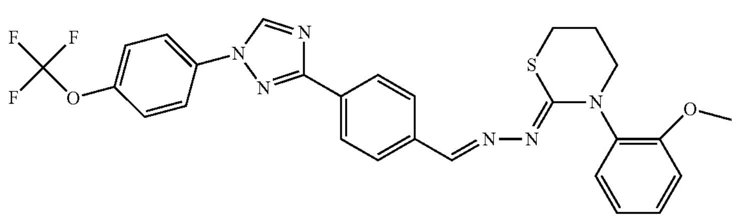 [SMILES: COc1ccccc1N1CCCS/C1=N\N=C\c1ccc(-c2ncn(-c3ccc(OC(F)(F)F)cc3)n2)cc1] |

TABLE 3-continued
Structures for Compounds
| ID | Structure |
|---|---|
| 192C | 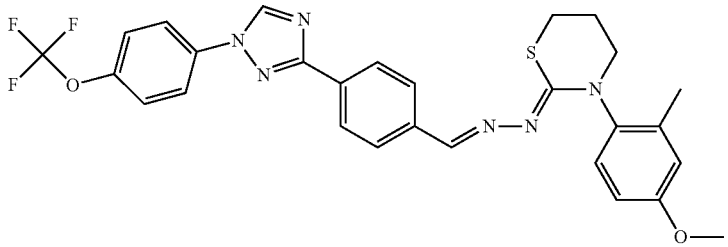 |
| 193C | 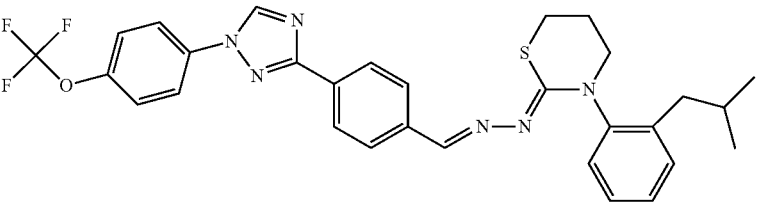 [SMILES: CC(C)Cc1ccccc1N1CCCS/C1=N\N=C\c1ccc(-c2ncn(-c3ccc(OC(F)(F)F)cc3)n2)cc1] |
| 194C | 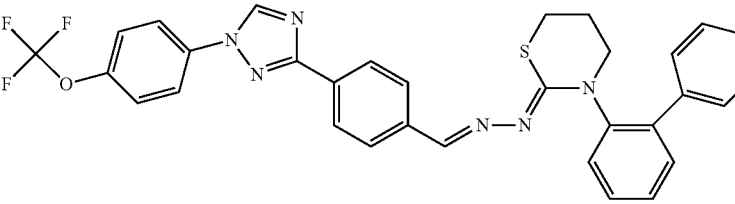 |
| 195C | 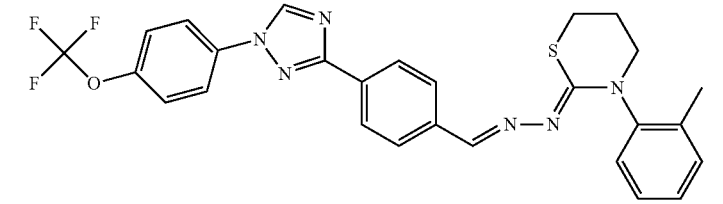 [SMILES: Cc1ccccc1N1CCCS/C1=N\N=C\c1ccc(-c2ncn(-c3ccc(OC(F)(F)F)cc3)n2)cc1] |
| 196C | 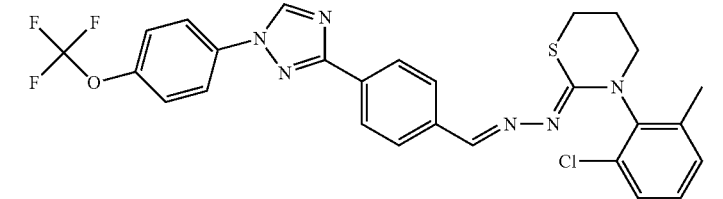 [SMILES: Cc1cccc(Cl)c1N1CCCS/C1=N\N=C\c1ccc(-c2ncn(-c3ccc(OC(F)(F)F)cc3)n2)cc1] |
| 197C | 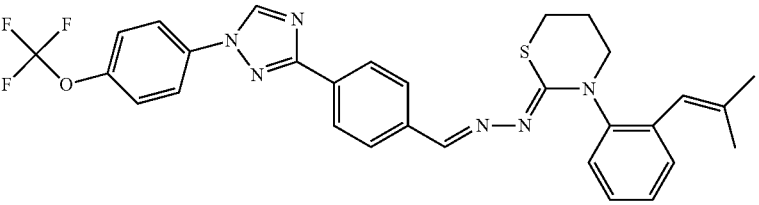 [SMILES: CC(C)=Cc1ccccc1N1CCCS/C1=N\N=C\c1ccc(-c2ncn(-c3ccc(OC(F)(F)F)cc3)n2)cc1] |
| 198C | 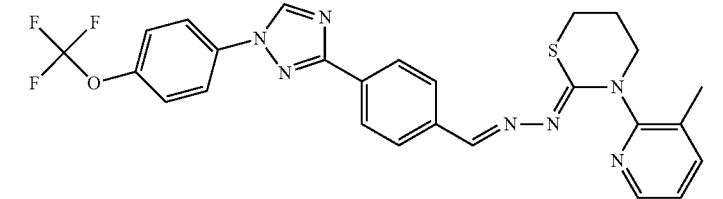 [SMILES: Cc1cccnc1N1CCCS/C1=N\N=C\c1ccc(-c2ncn(-c3ccc(OC(F)(F)F)cc3)n2)cc1] |

TABLE 3-continued
Structures for Compounds
| ID | Structure |
|---|---|
| 199C | 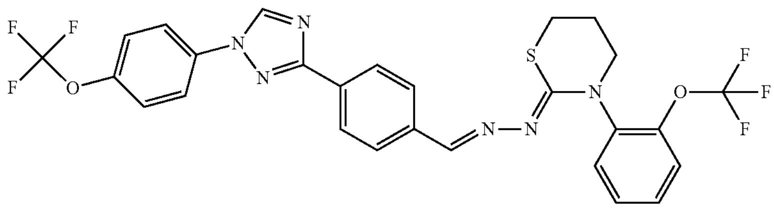 [SMILES: FC(F)(F)Oc1ccc(-n2cnc(-c3ccc(/C=N/N=C4\SCCCN4c4ccccc4OC(F)(F)F)cc3)n2)cc1] |
| 200C | 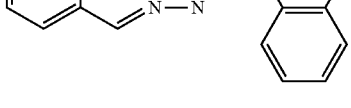 |
| 201C | 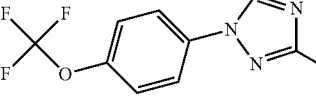 |
| 202C | 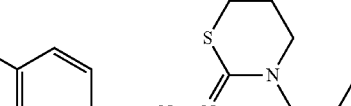 |
| 203C | 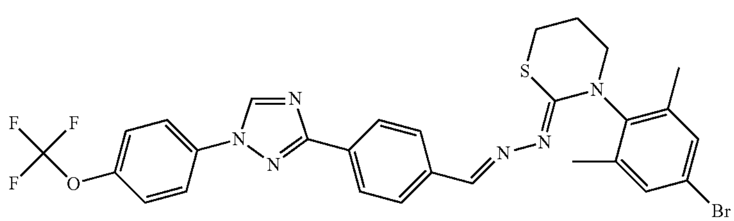 [SMILES: Cc1cc(Br)cc(C)c1N1CCCS/C1=N\N=C\c1ccc(-c2ncn(-c3ccc(OC(F)(F)F)cc3)n2)cc1] |
| 204C | 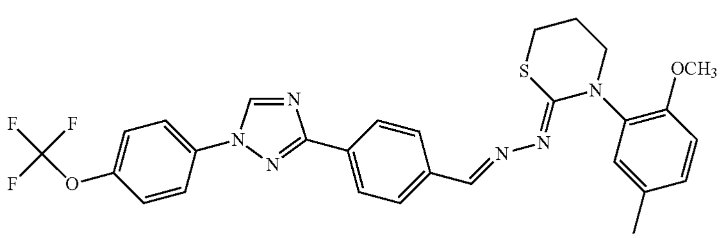 [SMILES: COc1ccc(C)cc1N1CCCS/C1=N\N=C\c1ccc(-c2ncn(-c3ccc(OC(F)(F)F)cc3)n2)cc1] |
| 205C | 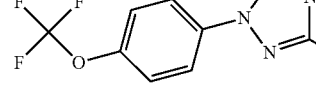 |

TABLE 3-continued
Structures for Compounds
| ID | Structure |
|---|---|
| 206C | 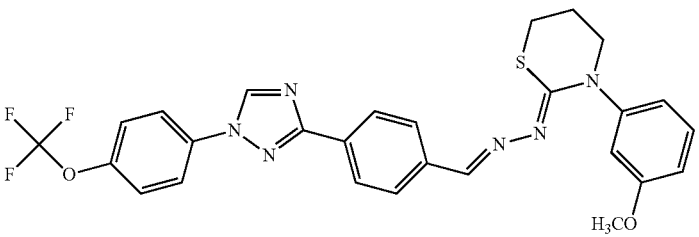 [SMILES: COc1cccc(N2CCCS/C2=N\N=C\c2ccc(-c3ncn(-c4ccc(OC(F)(F)F)cc4)n3)cc2)c1] |
| 207C | 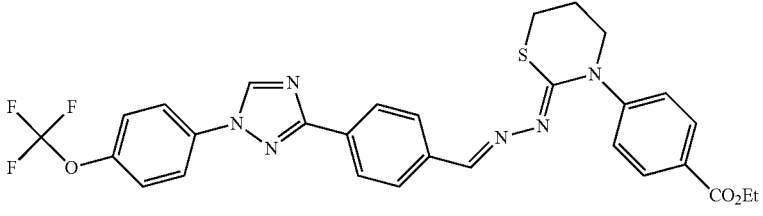 [SMILES: CCOC(=O)c1ccc(N2CCCS/C2=N\N=C\c2ccc(-c3ncn(-c4ccc(OC(F)(F)F)cc4)n3)cc2)cc1] |
| 208C | 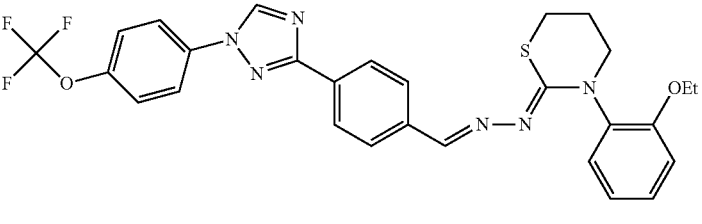 [SMILES: CCOc1ccccc1N1CCCS/C1=N\N=C\c1ccc(-c2ncn(-c3ccc(OC(F)(F)F)cc3)n2)cc1] |
| 209C | 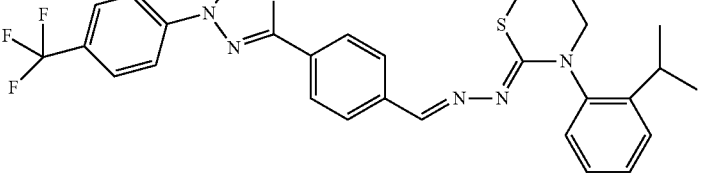 |
| 210C | 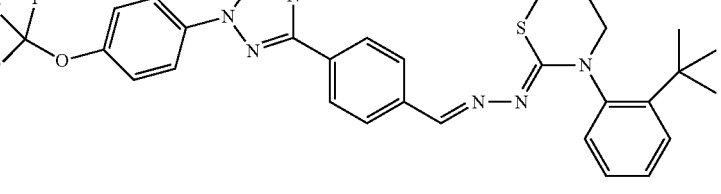 |
| 211C | 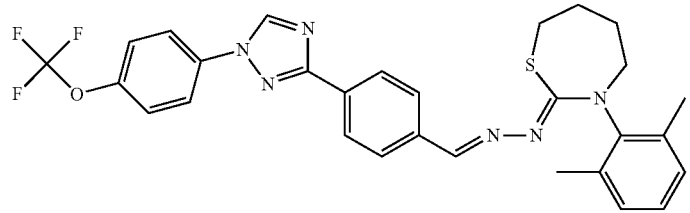 [SMILES: Cc1cccc(C)c1N1CCCCS/C1=N\N=C\c1ccc(-c2ncn(-c3ccc(OC(F)(F)F)cc3)n2)cc1] |
| 212C | 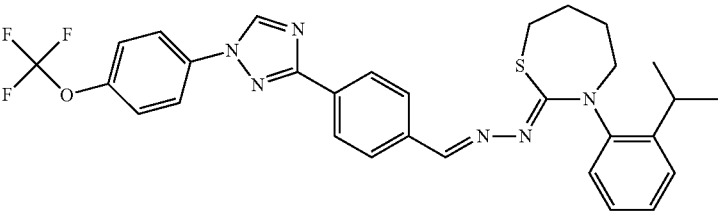 [SMILES: CC(C)c1ccccc1N1CCCCS/C1=N\N=C\c1ccc(-c2ncn(-c3ccc(OC(F)(F)F)cc3)n2)cc1] |

TABLE 3-continued

Structures for Compounds

| ID | Structure |
|---|---|
| 213C | 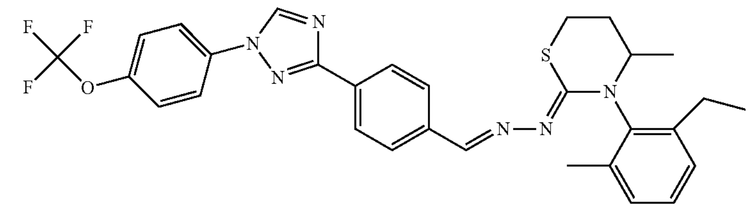 [SMILES: CCc1cccc(C)c1N1/C(=N/N=C/c2ccc(-c3ncn(-c4ccc(OC(F)(F)F)cc4)n3)cc2)SCCC1C] |
| 214C | 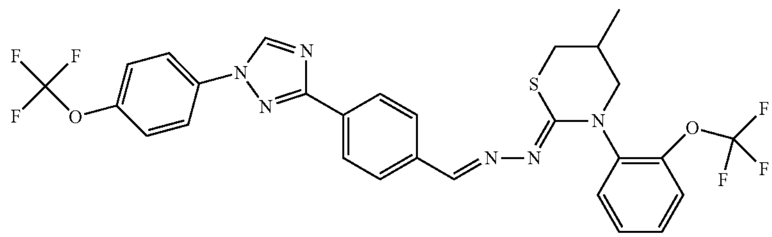 [SMILES: CC1CS/C(=N\N=C\c2ccc(-c3ncn(-c4ccc(OC(F)(F)F)cc4)n3)cc2)N(c2ccccc2OC(F)(F)F)C1] |
| 215C | 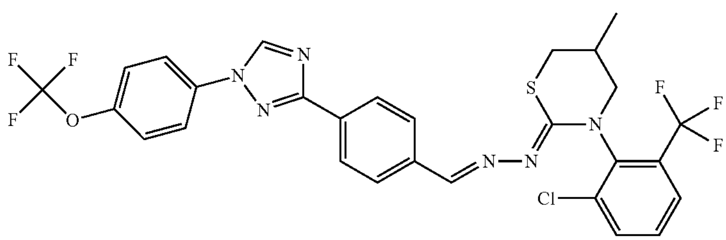 [SMILES: CC1CS/C(=N\N=C\c2ccc(-c3ncn(-c4ccc(OC(F)(F)F)cc4)n3)cc2)N(c2c(Cl)cccc2C(F)(F)F)C1] |
| 216C | 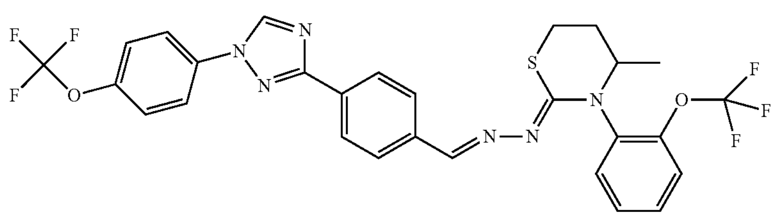 [SMILES: CC1CCS/C(=N\N=C\c2ccc(-c3ncn(-c4ccc(OC(F)(F)F)cc4)n3)cc2)N1c1ccccc1OC(F)(F)F] |
| 217C | 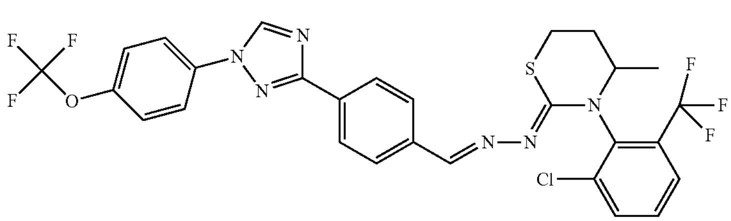 [SMILES: CC1CCS/C(=N\N=C\c2ccc(-c3ncn(-c4ccc(OC(F)(F)F)cc4)n3)cc2)N1c1c(Cl)cccc1C(F)(F)F] |
| 218C | 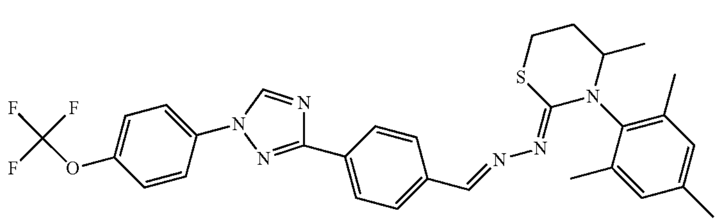 [SMILES: Cc1cc(C)c(N2/C(=N/N=C/c3ccc(-c4ncn(-c5ccc(OC(F)(F)F)cc5)n4)cc3)SCCC2C)c(C)c1] |

TABLE 3-continued

| Structures for Compounds | |
|---|---|
| ID | Structure |
| 219C | (structure) |
| 220C | (structure) |
| 221C | (structure) |
| 222C | (structure) |
| 223C | (structure) |
| 224C | (structure) |
| 225C | (structure) |

TABLE 3-continued

Structures for Compounds

| ID | Structure |
|---|---|
| 226C | 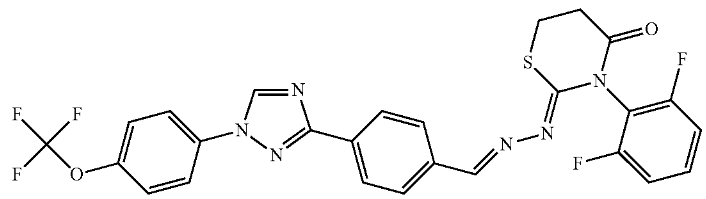 |
| 227C | 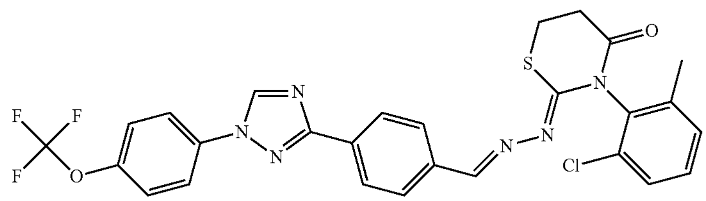 [SMILES: Cc1cccc(Cl)c1N1C(=O)CCS/C1=N\N=C\c1ccc(-c2ncn(-c3ccc(OC(F)(F)F)cc3)n2)cc1] |
| 228C | 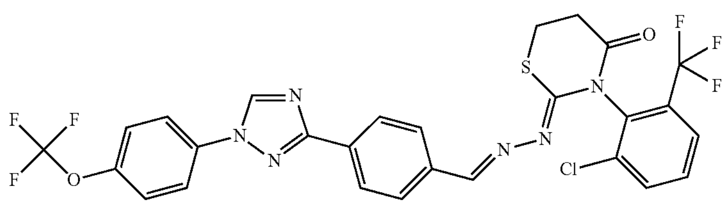 [SMILES: O=C1CCS/C(=N\N=C\c2ccc(-c3ncn(-c4ccc(OC(F)(F)F)cc4)n3)cc2)N1c1c(Cl)cccc1C(F)(F)F] |
| 229C | 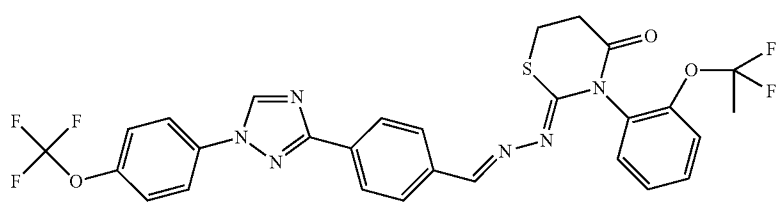 [SMILES: CC(F)(F)Oc1ccccc1N1C(=O)CCS/C1=N\N=C\c1ccc(-c2ncn(-c3ccc(OC(F)(F)F)cc3)n2)cc1] |
| 230C | 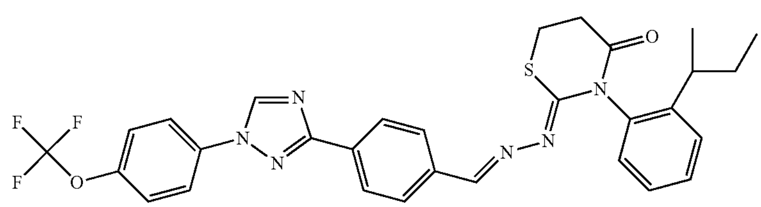 [SMILES: CCC(C)c1ccccc1N1C(=O)CCS/C1=N\N=C\c1ccc(-c2ncn(-c3ccc(OC(F)(F)F)cc3)n2)cc1] |
| 231C | 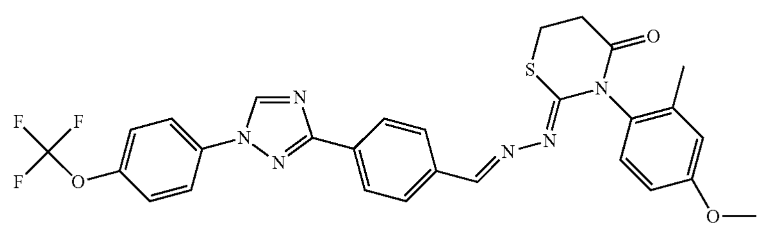 [SMILES: COc1ccc(N2C(=O)CCS/C2=N\N=C\c2ccc(-c3ncn(-c4ccc(OC(F)(F)F)cc4)n3)cc2)c(C)c1] |
| 232C | 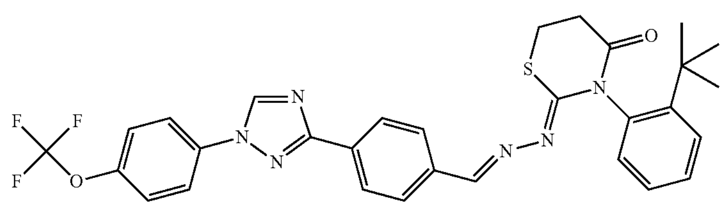 [SMILES: CC(C)(C)c1ccccc1N1C(=O)CCS/C1=N\N=C\c1ccc(-c2ncn(-c3ccc(OC(F)(F)F)cc3)n2)cc1] |

TABLE 3-continued

Structures for Compounds

| ID | Structure |
|---|---|
| 233C | 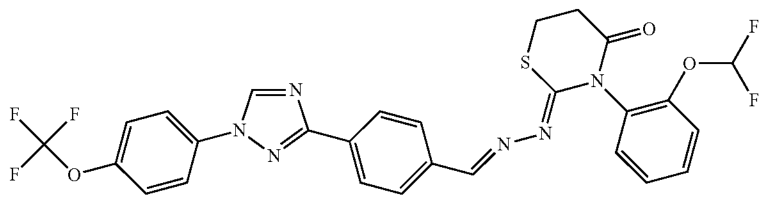 [SMILES: O=C1CCS/C(=N\N=C\c2ccc(-c3ncn(-c4ccc(OC(F)(F)F)cc4)n3)cc2)N1c1ccccc1OC(F)F] |
| 234C | 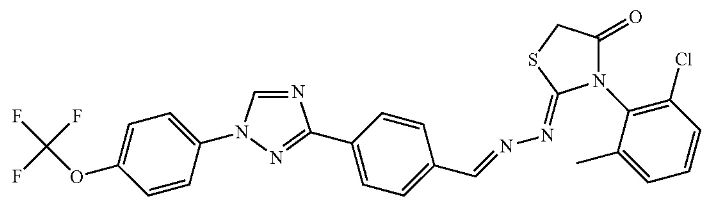 [SMILES: Cc1cccc(Cl)c1N1C(=O)CS/C1=N\N=C\c1ccc(-c2ncn(-c3ccc(OC(F)(F)F)cc3)n2)cc1] |
| 235C | 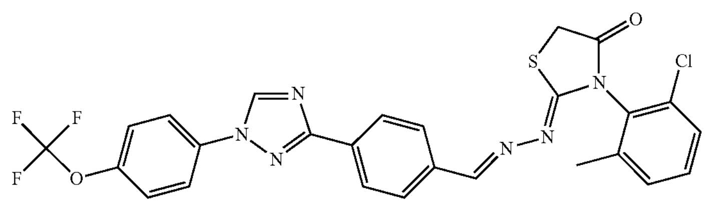 [SMILES: Cc1cccc(Cl)c1N1C(=O)CS/C1=N\N=C\c1ccc(-c2ncn(-c3ccc(OC(F)(F)F)cc3)n2)cc1] |
| 236C | 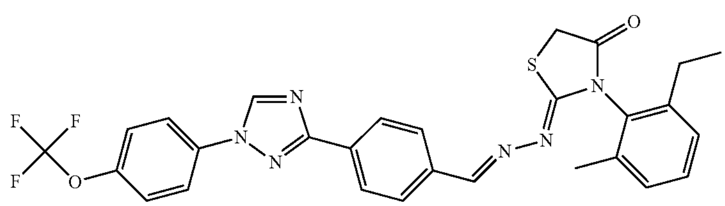 [SMILES: CCc1cccc(C)c1N1C(=O)CS/C1=N\N=C\c1ccc(-c2ncn(-c3ccc(OC(F)(F)F)cc3)n2)cc1] |
| 237C | 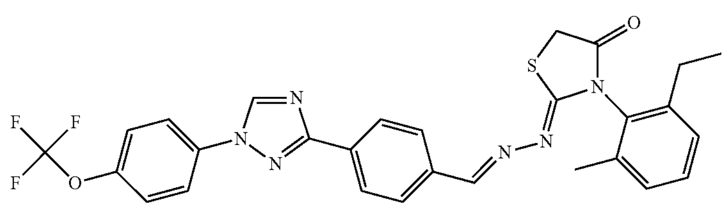 [SMILES: CCc1cccc(C)c1N1C(=O)CS/C1=N\N=C\c1ccc(-c2ncn(-c3ccc(OC(F)(F)F)cc3)n2)cc1] |
| 238C | 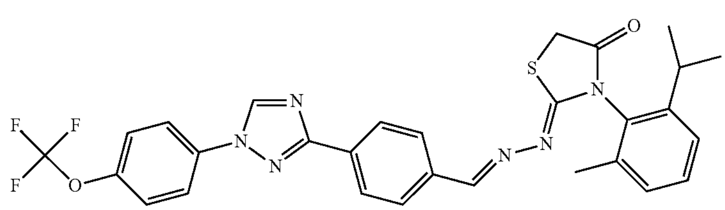 [SMILES: Cc1cccc(C(C)C)c1N1C(=O)CS/C1=N\N=C\c1ccc(-c2ncn(-c3ccc(OC(F)(F)F)cc3)n2)cc1] |
| 239C | 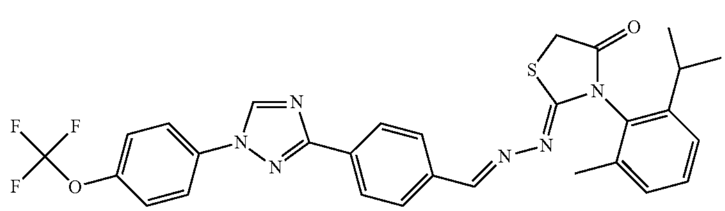 [SMILES: Cc1cccc(C(C)C)c1N1C(=O)CS/C1=N\N=C\c1ccc(-c2ncn(-c3ccc(OC(F)(F)F)cc3)n2)cc1] |

TABLE 4

Analytical Data for Compounds in Table 3

| ID | Synthesis Method | MS | mp (° C.) | ¹H NMR (δ)[1] |
|---|---|---|---|---|
| 1C | D | 540 (M+) | — | (DMSO-d$_6$) 8.61 (s, 1H), 8.48 (s, 1H), 8.22 (d, J = 8.24 Hz, 2H), 8.17 (s, 1H), 7.89 (d, J = 8.24 Hz, 2H), 7.80 (d, J = 8.28 Hz, 2H), 7.41 (d, J = 8.28 Hz, 2H), 7.19 (d, J = 8.24 Hz, 2H), 6.71 (d, J = 8.24 Hz, 2H), 2.99 (s, 6H), 2.42 (s, 3H) |
| 2C | D | 580 (M+) | 168-171 | (DMSO-d$_6$) 9.42 (s, 1H), 8.18-8.03 (m, 5H), 7.78-7.69 (m, 2H), 7.61 (d, J = 8.26 Hz, 2H), 7.44 (d, J = 8.24 Hz, 2H), 7.18 (m, 1H), 3.09-2.99 (m, 2H), 1.39-1.32 (m, 3H) |
| 3C | D | 594 (M+) | 180-182 | (DMSO-d$_6$) 9.42 (s, 1H), 8.18-8.04 (m, 5H), 7.78-7.69 (m, 2H), 7.61 (d, J = 8.26 Hz, 2H), 7.48 (d, J = 8.24 Hz, 2H), 7.19 (m, 1H), 3.06-3.02 (m, 2H), 1.78-1.64 (m, 2H), 1.04-0.96 (m, 3H) |
| 4C | D | 629 (M+) | | (DMSO-d$_6$) 8.57 (s, 1H), 8.48 (d, J = 5.5 Hz, 1H), 8.22 (d, J = 8.2 Hz, 2H), 7.91-7.75 (m, 5H), 7.38 (d, J = 8.7 Hz, 2H), 7.22-7.07 (m, 3H), 6.50-6.19 (m, 2H), 3.85 (d, J = 7.2 Hz, 1H), 3.75-3.64 (m, 1H), 2.33 (s, 6H) |
| 5C | E | 636 (M+) | | (300 MHz, CDCl$_3$) 8.56 (s, 1H), 8.54 (s, 1H), 8.23 (d, J = 8.3 Hz, 2H), 7.89 (d, J = 8.2 Hz, 3H), 7.79 (d, J = 9.0 Hz, 2H), 7.38 (d, J = 8.7 Hz, 2H), 7.23-7.00 (m, 4H), 6.88-6.74 (m, 2H), 4.44 (s, 2H), 2.33 (s, 6H) |
| 6C | D | 645 (M + H) | 196-198 | (methanol-d$_4$) 9.16 (s, 1H), 8.46 (s, 1H), 8.21 (d, J = 8.3 Hz, 2H), 8.03 (m, 6H), 7.52 (d, J = 8.3 Hz, 4H), 7.28-6.91 (m, 3H), 4.39 (s, 2H), 2.08 (s, 6H) |
| 7C | E | 636 (M+) | | (300 MHz, CDCl$_3$) 8.56 (m, 2H), 8.23 (d, J = 8.3 Hz, 2H), 7.88 (d, J = 8.3 Hz, 3H), 7.79 (d, J = 9.0 Hz, 2H), 7.55-7.42 (m, 1H), 7.37 (d, J = 9.0 Hz, 2H), 7.20-7.01 (m, 3H), 6.89-6.68 (m, 2H), 4.30 (s, 2H), 2.28 (s, 6H) |
| 8C | E | 684 (M+) | | (CDCl$_3$) 8.57 (s, 1H), 8.52 (s, 1H), 8.24 (d, J = 8.3 Hz, 2H), 7.91-7.84 (m, 3H), 7.80 (d, J = 9.1 Hz, 2H), 7.39 (d, J = 8.6 Hz, 4H), 7.18-7.03 (m, 5H), 4.32 (s, 2H), 2.29 (s, 6H) |
| 9C | E | 620 (M+) | | (CDCl$_3$) 8.57 (s, 1H), 8.47 (s, 1H), 8.23 (d, J = 8.3 Hz, 2H), 7.87 (d, J = 8.3 Hz, 2H), 7.80 (m, 3H), 7.39 (d, J = 8.4 Hz, 2H), 7.21-7.10 (m, 3H), 3.93 (s, 2H), 2.35 (s, 6H), 0.13 (s, 9H) |
| 10C | D | 600 (M+) | | (DMSO-d$_6$) 8.57 (s, 1H), 8.54 (s, 1H), 8.23 (d, J = 8.3 Hz, 2H), 7.89 (d, J = 8.3 Hz, 2H), 7.87 (s, 1H), 7.80 (d, J = 9.0 Hz, 2H), 7.44-7.32 (m, 4H), 7.31-7.19 (m, 3H), 7.19-7.00 (m, 3H), 4.34 (s, 2H), 2.31 (s, 6H) |
| 11C | D | 618 (M+) | | (DMSO-d$_6$) 8.57 (s, 1H), 8.55 (s, 1H), 8.23 (d, J = 8.3 Hz, 2H), 7.89 (d, J = 8.3 Hz, 2H), 7.86 (s, 1H), 7.83-7.73 (m, 2H), 7.48 (td, J = 7.6, 1.7 Hz, 1H), 7.38 (d, J = 8.5 Hz, 2H), 7.23-6.91 (m, 6H), 4.39 (s, 2H), 2.30 (s, 6H) |
| 12C | D | 658 (M+) | | (DMSO-d$_6$) 8.57 (s, 1H), 8.51 (s, 1H), 8.23 (d, J = 8.3 Hz, 2H), 7.94 (d, J = 8.3 Hz, 2H), 7.88 (d, J = 8.2 Hz, 2H), 7.86 (s, 1H), 7.79 (d, J = 9.0 Hz, 2H), 7.44 (d, J = 8.3 Hz, 2H), 7.38 (d, J = 8.6 Hz, 2H), 7.20-7.05 (m, 3H), 4.35 (s, 2H), 3.88 (s, 3H), 2.28 (s, 6H) |
| 13C | E | 679 (M+) | | (DMSO-d$_6$) 8.59 (s, 1H), 8.51 (s, 1H), 8.23 (d, J = 8.3 Hz, 2H), 7.93-7.76 (m, 7H), 7.53 (d, J = 8.2 Hz, 2H), 7.39 (d, J = 8.7 Hz, 2H), 7.20-7.06 (m, 3H), 4.88 (s, 2H), 4.36 (s, 2H), 2.28 (s, 6H) |
| 14C | E | 658 (M+) | | (CDCl$_3$) 8.57 (s, 1H), 8.52 (s, 1H), 8.23 (d, J = 8.3 Hz, 2H), 7.91-7.85 (m, 4H), 7.80 (d, J = 9.1 Hz, 2H), 7.73 (d, J = 6.8 Hz, 1H), 7.52 (dd, J = 8.8, 6.9 Hz, 1H), 7.39 (d, J = 9.0 Hz, 2H), 7.13-7.01 (m, 3H), 4.88 (s, 2H), 2.27 (s, 6H) |
| 15C | E | 667 (M+) | | (CDCl$_3$) 8.57 (s, 1H), 8.25-8.14 (m, 3H), 7.94-7.66 (m, 7H), 7.52-7.35 (m, 6H), 7.16-7.03 (m, 3H), 4.54 (s, 2H), 2.32 (s, 6H) |
| 16C | E | 658 (M+) | | (CDCl$_3$) 8.57 (s, 1H), 8.49 (s, 1H), 8.24 (d, J = 8.4 Hz, 2H), 7.88 (d, J = 8.3 Hz, 2H), |

TABLE 4-continued

Analytical Data for Compounds in Table 3

| ID | Synthesis Method | MS | mp (° C.) | $^1$H NMR ($\delta$)$^1$ |
|---|---|---|---|---|
| | | | | 7.83-7.77 (m, 3H), 7.39 (d, J = 8.3 Hz, 2H), 7.19-7.07 (m, 3H), 6.69-6.65 (m, 1H), 6.39-6.35 (m, 1H), 4.36 (s, 2H), 2.29 (s, 6H) |
| 17C | E | 678 (M+) | | (CDCl$_3$) 8.58 (s, 1H), 8.50 (s, 1H), 8.23 (d, J = 8.3 Hz, 2H), 7.94-7.74 (m, 7H), 7.59 (d, J = 8.4 Hz, 2H), 7.38 (d, J = 8.4 Hz, 2H), 7.20-7.04 (m, 3H), 4.37 (s, 2H), 3.01 (s, 3H), 2.29 (s, 6H) |
| 18C | E | 773 (M+) | | (CDCl$_3$) 8.59 (s, 1H), 8.46 (s, 1H), 8.22 (d, J = 8.4 Hz, 2H), 7.86 (d, J = 8.4 Hz, 2H), 7.83-7.75 (m, 3H), 7.63 (d, J = 8.4 Hz, 2H), 7.44 (d, J = 8.4 Hz, 2H), 7.38 (d, J = 8.4 Hz, 2H), 7.17-7.05 (m, 3H), 7.03-6.98 (m, 3H), 6.89 (t, J = 8.6 Hz, 2H), 4.30 (s, 2H), 2.24 (s, 6H) |
| 19C | E | 728 (M+) | | (CDCl$_3$) 8.59 (s, 2H), 8.26 (d, J = 8.3 Hz, 2H), 7.93 (d, J = 8.3 Hz, 2H), 7.89 (s, 1H), 7.82 (d, J = 9.1 Hz, 2H), 7.40 (d, J = 8.3 Hz, 2H), 7.20-7.05 (m, 3H), 6.86 (s, 1H), 4.49 (s, 2H), 3.98 (s, 3H), 2.31 (s, 6H) |
| 20C | E | 681 (M+) | | (CDCl$_3$) 8.58 (s, 1H), 8.38 (s, 1H), 8.23 (d, J = 8.3 Hz, 2H), 7.86 (d, J = 8.3 Hz, 3H), 7.81 (d, J = 9.1 Hz, 2H), 7.67-7.63 (m, 2H), 7.46-7.36 (m, 5H), 7.18-7.05 (m, 3H), 4.24 (s, 2H), 2.47 (s, 3H), 2.29 (s, 6H) |
| 21C | E | 596 (M+) | | (DMSO-d$_6$) 8.58 (s, 1H), 8.15 (d, J = 8.4 Hz, 2H), 7.80 (d, J = 9.0 Hz, 2H), 7.47-7.35 (m, 4H), 7.21-6.93 (m, 5H), 3.68 (t, J = 5.4 Hz, 2H), 3.35 (s, 3H), 2.65 (t, J = 6.2 Hz, 2H), 2.29 (s, 6H) |
| 22C | E | 626 (M+) | | (DMSO-d$_6$) 8.59 (s, 1H), 8.52 (s, 1H), 8.23 (d, J = 8.3 Hz, 2H), 7.95-7.75 (m, 5H), 7.39 (d, J = 8.4 Hz, 2H), 7.21-7.06 (m, 3H), 5.80 (s, 2H), 4.12 (s, 2H), 3.69-3.50 (m, 2H), 2.31 (s, 6H), 1.35-1.11 (m, 3H) |
| 23C | E | 731 (M+) | | (DMSO-d$_6$) 8.58 (s, 1H), 8.50 (s, 1H), 8.22 (d, J = 8.2 Hz, 2H), 7.93-7.70 (m, 5H), 7.45-7.28 (m, 8H), 7.23-7.03 (m, 3H), 5.79 (s, 2H), 5.38-5.27 (m, 1H), 5.11 (s, 2H), 4.07-3.98 (m, 2H), 2.30 (s, 6H) |
| 24C | E | 626 (M+) | | (DMSO-d$_6$) 8.58 (s, 1H), 8.51 (s, 1H), 8.22 (d, J = 8.3 Hz, 2H), 7.93-7.73 (m, 5H), 7.39 (d, J = 8.9 Hz, 2H), 7.21-7.07 (m, 3H), 5.76 (s, 2H), 5.05-4.70 (m, 1H), 2.32 (s, 6H), 1.38-1.17 (m, 6H) |
| 25C | E | 610 (M+) | | (DMSO-d$_6$) 8.59 (s, 1H), 8.52 (s, 1H), 8.23 (d, J = 8.3 Hz, 2H), 7.91-7.79 (m, 5H), 7.40 (d, J = 8.5 Hz, 2H), 7.18-7.06 (m, 3H), 5.73 (s, 2H), 2.70-2.45 (m, 1H), 2.32 (s, 6H), 1.15 (s, 6H) |
| 26C | E | 654 (M+) | | (DMSO-d$_6$) 8.58 (s, 1H), 8.21 (d, J = 8.4 Hz, 2H), 7.98 (d, J = 8.4 Hz, 2H), 7.81 (d, J = 6.9 Hz, 2H), 7.69 (s, 1H), 7.40 (d, J = 8.8 Hz, 2H), 6.63 (s, 2H), 5.73 (s, 2H), 3.80 (s, 3H), 2.64-2.53 (m, 1H), 2.58 (s, 3H), 2.28 (s, 6H), 1.17 (d, J = 7.0 Hz, 6H) |
| 27C | E | 640 (M+) | | (DMSO-d$_6$) 8.58 (s, 1H), 8.50 (s, 1H), 8.23 (d, J = 8.2 Hz, 2H), 7.88 (d, J = 8.3 Hz, 2H), 7.81 (d, J = 9.0 Hz, 2H), 7.74 (s, 1H), 7.39 (d, J = 8.6 Hz, 2H), 6.63 (s, 2H), 5.71 (s, 2H), 3.79 (s, 3H), 2.74-2.43 (m, 1H), 2.27 (s, 6H), 1.16 (d, J = 7.0 Hz, 6H) |
| 28C | E | 761 (M+) | | (300 MHz, CDCl$_3$) 8.58 (s, 1H), 8.48 (s, 1H), 8.22 (d, J = 8.3 Hz, 2H), 7.87 (d, J = 8.4 Hz, 2H), 7.80 (d, J = 9.0 Hz, 2H), 7.74 (s, 1H), 7.45-7.28 (m, 7H), 6.63 (s, 2H), 5.78 (s, 2H), 5.29 (m, 1H), 5.12 (s, 2H), 4.03 (d, J = 5.6 Hz, 2H), 3.79 (s, 3H), 2.27 (s, 6H) |
| 29C | E | 656 (M+) | | (300 MHz, CDCl$_3$) 8.58 (s, 1H), 8.49 (s, 1H), 8.23 (d, J = 8.3 Hz, 2H), 7.87 (d, J = 8.4 Hz, 2H), 7.81 (d, J = 9.0 Hz, 2H), 7.72 (s, 1H), 7.40 (d, J = 8.7 Hz, 2H), 6.63 (s, 2H), 5.78 (s, 2H), 4.11 (s, 2H), 3.80 (s, 3H), |

TABLE 4-continued

Analytical Data for Compounds in Table 3

| ID | Synthesis Method | MS | mp (° C.) | $^1$H NMR (δ)$^1$ |
|---|---|---|---|---|
| | | | | 3.59 (q, J = 7.0 Hz, 2H), 2.27 (s, 6H), 1.24 (t, J = 7.1 Hz, 3H) |
| 30C | E | 697 (M+) | | (300 MHz, CDCl$_3$) 8.60 (s, 1H), 8.50 (s, 1H), 8.22 (d, J = 8.3 Hz, 2H), 7.88 (d, J = 8.2 Hz, 2H), 7.82 (s, 1H), 7.80 (d, J = 9.0 Hz, 2H), 7.38 (d, J = 8.8 Hz, 3H), 7.23-7.02 (m, 3H), 5.78 (s, 2H), 3.96 (s, 2H), 2.31 (s, 6H), 1.44 (s, 9H) |
| 31C | E | 582 (M+) | | (300 MHz, CDCl$_3$) 8.58 (s, 1H), 8.52 (s, 1H), 8.23 (d, J = 8.3 Hz, 2H), 7.88 (m, 3H), 7.80 (d, J = 9.0 Hz, 2H), 7.38 (d, J = 8.6 Hz, 2H), 7.14 (m, 3H), 5.72 (s, 2H), 2.32 (s, 6H), 2.09 (s, 3H) |
| 32C | E | 697 (M+) | | (CDCl$_3$) (Mixture of atropisomers) [8.61 (s), 8.58 (s), 8.56 (s), 8.51 (s), 8.37 (d, J = 8.3 Hz), 8.23 (d, J = 8.4 Hz), 8.21-8.14 (m), 8.00 (d, J = 8.4 Hz), 7.89 (d, J = 8.2 Hz), 7.84-7.77 (m), 7.45-7.35 (m); 11H], 6.94 (s, 2H), [5.87 (s), 5.80 (s); 2H], [4.12 (s), 4.11 (s); 2H], 3.83 (s, 3H), 3.69-3.44 (m, 2H), 1.38-1.10 (m, 3H) |
| 33C | E | 697 (M+) | | (CDCl$_3$) 8.57 (s, 1H), 8.51 (s, 1H), 8.23 (d, J = 8.3 Hz, 2H), 7.88 (d, J = 8.4 Hz, 2H), 7.83-7.77 (m, 3H), 7.39 (d, J = 8.4 Hz, 2H), 6.94 (s, 2H), 5.76 (s, 2H), 4.96-4.77 (m, 1H), 3.82 (s, 3H), 1.30 (d, J = 6.3 Hz, 6H) |
| 34C | E | 681 (M+) | | (CDCl$_3$) 8.57 (s, 1H), 8.51 (s, 1H), 8.23 (d, J = 8.3 Hz, 2H), 7.92-7.76 (m, 5H), 7.39 (d, J = 8.4 Hz, 2H), 6.93 (s, 2H), 5.73 (s, 2H), 3.82 (s, 3H), 2.59 (m, 1H), 1.17 (d, J = 7.0 Hz, 6H) |
| 35C | E | 636 (M+) | | (CDCl$_3$) 8.57 (s, 1H), 8.50 (s, 1H), 8.23 (d, J = 8.4 Hz, 2H), 7.92-7.73 (m, 5H), 7.38 (d, J = 8.3 Hz, 2H), 7.20-6.92 (m, 3H), 5.72 (s, 2H), 2.94-2.63 (m, 1H), 2.31 (s, 6H), 2.02-1.38 (m, 8H) |
| 36C | E | 624 (M+) | | (CDCl$_3$) 8.56 (s, 1H), 8.49 (s, 1H), 8.23 (d, J = 8.3 Hz, 2H), 7.87 (d, J = 8.3 Hz, 2H), 7.84 (s, 1H), 7.79 (d, J = 9.0 Hz, 2H), 7.38 (d, J = 8.4 Hz, 2H), 7.19-7.05 (m, 3H), 5.71 (s, 2H), 2.31 (s, 6H), 1.20 (s, 9H) |
| 37C | E | 691 (M + H) | | (CDCl$_3$) 8.59 (s, 1H), 8.50 (s, 1H), 8.23 (d, J = 8.3 Hz, 2H), 7.93-7.77 (m, 4H), 7.72 (s, 1H), 7.40 (d, J = 9.0 Hz, 2H), 6.63 (s, 2H), 5.71 (s, 2H), 3.80 (s, 3H), 2.68-2.48 (m, 1H), 2.28 (s, 6H), 1.16 (d, J = 7.0 Hz, 6H) |
| 38C | E | 724 (M+) | | (CDCl$_3$) 8.58 (s, 1H), 8.47 (s, 1H), 8.23 (d, J = 8.3 Hz, 2H), 7.87 (d, J = 8.3 Hz, 2H), 7.81 (d, J = 9.1 Hz, 2H), 7.71 (s, 1H), 7.39 (d, J = 9.0 Hz, 2H), 6.64 (s, 2H), 5.76 (dd, J = 37.3, 11.0 Hz, 2H), 4.19 (q, J = 6.9 Hz, 1H), 4.14-3.97 (m, 1H), 3.80 (s, 3H), 3.79-3.68 (m, 1H), 2.27 (s, 6H), 1.47 (d, J = 6.9 Hz, 3H) |
| 39C | E | 694 (M+) | | (CDCl$_3$) 8.58 (s, 1H), 8.48 (s, 1H), 8.24 (d, J = 8.3 Hz, 2H), 7.87 (d, J = 8.3 Hz, 2H), 7.83 (s, 1H), 7.81 (d, J = 9.1 Hz, 2H), 7.39 (d, J = 8.3 Hz, 2H), 7.23-6.99 (m, 3H), 5.77 (dd, J = 36.4, 11.0 Hz, 2H), 4.19 (q, J = 6.9 Hz, 1H), 4.14-3.97 (m, 1H), 3.84-3.65 (m, 1H), 2.31 (s, 6H), 1.47 (d, J = 6.9 Hz, 3H) |
| 40C | E | 654 (M+) | | (CDCl$_3$) 8.57 (s, 1H), 8.48 (s, 1H), 8.23 (d, J = 8.3 Hz, 2H), 7.87 (d, J = 8.3 Hz, 2H), 7.80 (d, J = 9.0 Hz, 2H), 7.72 (s, 1H), 7.38 (d, J = 8.4 Hz, 2H), 6.62 (s, 2H), 5.70 (s, 2H), 3.79 (s, 3H), 2.27 (s, 6H), 1.20 (s, 9H) |
| 41C | E | 670 (M+) | | (CDCl$_3$) 8.58 (s, 1H), 8.49 (s, 1H), 8.23 (d, J = 8.3 Hz, 2H), 7.87 (d, J = 8.3 Hz, 2H), 7.84 (s, 1H), 7.80 (d, J = 9.0 Hz, 2H), 7.38 (d, J = 8.4 Hz, 2H), 7.23-6.96 (m, 3H), 5.77 (dd, J = 27.4, 10.9 Hz, 2H), 4.07 (q, J = 6.9 Hz, 1H), 3.78-3.70 (m, 1H), 3.66-3.39 (m, 3H), 3.35 (s, 3H), 2.31 (s, 6H), 1.42 (d, J = 6.9 Hz, 3H) |
| 42C | E | 700 (M+) | | (CDCl$_3$) 8.58 (s, 1H), 8.48 (s, 1H), 8.23 (d, J = 8.4 Hz, 2H), 7.87 (d, J = 8.3 Hz, 2H), |

TABLE 4-continued

Analytical Data for Compounds in Table 3

| ID | Synthesis Method | MS | mp (° C.) | $^1$H NMR (δ)$^1$ |
|---|---|---|---|---|
| | | | | 7.80 (d, J = 9.1 Hz, 2H), 7.71 (s, 1H), 7.39 (d, J = 8.3 Hz, 2H), 6.63 (s, 2H), 5.76 (dd, J = 27.8, 10.9 Hz, 2H), 4.07 (q, J = 6.9 Hz, 1H), 3.79 (s, 3H), 3.79-3.70 (m, 1H), 3.63-3.45 (m, 3H), 3.35 (s, 3H), 2.27 (s, 6H), 1.42 (d, J = 6.9 Hz, 3H) |
| 43C | E | 666 (M+) | | (CDCl$_3$) 8.57 (s, 1H), 8.49 (s, 1H), 8.22 (d, J = 8.3 Hz, 2H), 7.87 (d, J = 8.3 Hz, 2H), 7.79 (d, J = 9.1 Hz, 2H), 7.74 (s, 1H), 7.38 (d, J = 8.3 Hz, 2H), 6.62 (s, 2H), 5.71 (s, 2H), 3.79 (s, 3H), 2.85-2.65 (m, 1H), 2.27 (s, 6H), 1.98-1.51 (m, 8H) |
| 44C | E | 668 (M+) | | (CDCl$_3$) 8.59 (s, 1H), 8.55 (s, 1H), 8.22 (d, J = 8.3 Hz, 2H), 7.87 (d, J = 8.3 Hz, 2H), 7.84-7.74 (m, 3H), 7.38 (d, J = 8.4 Hz, 2H), 6.63 (s, 2H), 5.85-5.73 (m, 2H), 4.54-4.47 (m, 1H), 4.03 (dd, J = 14.7, 6.9 Hz, 1H), 3.91 (dd, J = 13.8, 7.4 Hz, 1H), 3.79 (s, 3H), 2.27 (s, 6H), 2.09-1.83 (m, 4H) |
| 45C | E | 746 (M + H) | 132-137 | (CDCl$_3$) 8.68 (s, 1H), 8.49 (s, 1H), 8.24 (d, J = 8.3 Hz, 2H), 7.93 (d, J = 8.4 Hz, 2H), 7.88 (d, J = 8.3 Hz, 2H), 7.81 (d, J = 8.5 Hz, 2H), 7.73 (s, 1H), 7.35 (s, 5H), 6.64 (s, 2H), 5.78 (s, 2H), 5.24 (s, 1H), 5.12 (s, 2H), 4.04 (d, J = 5.5 Hz, 2H), 3.80 (s, 3H), 2.28 (s, 6H) |
| 46C | E | 624 | 108-113 | (CDCl$_3$) 8.68 (s, 1H), 8.50 (s, 1H), 8.24 (d, J = 8.3 Hz, 2H), 7.98-7.69 (m, 7H), 6.63 (s, 2H), 5.71 (s, 2H), 3.80 (s, 3H), 2.59 (heptet, J = 7.0 Hz, 1H), 2.29 (d, J = 6.9 Hz, 6H), 1.16 (d, J = 7.0 Hz, 6H) |
| 47C | E | | 149-151 | (acetone-d$_6$) 9.20 (s, 1H), 8.52 (s, 1H), 8.40-8.21 (m, 2H), 8.21-8.01 (m, 4H), 7.61 (d, J = 8.3 Hz, 2H), 7.32-6.94 (m, 3H), 3.83 (s, 2H), 2.34 (s, 6H) |
| 48C | E | 599 (M + H) | 128-137 | (acetone-d$_6$) 9.18 (s, 1H), 8.83 (s, 1H), 8.67-7.82 (m, 8H), 7.60 (d, J = 8.4 Hz, 2H), 6.78 (s, 2H), 3.99-3.72 (m, 3H), 2.41-2.20 (m, 6H) |
| 49C | E | 619 (M + H) | 177-185 | (methanol-d$_4$) 9.23 (s, 1H), 8.62 (s, 1H), 8.29 (m, 2H), 8.17-7.98 (m, 4H), 7.60-7.45 (m, 2H), 7.41-7.19 (m, 3H), 4.22 (s, 2H), 2.34 (s, 6H) |
| 50C | E | 635 (M + H) | 193-196 | (methanol-d$_4$) 9.23 (s, 1H), 8.57 (s, 1H), 8.28 (m, 3H), 8.09-7.98 (m, 4H), 7.50 (m, 4H), 4.19-4.11 (m, 2H), 3.85 (s, 3H), 2.36 (s, 3H) |
| 51C | E | 649 (M + H) | 176-179 | (methanol-d$_4$) 9.23 (s, 1H), 8.60 (s, 1H), 8.30 (m, 2H), 8.14-8.00 (m, 4H), 7.52 (m, 2H), 6.81 (s, 2H), 4.22 (s, 2H), 3.84-3.81 (m, 3H), 2.33 (s, 6H) |
| 52C | E | 599 (M + H) | 168-178 | (methanol-d$_4$) 9.21 (s, 1H), 8.44 (s, 1H), 8.27 (d, J = 8.1 Hz, 2H), 8.09-7.98 (m, 4H), 7.52 (d, J = 8.3 Hz, 2H), 7.40 (d, J = 8.7 Hz, 2H), 6.97 (d, J = 8.8 Hz, 2H), 5.40 (s, 1H), 4.37-4.13 (m, 2H), 3.79 (s, 3H), 1.79 (m, 3H) |
| 53C | E | 617 (M + H) | 168-170 | (methanol-d$_4$) 9.21 (s, 1H), 8.44 (m, 1H), 8.28 (d, J = 8.2 Hz, 2H), 8.11-7.99 (m, 4H), 7.52 (d, J = 8.4 Hz, 2H), 7.25 (m, 2H), 7.14 (t, J = 8.5 Hz, 1H), 5.42 (m, 1H), 4.25 (m, 2H), 3.88 (s, 3H), 1.75 (m, 3H) |
| 54C | E | 569 (M + H) | 167-170 | (methanol-d$_4$) 9.23 (s, 1H), 8.46 (s, 1H), 8.27 (m, 2H), 8.05 (m, 4H), 7.57-7.39 (m, 7H), 5.41 (m, 1H), 4.24 (m, 2H), 1.79 (m, 3H) |
| 55C | E | 624 (M + H) | 90-97 | (methanol-d$_4$) 9.12 (s, 1H), 8.46 (s, 1H), 8.14 (m, 2H), 7.99 (m, 3H), 7.78 (s, 1H), 7.49 (d, J = 8.5 Hz, 2H), 7.12 (m, 3H), 3.69 (s, 2H), 3.22-2.80 (m, 2H), 2.25 (s, 6H), 2.03 (s, 2H), 1.93-1.66 (m, 1H), 0.92 (m, J = 9.7 Hz, 6H) |
| 56C | E | 765 (M + H) | 148-151 | (methanol-d$_4$) 9.18 (s, 1H), 8.59 (s, 1H), 8.30 (d, J = 8.1 Hz, 2H), 8.12 (m, 2H), 8.07-8.00 (m, 2H), 7.58-7.43 (m, 2H), 7.33 (dd, J = 8.6, 6.5 Hz, 1H), 7.25 (d, J = 7.6 Hz, |

TABLE 4-continued

Analytical Data for Compounds in Table 3

| ID | Synthesis Method | MS | mp (° C.) | $^1$H NMR (δ)$^1$ |
|---|---|---|---|---|
| 57C | E | 737 (M + H) | 151-153 | 2H), 4.02 (m, 2H), 3.97-3.75 (m, 2H), 3.21 (d, J = 6.9 Hz, 2H), 2.90 (m, 1H), 2.59 (m, 1H), 2.35 (s, 6H), 1.84 (m, 2H), 1.78-1.63 (m, 9H), 1.44 (s, 9H), 1.29 (m, 3H) (methanol-d$_4$) 9.20 (s, 1H), 8.65 (s, 1H), 8.30 (m, 2H), 8.21-7.96 (m, 4H), 7.53 (d, J = 8.4 Hz, 2H), 7.35 (dd, J = 8.5, 6.5 Hz, 1H), 7.28 (d, J = 7.5 Hz, 2H), 4.44 (s, 2H), 3.91-3.40 (m, 9H), 2.38 (s, 6H), 1.50 (s, 9H) |
| 58C | E | 725 (M + H) | 125-127 | (methanol-d$_4$) 9.18 (s, 1H), 8.61 (s, 1H), 8.31 (m, 2H), 8.14 (m, 2H), 8.06 (d, J = 9.0 Hz, 2H), 7.53 (d, J = 8.5 Hz, 2H), 7.32 (dt, J = 26.0, 7.0 Hz, 3H), 4.02 (s, 2H), 3.38-3.34 (m, 2H), 3.22-3.03 (m, 2H), 2.37 (s, 6H), 1.74 (m, 2H), 1.45 (s, 9H) |
| 59C | E | 755 (M + H) | 147-149 | (methanol-d$_4$) 9.18 (s, 1H), 8.62 (s, 1H), 8.38-7.97 (m, 6H), 7.51 (d, J = 8.4 Hz, 2H), 7.32 (dd, J = 8.5, 6.6 Hz, 1H), 7.25 (d, J = 7.6 Hz, 2H), 4.40 (s, 1H), 4.06 (m, 2H), 3.91-3.74 (m, 2H), 3.56-3.41 (m, 1H), 2.36 (s, 6H), 1.44 (s, 9H) |
| 60C | E | 755 (M + H) | 136-139 | (methanol-d$_4$) 9.16 (s, 1H), 8.58 (s, 1H), 8.28 (d, J = 7.4 Hz, 2H), 8.16-7.76 (m, 4H), 7.52 (p, J = 8.8 Hz, 2H), 6.83 (m, 2H), 4.04 (d, J = 8.5 Hz, 2H), 3.90-3.73 (m, 3H), 3.55-3.37 (m, 2H), 3.14-2.75 (m, 3H), 2.30 (s, 6H), 1.99-1.80 (m, 2H), 1.43-1.31 (m, 2H) |
| 61C | E | 738 (M + H) | 70-79 dec | (methanol-d$_4$) 9.12 (s, 1H), 8.12-8.07 (m, 2H), 8.02-7.96 (m, 2H), 7.55-7.50 (m, 2H), 7.50-7.45 (m, 2H), 7.43 (d, J = 7.7 Hz, 1H), 7.31 (d, J = 7.6 Hz, 2H), 4.03 (s, 2H), 3.25 (dt, J = 15.5, 7.0 Hz, 4H), 2.84 (s, 3H), 2.04 (s, 6H), 1.81-1.66 (m, 2H), 1.44 (s, 9H) |
| 62C | K | 665 (M + H) | 110-120 | (methanol-d$_4$) δ 9.18 (s, 1H), 8.56 (m, 1H), 8.26 (m, 2H), 8.16-7.84 (m, 4H), 7.52 (m, 2H), 7.27 (m, 1H), 7.22 (m, 2H), 4.00 (s, 2H), 3.28 (m, 3H), 3.06-2.83 (m, 1H), 2.75 (t, J = 12.2 Hz, 1H), 2.34 (s, 6H), 2.21-1.83 (m, 4H), 1.72 (m, 1H), 1.47-1.19 (m, 2H) |
| 63C | K | 655 (M + H) | 98-110 | (methanol-d$_4$) 9.18 (s, 1H), 8.63 (s, 1H), 8.28 (m, 2H), 8.13-7.97 (m, 4H), 7.51 (d, J = 8.3 Hz, 2H), 7.31 (dd, J = 8.5, 6.5 Hz, 1H), 7.24 (d, J = 7.6 Hz, 2H), 4.32-4.07 (m, 3H), 3.98-3.81 (m, 1H), 3.72 (s, 1H), 2.35 (s, 6H) |
| 64C | K | 655 (M + H) | 83-112 | (methanol-d$_4$) 9.19 (s, 1H), 8.58 (s, 1H), 8.28 (m, 2H), 8.14-7.97 (m, 4H), 7.51 (m, 2H), 6.78 (s, 2H), 4.00 (m, 2H), 3.81 (s, 3H), 3.10-2.93 (m, 4H), 2.30 (s, 6H), 1.91 (m, 2H) |
| 65C | K | 667 (M + H) | 128 dec | (methanol-d$_4$) 9.20 (s, 1H), 8.65 (s, 1H), 8.27 (m 2H), 8.11-7.99 (m, 4H), 7.52 (d, J = 8.3 Hz, 2H), 6.78 (s, 2H), 4.40 (s, 2H), 3.87 (m, 4H), 3.53 (s, 3H), 2.32 (s, 6H), 1.33 (m, 4H) |
| 66C | K | 625 (M + H) | 100-105 | (methanol-d$_4$) 9.20 (s, 1H), 8.56 (s, 1H), 8.27 (m, 2H), 8.12-7.99 (m, 3H), 7.53 (d, J = 8.4 Hz, 2H), 7.24 (m, 4H), 3.99 (s, 2H), 3.42 (m, 2H), 3.05 (m, 2H), 2.36 (s, 6H), 1.99-1.88 (m, 2H) |
| 67C | K | 636 (M + H) | 237-240 dec | (methanol-d$_4$) 9.20 (s, 1H), 8.74 (s, 1H), 8.33-8.25 (m, 2H), 8.12-7.98 (m, 4H), 7.53 (d, J = 8.3 Hz, 2H), 7.33 (dd, J = 8.5, 6.4 Hz, 1H), 7.26 (d, J = 7.5 Hz, 2H), 4.55 (s, 2H), 3.92 (m, 4H), 3.37 (m, 2H), 3.31 (m, 2H), 2.38 (s, 6H) |
| 69C | F | 581 (M + H) | 188-190 | (CDCl$_3$) 8.56 (s, 1H), 8.33 (s, 1H), 8.22 (d, J = 8.1 Hz, 2H), 7.90-7.70 (m, 4H), 7.39 (d, J = 8.7 Hz, 2H), 6.72 (s, 2H), 4.01 (s, 2H), 3.87-3.73 (s, 3H), 2.18 (s, 6H) |

TABLE 4-continued

Analytical Data for Compounds in Table 3

| ID | Synthesis Method | MS | mp (° C.) | ¹H NMR (δ)[1] |
|---|---|---|---|---|
| 70C | F | 592 (M+) | 134-138 | (CDCl₃) 8.65 (s, 1H), 8.31 (s, 1H), 8.23 (d, J = 8.3 Hz, 2H), 7.83 (m, 4H), 7.50 (d, J = 8.1 Hz, 2H), 7.45-7.38 (m, 3H), 4.05 (s, 2H) |
| 71C | F | 551 (M + H) | 104-111 | (CDCl₃) 8.62 (s, 1H), 8.32 (s, 1H), 8.23 (d, J = 8.3 Hz, 2H), 7.88-7.74 (m, 4H), 7.40 (d, J = 8.3 Hz, 2H), 7.34-7.26 (m, 1H), 7.20 (d, J = 7.5 Hz, 2H), 4.02 (s, 2H), 2.22 (s, 6H) |
| 72C | F | 565 (M + H) | 118-121 | (CDCl₃) 8.58 (s, 1H), 8.33 (s, 1H), 8.23 (d, J = 8.3 Hz, 2H), 7.81 (m, 4H), 7.40 (d, J = 8.3 Hz, 2H), 7.01 (d, J = 0.4 Hz, 2H), 4.01 (s, 2H), 2.34 (s, 3H), 2.17 (s, 6H) |
| 73C | F | 565 (M + H) | 145-150 | (CDCl₃) 8.58 (s, 1H), 8.30 (s, 1H), 8.23 (d, J = 8.3 Hz, 1H), 7.81 (m, 2H), 7.49 (d, J = 4.0 Hz, 1H), 7.40 (d, J = 8.4 Hz, 1H), 7.34 (s, 1H), 7.18 (d, J = 7.8 Hz, 1H), 4.01 (d, J = 1.4 Hz, 1H), 2.83 (heptet, J = 6.8 Hz, 1H), 1.23 (t, J = 6.6 Hz, 3H). |
| 74C | G | 682 (M + H) | 190-193 | (methanol-d₄) 9.20 (s, 1H), 8.38 (s, 1H), 8.31-8.24 (m, 2H), 8.08-8.00 (m, 2H), 7.95-7.88 (m, 2H), 7.55-7.48 (m, 3H), 7.48-7.36 (m, 5H), 7.31 (d, J = 7.7 Hz, 2H), 3.60 (q, J = 7.2 Hz, 4H), 2.20 (s, 6H), 1.07 (t, J = 7.2 Hz, 6H); |
| 75C | G | 617 (M+) | | (CDCl₃) 8.56 (s, 1H), 8.23 (s, 1H), 8.19 (d, J = 8.4 Hz, 2H), 7.84-7.73 (m, 5H), 7.41-7.33 (m, 3H), 7.21 (d, J = 7.2 Hz, 2H), 7.16 (s, 1H), 7.12 (d, J = 3.2 Hz, 1H), 2.20 (s, 6H). |
| 76C | G | 711 (M+) | | (CDCl₃) 8.56 (s, 1H), 8.25 (s, 1H), 8.20 (d, J = 8.4 Hz, 2H), 7.80 (dd, J = 8.7, 5.6 Hz, 4H), 7.48-7.34 (m, 8H), 7.26 (d, J = 7.7 Hz, 2H), 7.08 (s, 1H), 2.20 (s, 6H) |
| 77C | G | 655 (M + H) | 261-263 | (methanol-d₄) 9.14 (s, 1H), 8.21-8.13 (m, 3H), 8.06-7.99 (m, 2H), 7.86-7.75 (m, 4H), 7.50 (d, J = 8.3 Hz, 2H), 7.28-7.18 (m, 3H), 7.14 (d, J = 7.9 Hz, 2H), 6.72 (s, 1H), 0.09--0.09 (m, 6H) |
| 78C | G | 694 (M + H) | | (CDCl₃) 8.55 (s, 1H), 8.22 (s, 1H), 8.18 (d, J = 8.3 Hz, 2H), 7.79 (dd, J = 8.7, 5.1 Hz, 4H), 7.37 (d, J = 9.0 Hz, 2H), 7.23-6.94 (m, 7H), 6.26 (s, 1H), 2.17 (s, 6H) |
| 79C | G | 678 (M + H) | | (CDCl₃) 8.55 (s, 1H), 8.23 (s, 1H), 8.19 (d, J = 8.3 Hz, 2H), 7.79 (d, J = 8.7 Hz, 4H), 7.43 (d, J = 8.3 Hz, 2H), 7.37 (d, J = 8.9 Hz, 2H), 7.23-7.16 (m, 3H), 7.08 (d, J = 7.4 Hz, 2H), 6.35 (s, 1H), 2.18 (s, 6H) |
| 80C | G | 609 (M + H) | 215-219 | (methanol-d₄) 9.23 (s, 1H), 8.40 (s, 1H), 8.26 (m, 2H), 8.22 (s, 1H), 8.07-8.00 (m, 3H), 7.91 (d, J = 8.4 Hz, 2H), 7.51 (d, J = 8.3 Hz, 2H), 6.90 (s, 1H), 3.88 (s, 3H), 2.13 (s, 6H) |
| 81C | I | 551 (M + H) | 209-213 | (CDCl₃) 9.42 (s, 1H), 8.59 (s, 1H), 8.28 (d, J = 8.4 Hz, 2H), 8.01 (d, J = 8.3 Hz, 2H), 7.80-7.77 (m, 2H), 7.43-7.34 (m, 2H), 7.07 (d, J = 7.5 Hz, 2H), 6.98 (dd, J = 8.2, 6.7 Hz, 1H), 3.90 (s, 2H), 2.17 (s, 6H) |
| 82C | I | 565 (M + H) | 225-232 | (CDCl₃) 9.46 (s, 1H), 8.60 (s, 1H), 8.29 (d, J = 8.4 Hz, 2H), 8.02 (d, J = 8.4 Hz, 2H), 7.89-7.76 (m, 2H), 7.40 (d, J = 8.3 Hz, 2H), 6.88 (s, 2H), 3.90 (s, 2H), 2.28 (s, 3H), 2.13 (s, 6H). |
| 83C | I | 581 (M + H) | 211-215 | (CDCl₃) 9.44 (s, 1H), 8.60 (s, 1H), 8.30 (d, J = 8.4 Hz, 2H), 8.02 (d, J = 8.4 Hz, 2H), 7.82 (d, J = 9.1 Hz, 2H), 7.40 (d, J = 8.3 Hz, 2H), 6.63 (s, 2H), 3.90 (s, 2H), 3.78 (s, 3H), 2.15 (s, 6H) |
| 84C | I | 591 | 250 dec | (CDCl₃) 9.42 (s, 1H), 8.40 (s, 1H), 8.18 (d, J = 8.24 Hz, 2H), 8.07 (d, J = 8.28 Hz, 2H), 7.89 (d, J = 8.24 Hz, 2H), 7.76 (d, J = 8.28 Hz, 2H), 7.64-7.58 (m, 3H), 4.42 (s, 2H) |
| 85C | I | 551 (M + H) | 146-149 | (CDCl₃) δ 9.36 (s, 1H), 8.60 (s, 1H), 8.30 (d, J = 8.4 Hz, 2H), 8.01 (d, J = 8.4 Hz, 2H), 7.86-7.77 (m, 2H), 7.40 (d, J = 8.3 Hz, 2H), 7.32 (dd, J = 6.9, 2.3 Hz, 1H), 7.24-7.12 (m, 2H), 6.91 (dd, J = 7.1, 2.0 Hz, 1H), |

TABLE 4-continued

Analytical Data for Compounds in Table 3

| ID | Synthesis Method | MS | mp (° C.) | $^1$H NMR (δ)$^1$ |
|---|---|---|---|---|
| | | | | 3.93 (s, 2H), 3.15-2.97 (m, 1H), 1.21 (d, J = 6.9 Hz, 6H) |
| 86C | J | 566 (M + H) | 163-169 | (CDCl$_3$) δ 8.81 (bs, 1H), 8.57 (s, 1H), 8.20 (d, J = 8.3 Hz, 2H), 7.87-7.75 (m, 4H), 7.39 (d, J = 8.3 Hz, 2H), 7.32-7.25 (m, 1H), 7.10 (2dt, J = 7.4, 1.5 Hz, 2H), 6.83 (d, J = 6.5 Hz, 1H), 3.96 (t, J = 6.1 Hz, 2H), 3.13 (heptet, J = 6.9 Hz, 1H), 2.99-2.88 (m, 2H), 2.49-2.36 (m, 2H), 1.29-1.21 (m, 6H). |
| 87C | J | 550 (M + H) | 187-189 | (CDCl$_3$) δ 8.81 (s, 1H), 8.66 (s, 1H), 8.21 (d, J = 8.3 Hz, 2H), 7.92 (d, J = 8.4 Hz, 2H), 7.81 (t, J = 10.2 Hz, 4H), 7.30-7.26 (m, 2H), 7.17-7.04 (m, 1H), 6.83 (d, J = 6.4 Hz, 1H), 3.96 (t, J = 6.1 Hz, 2H), 3.13 (heptet, J = 6.9 Hz, 1H), 2.97-2.90 (m, 2H), 2.47-2.38 (m, 2H), 1.25 (d, J = 7.5 Hz, 6H). |
| 88C | F | 579.2 (M + H) | 178-182 | (CDCl$_3$) δ 8.58 (s, 1H), 8.30 (s, 1H), 8.22 (d, J = 8.3 Hz, 2H), 7.82 (dd, J = 8.7, 7.2 Hz, 4H), 7.48 (dd, J = 4.1, 1.3 Hz, 2H), 7.40 (d, J = 8.3 Hz, 2H), 7.37-7.30 (m, 1H), 7.17 (m, 1H), 4.23 (dq, J = 14.5, 7.2 Hz, 1H), 2.83 (dd, J = 14.6, 6.9 Hz, 1H), 1.79 (d, J = 7.2 Hz, 3H), 1.22 (ddd, J = 12.1, 6.9, 1.9 Hz, 6H). |
| 89C | F | 559 (M + H) | 205-206 | (CDCl$_3$) δ 8.58 (s, 1H), 8.32 (s, 1H), 8.23 (d, J = 8.4 Hz, 2H), 7.90-7.75 (m, 4H), 7.52-7.44 (m, 1H), 7.40 (d, J = 8.3 Hz, 2H), 7.10 (dd, J = 8.6, 7.4 Hz, 2H), 4.04 (s, 2H). |
| 90C | F | 566 (M + H) | 148-151 | (CDCl$_3$) δ 8.58 (s, 1H), 8.31 (s, 1H), 8.23 (d, J = 8.3 Hz, 2H), 7.82 (t, J = 8.5 Hz, 4H), 7.46-7.31 (m, 3H), 7.25-7.18 (m, 2H), 4.02 (s, 2H), 2.53 (q, J = 7.6 Hz, 2H), 2.21 (s, 3H), 1.26-1.16 (m, 3H). |
| 91C | F | 554 (M + H) | 227-235 | (CDCl$_3$) δ 8.58 (s, 1H), 8.36 (s, 1H), 8.23 (d, J = 8.3 Hz, 2H), 7.88-7.76 (m, 4H), 7.49-7.35 (m, 3H), 7.01 (dd, J = 8.5, 2.5 Hz, 1H), 6.96 (dd, J = 7.8, 1.0 Hz, 1H), 6.91 (t, J = 2.2 Hz, 1H), 3.98 (s, 2H), 3.85 (s, 3H). |
| 92C | F | 554 (M + H) | 104-108 | (CDCl$_3$) δ 8.58 (s, 1H), 8.32 (s, 1H), 8.22 (d, J = 8.4 Hz, 2H), 7.86-7.77 (m, 4H), 7.50-7.43 (m, 1H), 7.40 (d, J = 8.3 Hz, 2H), 7.32-7.27 (m, 1H), 7.14-7.04 (m, 2H), 4.01 (d, J = 17.2 Hz, 1H), 3.94 (d, J = 17.3 Hz, 1H), 3.84 (s, 3H). |
| 93C | F | 572 (M + H) | 183-186 | (CDCl$_3$) δ 8.58 (s, 1H), 8.31 (s, 1H), 8.27-8.18 (m, 2H), 7.88-7.77 (m, 4H), 7.43-7.37 (m, 3H), 7.34 (t, J = 7.8 Hz, 1H), 7.30-7.26 (m, 1H), 4.07 (d, J = 17.4 Hz, 1H), 4.00 (d, J = 17.4 Hz, 1H), 2.29 (s, 3H). |
| 94C | F | 552 (M + H) | 134-136 | (CDCl$_3$) δ 8.58 (s, 1H), 8.31 (s, 1H), 8.23 (d, J = 8.4 Hz, 2H), 7.86-7.78 (m, 4H), 7.49-7.32 (m, 5H), 7.24-7.18 (m, 1H), 4.06-3.94 (m, 2H), 2.56 (q, J = 7.6 Hz, 2H), 1.26-1.18 (m, 3H). |
| 95C | F | 576.1 (M + H) | 195-201 | (CDCl$_3$) δ 8.59 (d, J = 4.8 Hz, 1H), 8.26 (m, 3H), 7.89-7.74 (m, 4H), 7.52-7.31 (m, 4H), 7.24-7.13 (m, 1H), 4.05 (d, J = 0.9 Hz, 2H). |
| 96C | F | 600 (M + H) | 182-185 | (300 MHz, CDCl$_3$) δ 8.58 (s, 1H), 8.33 (d, J = 7.9 Hz, 1H), 8.24 (s, 1H), 8.21 (s, 1H), 7.86-7.76 (m, 4H), 7.53 (t, J = 5.9 Hz, 3H), 7.44-7.29 (m, 8H), 3.80-3.73 (m, 1H), 3.59-3.51 (m, 1H). |
| 97C | F | 567 (M + H) | 234-236 | (CDCl$_3$) δ 8.57 (s, 1H), 8.37 (s, 1H), 8.23 (d, J = 8.4 Hz, 2H), 7.89-7.73 (m, 4H), 7.45-7.29 (m, 3H), 6.79 (dd, J = 8.2, 2.2 Hz, 1H), 6.70 (d, J = 1H), 6.57 (s, 1H), 3.96 (s, 2H), 2.98 (s, 6H) |
| 98C | F | 612 (M + H) | 225-226 | (CDCl$_3$) δ 8.55 (s, 1H), 8.29 (s, 1H), 8.21 (d, J = 8.4 Hz, 2H), 7.86-7.71 (m, 4H), 7.42-7.23 (m, 3H), 6.63 (d, J = 8.5 Hz, |

TABLE 4-continued

Analytical Data for Compounds in Table 3

| ID | Synthesis Method | MS | mp (° C.) | $^1$H NMR (δ)$^1$ |
|---|---|---|---|---|
| | | | | 2H), 4.07 (q, J = 7.0 Hz, 4H), 3.94 (s, 2H), 1.31 (t, J = 7.0 Hz, 6H) |
| 99C | F | 679 (M − H) | 230-231 | (CDCl$_3$) δ 8.58 (s, 1H), 8.32 (s, 1H), 8.23 (d, J = 8.4 Hz, 2H), 7.89-7.77 (m, 4H), 7.70 (d, J = 8.1 Hz, 2H), 7.40 (d, J = 8.3 Hz, 2H), 7.29-7.20 (m, 1H), 4.04 (s, 2H) |
| 100C | F | 602 (M + H) | 118-120 | (CDCl$_3$) δ 8.58 (s, 1H), 8.30 (s, 1H), 8.22 (d, J = 8.4 Hz, 2H), 7.93-7.70 (m, 4H), 7.39 (d, J = 9.0 Hz, 2H), 7.28 (t, 1H), 7.19 (d, J = 7.7 Hz, 2H), 4.01 (s, 2H), 2.21 (s, 6H). |
| 101C | F | 583 (M + H) | 106-107 | (CDCl$_3$) δ 8.60 (s, 1H), 8.32 (s, 1H), 8.23 (d, J = 8.4 Hz, 2H), 7.89-7.74 (m, 4H), 7.39 (d, J = 8.3 Hz, 2H), 6.56 (s, 1H), 4.01 (s, 2H), 3.94 (s, 3H), 2.32 (s, 3H), 2.16 (s, 3H) |
| 102C | F | 589 (M − H) | 123-126 | (CDCl$_3$) δ 8.27 (s, 1H), 7.95-7.71 (m, 5H), 7.60 (d, J = 1.3 Hz, 1H), 7.53-7.43 (m, 4H), 7.45-7.32 (m, 3H), 4.04 (s, 2H) |
| 103C | F | 551 (M + H) | 194-196 | (CDCl$_3$) δ 8.28 (s, 1H), 7.93 (dd, J = 5.4, 4.1 Hz, 3H), 7.78 (m, 4H), 7.36-7.23 (m, 3H), 7.19 (d, J = 7.6 Hz, 2H), 6.81 (d, J = 2.5 Hz, 1H), 4.00 (s, 2H), 2.21 (s, 6H) |
| 104C | F | 551 (M + H) | 100-102 | (CDCl$_3$) δ 8.27 (s, 1H), 8.16 (s, 1H), 8.03 (s, 1H), 7.80-7.71 (m, 4H), 7.57 (d, J = 8.3 Hz, 2H), 7.30 (dd, J = 28.7, 5.8 Hz, 3H), 7.19 (d, J = 7.6 Hz, 2H), 4.01 (s, 2H), 2.21 (s, 6H) |
| 105C | F | 586 (M + H) | 209-211 | (CDCl$_3$) δ 8.58 (s, 1H), 8.31 (s, 1H), 8.23 (d, J = 7.8 Hz, 2H), 7.82 (m, 4H), 7.39 (d, J = 8.0 Hz, 2H), 7.19 (s, 2H), 4.01 (s, 2H), 2.19 (s, 6H) |
| 106C | F | 558 (M + H) | 180-182 | (CDCl$_3$) δ 8.58 (s, 1H), 8.30 (s, 1H), 8.22 (d, J = 8.2 Hz, 2H), 7.81 (m, 4H), 7.58 (dd, J = 6.0, 3.3 Hz, 1H), 7.43 (ddd, J = 23.4, 11.3, 5.5 Hz, 5H), 4.02 (dd, J = 29.9, 17.4 Hz, 2H) |
| 107C | F | 596 (M + H) | 227-232 | (CDCl$_3$) δ 8.58 (s, 1H), 8.32 (s, 1H), 8.22 (dd, J = 10.0, 8.6 Hz, 4H), 7.82 (m, 4H), 7.49 (d, J = 8.5 Hz, 2H), 7.40 (d, J = 8.6 Hz, 2H), 4.42 (q, J = 7.1 Hz, 2H), 4.00 (s, 2H), 1.41 (t, J = 7.1 Hz, 3H) |
| 108C | F | 580 (M + H) | 167-171 | (CDCl$_3$) δ 8.58 (s, 1H), 8.28 (d, J = 15.0 Hz, 1H), 8.23 (d, J = 8.3 Hz, 2H), 7.87-7.76 (m, 4H), 7.53-7.30 (m, 5H), 7.18 (ddd, J = 7.8, 4.2, 1.2 Hz, 1H), 4.03-3.98 (m, 2H), 2.53 (dd, J = 14.1, 7.0 Hz, 1H), 1.77-1.56 (m, 2H), 1.26-1.16 (m, 3H), 0.78 (td, J = 7.4, 2.3 Hz, 3H). |
| 109C | F | 652 (M + H) | 105-111 | (CDCl$_3$) δ 8.25 (s, 1H), 7.73 (d, J = 7.4 Hz, 4H), 7.55-7.43 (m, 2H), 7.43-7.36 (m, 1H), 7.10 (t, J = 11.6 Hz, 4H), 4.90-4.79 (m, 1H), 4.04 (s, 2H), 3.76 (s, 3H), 3.73-3.62 (m, 1H), 3.52-3.35 (m, 1H) |
| 110C | F | 611 (M + H) | Oil | (CDCl$_3$) δ 8.25 (s, 1H), 7.82-7.64 (m, 4H), 7.30 (t, 1H), 7.22-6.99 (m, 6H), 4.83 (dd, J = 12.8, 6.5 Hz, 1H), 4.00 (s, 2H), 3.89-3.59 (m, 4H), 3.44 (dd, J = 17.2, 6.5 Hz, 1H), 2.20 (s, 6H). |
| 111C | F | 580 (M + H) | 209-210 | (CDCl$_3$) δ 8.58 (s, 1H), 8.30 (s, 1H), 8.23 (d, J = 8.4 Hz, 2H), 7.86-7.77 (m, 4H), 7.39 (t, J = 7.8 Hz, 3H), 7.34-7.27 (m, 1H), 7.20 (d, J = 7.4 Hz, 1H), 4.03 (s, 2H), 2.86-2.71 (m, 1H), 2.21 (s, 3H), 1.21 (2d, J = 6.7 Hz, 6H). |
| 112C | F | 564 (M + H) | 154-158 | (CDCl$_3$) δ 8.58 (s, 1H), 8.32 (s, 1H), 8.23 (d, J = 8.4 Hz, 2H), 7.87-7.75 (m, 4H), 7.43-7.33 (m, 4H), 7.26-7.19 (m, 2H), 4.02 (s, 2H), 1.86-1.77 (m, 1H), 0.90-0.83 (m, 2H), 0.77-0.68 (m, 1H), 0.67-0.59 (m, 1H). |
| 113C | F | 538 (M + H) | 111-116; 210-212 | (Acetone-D$_6$) δ 9.20 (s, 1H), 8.28 (d, J = 8.2 Hz, 3H), 8.13 (d, J = 9.0 Hz, 2H), 7.94 (d, J = 8.2 Hz, 2H), 7.60 (d, J = 8.8 Hz, 2H), |

TABLE 4-continued

Analytical Data for Compounds in Table 3

| ID | Synthesis Method | MS | mp (° C.) | $^1$H NMR (δ)$^1$ |
|---|---|---|---|---|
| | | | | 7.39 (t, J = 17.1 Hz, 4H), 4.15 (q, J = 17.3 Hz, 2H), 2.23 (s, 3H) |
| 114C | F | 568 (M + H) | 203-205 | (CDCl$_3$) δ 8.58 (s, 1H), 8.33 (s, 1H), 8.22 (d, J = 8.3 Hz, 2H), 7.88-7.67 (m, 4H), 7.38 (d, J = 8.4 Hz, 2H), 7.14 (d, J = 8.3 Hz, 1H), 6.87 (d, J = 8.9 Hz, 2H), 3.98 (s, 2H), 3.83 (s, 3H), 2.20 (s, 3H) |
| 115C | F | 554 (M + H) | 261-264 | (CDCl$_3$) δ 8.58 (s, 1H), 8.35 (s, 1H), 8.23 (d, J = 8.2 Hz, 2H), 7.82 (m, 4H), 7.40 (d, J = 8.6 Hz, 2H), 7.30 (d, 2H), 7.03 (d, J = 8.8 Hz, 2H), 3.97 (s, 2H), 3.86 (s, 3H) |
| 116C | F | 568 (M + H) | 92-97 | (CDCl$_3$) δ 8.58 (s, 1H), 8.31 (s, 1H), 8.22 (d, J = 8.3 Hz, 2H), 7.88-7.72 (m, 4H), 7.48-7.32 (m, 3H), 7.31-7.20 (m, 1H), 7.13-6.97 (m, 2H), 4.09 (q, J = 7.0 Hz, 2H), 3.95 (t, J = 11.7 Hz, 2H), 1.33 (t, J = 7.0 Hz, 3H) |
| 117C | F | 539 (M + H) | 127-132 | (CDCl$_3$) δ 8.59 (s, 1H), 8.54 (dd, J = 4.8, 1.3 Hz, 1H), 8.28 (s, 1H), 8.22 (d, J = 8.4 Hz, 2H), 7.84-7.77 (m, 4H), 7.77-7.72 (m, 1H), 7.38 (dd, J = 7.7, 5.0 Hz, 3H), 4.02 (d, J = 1.2 Hz, 2H), 2.30 (s, 3H) |
| 118C | F | 539 (M + H) | 215 (dec) | (CDCl$_3$) δ 8.67 (s, 1H), 8.59 (s, 1H), 8.24 (d, J = 8.4 Hz, 2H), 7.99 (d, J = 8.4 Hz, 1H), 7.84 (dd, J = 8.3, 3.8 Hz, 4H), 7.80 (s, 1H), 7.42-7.39 (m, 3H), 4.03 (d, J = 1.3 Hz, 2H), 2.26 (s, 3H). |
| 119C | F | 580 (M + H) | 124-138 | (CDCl$_3$) δ 8.58 (s, 1H), 8.29 (s, 1H), 8.23 (d, J = 8.4 Hz, 2H), 7.88-7.77 (m, 4H), 7.48-7.34 (m, 5H), 7.23-7.18 (m, 1H), 4.06-3.93 (m, 2H), 2.40 (qd, J = 14.2, 7.3 Hz, 2H), 1.94-1.81 (m, 1H), 0.89 (d, J = 6.6 Hz, 6H). |
| 120C | F | 549.7 (M + H) | 153-159 | (CDCl$_3$) δ 8.67 (s, 1H), 8.30 (s, 1H), 8.24 (d, J = 8.3 Hz, 2H), 7.92 (d, J = 8.5 Hz, 2H), 7.82 (m, 3H), 4.01 (d, J = 1.5 Hz, 2H), 3.80-3.64 (m, 2H), 2.91-2.76 (m, 2H), 1.30-1.14 (m, 6H) |
| 121C | F | 578 (M + H) | 143-147; 148-151 | (CDCl$_3$) δ 8.57 (d, J = 7.4 Hz, 1H), 8.30 (s, 1H), 8.23 (d, J = 8.4 Hz, 2H), 7.87-7.78 (m, 4H), 7.49-7.33 (m, 5H), 7.29-7.26 (m, 1H), 6.03 (s, 1H), 3.95 (s, 2H), 1.84 (d, J = 1.3 Hz, 3H), 1.71 (d, J = 1.2 Hz, 3H). |
| 122C | F | 579.3 (M + 1) | 169-171 | (CDCl3) δ 8.58 (s, 1H), 8.24-8.18 (m, 2H), 7.99-7.94 (m, 2H), 7.84-7.78 (m, 2H), 7.47 (dd, J = 5.0, 1.1 Hz, 2H), 7.40 (d, J = 8.3 Hz, 2H), 7.34 (ddd, J = 7.9, 5.1, 3.7 Hz, 1H), 7.18 (d, J = 7.6 Hz, 1H), 4.00 (d, J = 1.5 Hz, 2H), 3.72 (dd, J = 7.0, 5.1 Hz, 2H), 2.94-2.80 (m, 1H), 2.22 (s, 3H), 1.23 (m, 9H). |
| 123C | F | 553 (M + H) | 130-135 | (CDCl$_3$) δ 8.62 (s, 1H), 8.54 (d, J = 3.2 Hz, 1H), 8.28-8.19 (m, 3H), 7.82 (d, J = 8.8 Hz, 5H), 7.43-7.37 (m, 3H), 4.02 (s, 2H), 2.63 (d, J = 7.6 Hz, 2H), 1.22 (s, 3H) |
| 124C | F | 608 (M + H) | 140-145 | (CDCl$_3$) δ 8.58 (s, 1H), 8.29 (s, 1H), 8.23 (d, J = 8.4 Hz, 2H), 7.89-7.75 (m, 4H), 7.58-7.51 (m, 1H), 7.49-7.36 (m, 5H), 4.04 (d, J = 17.4 Hz, 1H), 3.97 (d, J = 17.4 Hz, 1H). |
| 125C | F | 580 (M + H) | 130-140 | (CDCl$_3$) δ 8.58 (s, 1H), 8.31 (s, 1H), 8.22 (d, J = 8.4 Hz, 2H), 7.86-7.78 (m, 4H), 7.65 (dd, J = 8.1, 1.4 Hz, 1H), 7.49-7.42 (m, 1H), 7.40 (d, J = 8.3 Hz, 2H), 7.35 (dt, J = 7.6, 1.5 Hz, 1H), 7.05 (dd, J = 7.8, 1.5 Hz, 1H), 3.95 (s, 2H), 1.38 (s, 9H). |
| 126C | F | 590 (M + H) | 175-177 | (CDCl$_3$) δ 8.58 (s, 1H), 8.29 (s, 1H), 8.23 (d, J = 8.4 Hz, 2H), 7.87-7.77 (m, 4H), 7.52 (ddd, J = 8.1, 6.0, 3.4 Hz, 1H), 7.44-7.34 (m, 5H), 6.46 (t, J$_{HF}$ = 73.5 Hz, 1H), 4.05-3.95 (m, 2H). |
| 127C | F | 578 (M + H) | 112-115 | (CDCl$_3$) δ 8.58 (s, 1H), 8.32 (s, 1H), 8.22 (d, J = 8.3 Hz, 2H), 7.87-7.75 (m, 4H), 7.43-7.32 (m, 4H), 7.26-7.24 (m, 2H), 4.23 (q, J = 7.3 Hz, 1H), 1.85-1.78 (m, |

TABLE 4-continued

Analytical Data for Compounds in Table 3

| ID | Synthesis Method | MS | mp (° C.) | $^1$H NMR (δ)$^1$ |
|---|---|---|---|---|
| | | | | 4H), 0.90-0.78 (m, 2H), 0.78-0.69 (m, 1H), 0.65-0.55 (m, 1H). |
| 128C | F | 580 (M + H) | 164-171 | (CDCl$_3$) δ 8.58 (s, 1H), 8.29 (d, J = 7.8 Hz, 1H), 8.22 (d, J = 8.3 Hz, 2H), 7.88-7.74 (m, 4H), 7.48-7.30 (m, 5H), 7.20 (t, J = 11.1 Hz, 1H), 4.26-4.14 (m, 1H), 2.50-2.46 (m, 2H), 1.79 (d, J = 7.3 Hz, 3H), 1.69-1.56 (m, 2H), 0.93 (t, J = 7.3 Hz, 3H). |
| 129C | F | 606 (M + H) | 140-142 | (CDCl$_3$) δ 8.58 (s, 1H), 8.30 (s, 1H), 8.22 (d, J = 8.4 Hz, 2H), 7.87-7.76 (m, 4H), 7.53-7.47 (m, 2H), 7.44-7.35 (m, 3H), 4.27 (q, J = 7.3 Hz, 1H), 1.82 (d, J = 7.3 Hz, 3H). |
| 130C | F | 590 (M + H) | 93-97; 191-194 | (CDCl$_3$) δ 8.58 (s, 1H), 8.31 (s, 1H), 8.22 (d, J = 8.4 Hz, 2H), 7.88-7.76 (m, 4H), 7.48-7.34 (m, 4H), 7.20 (tt, J = 12.4, 6.1 Hz, 1H), 4.35-4.18 (m, 1H), 1.81 (2d, J = 7.3 Hz, 3H). |
| 131C | F | 572 (M − H) | 93-98; 185-186 | (CDCl$_3$) δ 8.58 (s, 1H), 8.32 (s, 1H), 8.26-8.20 (m, 2H), 7.86-7.78 (m, 4H), 7.53-7.42 (m, 1H), 7.40 (d, J = 8.3 Hz, 2H), 7.09 (t, J = 8.1 Hz, 2H), 4.26 (q, J = 7.3 Hz, 1H), 1.80 (d, J = 7.3 Hz, 3H). |
| 132C | J | 552 (M + H) | 193-196 | (CDCl$_3$) δ 8.56 (s, 1H), 8.22 (s, 1H), 8.17 (d, J = 8.4 Hz, 2H), 7.80 (ddd, J = 9.5, 6.9, 4.9 Hz, 4H), 7.43-7.33 (m, 4H), 7.31-7.21 (m, 2H), 4.05 (td, J = 9.4, 7.1 Hz, 1H), 3.97-3.87 (m, 1H), 3.42-3.33 (m, 1H), 3.33-3.24 (m, 1H), 3.12 (heptet, J = 6.8 Hz, 1H), 1.27 (d, J = 6.8 Hz, 3H), 1.22 (d, J = 6.9 Hz, 3H). |
| 133C | J | 538 (M + H) | 167-169 | (CDCl$_3$) δ 8.55 (d, J = 7.1 Hz, 1H), 8.23 (s, 1H), 8.17 (d, J = 8.4 Hz, 2H), 7.80 (dt, J = 11.4, 6.2 Hz, 4H), 7.43-7.23 (m, 6H), 4.00 (s, 2H), 3.32 (s, 2H), 2.67 (q, J = 7.6 Hz, 2H), 1.25 (dd, J = 9.6, 5.5 Hz, 3H). |
| 134C | J | 536 (M + H) | 217-220; 230-232 | (CDCl$_3$) δ 8.65 (s, 1H), 8.22 (s, 1H), 8.18 (d, J = 8.4 Hz, 2H), 7.94-7.88 (m, 2H), 7.81-7.78 (m, 4H), 7.41 (dd, J = 7.8, 1.5 Hz, 1H), 7.39-7.33 (m, 1H), 7.30-7.24 (m, 1H), 7.23 (dd, J = 7.8, 1.5 Hz, 1H), 4.09-4.02 (m, 1H), 3.98-3.88 (m, 1H), 3.43-3.24 (m, 2H), 3.12 (heptet, J = 6.9 Hz, 1H), 1.27 (d, J = 6.8 Hz, 3H), 1.22 (d, J = 6.9 Hz, 3H). |
| 135C | J | 566 (M + H) | 167-169 | (CDCl$_3$) δ 8.56 (s, 1H), 8.19 (dd, J = 12.7, 9.0 Hz, 3H), 7.84-7.74 (m, 4H), 7.37 (dd, J = 14.9, 6.1 Hz, 4H), 7.26 (s, 1H), 7.21 (d, J = 7.6 Hz, 1H), 4.17-3.85 (m, 2H), 3.42-3.22 (m, 2H), 2.82 (d, J = 23.6 Hz, 1H), 1.80-1.55 (m, 2H), 1.23 (2d, J = 6.9 Hz, 3H), 0.82 (2t, J = 7.4 Hz, 3H). |
| 136C | J | 552 (M + H) | 143-147 | (CDCl$_3$) δ 8.56 (s, 1H), 8.22 (s, 1H), 8.17 (d, J = 8.4 Hz, 2H), 7.84-7.74 (m, 4H), 7.39 (d, J = 8.3 Hz, 2H), 7.24 (d, J = 7.5 Hz, 1H), 7.19 (d, J = 6.4 Hz, 1H), 7.15 (d, J = 7.3 Hz, 1H), 3.92 (qt, J = 10.1, 7.3 Hz, 2H), 3.43-3.28 (m, 2H), 2.72-2.51 (m, 2H), 2.27 (s, 3H), 1.25 (t, J = 7.6 Hz, 3H). |
| 137C | J | 554 (M + H) | 183-186 | (CDCl$_3$) δ 8.56 (d, J = 5.3 Hz, 1H), 8.26 (s, 1H), 8.17 (d, J = 8.4 Hz, 2H), 7.84-7.74 (m, 4H), 7.39 (d, J = 8.3 Hz, 2H), 7.18 (d, J = 8.5 Hz, 1H), 6.81 (dt, J = 8.4, 2.9 Hz, 2H), 3.96 (t, J = 6.6 Hz, 2H), 3.81 (s, 3H), 3.30 (t, J = 6.9 Hz, 2H), 2.28 (s, 3H). |
| 138C | J | 568 (M + H) | 231-233 | (CDCl$_3$) δ 8.56 (d, J = 5.4 Hz, 1H), 8.25 (s, 1H), 8.17 (d, J = 8.4 Hz, 2H), 7.84-7.72 (m, 4H), 7.39 (d, J = 8.3 Hz, 2H), 6.67 (s, 2H), 3.92-3.85 (m, 2H), 3.79 (s, 3H), 3.34 (t, J = 7.1 Hz, 2H), 2.25 (s, 6H). |
| 139C | J | 552 (M + H) | 195-197 | (CDCl$_3$) δ 8.56 (s, 1H), 8.24 (s, 1H), 8.17 (d, J = 8.3 Hz, 2H), 7.83-7.73 (m, 4H), 7.39 (d, J = 8.3 Hz, 2H), 6.95 (s, 2H), 3.90 (t, J = 7.1 Hz, 2H), 3.35 (t, J = 7.1 Hz, 2H), 2.30 (s, 3H), 2.23 (s, 6H). |

TABLE 4-continued

Analytical Data for Compounds in Table 3

| ID | Synthesis Method | MS | mp (° C.) | ¹H NMR (δ)[1] |
|---|---|---|---|---|
| 140C | J | 540 (M + H) | 181-184 | (CDCl₃) δ 8.56 (s, 1H), 8.24 (s, 1H), 8.17 (d, J = 8.3 Hz, 2H), 7.84-7.75 (m, 4H), 7.43-7.36 (m, 3H), 7.30 (ddd, J = 12.6, 6.9, 3.1 Hz, 1H), 7.06-6.97 (m, 2H), 4.04 (t, J = 7.0 Hz, 2H), 3.86 (s, 3H), 3.29 (t, J = 7.0 Hz, 2H). |
| 141C | J | 524 (M + H) | 173-176 | (CDCl₃) δ 8.56 (s, 1H), 8.25 (s, 1H), 8.18 (d, J = 8.4 Hz, 2H), 7.83-7.75 (m, 4H), 7.39 (d, J = 8.3 Hz, 2H), 7.34-7.23 (m, 4H), 4.01 (t, J = 6.9 Hz, 2H), 3.32 (t, J = 6.9 Hz, 2H), 2.31 (s, 3H). |
| 142C | J | 538 (M + H) | 210-213 | (CDCl₃) δ 8.56 (s, 1H), 8.23 (s, 1H), 8.17 (d, J = 8.4 Hz, 2H), 7.84-7.74 (m, 4H), 7.39 (d, J = 8.3 Hz, 2H), 7.22-7.10 (m, 3H), 3.92 (t, J = 7.1 Hz, 2H), 3.36 (t, J = 7.1 Hz, 2H), 2.28 (s, 6H). |
| 143C | J | 562 (M + H) | 221-224 | (CDCl₃) δ 8.56 (s, 1H), 8.23 (s, 1H), 8.18 (d, J = 8.4 Hz, 2H), 7.83-7.74 (m, 4H), 7.38 (d, J = 8.3 Hz, 2H), 7.30 (dt, J = 7.4, 4.8 Hz, 2H), 7.15-7.09 (m, 1H), 4.05 (ddd, J = 9.4, 7.3, 5.2 Hz, 1H), 4.00-3.89 (m, 1H), 3.46-3.30 (m, 2H). |
| 144C | J | 586 (M + H) | 117-123; 134-138 | (300 MHz, CDCl₃) δ 8.56 (d, J = 4.3 Hz, 1H), 8.34 (s, 1H), 8.21 (s, 1H), 8.18 (s, 1H), 7.81 (dd, J = 8.9, 2.3 Hz, 4H), 7.52 (d, J = 6.7 Hz, 1H), 7.50-7.31 (m, 10H), 3.53-3.49 (m, 2H), 2.95-2.90 (d, J = 6.8 Hz, 2H). |
| 145C | J | 550 (M + H) | 207-209 | (CDCl₃) δ 8.56 (s, 1H), 8.26 (s, 1H), 8.18 (d, J = 8.3 Hz, 2H), 7.84-7.74 (m, 4H), 7.39 (d, J = 8.3 Hz, 2H), 7.32-7.21 (m, 3H), 7.01 (dd, J = 8.9, 2.5 Hz, 1H), 4.12-4.04 (s, 2H), 3.34 (t, J = 6.9 Hz, 2H), 2.09-1.98 (m, 1H), 0.95 (dd, J = 8.5, 1.7 Hz, 2H), 0.72 (bs, 2H). |
| 146C | J | 554 (M + H) | 141-144 | (CDCl₃) δ 8.56 (d, J = 5.2 Hz, 1H), 8.24 (s, 1H), 8.17 (d, J = 8.3 Hz, 2H), 7.80 (dt, J = 8.2, 4.6 Hz, 4H), 7.45-7.36 (m, 3H), 7.30-7.24 (m, 1H), 7.05-6.95 (m, 2H), 4.13-4.02 (m, 4H), 3.28 (t, J = 7.0 Hz, 2H), 1.44-1.35 (m, 3H). |
| 147C | J | 540 (M + H) | 168-170 | (CDCl₃) δ 8.57 (s, 1H), 8.37 (s, 1H), 8.21 (d, J = 8.3 Hz, 2H), 7.87-7.76 (m, 4H), 7.40 (d, J = 8.4 Hz, 2H), 7.29 (dd, J = 14.2, 6.0 Hz, 1H), 7.24 (d, J = 2.3 Hz, 1H), 7.09-7.02 (m, 1H), 6.72 (dd, J = 8.0, 2.1 Hz, 1H), 4.20 (t, J = 6.9 Hz, 2H), 3.83 (d, J = 8.7 Hz, 3H), 3.24 (t, J = 6.9 Hz, 2H). |
| 148C | J | 546 (M + H) | 213-216 | (CDCl₃) δ 8.56 (s, 1H), 8.24 (s, 1H), 8.18 (d, J = 8.3 Hz, 2H), 7.80 (dt, J = 4.0, 2.5 Hz, 4H), 7.39 (d, J = 8.3 Hz, 2H), 7.30 (ddd, J = 8.5, 7.4, 4.2 Hz, 1H), 7.05-6.97 (m, 2H), 4.02 (t, J = 6.9 Hz, 2H), 3.36 (t, J = 6.9 Hz, 2H). |
| 149C | J | 612 (M + H) | 200-203 | (CDCl₃) δ 8.56 (s, 1H), 8.18 (d, J = 2.6 Hz, 2H), 8.16 (s, 1H), 7.80 (dt, J = 8.3, 4.7 Hz, 4H), 7.71 (t, J = 8.6 Hz, 2H), 7.47 (t, J = 7.7 Hz, 1H), 7.39 (d, J = 8.3 Hz, 2H), 4.18-4.07 (m, 1H), 3.93-3.84 (m, 1H), 3.46 (td, J = 10.7, 7.3 Hz, 1H), 3.35-3.25 (m, 1H). |
| 150C | J | 566 (M + H) | 169-172 | (CDCl₃) δ 8.56 (s, 1H), 8.22 (s, 1H), 8.17 (d, J = 8.4 Hz, 2H), 7.80 (dt, J = 11.5, 6.2 Hz, 4H), 7.39 (d, J = 8.3 Hz, 2H), 7.31-7.27 (m, 3H), 7.26-7.24 (m, 1H), 4.10-3.89 (m, 2H), 3.38-3.32 (m, 2H), 2.48 (s, 2H), 2.01-1.84 (m, 1H), 0.91 (d, J = 6.2 Hz, 6H). |
| 151C | J | 564 (M + H) | 149-153 | (CDCl₃) δ 8.57 (s, 1H), 8.25 (s, 1H), 8.18 (d, J = 8.3 Hz, 2H), 7.99 (s, 1H), 7.81 (dt, J = 8.3, 4.5 Hz, 4H), 7.39 (dd, J = 6.1, 3.5 Hz, 3H), 7.33-7.27 (m, 2H), 6.21 (s, 1H), 3.92 (t, J = 6.9 Hz, 2H), 3.26 (t, J = 6.8 Hz, 2H), 1.89 (d, J = 1.1 Hz, 3H), 1.79 (d, J = 1.1 Hz, 3H). |

TABLE 4-continued

Analytical Data for Compounds in Table 3

| ID | Synthesis Method | MS | mp (° C.) | ¹H NMR (δ)¹ |
|---|---|---|---|---|
| 152C | J | 576 (M + H) | 161-163 | (CDCl₃) δ 8.57 (s, 1H), 8.23-8.16 (m, 3H), 7.83-7.77 (m, 4H), 7.48 (dd, J = 7.5, 2.0 Hz, 1H), 7.39 (d, J = 8.3 Hz, 2H), 7.33 (dt, J = 7.2, 2.1 Hz, 2H), 7.28 (dd, J = 9.8, 1.9 Hz, 1H), 6.52 (t, $J_{HF}$ = 74.1 Hz, 1H), 4.06 (t, J = 6.9 Hz, 2H), 3.33 (t, J = 6.9 Hz, 2H). |
| 153C | J | 594 (M + H) | 195-197 | (CDCl₃) δ 8.57 (s, 1H), 8.25 (s, 1H), 8.19 (d, J = 8.4 Hz, 2H), 7.81 (dt, J = 4.1, 2.6 Hz, 4H), 7.58-7.52 (m, 1H), 7.42-7.33 (m, 5H), 4.05 (t, J = 6.9 Hz, 2H), 3.31 (t, J = 6.9 Hz, 2H). |
| 154C | J | 538 (M + H) | 164-167 | CDCl₃) δ 8.56 (s, 1H), 8.23 (d, J = 9.8 Hz, 1H), 8.17 (d, J = 8.3 Hz, 2H), 7.84-7.74 (m, 4H), 7.39 (d, J = 8.3 Hz, 2H), 7.35-7.27 (m, 3H), 7.19 (s, 1H), 3.54-3.31 (m, 1H), 3.07-2.93 (m, 1H), 2.31 (d, J = 9.0 Hz, 3H), 1.62-1.56 (m, 1H), 1.31-1.19 (m, 3H). |
| 155C | J | 566 (M + H) | 201-204 | Two Isomers (CDCl₃) δ 8.56 (s, 2H), 8.18 (dd, J = 10.8, 7.4 Hz, 6H), 7.84-7.73 (m, 8H), 7.45-7.30 (m, 8H), 7.30-7.23 (m, 2H), 7.20 (d, J = 6.7 Hz, 1H), 7.12 (dd, J = 7.8, 1.2 Hz, 1H), 4.43-4.33 (m, 1H), 4.16 (dd, J = 12.6, 6.3 Hz, 1H), 3.48 (dt, J = 13.3, 6.7 Hz, 1H), 3.37 (dd, J = 10.8, 6.2 Hz, 1H), 3.24 (dt, J = 13.7, 6.9 Hz, 1H), 3.08-2.92 (m, 3H), 1.33-1.16 (m, 18H). |
| 156C | J | 566 (M + H) | 105-110 | (CDCl₃) δ 8.56 (s, 1H), 8.20 (d, J = 3.4 Hz, 1H), 8.16 (d, J = 8.4 Hz, 2H), 7.84-7.73 (m, 4H), 7.39 (d, J = 8.3 Hz, 2H), 7.25-7.09 (m, 3H), 4.39-4.23 (m, 1H), 3.53-3.35 (m, 1H), 3.04-3.00 (m, 1H), 2.78-2.49 (m, 2H), 2.28 (2s, 3H), 1.34-1.08 (m, 6H). |
| 157C | J | 592 (M + H) | 175-176 | (CDCl₃) δ 8.56 (d, J = 0.6 Hz, 1H), 8.21 (s, 1H), 8.17 (d, J = 8.2 Hz, 2H), 7.82-7.77 (m, 4H), 7.49-7.35 (m, 4H), 7.30-7.28 (m, 1H), 4.64-4.57 (m, 1H), 3.44 (dd, J = 10.2, 6.3 Hz, 1H), 3.16-3.01 (m, 1H), 1.27 (d, J = 6.3 Hz, 3H). |
| 158C | J | 572 (M + H) | 99-102 | Two Isomers (CDCl₃) δ 8.56 (s, 2H), 8.20 (s, 2H), 8.19-8.12 (m, 4H), 7.84-7.73 (m, 8H), 7.39 (d, J = 8.3 Hz, 4H), 7.36-7.29 (m, 2H), 7.25-7.17 (m, 4H), 4.78-4.55 (m, 1H), 4.35 (dt, J = 9.4, 6.3 Hz, 1H), 3.48 (dd, J = 10.7, 6.5 Hz, 1H), 3.38 (dd, J = 10.7, 6.2 Hz, 1H), 3.11 (dd, J = 10.7, 9.4 Hz, 1H), 3.01 (dd, J = 10.7, 8.3 Hz, 1H), 2.35 (s, 3H), 2.30 (s, 3H), 1.26 (d, J = 6.3 Hz, 3H), 1.21 (d, J = 6.4 Hz, 3H) |
| 159C | J | 607 (M + H) | 85 (dec) | (CDCl₃) δ 8.56 (s, 1H), 8.18 (dd, J = 11.9, 5.3 Hz, 3H), 7.79 (dd, J = 8.7, 6.5 Hz, 4H), 7.47 (dd, J = 7.8, 2.3 Hz, 1H), 7.42-7.32 (m, 5H), 4.48-4.29 (m, 1H), 3.45 (dd, J = 10.7, 6.4 Hz, 1H), 2.98 (dd, J = 10.7, 7.1 Hz, 1H), 1.26 (d, J = 6.3 Hz, 3H) |
| 160C | J | 626 (M + H) | 93 (dec) | Two Isomers (CDCl3) δ 8.56 (s, 2H), 8.19-8.12 (m, 6H), 7.84-7.73 (m, 10H), 7.71 (d, J = 8.2 Hz, 2H), 7.47 (t, J = 8.0 Hz, 2H), 7.39 (d, J = 8.3 Hz, 4H), 4.76-4.64 (m, 1H), 4.48 (dd, J = 14.6, 6.3 Hz, 1H), 3.43 (dd, J = 10.6, 6.2 Hz, 1H), 3.29 (dd, J = 10.5, 5.5 Hz, 1H), 3.16-3.00 (m, 2H), 1.27 (d, J = 6.4 Hz, 3H), 1.17 (d, J = 6.4 Hz, 3H) |
| 161C | J | 566 (M + H) | 105 (dec) | (CDCl₃) δ 8.56 (s, 1H), 8.22 (s, 1H), 8.16 (d, J = 8.4 Hz, 2H), 7.83-7.70 (m, 4H), 7.39 (d, J = 8.3 Hz, 2H), 6.94 (d, J = 9.3 Hz, 2H), 4.43-4.22 (m, 1H), 3.42 (dd, J = 10.8, 6.5 Hz, 1H), 3.00 (dd, J = 10.8, 8.5 Hz, 1H), 2.30 (s, 3H), 2.25 (s, 3H), 2.21 (s, 3H), 1.20 (d, J = 6.3 Hz, 3H) |
| 162C | J | 568 (M + H) | 100 (dec) | (CDCl₃) δ 8.56 (s, 1H), 8.24 (s, 1H), 8.17 (d, J = 8.4 Hz, 2H), 7.83-7.73 (m, 4H), 7.39 (d, J = 8.3 Hz, 2H), 7.18-7.09 (m, 1H), 6.86-6.76 (m, 2H), 4.33-4.19 (m, |

TABLE 4-continued

Analytical Data for Compounds in Table 3

| ID | Synthesis Method | MS | mp (° C.) | $^1$H NMR (δ)$^1$ |
|---|---|---|---|---|
| | | | | 1H), 3.82 (s, 3H), 3.47-3.38 (m, 1H), 3.00-2.99 (m, 1H), 2.29-2.27 (m, 3H), 1.33-1.15 (m, 3H) |
| 163C | J | 580 (M + H) | 92-102 | (CDCl$_3$) δ 8.56 (s, 2H), 8.18 (dd, J = 10.7, 5.3 Hz, 6H), 7.84-7.74 (m, 8H), 7.42-7.30 (m, 8H), 7.23-7.10 (m, 2H), 4.37 (dd, J = 19.5, 13.6 Hz, 1H), 4.16 (dd, J = 13.1, 6.6 Hz, 1H), 3.56-3.42 (m, 1H), 3.34 (dd, J = 10.8, 6.0 Hz, 1H), 3.08-2.87 (m, 3H), 2.70 (dd, J = 16.0, 7.0 Hz, 1H), 1.71-1.56 (m, 4H), 1.34-1.25 (m, 6H), 1.24-1.14 (m, 6H), 0.93-0.73 (m, 6H) |
| 164C | J | 589 (M + H) | 80 (dec) | (CDCl$_3$) δ 8.56 (s, 1H), 8.22-8.14 (m, 3H), 7.84-7.76 (m, 4H), 7.42-7.27 (m, 6H), 6.51 (t, J$_{HF}$ = 74.3 Hz, 1H), 4.52-4.31 (m, 1H), 3.44 (dd, J = 10.8, 6.5 Hz, 1H), 2.99 (dd, J = 10.8, 7.6 Hz, 1H), 1.25 (d, J = 6.3 Hz, 3H) |
| 165C | J | 580 (M + H) | 143 (dec) | Two Isomers (CDCl$_3$) δ 8.56 (s, 2H), 8.22 (s, 1H), 8.20 (s, 1H), 8.16 (d, J = 8.3 Hz, 4H), 7.84-7.74 (m, 8H), 7.58 (ddd, J = 9.7, 8.0, 1.7 Hz, 2H), 7.39 (d, J = 8.4 Hz, 4H), 7.36-7.27 (m, 4H), 7.15 (dd, J = 7.7, 1.6 Hz, 1H), 7.09 (dd, J = 7.6, 1.7 Hz, 1H), 4.38-4.22 (m, 2H), 3.61 (dd, J = 10.8, 7.0 Hz, 1H), 3.24 (dd, J = 10.7, 5.6 Hz, 1H), 3.07-2.94 (m, 1H), 2.91 (dd, J = 10.8, 1.5 Hz, 1H), 1.47-1.38 (m, 24H) |
| 166C | J | 552 (M + H) | 93 (dec) | (CDCl$_3$) δ 8.56 (s, 1H), 8.21 (s, 1H), 8.16 (d, J = 8.4 Hz, 2H), 7.84-7.73 (m, 4H), 7.39 (d, J = 8.3 Hz, 2H), 7.32-7.28 (m, 3H), 7.20 (s, 1H), 4.20-4.06 (m, 1H), 3.41 (s, 1H), 3.05 (dd, J = 10.8, 8.2 Hz, 1H), 2.31-32.30 (m, 3H), 1.66 (s, 2H), 0.90-0.88 (m, 3H) |
| 167C | J | 586 (M + H) | 105 (dec) | Two Isomers (CDCl$_3$) δ 8.56 (s, 2H), 8.20 (s, 2H), 8.16 (d, J = 8.3 Hz, 4H), 7.83-7.74 (m, 8H), 7.43-7.28 (m, 6H), 7.21 (dd, J = 5.4, 3.3 Hz, 4H), 4.49-4.36 (m, 1H), 4.17-4.05 (m, 1H), 3.49 (dd, J = 10.7, 6.6 Hz, 1H), 3.40 (dd, J = 10.7, 6.3 Hz, 1H), 3.10 (dd, J = 10.7, 9.4 Hz, 1H), 3.04 (dd, J = 10.8, 8.2 Hz, 1H), 2.34 (s, 3H), 2.30 (s, 3H), 1.73-1.48 (m, 4H), 0.91 (m, 6H) |
| 168C | J | 560 (M + H) | 199-200 | (CDCl$_3$) δ 8.56 (s, 1H), 8.18 (m,, 2H), 7.79 (m, 4H), 7.47 (dd, J = 7.8, 2.3 Hz, 1H), 7.42-7.32 (m, 5H), 4.48-4.29 (m, 1H), 3.45 (dd, J = 10.7, 6.4 Hz, 1H), 2.98 (dd, J = 10.7, 7.1 Hz, 1H), 1.26 (d, J = 6.3 Hz, 3H) |
| 169C | G | 623 (M + H) | Oil | (CDCl$_3$) δ 10.45 (s, 1H), 8.59 (s, 1H), 8.25 (d, J = 8.3 Hz, 2H), 7.88 (d, J = 8.3 Hz, 2H), 7.81 (d, J = 8.9 Hz, 2H), 7.61 (t, J = 7.5 Hz, 2H), 7.40 (d, J = 8.7 Hz, 2H), 7.11 (t, J = 8.0 Hz, 1H), 5.71 (d, J = 1.1 Hz, 1H), 2.35 (s, 3H) $^{19}$F NMR (376 MHz, CDCl$_3$) δ −58.02, −62.31 |
| 170C | G | 606 (M + H) | 157-159 | (CDCl$_3$) δ 8.56 (s, 1H), 8.19-8.14 (m, 3H), 7.79 (m, 4H), 7.56-7.46 (m, 2H), 7.46-7.43 (m, 2H), 7.39 (d, J = 8.3 Hz, 2H), 5.88 (d, J = 1.3 Hz, 1H), 1.86 (d, J = 1.2 Hz, 3H) |
| 171C | G | 558 (M + H) | 236-237 | (CDCl$_3$) δ 8.56 (s, 1H), 8.19 (d, J = 5.9 Hz, 2H), 8.16 (s, 1H), 7.83-7.76 (m, 4H), 7.45 (tt, J = 8.4, 6.1 Hz, 1H), 7.39 (d, J = 8.3 Hz, 2H), 7.10 (dd, J = 8.5, 7.3 Hz, 2H), 5.90 (d, J = 1.3 Hz, 1H), 1.92 (s, 3H) |
| 172C | G | 580 (M + H) | 103-108 | (CDCl$_3$) δ 8.56 (d, J = 3.7 Hz, 1H), 8.21 (s, 1H), 8.16 (d, J = 8.4 Hz, 2H), 7.84-7.72 (m, 4H), 7.39 (d, J = 8.3 Hz, 2H), 6.72 (s, 2H), 5.89 (d, J = 1.3 Hz, 1H), 3.82 (s, 3H), 2.14 (s, 6H), 1.75 (d, J = 1.2 Hz, 3H). |
| 173C | G | 536 (M + H) | 87 (dec) | (CDCl$_3$) δ 8.56 (s, 1H), 8.19-8.15 (m, 3H), 7.82-7.75 (m, 4H), 7.43-7.30 (m, 5H), 7.24 (d, J = 7.3 Hz, 1H), 5.88 (s, 1H), 2.21 (s, 3H), 1.80 (d, J = 1.2 Hz, 3H) |

TABLE 4-continued

Analytical Data for Compounds in Table 3

| ID | Synthesis Method | MS | mp (° C.) | $^1$H NMR (δ)$^1$ |
|---|---|---|---|---|
| 174C | G | 570 (M + H) | 95 (dec) | (CDCl$_3$) δ 8.56 (s, 1H), 8.20-8.12 (m, 3H), 7.83-7.74 (m, 4H), 7.43-7.36 (m, 3H), 7.32 (t, J = 7.7 Hz, 1H), 7.29-7.27 (m, 1H), 5.92 (d, J = 1.3 Hz, 1H), 2.26 (s, 3H), 1.81 (d, J = 1.2 Hz, 3H) |
| 175C | G | 550 (M + H) | 132-136 | (CDCl$_3$) δ 8.56 (d, J = 5.0 Hz, 1H), 8.21-8.13 (m, 3H), 7.83-7.74 (m, 4H), 7.39 (d, J = 8.2 Hz, 2H), 7.29-7.23 (m, 1H), 7.19 (d, J = 7.7 Hz, 2H), 5.92 (d, J = 1.3 Hz, 1H), 2.18 (s, 6H), 1.75 (d, J = 1.2 Hz, 3H). |
| 176C | G | 564 (M + H) | 123-138 | (CDCl$_3$) δ 8.56 (s, 1H), 8.19-8.14 (m, 3H), 7.83-7.75 (m, 4H), 7.49-7.43 (m, 2H), 7.39 (d, J = 8.3 Hz, 2H), 7.33 (ddd, J = 7.8, 5.9, 3.0 Hz, 1H), 7.19-7.17 (m, 1H), 5.88 (d, J = 1.3 Hz, 1H), 2.96-2.76 (m, 1H), 1.81 (d, J = 1.2 Hz, 3H), 1.24 (t, J = 6.4 Hz, 3H), 1.22-1.16 (m, 3H). |
| 177C | J | 566 (M + H) | 185-187 | (CDCl$_3$) δ 8.55 (s, 1H), 8.14 (d, J = 8.4 Hz, 2H), 8.05 (s, 1H), 7.84-7.77 (m, 2H), 7.74 (d, J = 8.3 Hz, 2H), 7.42-7.35 (m, 3H), 7.32 (dd, J = 10.6, 4.3 Hz, 1H), 7.28-7.24 (m, 1H), 7.18 (dd, J = 7.8, 1.4 Hz, 1H), 3.80-3.69 (m, 1H), 3.59-3.48 (m, 1H), 3.11 (dd, J = 13.2, 6.8 Hz, 3H), 2.41-2.27 (m, 2H), 1.22 (t, J = 5.6 Hz, 6H). |
| 178C | J | 580 (M + H) | 186-190 | (CDCl$_3$) δ 8.55 (d, J = 3.6 Hz, 1H), 8.14 (d, J = 8.4 Hz, 2H), 8.06 (s, 1H), 7.84-7.77 (m, 2H), 7.74 (d, J = 8.4 Hz, 2H), 7.38 (d, J = 9.0 Hz, 3H), 7.32 (td, J = 7.5, 1.4 Hz, 1H), 7.26 (s, 1H), 7.17 (t, J = 7.1 Hz, 1H), 3.69-3.26 (m, 1H), 3.55-3.37 (m, 1H), 3.18-2.98 (m, 2H), 2.93-2.80 (m, 1H), 2.47 (d, J = 35.9 Hz, 1H), 1.31-1.12 (m, 9H). |
| 179C | J | 550 (M + H) | 212-213 | (CDCl$_3$) δ 8.64 (s, 1H), 8.15 (d, J = 8.4 Hz, 2H), 8.06 (s, 1H), 7.91 (d, J = 8.5 Hz, 2H), 7.79 (d, J = 8.6 Hz, 2H), 7.75 (d, J = 8.4 Hz, 2H), 7.38 (dd, J = 7.8, 1.6 Hz, 1H), 7.33 (td, J = 7.5, 1.4 Hz, 1H), 7.29-7.23 (m, 1H), 7.18 (dd, J = 7.8, 1.4 Hz, 1H), 3.78-3.72 (m, 1H), 3.59-3.48 (m, 1H), 3.18-3.04 (m, 3H), 2.40-2.30 (m, 2H), 1.26-1.20 (m, 6H). |
| 180C | J | 566 (M + H) | 127-133 | (300 MHz, CDCl$_3$) δ 8.55 (s, 1H), 8.13 (d, J = 8.3 Hz, 2H), 8.05 (s, 1H), 7.76 (dd, J = 17.0, 8.7 Hz, 4H), 7.37 (t, J = 8.4 Hz, 2H), 7.18 (dd, J = 12.7, 9.6 Hz, 3H), 3.54-3.49 (m, 2H), 3.12-3.08 (m, 2H), 2.70-2.55 (m, 2H), 2.39-2.31 (m, 2H), 2.28 (s, 3H), 1.25 (t, J = 7.6 Hz, 3H). |
| 181C | J | 582 (M + H) | 170-174 | (CDCl$_3$) δ 8.55 (s, 1H), 8.14 (d, J = 8.3 Hz, 2H), 8.08 (s, 1H), 7.84-7.76 (m, 2H), 7.74 (d, J = 8.3 Hz, 2H), 7.38 (d, J = 8.3 Hz, 2H), 6.65 (s, 2H), 3.79 (s, 3H), 3.52-3.45 (m, 2H), 3.10-3.07 (m, 2H), 2.38-2.31 (d, J = 5.7 Hz, 2H), 2.25 (s, 6H). |
| 182C | J | 552 (M + H) | 148-155; 166-168 | (300 MHz, CDCl$_3$) δ 8.55 (d, J = 1.0 Hz, 1H), 8.14 (d, J = 8.4 Hz, 2H), 8.05 (s, 1H), 7.83-7.76 (m, 2H), 7.74 (d, J = 8.4 Hz, 2H), 7.38 (d, J = 9.0 Hz, 2H), 7.14-7.09 (m, 3H), 3.51 (dd, J = 9.1, 3.5 Hz, 2H), 3.15-3.03 (m, 2H), 2.36 (s, 2H), 2.28 (s, 6H). |
| 183C | J | 580 (M + H) | 159-162 | (CDCl$_3$) δ 8.55 (d, J = 3.7 Hz, 1H), 8.14 (d, J = 8.4 Hz, 2H), 8.03 (d, J = 19.3 Hz, 1H), 7.84-7.77 (m, 2H), 7.74 (d, J = 8.4 Hz, 2H), 7.38 (d, J = 8.3 Hz, 2H), 7.32 (d, J = 3.8 Hz, 2H), 7.25 (d, J = 6.6 Hz, 1H), 7.19 (t, J = 8.0 Hz, 1H), 3.76 (ddd, J = 24.2, 12.0, 5.9 Hz, 1H), 3.58-3.46 (m, 1H), 3.11 (dd, J = 15.3, 6.1 Hz, 2H), 2.82 (dd, J = 14.6, 7.2 Hz, 1H), 2.41-2.29 (m, 2H), 1.71-1.55 (m, 2H), 1.20 (d, J = 6.8 Hz, 3H), 0.87-0.76 (m, 3H). |
| 184C | J | 566 (M + H) | 194-198 | (CDCl$_3$) δ 8.55 (s, 1H), 8.14 (d, J = 8.4 Hz, 2H), 8.07 (s, 1H), 7.83-7.76 (m, 2H), 7.74 (d, J = 8.4 Hz, 2H), 7.40 (t, J = 10.1 Hz, |

TABLE 4-continued

Analytical Data for Compounds in Table 3

| ID | Synthesis Method | MS | mp (° C.) | ¹H NMR (δ)¹ |
|---|---|---|---|---|
| | | | | 2H), 6.93 (s, 2H), 3.53-3.47 (m, 2H), 3.12-3.05 (m, 2H), 2.34 (dt, J = 11.7, 5.8 Hz, 2H), 2.30 (s, 3H), 2.23 (s, 6H). |
| 185C | J | 552 (M + H) | 157-160 | (CDCl₃) δ 8.55 (s, 1H), 8.14 (d, J = 8.4 Hz, 2H), 8.06 (s, 1H), 7.83-7.77 (m, 2H), 7.74 (d, J = 8.3 Hz, 2H), 7.38 (d, J = 8.3 Hz, 2H), 7.36-7.27 (m, 3H), 7.23-7.19 (m, 1H), 3.74 (m, 1H), 3.50 (m, 1H), 3.10 (d, J = 5.9 Hz, 2H), 2.64 (q, J = 7.6 Hz, 2H), 2.40-2.29 (m, 2H), 1.28-1.21 (m, 3H). |
| 186C | J | 564 (M + H) | 173-177 | (CDCl₃) δ 8.55 (s, 1H), 8.14 (d, J = 8.4 Hz, 2H), 8.09 (s, 1H), 7.83-7.77 (m, 2H), 7.81-7.77 (m, 2H), 7.38 (d, J = 8.3 Hz, 2H), 7.24-7.22 (m, 3H), 7.05-6.95 (m, 1H), 3.77-3.63 (m, 2H), 3.14-3.07 (m, 2H), 2.45-2.29 (m, 2H), 2.09-1.92 (m, 1H), 0.97-0.82 (m, 3H), 0.53 (bs, 1H). |
| 187C | J | 593 (M + H) | 180-182 | (300 MHz, CDCl₃) δ 8.55 (s, 1H), 8.14 (d, J = 8.4 Hz, 2H), 8.05 (d, J = 4.9 Hz, 1H), 7.77 (dd, J = 11.4, 8.6 Hz, 4H), 7.39 (t, J = 8.1 Hz, 4H), 7.21 (dd, J = 13.2, 5.6 Hz, 1H), 3.65-3.58 (m, 2H), 3.09 (t, J = 5.5 Hz, 2H), 2.45-2.35 (m, 2H). |
| 188C | J | 576 (M + H) | 209-212 | (CDCl₃) δ 8.56 (s, 1H), 8.15 (d, J = 8.4 Hz, 2H), 8.07 (s, 1H), 7.79 (ddd, J = 15.8, 7.8, 5.8 Hz, 4H), 7.38 (d, J = 8.3 Hz, 2H), 7.31-7.21 (m, 2H), 7.10 (ddd, J = 9.7, 7.8, 2.0 Hz, 1H), 3.64 (t, J = 5.4 Hz, 2H), 3.11 (t, J = 6.0 Hz, 2H), 2.46-2.33 (m, 2H). |
| 189C | J | 560 (M + H) | 217-219 | (CDCl₃) δ 8.56 (s, 1H), 8.15 (d, J = 8.4 Hz, 2H), 8.08 (s, 1H), 7.83-7.74 (m, 4H), 7.38 (d, J = 8.3 Hz, 2H), 7.31-7.21 (m, 1H), 7.03-6.94 (m, 2H), 3.72-3.62 (m, 2H), 3.15-3.07 (m, 2H), 2.40-2.34 (m, 2H). |
| 190C | J | 626 (M + H) | 190-193 | (CDCl₃) δ 8.55 (s, 1H), 8.14 (d, J = 8.3 Hz, 2H), 8.00 (s, 1H), 7.83-7.73 (m, 4H), 7.71 (d, J = 8.1 Hz, 1H), 7.67 (d, J = 7.7 Hz, 1H), 7.40 (dd, J = 15.8, 8.2 Hz, 3H), 3.79-3.69 (m, 1H), 3.55-3.49 (m, 1H), 3.16-3.04 (m, 2H), 2.47-2.31 (m, 2H). |
| 191C | J | 554 (M + H) | 150-155 | (CDCl₃) δ 8.54 (d, J = 4.3 Hz, 1H), 8.13 (d, J = 8.3 Hz, 2H), 8.05 (d, J = 6.3 Hz, 1H), 7.77 (dd, J = 15.4, 8.7 Hz, 4H), 7.38 (d, J = 8.3 Hz, 2H), 7.29 (dd, J = 8.0, 4.8 Hz, 2H), 7.04-6.93 (m, 2H), 3.85 (s, 3H), 3.65-3.61 (m, 2H), 3.10-3.06 (m, 2H), 2.36-2.28 (s, 2H). |
| 192C | J | 568 (M + H) | 164-167; 168-173 | (CDCl₃) δ 8.55 (s, 1H), 8.14 (d, J = 8.4 Hz, 2H), 8.09 (s, 1H), 7.82-7.77 (m, 2H), 7.74 (d, J = 6.7 Hz, 2H), 7.38 (d, J = 8.3 Hz, 2H), 7.13 (d, J = 8.3 Hz, 1H), 6.79 (dd, J = 11.9, 3.3 Hz, 2H), 3.81 (s, 3H), 3.74-3.66 (m, 1H), 3.57-3.48 (m, 1H), 3.12-3.04 (m, 2H), 2.36-2.30 (m, 2H), 2.25 (s, 3H). |
| 193C | J | 580 (M + H) | 155-158 | (CDCl₃) δ 8.55 (s, 1H), 8.14 (d, J = 8.4 Hz, 2H), 8.04 (s, 1H), 7.83-7.77 (m, 2H), 7.74 (d, J = 8.4 Hz, 2H), 7.38 (d, J = 8.3 Hz, 2H), 7.31-7.24 (m, 3H), 7.23-7.20 (m, 1H), 3.82-3.71 (m, 1H), 3.56-3.47 (m, 1H), 3.17-3.02 (m, 2H), 2.46 (t, J = 6.7 Hz, 2H), 2.39-2.27 (m, 2H), 1.99 (heptet, J = 6.8 Hz, 1H), 0.95-0.92 (m, 6H). |
| 194C | J | 600 (M + H) | 102-108 | (CDCl₃) δ 8.56 (s, 1H), 8.17 (m 3H), 7.80 (m, 4H), 7.52-7.47 (m, 2H), 7.47-7.31 (m, 9H), 3.42-3.05 (m, 2H), 2.86 (bs, 2H), 2.04-1.71 (m, 2H). |
| 195C | J | 538 (M + H) | 159-162 | (CDCl₃) δ 8.55 (s, 1H), 8.14 (d, J = 8.3 Hz, 2H), 8.08 (s, 1H), 7.84-7.77 (m, 2H), 7.75 (d, J = 8.4 Hz, 2H), 7.38 (d, J = 8.5 Hz, 2H), 7.31-7.19 (m, 4H), 3.81-3.47 (m, 2H), 3.20-3.00 (m, 2H), 2.35 (dt, J = 11.7, 5.8 Hz, 2H), 2.28 (s, 3H). |
| 196C | J | 572 (M + H) | 140-143 | (CDCl₃) δ 8.55 (s, 1H), 8.14 (d, J = 8.1 Hz, 2H), 8.05 (s, 1H), 7.80 (d, J = 8.9 Hz, 2H), 7.75 (d, J = 8.2 Hz, 2H), 7.38 (d, J = 8.8 Hz, |

TABLE 4-continued

Analytical Data for Compounds in Table 3

| ID | Synthesis Method | MS | mp (° C.) | $^1$H NMR (δ)$^1$ |
|---|---|---|---|---|
| | | | | 2H), 7.33 (dd, J = 6.1, 3.4 Hz, 1H), 7.21-7.15 (m, 2H), 3.72-3.66 (m, 1H), 3.55-3.41 (m, 1H), 3.16-3.05 (m, 2H), 2.48-2.34 (m, 2H), 2.32 (s, 3H). |
| 197C | J | 578 (M + H) | 151-155 | (CDCl$_3$) δ 8.55 (s, 1H), 8.14 (d, J = 8.2 Hz, 2H), 8.06 (s, 1H), 7.80 (d, J = 8.9 Hz, 2H), 7.75 (d, J = 8.2 Hz, 2H), 7.38 (d, J = 8.8 Hz, 2H), 7.29 (dd, J = 10.7, 4.6 Hz, 4H), 6.20 (s, 1H), 3.59-3.48 (m, 2H), 3.10-3.01 (m, 2H), 2.34-2.20 (m, 2H), 1.90 (s, 3H), 1.78 (s, 3H). |
| 198C | J | 539 (M + H) | 186-189 | (CDCl$_3$) δ 8.56 (s, 1H), 8.36 (dd, J = 4.8, 1.3 Hz, 1H), 8.15 (d, J = 8.3 Hz, 2H), 8.09 (s, 1H), 7.78 (m, 4H), 7.54 (dd, J = 7.5, 0.9 Hz, 1H), 7.37 (d, J = 8.5 Hz, 2H), 7.13 (dd, J = 7.4, 4.8 Hz, 1H), 3.87 (t, J = 5.7 Hz, 2H), 3.12-3.03 (m, 2H), 2.40-2.32 (m, 2H), 2.24 (s, 3H). |
| 199C | J | 608 (M + H) | 207-208 | (CDCl$_3$) δ 8.55 (s, 1H), 8.15 (d, J = 8.4 Hz, 2H), 8.05 (s, 1H), 7.83-7.78 (m, 2H), 7.76 (d, J = 8.4 Hz, 2H), 7.43-7.36 (m, 3H), 7.34 (t, J = 4.7 Hz, 3H), 3.71-3.64 (m, 2H), 3.12-3.06 (m, 2H), 2.39-2.30 (m, 2H). |
| 200C | J | 590 (M + H) | 170-172 | (CDCl$_3$) δ 8.56 (s, 1H), 8.15 (d, J = 8.4 Hz, 2H), 8.03 (s, 1H), 7.83-7.77 (m, 2H), 7.76 (d, J = 8.3 Hz, 2H), 7.42-7.27 (m, 6H), 6.74-6.29 (m, 1H), 3.70-3.64 (m, 2H), 3.13-3.06 (m, 2H), 2.40-2.31 (m, 2H). |
| 201C | J | 626 (M + H) | 190-193 | (CDCl$_3$) δ 8.55 (s, 1H), 8.14 (d, J = 8.3 Hz, 2H), 8.00 (s, 1H), 7.83-7.73 (m, 4H), 7.71 (d, J = 8.1 Hz, 1H), 7.67 (d, J = 7.7 Hz, 1H), 7.40 (dd, J = 15.8, 8.2 Hz, 3H), 3.79-3.69 (m, 1H), 3.55-3.49 (m, 1H), 3.16-3.04 (m, 2H), 2.47-2.31 (m, 2H). |
| 202C | J | 554 (M + H) | 231-234 | (CDCl$_3$) δ 8.56 (s, 1H), 8.19-8.08 (m, 3H), 7.84-7.72 (m, 4H), 7.39 (d, J = 8.4 Hz, 2H), 7.25-7.20 (m, 2H), 6.96-6.88 (m, 2H), 3.83 (s, 3H), 3.76-3.68 (m, 2H), 3.13-3.03 (m, 2H), 2.39-2.27 (m, 2H). |
| 203C | J | 631 (M + H) | 200-201 | (CDCl$_3$) δ 8.56 (s, 1H), 8.15 (d, J = 8.2 Hz, 2H), 8.06 (s, 1H), 7.83-7.77 (m, 2H), 7.75 (d, J = 8.2 Hz, 2H), 7.39 (d, J = 8.5 Hz, 2H), 7.28-7.25 (m, 2H), 3.51-3.42 (m, 2H), 3.14-3.05 (m, 2H), 2.35 (s, 2H), 2.25 (s, 6H). |
| 204C | J | 568 (M + H) | 193-196 | (CDCl$_3$) δ 8.55 (s, 1H), 8.14 (d, J = 8.4 Hz, 2H), 8.09 (s, 1H), 7.84-7.77 (m, 2H), 7.75 (d, J = 8.4 Hz, 2H), 7.38 (d, J = 8.3 Hz, 2H), 7.08 (t, J = 4.0 Hz, 2H), 6.88 (d, J = 8.6 Hz, 1H), 3.82 (s, 3H), 3.66-3.58 (m, 2H), 3.11-3.03 (m, 2H), 2.36-2.27 (m, 5H). |
| 205C | J | 539 (M + H) | Oil | (CDCl$_3$) δ 8.55 (s, 1H), 8.45 (dd, J = 4.8, 1.6 Hz, 1H), 8.18-8.12 (m, 2H), 8.06 (s, 1H), 7.82-7.72 (m, 4H), 7.53 (dd, J = 7.9, 1.6 Hz, 1H), 7.40-7.33 (m, 2H), 7.24-7.18 (m, 1H), 3.63 (br s, 2H), 3.18-3.03 (m, 2H), 2.51 (s 3H), 2.35 (dt, J = 11.7, 5.7 Hz, 2H) |
| 206C | J | 554 (M + H) | 177-178 | (CDCl$_3$) δ 8.56 (s, 1H), 8.16 (d, J = 8.9 Hz, 3H), 7.84-7.73 (m, 4H), 7.39 (d, J = 8.8 Hz, 2H), 7.30 (t, J = 8.1 Hz, 1H), 6.95-6.85 (m, 2H), 6.78 (dt, J = 11.1, 5.5 Hz, 1H), 3.81 (s, 3H), 3.79-3.73 (m, 2H), 3.12-3.04 (m, 2H), 2.38-2.28 (m, 2H). |
| 207C | J | 596 (M + H) | 171-173 | (CDCl$_3$) δ 8.57 (s, 1H), 8.23-8.13 (m, 3H), 8.06 (d, J = 8.5 Hz, 2H), 7.80 (dd, J = 8.5, 4.5 Hz, 4H), 7.39 (d, J = 8.5 Hz, 4H), 4.38 (q, J = 7.2 Hz, 2H), 3.82 (t, J = 6.0 Hz, 2H), 3.14-3.03 (m, 2H), 2.37 (s, 2H), 1.40 (t, J = 7.1 Hz, 3H). |
| 208C | J | 568 (M + H) | 171-173 | (CDCl$_3$) δ 8.55 (s, 1H), 8.14 (d, J = 8.3 Hz, 2H), 8.07 (s, 1H), 7.84-7.77 (m, 2H), 7.75 (d, J = 8.3 Hz, 2H), 7.38 (d, J = 8.3 Hz, 2H), 7.32-7.23 (m, 2H), 6.99 (ddd, J = 8.3, 5.5, 1.4 Hz, 2H), 4.08 (q, J = 7.0 Hz, 2H), 3.69-3.57 (m, 2H), 3.16-3.02 (m, 2H), 2.32 (dt, |

TABLE 4-continued

Analytical Data for Compounds in Table 3

| ID | Synthesis Method | MS | mp (° C.) | $^1$H NMR ($\delta$)$^1$ |
|---|---|---|---|---|
| | | | | J = 11.7, 5.9 Hz, 2H), 1.39 (t, J = 7.0 Hz, 3H). |
| 209C | J | 550 (M + H) | 212-213 | (CDCl$_3$) $\delta$ 8.64 (s, 1H), 8.15 (d, J = 8.4 Hz, 2H), 8.06 (s, 1H), 7.91 (d, J = 8.5 Hz, 2H), 7.79 (d, J = 8.6 Hz, 2H), 7.75 (d, J = 8.4 Hz, 2H), 7.38 (dd, J = 7.8, 1.6 Hz, 1H), 7.33 (td, J = 7.5, 1.4 Hz, 1H), 7.29-7.23 (m, 1H), 7.18 (dd, J = 7.8, 1.4 Hz, 1H), 3.78-3.72 (m, 1H), 3.59-3.48 (m, 1H), 3.18-3.04 (m, 3H), 2.40-2.30 (m, 2H), 1.26-1.20 (m, 6H). |
| 210C | J | 580 (M + H) | 136-139 | (CDCl$_3$) $\delta$ 8.55 (s, 1H), 8.14 (d, J = 8.4 Hz, 2H), 8.07 (s, 1H), 7.83-7.77 (m, 2H), 7.75 (d, J = 8.4 Hz, 2H), 7.55-7.49 (m, 1H), 7.38 (d, J = 8.3 Hz, 2H), 7.32-7.26 (m, 2H), 7.19-7.13 (m, 1H), 3.72 (ddd, J = 12.9, 9.3, 3.8 Hz, 1H), 3.60-3.51 (m, 1H), 3.15 (ddd, J = 13.3, 9.4, 4.0 Hz, 1H), 3.10-3.01 (m, 1H), 2.51-2.36 (m, 1H), 2.36-2.22 (m, 1H), 1.43 (s, 9H). |
| 211C | J | 566 (M + H) | 100-106 | (CDCl$_3$) $\delta$ 8.55 (s, 1H), 8.15 (d, J = 8.4 Hz, 2H), 8.10 (s, 1H), 7.79 (dt, J = 10.4, 5.8 Hz, 4H), 7.38 (d, J = 8.3 Hz, 2H), 7.11 (s, 3H), 3.85-3.78 (m, 2H), 3.20-3.12 (m, 2H), 2.30 (s, 6H), 2.13-2.07 (m, 2H), 1.87-1.82 (m, 2H). |
| 212C | J | 580 (M + H) | 186-188 | (CDCl$_3$) $\delta$ 8.55 (s, 1H), 8.19-8.10 (m, 3H), 7.79 (dt, J = 10.7, 5.9 Hz, 4H), 7.38 (dd, J = 8.5, 2.6 Hz, 3H), 7.30 (td, J = 7.5, 1.4 Hz, 1H), 7.23 (td, J = 7.5, 1.7 Hz, 1H), 7.13 (dd, J = 7.8, 1.4 Hz, 1H), 3.94 (bs, 2H), 3.24-3.02 (m, 3H), 2.13-2.05 (m, 2H), 1.84-1.73 (m, 2H), 1.24 (t, J = 10.5 Hz, 6H). |
| 213C | J | 580 (M + H) | 123-127 | (CDCl$_3$) $\delta$ 8.55 (s, 1H), 8.13 (d, J = 8.4 Hz, 2H), 8.03 (d, J = 4.4 Hz, 1H), 7.83-7.76 (m, 2H), 7.74 (d, J = 8.0 Hz, 2H), 7.38 (d, J = 8.4 Hz, 2H), 7.24-7.15 (m, 2H), 7.12 (dd, J = 11.9, 4.6 Hz, 1H), 3.82-3.71 (m, 1H), 3.30-3.18 (m, 1H), 3.07-2.94 (m, 1H), 2.72-2.40 (m, 3H), 2.30-2.16 (m, 4H), 1.30-1.12 (m, 6H). |
| 214C | J | 622 (M + H) | 160-162 | (CDCl$_3$) $\delta$ 8.55 (s, 1H), 8.15 (d, J = 8.4 Hz, 2H), 8.06 (s, 1H), 7.83-7.72 (m, 4H), 7.38 (m, 3H), 7.34 (dd, J = 2.9, 1.5 Hz, 3H), 3.58 (ddd, J = 12.3, 3.9, 1.4 Hz, 1H), 3.39 (dd, J = 12.2, 9.2 Hz, 1H), 3.04 (ddd, J = 12.2, 3.9, 1.4 Hz, 1H), 2.84 (dd, J = 12.2, 9.5 Hz, 1H), 2.61-2.42 (m, 1H), 1.18 (d, J = 6.7 Hz, 3H) |
| 215C | J | 640 (M + H) | 116 (dec) | (CDCl$_3$) $\delta$ 8.55 (s, 1H), 8.14 (dd, J = 8.3, 1.5 Hz, 2H), 8.00 (d, J = 4.0 Hz, 1H), 7.84-7.72 (m, 4H), 7.72-7.63 (m, 2H), 7.45-7.32 (m, 3H), 3.60-3.44 (m, 1H), 3.37-3.27 (m, 1H), 3.03-2.92 (m, 1H), 2.92-2.82 (m, 1H), 2.69-2.54 (m, 1H), 1.19-1.12 (m, 3H) |
| 216C | J | 622 (M + H) | 132-135 | (CDCl$_3$) $\delta$ 8.55 (s, 1H), 8.14 (d, J = 8.4 Hz, 2H), 8.02 (s, 1H), 7.82-7.71 (m, 4H), 7.44-7.30 (m, 6H), 3.87 (d, J = 6.3 Hz, 1H), 3.23 (td, J = 11.9, 3.8 Hz, 1H), 3.07-2.94 (m, 1H), 2.54-2.43 (m, 1H), 2.19 (ddd, J = 13.9, 9.0, 5.0 Hz, 1H), 1.31 (d, J = 6.6 Hz, 3H) |
| 217C | J | 640 (M + H) | 93 (dec) | Two isomers (CDCl$_3$) $\delta$ 8.55 (s, 2H), 8.14 (dd, J = 8.4, 2.7 Hz, 4H), 7.98 (d, J = 4.2 Hz, 2H), 7.83-7.72 (m, 8H), 7.67 (dt, J = 12.9, 7.4 Hz, 4H), 7.40 (dd, J = 15.3, 8.1 Hz, 6H), 4.17 (s, 1H), 3.96 (td, J = 6.6, 3.1 Hz, 1H), 3.24-3.12 (m, 2H), 3.12-3.01 (m, 2H), 2.41 (dddd, J = 10.8, 10.0, 8.9, 4.2 Hz, 2H), 2.30-2.15 (m, 2H), 1.24 (d, J = 6.7 Hz, 3H), 1.04 (d, J = 6.7 Hz, 3H) |
| 218C | J | 580 (M + H) | 95 (dec) | (CDCl$_3$) $\delta$ 8.55 (s, 1H), 8.18-8.10 (m, 2H), 8.05 (s, 1H), 7.83-7.76 (m, 2H), 7.73 (d, J = 8.4 Hz, 2H), 7.41-7.37 (m, 2H), 6.93 (d, J = 9.4 Hz, 2H), 3.76 (dd, J = 10.8, 4.6 Hz, |

TABLE 4-continued

Analytical Data for Compounds in Table 3

| ID | Synthesis Method | MS | mp (° C.) | $^1$H NMR (δ)$^1$ |
|---|---|---|---|---|
| | | | | 1H), 3.29-3.16 (m, 1H), 2.99 (ddd, J = 12.2, 5.9, 3.9 Hz, 1H), 2.54-2.37 (m, 1H), 2.31 (s, 3H), 2.22 (d, J = 6.4 Hz, 7H), 1.19 (d, J = 6.7 Hz, 3H) |
| 219C | J | 592 (M + H) | 100 (dec) | (CDCl$_3$) δ 8.55 (s, 1H), 8.14-8.06 (m, 3H), 7.91-7.65 (m, 4H), 7.44-7.37 (m, 2H), 7.16-7.09 (m, 1H), 6.93-6.77 (m, 2H), 4.06-3.64 (m, 4H), 3.31-3.16 (m, 1H), 3.02-2.92 (m, 1H), 2.51-2.40 (m, 1H), 2.25-2.17 (m, 4H), 1.41-1.14 (m, 3H) |
| 220C | J | 593 (M + H) | 95 (dec) | Two isomers: (CDCl$_3$) δ 8.55 (s, 1H), 8.16-8.09 (m, 2H), 8.01 (m, 1H), 7.86-7.76 (m, 2H), 7.76-7.70 (m, 2H), 7.64-7.28 (m, 4H), 7.24-7.14 (m, 2H), 4.08-3.65 (m, 1H), 3.37-3.15 (m, 1H), 3.09-2.92 (m, 1H), 2.80 (td, J = 14.2, 6.8 Hz, 1H), 2.45 m, 1H), 2.35-2.09 (m, 1H), 1.76-1.58 (m, 1H), 1.48-1.35 (m, 2H), 1.27-1.19 (m, 2H), 1.19-1.13 (m, 2H), 1.06-0.92 (m, 1H), 0.92-0.72 (m, 3H) |
| 221C | J | 603 (M + H) | 113 (dec) | (400 MHz, CDCl$_3$) δ 8.56 (s, 1H), 8.20-8.10 (m, 2H), 8.00 (s, 1H), 7.83-7.77 (m, 2H), 7.75 (d, J = 8.4 Hz, 2H), 7.42-7.28 (m, 6H), 6.72-6.25 (m, 1H), 3.90 (d, J = 6.4 Hz, 1H), 3.24 (td, J = 12.0, 3.6 Hz, 1H), 3.05-2.93 (m, 1H), 2.49 (tt, J = 11.7, 4.0 Hz, 1H), 2.21 (td, J = 8.7, 4.4 Hz, 1H), 1.29 (d, J = 6.6 Hz, 3H) |
| 222C | J | 594 (M + H) | 124 (dec) | (CDCl$_3$) δ 8.55 (s, 1H), 8.14 (dd, J = 8.4, 2.1 Hz, 2H), 8.05 (d, J = 2.8 Hz, 1H), 7.87-7.72 (m, 4H), 7.61-7.49 (m, 1H), 7.38 (d, J = 8.3 Hz, 2H), 7.33-7.21 (m, 2H), 7.15-7.05 (m, 1H), 3.79-3.68 (m, 1H), 3.51-3.29 (m, 1H), 3.12-2.93 (m, 1H), 2.66-2.52 (m, 1H), 2.18-2.12 (m, 1H), 1.43 (m, 12H) |
| 223C | L | 566 (M + H) | 75-87 | (CDCl$_3$) δ 8.58 (s, 1H), 8.21 (d, J = 8.4 Hz, 2H), 8.16 (s, 1H), 7.85-7.77 (m, 4H), 7.40 (d, J = 8.3 Hz, 2H), 7.23 (dd, J = 8.4, 6.6 Hz, 1H), 7.15 (d, J = 7.5 Hz, 2H), 3.24-3.14 (m, 4H), 2.18 (s, 6H). |
| 224C | L | 580 (M + H) | 118 (dec) | (CDCl$_3$) δ 8.57 (s, 1H), 8.21 (d, J = 8.4 Hz, 2H), 8.16 (s, 1H), 7.85-7.75 (m, 4H), 7.46-7.36 (m, 4H), 7.33-7.26 (m, 1H), 7.10 (d, J = 7.6 Hz, 1H), 3.26-3.14 (m, 4H), 2.81 (sept, J = 6.9 Hz, 1H), 1.21 (t, J = 7.2 Hz, 6H). |
| 225C | L | 580 (M + H) | 111 (dec) | (CDCl$_3$) δ 8.57 (s, 1H), 8.21 (d, J = 8.4 Hz, 2H), 8.15 (s, 1H), 7.86-7.76 (m, 4H), 7.39 (d, J = 8.3 Hz, 2H), 7.29 (t, J = 7.6 Hz, 1H), 7.21-7.15 (m, 2H), 3.27-3.10 (m, 4H), 2.50 (q, J = 7.5 Hz, 2H), 2.18 (s, 3H), 1.20 (t, J = 7.6 Hz, 3H). |
| 226C | L | 573 (M + H) | 196-200 | (CDCl$_3$) δ 8.57 (s, 1H), 8.24-8.16 (m, 3H), 7.85-7.76 (m, 4H), 7.43-7.34 (m, 3H), 7.03 (dd, J = 8.5, 7.4 Hz, 2H), 3.21 (s, 4H) |
| 227C | L | 586 (M + H) | Oil | (CDCl$_3$) δ 8.57 (s, 1H), 8.21 (d, J = 8.3 Hz, 2H), 8.15 (s, 1H), 7.81 (t, J = 9.1 Hz, 4H), 7.43-7.31 (m, 3H), 7.28-7.21 (m, 2H), 3.36-3.07 (m, 4H), 2.24 (s, 3H); $^{19}$F NMR (376 MHz, CDCl$_3$) δ −58.02 |
| 228C | L | 640 (M + H) | 99 (dec) | (CDCl$_3$) δ 8.57 (s, 1H), 8.21 (d, J = 8.3 Hz, 2H), 8.11 (s, 1H), 7.81 (dd, J = 11.5, 4.7 Hz, 4H), 7.72 (dd, J = 17.3, 8.0 Hz, 2H), 7.51 (dd, J = 10.0, 5.4 Hz, 1H), 7.39 (d, J = 8.3 Hz, 2H), 3.36-3.03 (m, 4H) |
| 229C | L | 622 (M + H) | 95 (dec) | (CDCl$_3$) δ 8.57 (s, 1H), 8.21 (d, J = 8.4 Hz, 2H), 8.13 (s, 1H), 7.80 (dt, J = 5.5, 4.9 Hz, 4H), 7.44-7.34 (m, 6H), 3.29-3.10 (m, 4H) |
| 230C | L | 594 (M + H) | 94 (dec) | (CDCl$_3$) δ 8.57 (s, 1H), 8.21 (d, J = 8.3 Hz, 2H), 8.14 (d, J = 15.4 Hz, 1H), 7.83-7.76 (m, 4H), 7.43-7.37 (m, 4H), 7.32-7.26 (m, 1H), 7.16-7.09 (m, 1H), 3.24-3.12 (m, 4H), 2.61-2.44 (m, 1H), 1.75-1.50 (m, |

TABLE 4-continued

Analytical Data for Compounds in Table 3

| ID | Synthesis Method | MS | mp (° C.) | $^1$H NMR (δ)[1] |
|---|---|---|---|---|
| | | | | 2H), 1.17 (dd, J = 6.9, 3.3 Hz, 3H), 0.87-0.73 (m, 3H) |
| 231C | L | 582 (M + H) | 105 (dec) | (CDCl$_3$) δ 8.58 (s, 1H), 8.22 (s, 1H), 8.19 (d, J = 5.0 Hz, 2H), 7.81 (dd, J = 8.7, 5.5 Hz, 4H), 7.40 (d, J = 8.3 Hz, 2H), 7.05 (d, J = 8.3 Hz, 1H), 6.90-6.76 (m, 2H), 3.83 (s, 3H), 3.22-3.11 (m, 4H), 2.16 (s, 3H) |
| 232C | L | 593 (M + H) | 120 (dec) | (CDCl$_3$) δ 8.57 (s, 1H), 8.21 (d, J = 8.4 Hz, 2H), 8.16 (s, 1H), 7.81 (dd, J = 8.7, 5.3 Hz, 4H), 7.58 (dd, J = 8.1, 1.5 Hz, 1H), 7.38 (dd, J = 13.2, 5.1 Hz, 3H), 7.33-7.27 (m, 1H), 7.02-6.96 (m, 1H), 3.37-3.01 (m, 4H), 1.36 (s, 9H) |
| 233C | L | 604 (M + H) | 92 (dec) | (CDCl$_3$) δ 8.58 (s, 1H), 8.21 (d, J = 8.4 Hz, 2H), 8.14 (s, 1H), 7.86-7.72 (m, 4H), 7.48-7.28 (m, 6H), 6.40 (t, J$_{HF}$ = 74.3 Hz, 1H), 3.25-3.11 (m, 4H) |

[1]NMR spectral data were acquired using a 400 MHz instrument except where noted.

TABLE 4A

Analytical Data for Optically Active Compounds in Table 3

| ID | Separation Method | MS | Chiral Purity (%) | $^1$H NMR (δ)[1] |
|---|---|---|---|---|
| 234C | A | 571 (M + H) | 98.73 | (CDCl$_3$) δ 8.58 (s, 1H), 8.31 (s, 1H), 8.23 (d, J = 8.4 Hz, 2H), 7.87 – 7.78 (m, 4H), 7.41 (t, J = 6.3 Hz, 3H), 7.37 – 7.31 (m, 1H), 7.28 (d, J = 7.0 Hz, 1H), 4.09 – 3.98 (m, 2H), 2.29 (s, 3H) |
| 235C | A | 571 (M + H) | 95.75 | (CDCl$_3$) δ 8.58 (s, 1H), 8.31 (s, 1H), 8.23 (d, J = 8.3 Hz, 2H), 7.87 – 7.78 (m, 4H), 7.41 (dd, J =7.0, 5.6 Hz, 3H), 7.34 (t, J = 7.8 Hz, 1H), 7.28 (d, J = 6.0 Hz, 1H), 4.09 – 3.98 (m, 2H), 2.29 (s, 3H) |
| 236C | A | 565 (M + H) | 96.32 | (CDCl$_3$) δ 8.58 (s, 1H), 8.31 (s, 1H), 8.23 (d, J = 8.4 Hz, 2H), 7.81 (dd, J = 11.7, 5.1 Hz, 4H), 7.40 (d, J = 8.4 Hz, 2H), 7.35 (t, J = 7.7 Hz, 1H), 7.24 – 7.18 (m, 2H), 4.02 (s, 2H), 2.53 (q, J = 7.5 Hz, 2H), 2.21 (s, 3H), 1.21 (t, J = 7.6 Hz, 3H) |
| 237C | A | 565 (M + H) | 92.33 | (CDCl$_3$) δ 8.58 (s, 1H), 8.31 (s, 1H), 8.23 (d, J = 8.4 Hz, 2H), 7.81 (dd, J = 11.7, 5.1 Hz, 4H), 7.40 (d, J = 8.3 Hz, 2H), 7.35 (dd, J = 10.4, 4.9 Hz, 1H), 7.24 – 7.20 (m, 2H), 4.02 (s, 2H), 2.59 – 2.45 (m, 2H), 2.21 (s, 3H), 1.21 (t, J = 7.6 Hz, 3H) |
| 238C | B | 579 (M + H) | 95.41 | (CDCl$_3$) δ 8.58 (s, 1H), 8.29 (d, J = 3.9 Hz, 1H), 8.23 (d, J = 8.4 Hz, 2H), 7.82 (t, J = 8.8 Hz, 4H), 7.40 (d, J = 8.3 Hz, 3H), 7.31 (d, J = 6.9 Hz, 1H), 7.19 (dd, J = 7.6, 5.2 Hz, 1H), 4.03 (s, 2H), 2.83 – 2.73 (m, 1H), 2.21 (s, 3H), 1.25 – 1.18 (m, 6H) |
| 239C | B | 579 (M + H) | 92.68 | (CDCl$_3$) δ 8.58 (s, 1H), 8.30 (s, 1H), 8.22 (t, J = 8.7 Hz, 2H), 7.82 (t, J = 8.7 Hz, 4H), 7.40 (d, J = 8.2 Hz, 3H), 7.31 (d, J = 8.0 Hz, 1H), 7.20 (d, J = 7.3 Hz, 1H), 4.03 (s, 2H), 2.83 – 2.73 (m, 1H), 2.21 (s, 3H), 1.25 – 1.18 (m, 6H) |

[1]NMR spectral data were acquired using a 400 MHz instrument except where noted.

TABLE 5

Biological Results

| Compound Number | % Mortality CEW 50 μg/cm$^2$ | % Mortality BAW 50 μg/cm$^2$ | % Mortality GPA 200 ppm |
|---|---|---|---|
| 1C | A | A | D |
| 2C | A | A | D |
| 3C | A | A | D |
| 4C | A | A | B |
| 5C | A | A | B |
| 6C | A | A | D |
| 7C | A | D | D |
| 8C | A | A | B |
| 9C | A | A | D |
| 10C | A | A | D |
| 11C | A | A | D |
| 12C | A | A | B |
| 13C | A | A | B |
| 14C | A | A | B |
| 15C | A | A | A |
| 16C | A | A | D |
| 17C | A | A | B |
| 18C | A | A | B |
| 19C | A | A | B |
| 20C | A | A | D |
| 21C | C | C | D |
| 22C | A | A | B |
| 23C | A | A | D |
| 24C | A | A | B |
| 25C | A | A | D |
| 26C | C | C | D |
| 27C | A | A | B |
| 28C | A | A | B |
| 29C | A | A | B |
| 30C | A | A | B |
| 31C | A | A | B |
| 32C | C | C | B |
| 33C | A | A | B |
| 34C | C | C | B |
| 35C | A | A | B |
| 36C | A | A | D |
| 37C | A | A | D |
| 38C | A | A | D |
| 39C | C | C | B |
| 40C | A | A | B |
| 41C | A | A | D |
| 42C | A | A | D |
| 43C | A | A | B |
| 44C | A | A | D |

TABLE 5-continued

Biological Results

| Compound Number | % Mortality CEW 50 µg/cm² | % Mortality BAW 50 µg/cm² | % Mortality GPA 200 ppm |
|---|---|---|---|
| 45C | A | A | C |
| 46C | A | A | D |
| 47C | A | A | B |
| 48C | A | A | C |
| 49C | A | A | B |
| 50C | A | A | C |
| 51C | A | A | D |
| 52C | D | B | B |
| 53C | D | B | B |
| 54C | A | A | D |
| 55C | A | A | D |
| 56C | A | A | C |
| 57C | A | A | B |
| 58C | A | A | B |
| 59C | A | A | B |
| 60C | A | A | D |
| 61C | A | A | C |
| 62C | A | A | B |
| 63C | A | A | D |
| 64C | A | A | D |
| 65C | A | A | B |
| 66C | A | A | B |
| 67C | A | A | D |
| 68C | A | A | B |
| 69C | A | A | C |
| 70C | A | A | D |
| 71C | A | A | D |
| 72C | A | A | B |
| 73C | A | A | B |
| 74C | A | A | D |
| 75C | A | A | B |
| 76C | A | A | B |
| 77C | A | A | B |
| 78C | A | A | B |
| 79C | A | A | B |
| 80C | A | A | D |
| 81C | A | A | D |
| 82C | A | A | C |
| 83C | A | A | C |
| 84C | A | A | D |
| 85C | A | A | B |
| 86C | A | A | D |
| 87C | C | C | B |
| 88C | A | A | B |
| 89C | A | A | D |
| 90C | A | A | B |
| 91C | D | D | C |
| 92C | A | A | B |
| 93C | A | A | D |
| 94C | A | A | D |
| 95C | A | A | B |
| 96C | A | A | B |
| 97C | A | A | C |
| 98C | C | A | C |
| 99C | A | A | C |
| 100C | A | A | C |
| 101C | A | A | C |
| 102C | A | A | C |
| 103C | A | A | C |
| 104C | A | A | C |
| 105C | A | A | C |
| 106C | A | A | C |
| 107C | D | D | C |
| 108C | A | A | D |
| 109C | A | A | C |
| 110C | A | A | C |
| 111C | A | A | B |
| 112C | A | A | B |
| 113C | A | A | C |
| 114C | A | A | C |
| 115C | D | B | C |
| 116C | A | A | C |
| 117C | A | A | D |
| 118C | A | A | D |
| 119C | A | A | D |
| 120C | A | A | C |
| 121C | A | A | B |
| 122C | A | A | C |
| 123C | A | A | C |
| 124C | A | A | C |
| 125C | A | A | C |
| 126C | A | A | C |
| 127C | A | A | C |
| 128C | A | A | C |
| 129C | A | A | C |
| 130C | A | A | C |
| 131C | A | A | D |
| 132C | A | A | B |
| 133C | A | A | B |
| 134C | A | A | C |
| 135C | A | A | D |
| 136C | A | A | D |
| 137C | A | A | D |
| 138C | A | A | B |
| 139C | A | A | B |
| 140C | A | A | B |
| 141C | A | A | D |
| 142C | A | A | D |
| 143C | A | A | C |
| 144C | A | A | C |
| 145C | A | A | B |
| 146C | A | A | B |
| 147C | A | A | B |
| 148C | A | A | C |
| 149C | A | A | D |
| 150C | A | A | D |
| 151C | A | A | B |
| 152C | A | A | C |
| 153C | A | d | C |
| 154C | A | A | B |
| 155C | A | A | D |
| 156C | A | A | B |
| 157C | A | A | B |
| 158C | A | A | B |
| 159C | A | A | C |
| 160C | A | A | C |
| 161C | A | A | C |
| 162C | A | A | C |
| 163C | A | A | C |
| 164C | A | A | C |
| 165C | A | A | C |
| 166C | A | A | C |
| 167C | A | A | C |
| 168C | A | A | D |
| 169C | A | A | C |
| 170C | A | A | C |
| 171C | A | A | C |
| 172C | A | A | D |
| 173C | A | A | D |
| 174C | A | A | B |
| 175C | A | A | D |
| 176C | A | A | C |
| 177C | A | A | D |
| 178C | A | A | D |
| 179C | A | A | D |
| 180C | A | A | B |
| 181C | A | A | B |
| 182C | A | A | B |
| 183C | A | A | D |
| 184C | A | A | D |
| 185C | A | A | D |
| 186C | A | A | B |
| 187C | A | A | D |
| 188C | A | A | B |
| 189C | A | A | B |
| 190C | A | A | B |

TABLE 5-continued

Biological Results

| Compound Number | % Mortality CEW 50 μg/cm² | % Mortality BAW 50 μg/cm² | % Mortality GPA 200 ppm |
|---|---|---|---|
| 191C | A | A | D |
| 192C | A | A | B |
| 193C | A | A | B |
| 194C | A | A | B |
| 195C | A | A | B |
| 196C | A | A | D |
| 197C | A | A | D |
| 198C | A | A | D |
| 199C | A | A | C |
| 200C | A | A | C |
| 201C | A | A | B |
| 202C | A | A | B |
| 203C | A | A | B |
| 204C | A | A | B |
| 205C | A | A | B |
| 206C | A | A | D |
| 207C | d | D | C |
| 208C | A | A | D |
| 209C | A | A | D |
| 210C | A | A | C |
| 211C | A | A | D |
| 212C | A | A | D |
| 213C | A | A | B |
| 214C | A | A | C |
| 215C | A | A | C |
| 216C | A | A | C |
| 217C | A | A | C |
| 218C | A | A | C |
| 219C | A | A | C |
| 220C | A | A | C |
| 221C | A | A | C |
| 222C | A | A | C |
| 223C | A | A | C |
| 224C | A | A | B |
| 225C | A | A | C |
| 226C | A | A | C |
| 227C | A | A | C |
| 228C | A | A | C |
| 229C | A | A | C |
| 230C | A | A | C |
| 231C | A | A | C |
| 232C | A | A | C |
| 233C | A | A | C |
| 234C | A | A | C |
| 235C | A | A | C |
| 236C | A | A | C |
| 237C | A | A | C |
| 238C | A | A | C |
| 239C | A | A | C |

We claim:

1. A process to control a pest, said process comprising applying to an area, in an amount sufficient to control such pest, a composition comprising a carrier and a molecule according to Formulas One or Two Formula 1

$Ar_1-Het-Ar_2-C(R_1)=N_1-N_2(R_2)-CH(SR_3)(N_3R_4)$

Formula 2

$Ar_1-Het-Ar_2-C(R_1)=N_1-N_2=C(S-R_5)(N_3R_4)$ wherein:

(a) $Ar_1$ is
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl, and substituted phenoxy,
  wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl)phenyl, and phenoxy;

(b) Het is a 1,2,4-triazolyl $Ar_1-N-N=C(Ar_2)-N$ (1,2,4-triazolyl linking $Ar_1$ and $Ar_2$)

(c) $Ar_2$ is
  (1) furanyl, phenyl, pyridazinyl, pyridyl, pyrimidinyl, thienyl, or
  (2) substituted furanyl, substituted phenyl, substituted pyridazinyl, substituted pyridyl, substituted pyrimidinyl, or substituted thienyl,
    wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy, wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(d) R1 is selected from H, CN, F, Cl, Br, I, $C_1$-$C_6$ alkyl, $C_3$-$C_6$ cycloalkyl, $C_3$-$C_6$ cycloalkoxy, $C_1$-$C_6$ alkoxy, $C_2$-$C_6$ alkenyl, $C_2$-$C_6$ alkynyl, $S(=O)_n(C_1$-$C_6$ alkyl), $OSO_2(C_1$-$C_6$ alkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, or phenoxy, wherein each alkyl, cycloalkyl, cycloalkoxy, alkoxy, alkenyl, alkynyl, phenyl, and phenoxy, are optionally substituted with one or more substituents independently selected from F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(e) R2 is H, $C_1$-$C_6$ alkyl, $C_3$-$C_6$ cycloalkyl, $C_2$-$C_6$ alkenyl, $C_2$-$C_6$ alkynyl, $C(=O)H$, $C(=O)(C_1$-$C_6$ alkyl), $C(=O)O(C_1$-$C_6$ alkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O$ ($C_1$-$C_6$ alkyl), phenyl, $C_1$-$C_6$ alkylphenyl, $C_1$-$C_6$ alkyl-O-phenyl, $C(=O)$Het-1, Het-1, $C_1$-$C_6$ alkylHet-1, or $C_1$-$C_6$ alkyl-O-Het-1, wherein each alkyl, cycloalkyl, alkenyl, alkynyl, phenyl, and Het-1 are optionally substituted with one or more substituents independently selected from F, Cl, Br, I, CN, $NO_2$, $NR_xR_y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, and Het-1;

(f) R3 is $C_1$-$C_6$ alkyl, $C_3$-$C_6$ cycloalkyl, $C_2$-$C_6$ alkenyl, $C_2$-$C_6$ alkynyl, $C(=O)H$, $C(=O)(C_1$-$C_6$ alkyl), $C(=O)O(C_1$-$C_6$ alkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O$ ($C_1$-$C_6$ alkyl), phenyl, $C_1$-$C_6$ alkylphenyl, $C_1$-$C_6$ alkyl-O-phenyl, $C(=O)$Het-1, Het-1, $C_1$-$C_6$ alkylHet-1, $C_1$-$C_6$ alkyl-O—$C(=O)C_1$-$C_6$ alkyl-O—$C_1$-$C_6$ alkyl, $C_1$-$C_6$ alkyl-O—$C(=O)C_1$-$C_6$ alkyl-O—$C_1$-$C_6$ alkyl-O—$C_1$-$C_6$ alkyl, $C_1$-$C_6$ alkyl-O—$C(=O)C_1$-$C_6$ alkyl-O—$C_1$-$C_6$ haloalkyl, $C_1$-$C_6$ alkyl-O—$C(=O)C_1$-$C_6$ alkyl-$N(R_x)C(=O)$—O-phenyl, $C_1$-$C_6$ alkyl-O—$C(=O)C_1$-$C_6$ alkyl-$N(R_x)C(=O)$—O—$C_1$-$C_6$ alkylphenyl, $C_1$-$C_6$ alkyl$C(=O)N(R_x)C_1$-$C_6$ alkyl, $C_1$-$C_6$ alkyl$C(=O)N(R_x)C_1$-$C_6$ alkylHet-1$C(=O)$—O—$C_1$-$C_6$ alkyl, $C_1$-$C_6$ alkyl$C(=O)N(R_x)C_1$-$C_6$ alkylHet-1, $C_1$-$C_6$ alkyl$C(=O)$Het-1, $C_1$-$C_6$ alkyl$C(=O)N(R_x)C_1$-$C_6$ alkyl$(N(R_x)(R_y))(C(=O)OH)$, $C_1$-$C_6$ alkyl$C(=O)N(R_x)C_1$-$C_6$ alkyl$N(R_x)(R_x$, $C_1$-$C_6$ alkyl$C(=O)N(R_x(C_1$-$C_6$ alkyl$N(R_xC(=O)$—O—$C_1$-$C_6$ alkyl, $C_1$-$C_6$ alkyl$C(=O)N(R_x)C_1$-$C_6$ alkyl$(N(R_x)C(=O)$—O—$C_1$-$C_6$ alkyl$)(C(=O)OH)$, $C_1$-$C_6$ alkyl$C(=O)$Het-1$C(=O)$—O—$C_1$-$C_6$ alkyl, $C_1$-$C_6$ alkyl-O—$C(=O)$—O—$C_1$-$C_6$ alkyl, $C_1$-$C_6$ alkyl-O—$C(=O)C_1$-$C_6$ alkyl, $C_1$-$C_6$ alkyl-O—$C(=O)C_3$-$C_6$ cycloalkyl, $C_1$-$C_6$ alkyl-O—$C(=O)$Het-1, $C_1$-$C_6$ alkyl-O—$C(=O)C_1$-$C_6$ alkyl-$N(R_x)C(=O)$—O—$C_1$-$C_6$ alkyl, $C_1$-$C_6$ alkyl-$NR_xR_y$, or $C_1$-$C_6$ alkyl-O-Het-1, wherein each alkyl, cycloalkyl, alkenyl, alkynyl, phenyl, and Het-1 are optionally substituted with one or more substituents independently selected from F, Cl, Br, I, CN, $NO_2$, $NR_xR_y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)OH$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, $Si(C_1$-$C_6$ alkyl$)_3$, $S(=O)_nNR_xR_y$, and Het-1;

(g) R4 is H, $C_1$-$C_6$ alkyl, $C_3$-$C_6$ cycloalkyl, $C_2$-$C_6$ alkenyl, $C_2$-$C_6$ alkynyl, C(=O)H, C(=O)($C_1$-$C_6$ alkyl), C(=O)O($C_1$-$C_6$ alkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, $C_1$-$C_6$ alkylphenyl, $C_1$-$C_6$ alkyl-O-phenyl, C(=O)Het-1, Het-1, $C_1$-$C_6$ alkylHet-1, or $C_1$-$C_6$ alkyl-O-Het-1, wherein each alkyl, cycloalkyl, alkenyl, alkynyl, phenyl, and Het-1 are optionally substituted with one or more substituents independently selected from F, Cl, Br, I, CN, $NO_2$, $NR_xR_y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, and Het-1;

(h) R5 is a 2 to 4 membered saturated or unsaturated hydrocarbyl linkage where said linkage may also be substituted with F, Cl, Br, I, CN, $NO_2$, oxo, $NR_xR_y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, and Het-1, wherein each alkyl, cycloalkyl, cycloalkoxy, alkoxy, alkenyl, alkynyl, phenyl, phenoxy, and Het-1, are optionally substituted with one or more substituents independently selected from F, Cl, Br, I, CN, $NO_2$, oxo, $NR_xR_y$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)$NR_xR_y$, ($C_1$-$C_6$ alkyl)$NR_xR_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, halophenyl, phenoxy, and Het-1;

(i) n=0, 1, or 2; and (j) $R_x$ and $R_y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), and phenyl, wherein each alkyl, cycloalkyl, cycloalkoxy, alkoxy, alkenyl, alkynyl, phenyl, phenoxy, and Het-1, are optionally substituted with one or more substituents independently selected from F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)H, C(=O)OH, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, halophenyl, phenoxy, and Het-1, or $R_x$ and $R_y$ together can optionally form a 5- to 7-membered saturated or unsaturated cyclic group which may contain one or more heteroatoms selected from nitrogen, sulfur, and oxygen, and where said cyclic group can contain >C=O or >C=S, and where said cyclic group may be substituted with F, Cl, Br, I, CN, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_3$-$C_6$ cycloalkenyl, $C_2$-$C_6$ alkynyl, $S(=O)_n$($C_1$-$C_6$ alkyl), $S(=O)_n$($C_1$-$C_6$ haloalkyl), $OSO_2$($C_1$-$C_6$ alkyl), $OSO_2$($C_1$-$C_6$ haloalkyl), C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, substituted phenyl, phenoxy, and Het-1; and (k) Het-1 is a 5- or 6-membered, saturated or unsaturated, heterocyclic ring, containing one or more heteroatoms independently selected from nitrogen, sulfur or oxygen.

2. A process according to claim 1 wherein said molecule $Ar_1$ is a substituted phenyl wherein said substituted phenyl has one or more substituents independently selected from $C_1$-$C_6$ haloalkyl and $C_1$-$C_6$ haloalkoxy.

3. A process according to claim 1 wherein said molecule $Ar_1$ is a substituted phenyl wherein said substituted phenyl, has one or more substituents independently selected from $CF_3$, $OCF_3$, and $OCF_2CF_3$.

4. A process according to claim 1 wherein said $Ar_2$ is a phenyl.

5. A process according to claim 1 wherein said R1 is H or $C_1$-$C_6$ alkyl.

6. A process according to claim 1 wherein said R1 is H or $CH_3$.

7. A process according to claim 1 wherein said R2 is H.

8. A process according to claim 1 wherein said R3 is $C_1$-$C_6$ alkyl, $C_2$-$C_6$ alkenyl, $C_2$-$C_6$ alkynyl, $C_1$-$C_6$ alkylphenyl, $C_1$-$C_6$ alkylHet-1, $C_1$-$C_6$ alkyl-O—C(=O)$C_1$-$C_6$ alkyl-O—$C_1$-$C_6$ alkyl, $C_1$-$C_6$ alkyl-O—C(=O)$C_1$-$C_6$ alkyl-O—$C_1$-$C_6$ alkyl-O—$C_1$-$C_6$ alkyl, $C_1$-$C_6$ alkyl-O—C(=O)$C_1$-$C_6$ alkyl-O—$C_1$-$C_6$ haloalkyl, $C_1$-$C_6$ alkyl-O—C(=O)$C_1$-$C_6$ alkyl-N($R_x$)C(=O)—O-phenyl, $C_1$-$C_6$ alkyl-O—C(=O)$C_1$-$C_6$ alkyl-N($R_x$)C(=O)—O—$C_1$-$C_6$ alkylphenyl, $C_1$-$C_6$ alkylC (=O)N(R$_x$)C$_1$-C$_6$ alkyl, C$_1$-C$_6$ alkylC(=O)N(R$_x$)C$_1$-C$_6$ alkylHet-1C(=O)—O—C$_1$-C$_6$ alkyl, C$_1$-C$_6$ alkylC(=O)N(R$_x$)C$_1$-C$_6$ alkylHet-1, C$_1$-C$_6$ alkylC(=O)Het-1, C$_1$-C$_6$ alkylC(=O)N(R$_x$)C$_1$-C$_6$ alkyl(N(R$_x$)(R$_y$))(C(=O)OH), C$_1$-C$_6$ alkylC(=O)N(R$_x$)C$_1$-C$_6$ alkylN(R$_x$)(R$_y$), C$_1$-C$_6$ alkylC(=O)N(R$_x$)C$_1$-C$_6$ alkylN(R$_x$)C(=O)—O—C$_1$-C$_6$ alkyl, C$_1$-C$_6$ alkylC(=O)N(R$_x$)C$_1$-C$_6$ alkyl(N(R$_x$)C(=O)—O—C$_1$-C$_6$ alkyl)(C(=O)OH), C$_1$-C$_6$ alkylC(=O)Het-1C(=O)—O—C$_1$-C$_6$ alkyl, C$_1$-C$_6$ alkyl-O—C(=O)—O—C$_1$-C$_6$ alkyl, C$_1$-C$_6$ alkyl-O—C(=O)C$_1$-C$_6$ alkyl, C$_1$-C$_6$ alkyl-O—C(=O)C$_3$-C$_6$ cycloalkyl, C$_1$-C$_6$ alkyl-O—C(=O)Het-1, or C$_1$-C$_6$ alkyl-O—C(=O)C$_1$-C$_6$ alkyl-N(R$_x$)C(=O)—O—C$_1$-C$_6$ alkyl wherein each alkyl, alkenyl, alkynyl, phenyl, and Het-1 are optionally substituted with one or more substituents independently selected from F, Cl, Br, C$_1$-C$_6$ alkyl, C$_1$-C$_6$ haloalkyl, C$_1$-C$_6$ haloalkoxy, S(=O)$_n$(C$_1$-C$_6$ alkyl), C(=O)OH, C(=O)O(C$_1$-C$_6$ alkyl), phenyl, Si(C$_1$-C$_6$ alkyl)$_3$, and S(=O)$_n$NR$_x$R$_y$.

9. A process according to claim 1 wherein said R$_4$ is phenyl, C$_1$-C$_6$ alkylphenyl, or C$_1$-C$_6$ alkyl-O-phenyl, wherein each alkyl and phenyl are optionally substituted with one or more substituents independently selected from F, Cl, NR$_x$R$_y$, C$_1$-C$_6$ alkyl, or C$_1$-C$_6$ alkoxy.

10. A process according to claim 1 wherein said
Ar$_1$ is a substituted phenyl wherein said substituted phenyl, has one or more C$_1$-C$_6$ haloalkoxy;
Het is a triazolyl;
Ar$_2$ is a phenyl;
R1 is H;
R2 is H;
R3 is C$_1$-C$_6$ alkylHet-1 wherein said alkyl and Het-1 are optionally substituted with one or more substituents independently selected from F, Cl, Br, C$_1$-C$_6$ alkyl, C$_1$-C$_6$ haloalkyl, C$_1$-C$_6$ haloalkoxy, S(=O)$_n$(C$_1$-C$_6$ alkyl), C(=O)OH, C(=O)O(C$_1$-C$_6$ alkyl), phenyl, Si(C$_1$-C$_6$ alkyl)$_3$, and S(=O)$_n$NR$_x$R$_y$;
R4 is phenyl, wherein said phenyl is optionally substituted with one or more substituents independently selected from F, Cl, NR$_x$R$_y$, C$_1$-C$_6$ alkyl, or C$_1$-C$_6$ alkoxy; and
n=0, 1, or 2;
R$_x$ and R$_y$ are independently selected from H and phenyl, wherein said phenyl, may be optionally substituted with one or more substituents independently selected from F and Cl; and
Het-1 is wherein Het-1 is a 5- or 6-membered, saturated or unsaturated, heterocyclic ring, containing one or more heteroatoms independently selected from nitrogen, sulfur or oxygen.

11. A process according to claim 1 wherein said molecule is selected from

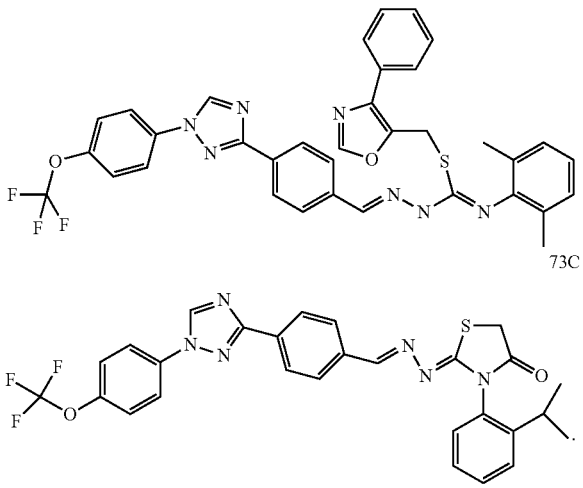

12. A process according to claim 1 wherein said area is an area where apples, corn, cotton, soybeans, canola, wheat, rice, sorghum, barley, oats, potatoes, oranges, alfalfa, lettuce, strawberries, tomatoes, peppers, crucifers, pears, tobacco, almonds, sugar beets, or beans, are growing, or the seeds thereof are going to be planted.

13. A process according to claim 1 wherein said molecule is a pesticidally acceptable acid addition salt, a salt derivative, a solvate, or an ester derivative.

14. A process according to claim 1 wherein said composition further comprises and at least one other compound selected from the Insecticide Group, Acaricide Group, Nematicide Group, Fungicide Group, Herbicide Group, AI Group, or Synergist Group.

15. A process according to claim 1 wherein said composition further comprises at least one compound that has a mode of action selected from acetylcholinesterase inhibitor, sodium channel modulator, chitin biosynthesis inhibitor, GABA-gated chloride channel antagonist, GABA and glutamate-gated chloride channel agonist, acetylcholine receptor agonist, MET I inhibitor, Mg-stimulated ATPase inhibitor, nicotinic acetylcholine receptor, Midgut membrane disrupter, oxidative phosphorylation disrupter, and ryanodine receptor (RyRs).

* * * * *